United States Patent [19]

Daniels et al.

[11] Patent Number: 4,771,384

[45] Date of Patent: Sep. 13, 1988

[54] SYSTEM AND METHOD FOR FRAGMENTATION MAPPING

[75] Inventors: Donna L. Daniels, Cross Plains; John L. Schroeder; Frederick R. Blattner, both of Madison, all of Wis.; Michael Waterman, Culver City,, Calif.

[73] Assignee: Dnastar, Inc., Madison, Wis.

[21] Appl. No.: 889,981

[22] Filed: Jul. 24, 1986

[51] Int. Cl.[4] .......................... G05F 15/42; G06G 7/58

[52] U.S. Cl. .............................. 364/413.01; 204/182.8; 364/497; 364/499; 935/75; 935/76

[58] Field of Search ............... 364/413, 497, 498, 499; 204/182.8, 182.9; 935/3, 9, 75, 76

[56] References Cited

U.S. PATENT DOCUMENTS

| | | | |
|---|---|---|---|
| 4,412,288 | 10/1983 | Herman | 364/413 |
| 4,518,690 | 5/1985 | Guntaka | 935/8 |
| 4,675,283 | 6/1987 | Roninson | 204/182.8 |

FOREIGN PATENT DOCUMENTS

| | | | |
|---|---|---|---|
| 3300632 | 7/1984 | Fed. Rep. of Germany | 935/76 |
| 59-182366 | 10/1984 | Japan | 364/413 |
| 59-193355 | 11/1984 | Japan | 364/413 |

OTHER PUBLICATIONS

Pearson, William R., Automatic Construction of Restriction Site Maps, *Nucleic Acids Research,* vol. 10 No. 1 1982.

Nolan, Garry P. et al., Plasmid Mapping Computer Program, *Nucleic Acids Research,* vol. 12 No. 1 1984.

Durand and Gregegere, An Efficient Program to Construct Restriction Maps from Experimental Data with Realistic Error Levels, *Nucleic Acids Research,* vol. 12 No. 1 1984.

Wulkan and Lott, Computer-Aided Construction of Nucleic Acid Restriction Maps Using Defined Vectors, *Cabios,* vol. 1, No. 4 1985.

Fitch, Smith & Ralph, Mapping the Order of DNA Restriction Fragments, *Gene,* vol. 22 1983.

*Primary Examiner*—R. R. Kucia

*Attorney, Agent, or Firm*—Isaksen, Lathrop, Esch, Hart & Clark

[57] ABSTRACT

A system and method for the construction of one-dimensional maps from fragmentation data is disclosed. Particularly useful for construction of restriction maps of DNA, the system and method completely permutes sites, single digest fragments, and any available multiple digest fragments, and displays maps in rank-order according to a quality factor. Display of constructed maps includes information about relative ordering of all fragments, sites, and particularly about closely-spaced sites and fragments.

11 Claims, 11 Drawing Sheets c)

| ECO | HIN | BAM | ECO+HIN | ECO+BAM | HIN+BAM |
|---|---|---|---|---|---|
| 6000 | 6400 | 5000 | 6000 | 2400 | 2700 |
| 2000 | 3300 | 2400 | 1700 | 2300 | 2400 |
| 1700 | | 1300 | 1600 | 2000 | 2300 |
| | | 1000 | 400 | 1300 | 1300 |
| | | | | 1000 | 1000 |
| | | | | 700 | |

Fig. 2a
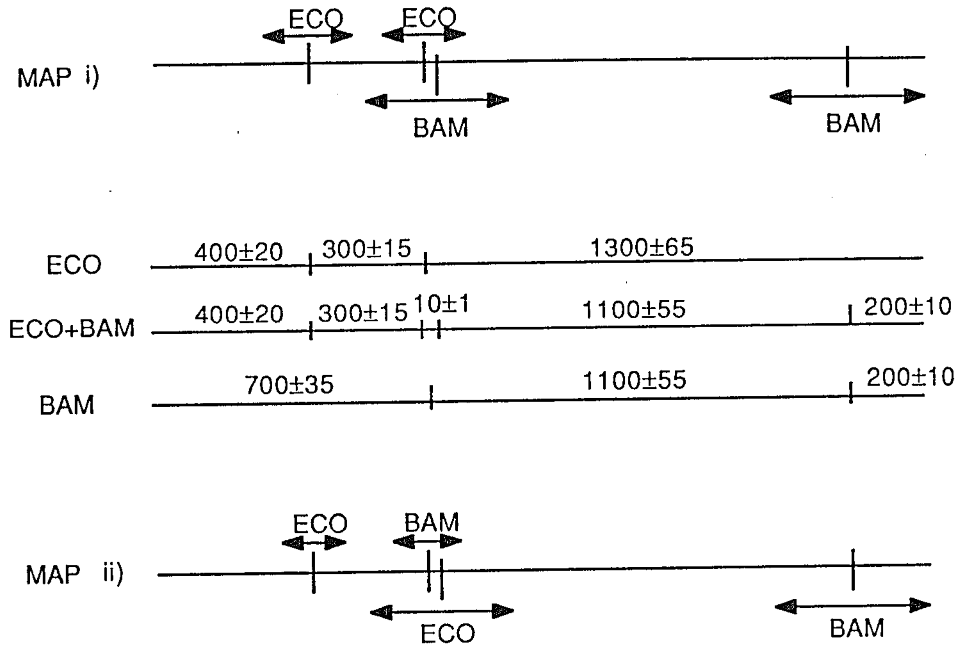
Fig. 2b
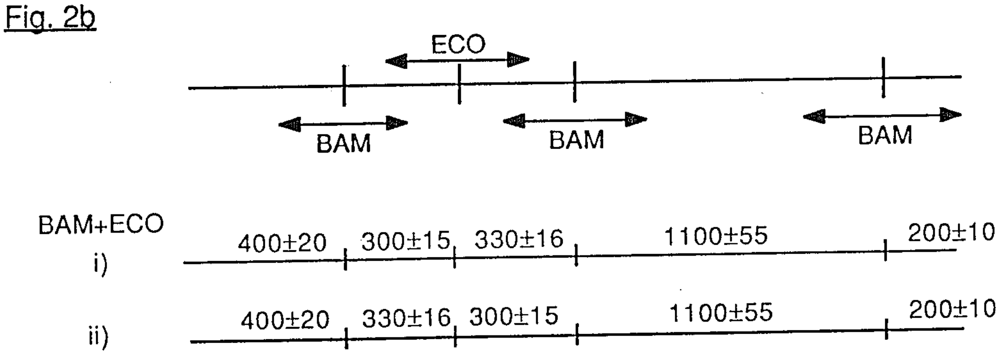
Fig. 2

CASE 1:
THE PREVIOUS SITE IN THE A+B MAP IS NOT THE GROWING POINT ENZYME

CASE 2:
THE PREVIOUS SITE IN THE A+B DIGEST IS THE GROWING POINT ENZYME

STARTING A CIRCULAR MAP:
FITTING MULTIPLE DIGEST FRAGMENTS USING WEAK RULES

SYSTEM AND METHOD FOR FRAGMENTATION MAPPING

FIELD OF THE INVENTION

The present invention relates to the computer-assisted construction of one-dimensional linear or circular maps from fragment size data. The preferred embodiment allows construction of restriction maps of deoxyribonucleic acid (DNA) for use by experimenters in the fields of molecular biology, molecular genetics and genetic engineering.

BACKGROUND OF THE INVENTION

Restriction enzymes are endonucleases (see Glossary of Terms) which cleave DNA at short, specific nucleotide sequences. Purified DNA can be cleaved at these specific sites on the molecule and the length of the cleavage products measured. By a variety of experimental techniques, the order of these fragments in the molecule can be determined and thus one can "map" the restriction sites of a genome. At minimum, a map is an ordered list of restriction sites and their positions on the DNA molecule. A map may also contain an identification of every fragment in the data set as belonging to an interval on the map. For most purposes, the usefulness of a map is dependent on this information. Such a map is a physical map of the genome and can be correlated with a genetic map or with physical maps derived by other means (such as EM Heteroduplex analysis).

Restriction enzymes have proven useful for the physical dissection of the genomes of organisms ranging from bacteria to mammals. These endonucleases have been used to map and compare genomes, to produce DNA fragments for DNA sequencing and to construct recombinant DNA molecules. Maps are useful both for the isolation of defined regions of the genome and in the analysis of hybrid chromosomes and deletion mutants.

For example, restriction enzymes are the "scissors" used to cut large genomes (billions of nucleotides (bases) long) into pieces for subsequent molecular cloning. It was only the discovery of restriction enzymes and their characteristics which allowed the development of the analysis techniques collectively known as "recombinant DNA technology". The ability to clone pieces of DNA of interest out of the huge background of the genome and replicate them along with the cloning vector permits the isolation of useful amounts of reasonably pure DNA for study. This has led to experiments for the elucidation of molecular genetic details about gene structure and function that were impossible a decade ago.

Restriction enzymes are also an important tool of genome analysis. For example, when screening a "shotgun" (large, mixed collection of all clones of a genome) for a particular feature of interest, an experimenter generally finds a number of positive candidates. The relationship of the candidates can be elucidated by restriction mapping. Two candidates might be identical (and would thus have an identical restriction map), they might be overlapping (and would thus each have a part of its map identical with the other) or they might be unrelated (and would thus have quite different restriction maps). In the case of overlapping clones, this kind of analysis further locates the feature selected for when isolating the positive candidates to the DNA contained in both clones (i.e., the overlapping region of the restriction maps). If two of the candidates selected have unrelated maps, this suggests that two different regions of the genome (two different "genes") can produce the same feature selected for.

Similarly, genomes related in a number of ways can be compared by their restriction maps. For example, two related but distinct organisms (such as bacteriophage lambda and bacteriophage phi 80) can genetically recombine to yield recombinent progeny with some of the features of each parent. If one determines a restriction map of the recombinant and compares it with the maps of the parents, one can determine which region of the genome came from which parent, where the recombination events occured in the DNA, and may be able to assign some of the features to particular regions in the DNA.

In recent years it has become possible to determine the nucleotide sequence of DNA in a particular gene or region of interest. DNA is a linear string of subunits, each subunit can be one of four types (A,G,C, or T). The experiments to determine the sequence or order of subunits in a given region of DNA are greatly facilitated by having a restriction map of the region of interest.

DESCRIPTION OF THE PRIOR ART

Since maps are so useful, constructing restriction maps from fragment size data (usually derived from gel electrophoresis of digested DNA) is a common activity of molecular biologists. One method frequently used is referred to in the literature as "by inspection". This generally means that DNA which has been digested to completion by a particular restriction enzyme is run in one channel of an electrophoresis gel, a second complete digest with a different enzyme in another channel and the complete digest with both enzymes together in a channel between the two. Electrophoresis is known to separate DNA fragments on the basis of size. The sizes of the DNA fragments in the digestion are then measured by comparing their mobility on the gel to the mobility of a set of known size standards.

The researcher then tries to piece together all of these fragments, much like a jigsaw puzzle. He/she tries to determine an ordering of every fragment in each of the three digests. In doing so, the researcher follows rules which express the underlying logic of the original arrangement of the fragments. For example, each fragment in each single digest must be identified with some subset of the fragments in the double digest whose sum of lengths adds up within error to the length of the single digest fragment. Similarly, each end of each double digest fragment must be identified with an end of a fragment from one or the other of the single digests.

The result is a linear map of the original DNA with an ordering and position (plus or minus error) of each site for both enzymes and an identification of every fragment on the gel to an interval between two sites on the map and of every interval on the map to a fragment on the gel.

Mapping "by inspection" (i.e. by hand) is most common among molecular biologists. However, several computer programs or algorithms have been reported in the literature which claim to find all possible maps. All use as input data the fragment sizes of fragments in single and multiple digests. As will be discussed below, each of the prior art systems suffers from some inherent defect which leave much to be desired by the genetic researcher.

Prior Art Algorithms and Computer Programs

Stefik—Artificial Inteligence (1978) 11:85–114. Doctoral Dissertation—1980.

Implemented for Stanford Sumex system. This method permutes sites and intervals, termed "segments", and rejects maps using heuristic rules. It is not an algorithm, but is a set of heuristic rules. According to Stefik's dissertation, the method is not intended to be a complete solution generator, but is only a small subset of the possible solution implemented as a rule-driven artificial intelligence program.

Pearson NAR (1982) 10:217–227.

Implemented on a DEC-10 minicomputer. Permutes only fragments from single digests. This method "predicts" double digestion fragments (by an unexplained method), assigns double digestion fragments to these predictions in order, and takes least sum of squares of absolute differences as the goodness of fit. The configuration space identified as (A!×B!). The method is said to be extendable to more than two enzymes. It computes pairs first, then adds third, etc. to list of possible maps.

The Pearson method does not permute double digest fragments nor does it consider alternative orders of closly spaced sites. On particular sets of input data, this method has been shown to miss the correct map.

Fitch, et. al. Gene (1983) 22:19–29.

This approach is a branch and bounds method. The method is limited to two enzymes and 3 digests. There is no indication of any ability to handle additional enzymes.

The method appears to attempt to do what is commonly done by hand in a "systematic" way. The "bounding rules" described are complex and their interaction with each other and the procedure cannot be clearly understood from the description.

Fitch, et al. start by trying to determine all possible "contained-in" relationships for the smallest single digest fragment. The method uses local error calculations to verify that the sum of double digest fragments' length could fit within a selected single digest fragment. A difficulty in this approach is that the method attaches great value to assigning uncut fragments (a necessarily tentative initial assignment). The method then tries to make the uncut assignment definite by other information. When all "contained-in" possibilities are enumerated for every single digest, they have to be resolved into all possible consistent sets of one per fragment and then maps extracted for each set.

Durand, et. al. NAR (1984) 12:703–716.

Durand, et al. propose another method using branch and bounds (although not called such in the paper). The method handles many enzymes at once, and builds from the left end of the molecule. The method does not assign double digest fragments, however. It also does not consider alternative orderings of closely spaced sites. No use of local error is made, thus preventing the method from computing long maps efficiently (although the paper suggests starting from both ends at once). The algorithm can accept as input partial information about the map.

Wulkan et. al. CABIOS (1985) 1:4 pp 235–239.

Wulkan et. al. present an implementation of the method of Pearson for a microcomputer. The addition of "clues" such as the contained-within relationships of the data speeds computation of maps.

Nolan, et. al. NAR (1984) 12:717

This method produces maps using a branch and bounds method involving construction of "forks" and permuting them. "Forks" are sets of fragments from one double digest that sum to the same length within error as one fragment from a single digest. As in Fitch, et al., the first step is to determine all possible forks in the data set.

The method is inherently limited to two enzymes and one double digest. Two versions of the method exist for circular and linear maps. It is not clear whether the "fork" generation method covers all combinations. (Combinatorics of the permutation method are: F!+sum($F_i$!) where F is the number of forks and $F_i$ is the number of double digest fragments in the i'th fork.) It builds forks together using global error. A set of heuristics is also presented which is intended to bound the set of fork permutations.

BRIEF DESCRIPTION OF THE FIGURES

FIG. 2 depicts two examples (a and b) of pairs of different restriction maps which prior art mapping algorithms would not identify as different.

INTRODUCTION TO AN UNDERSTANDING OF THE PRESENT INVENTION

In accordance with the present invention, there is provided a method for constructing restriction maps of DNA from data derived from single and multiple digestions of purified DNA with various restriction enzymes. Such data typically consists of the number of fragments produced by digestion and their sizes. After digestion of a DNA molecule with one or more restriction enzymes, the resulting fragments are separated by gel electrophoresis. When compared to standard compounds of known length (or molecular weight), the fragments may be listed with their approximate length. (The error inherent in such a procedure is on the order of 1–10%.)

Even if there were no error in measurement of the lengths of the restricition fragments, there could be alternative arrangements of the fragment data which would be consistent with the known information about the genome of interest. For instance, if a linear DNA molecule were being studied, and if the identities of both of the ends were known with certainty (perhaps through radio-labelling), there might still be ambiguity in the data if two or more fragments having the same end moieties and identical lengths resulted from a multiple digestion.

Given the error inherent in the measuring procedures employed, the number of possible arrangements of fragments consistent with the data is very large. The mapping problem is of the type "NP Complete", which indicates that no program can be written which solves all cases in less than exponential time.

Although the complete solution to the mapping problem has been claimed by researchers in the art, investigations by the present inventors have revealed that each solution proposed in the prior art has been deficient. Since the correct solution is known to exist (i.e., a DNA molecule does have a sequence, and a map), generation of that solution among several possibilities is one crucial measure of prior art methods. Any algorithm which fails to give the correct result has either failed to generate that result through an incomplete definition of the configuration space of the mapping problem, or has rejected a generated solution for incorrect or invalid reasons.

Once a set of possible maps for a given set of data has been produced, the next desirable step is the ability to rank-order those possible solutions in accordance with their conformity with the data. In this way, the investigator may easily focus his or her efforts on those possible solutions which hold the most promise.

In accordance with the present invention a map generation system correctly and completely defines the configuration space of the mapping problem, evaluates possible maps on the basis of their conformity with the experimental data, and displays the possible maps generated to the user in novel and useful formats.

Explanation of restriction mapping in molecular biology

What is a map?

Figure 1:
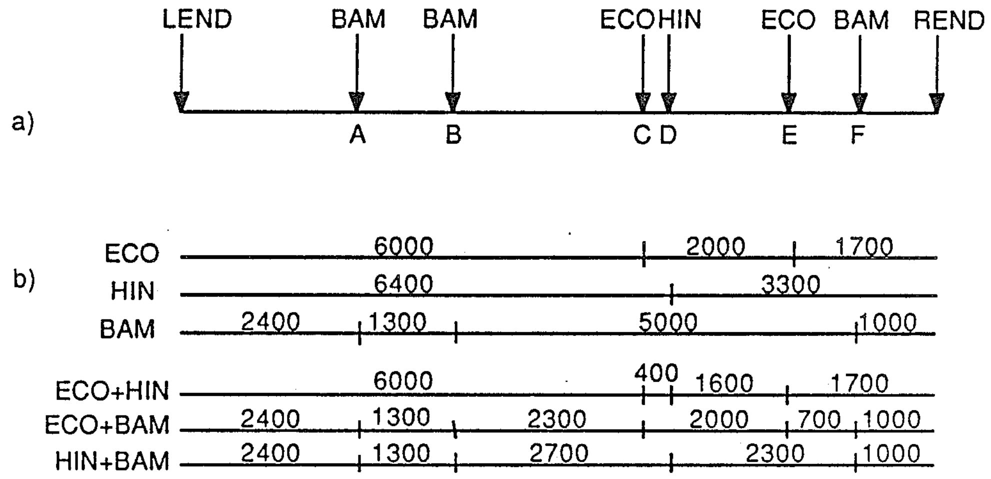
FIG. 1 is an example of a restriction map and fragment size data.

Referring now to FIG. 1(*a*) there is shown a restriction map of a DNA molecule. The DNA is cut by restriction enzymes labeled Eco, Bam, and Hin at specific sites located at positions labeled A to F. This particular DNA is linear and the left and right ends are denoted LEND and REND. (The left and right ends are not inherently different and which is which is just a convention accepted by scientists working on that particular DNA).

FIG. 1(*b*) shows the fragments obtained by digestion of the DNA with any one of the enzymes on the map or with any two in combination.

FIG. 1(*c*) shows the sizes of fragments in the various digests in sorted (decreasing) order. This is the form of the data obtained by experiments. The goal of mapping is to deduce the fragment arrangement (as in 1(*b*)) and thus the map (as in 1(*a*)) from the fragmentation data. Since the map is one-dimensional and intervals on the map are additive, the test for correctness of a map is based on this additive property. Finding the correct map is greatly complicated by the fact that fragment-size measurements are not perfect, but have an inherent measurement error. It is possible, however, to put a bound on the magnitude of the measurement error. A further complication is that some fragments may be "missed" in the experiment, either because they are too small for the detection method or are not resolved from another very similarly sized fragment and thus not identified. The various digests can be checked against each other for internal consistency of fragments number and total size but "completeness" of the data is not guaranteed.

The researcher's problem is to deduce all possible maps which are consistent with the fragment size data (within error), and to identify the more likely ones.

Depending on the use to which he/she wishes to put the map, the experimenter will either do additional experiments to distinguish between the possibilities or will decide to work around the existing ambiguities in the map.

What constitutes a valid map, and whether two maps differ depends on the definition used, which may vary depending on the use to which the map is to be put. A map usually contains some or all of the following (not independent) information about the molecule.

1. An ordered list of sites generally with coordinates and perhaps with ± error on the coordinates 2. An ordering of fragments from the digests (which can include error of the fragments). Either an ordering of just the single digest fragments, or an ordering of fragments of all the digests.

3. An assignment of every fragment in the data to an interval on the map and of every interval on the map to a fragment in the data. (Note that this is essentially equivalent to "1"+"2".)

4. An enumeration of the relationships between fragments of different digests. Particularly those fragments from single-enzyme digests are related to those subfragments from all multiple digests involving that enzyme and vice versa. That is, for every pair of digests involving that enzyme, one single and one multiple, completely identify the contained-within and containing relationships. This information is generally needed for cloning and/or sequencing experiments and is completely predictable from "1"+"2".

"1" is the format in which maps are usually presented. However, it is important to note that because of error, "1" does not unambiguously predict "2", nor does "2" unambiguously predict "1".

FIG. 2(*a*) shows two possible maps which are both consistent with the experimentally-derived fragment size data. The maps have the same fragment order for all digests, both single and double, but differ in the relative ordering of sites. This means that in map (ii) the 300-long Eco fragment is cut by Bam into a very slightly shorter new fragment with one Eco end and one Bam end and a 10-long new fragment with one Eco end and one Bam end. The 1100-long Bam fragment is similarly cut by Eco in the double digest. In the second map (ii), however, the 300-long Eco fragment is not cut by Bam nor is the 1100-long Bam fragment cut by Eco. These differences may be critical in the design of some experiments, such as cloning or sequencing.

FIG. 2(*b*) shows two maps which have the same site order and error ranges on the coordinates but differ in the ordering of fragments in the double digest. Depending on the use, this difference may be very important and the experimenter may need to know that two alternatives exist. This is important for any experiment where one wishes to physically isolate a particular subregion of the DNA molecule for subsequent experiments, such as cloning, sequencing, or protein-binding assays.

As an example of the typical prior art procedure employed by researchers in the field, (other than computer methods referred to above as "prior art",) the following description may be useful.

Procedure for Restriction Mapping "by hand"

Do experiments to derive the data.

(a) Isolate DNA of a single molecular species. (Usually a plasmid from a bacteria or the genome from a virus).

(b) Digest aliquots of the DNA with a variety of restriction enzymes employed singly and in various combinations.

(c) Run the digestions on an electrophoretic gel to separate the fragments according to size.

Determining the map from the data involves several steps:

1. The researcher measures the length of fragments resulting from digestion by comparing the position of the bands on the gel with the positions of known length standards.

2. He/she notes significant facts (clues to the map as it were) about the pattern of the bands in the three lanes. (one lane for each of the two single and one double digests.)

(a) Which bands in the single digest are not in the double digest? (This means that there is at least one cut for the second enzyme between the two ends of the single digest fragment)

(b) Which bands in the single digests are (tentatively) also present in the double digest? (Its presence in both digests means that there is no site for the second enzyme between the two first enzyme sites which generated the fragment).

(c) Which bands in the double digest are (tentatively) identical to bands in which of the single digests and which bands are new? (This identifies the ends of the fragments as being both of one type or both of the other or one of each type.)

(d) Are the total number of fragments in the three digests consistent and is the number of new fragments in the double digest consistent with the number of cut fragments in the singles?

3. An effort is made to resolve discrepancies by careful reinspection of the gel. (see Table 1)

(a) Search for "missing" fragments. Two similarly sized fragments may not be resolved into two bands. A band on the gel composed of two fragments (a doublet) is generally recognizable as such because it stains more intensly than a singlet and it may be broader. The other cause of missing fragments is that they are so small they either ran off the bottom of the gel or do not stain intensely enough to be seen. If it is fairly certain that doublets have been identified, one tentatively assumes the existence of "not visible" fragments in the double digest which are smaller than some maximum (the size which would certainly have been visible).

(b) If the number of cut fragments and new fragments is inconsistent, there is a mis-assignment of a cut fragment in a single digest and a similarly-sized new fragment in the double digest as identical and uncut. Re-examination of the gel may detect this.

4. The researcher tries to construct a map which is consistent with all the above information. More than one map may be consistent and he/she tries to find all possibilities. The mental processes used and the rate of progress are highly dependent on the skill and experience of the mapper, as well as the peculiarities of the data being considered.

Generally, what is done is to find a small sub-region of the map which is "easy" (certain, self-evident, unambiguous, etc). He/she determines the containing and contained-within relationships for this region and constructs a map of this sub-section. He/she then proceeds in both directions, identifying overlapping fragments from the two single digests by which ones contain a double digest fragment in common, until a map is achieved. Progress becomes easier as more map is determined because the mapped region and fragments already assigned to them can be eliminated from further consideration in constructing the not-yet-mapped regions.

Figure 3:
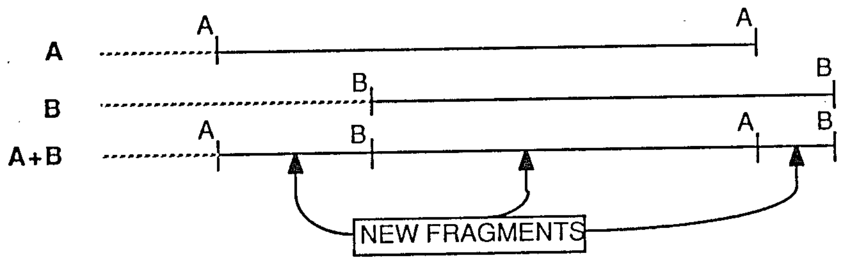
FIG. 3 is an example of a starting point used when mapping "by hand".

Most maps have a readily evident region which can be a starting point. For example, a large "new" fragment in a double digest can only be contained in an even larger "cut" fragment (necessarily one in each single). Frequently, there is only one choice for each of these. Subtraction of the size of the new fragment from the size of the containing single digest fragments yields a possible size for two other new fragments and if either or both exist, a possible map is started (see FIG. 3).

Similarly, a small cut fragment can only be cut into an even smaller new fragment, or a large uncut fragment must be a sub-region of an even larger cut fragment in the other single digest. In most data sets, there is usually a natural starting point for the mapping process. If not, what is usually done is to resort to a different experiment with a different, easier pair of enzymes. After some map is constructed, the more difficult enzymes can be added more readily.

Alternatively, there may already be a known section of the map. When mapping clones for example, the vector portion is already known.

Mapping by Computer

The construction of maps by hand using the human mind to perceive relationships is a difficult skill in which proficiency comes only with practice. Therefore it cannot usually be assigned to unskilled personel. In complex maps the number of possibilities is understood to exceed the ability of the human to solve. Computational assistance is therefore definitly welcome, not only because of the time saved but because of potentially greater accuracy. Even the most experienced and skilled practitioner of this art is aware and concerned that the map he/she has deduced (really induced) might not be the only one or even the best that fits the data. Just as the human mind is good at solving puzzles by intuitive leaps, it is also easy to fixate on one approach leaving blind spots that may mask the truth.

BRIEF DESCRIPTION OF THE INVENTION

The present invention comprises a computer-assisted method for determining the order (map) of fragments in a one-dimensional array (either linear or circular), based on fragment length and fragment termination data. While the invention may have utility in other types of problems, its primary utility is that of restriction mapping of DNA molecules.

With reference to DNA restriction mapping, the method of this invention comprises constructing hypotheses of possible maps by permuting at least some, and preferably all, arrangements of fragments (each of a characteristic fragment length) and some, and preferably all, fragment termination information, known as "sites". The number and types of sites in the molecule are determined by counting the numbered fragments in restriction enzyme digestions, and fragment length is one of a number of possible method such as, for example, by gel elctrophoresis. Each such permutation is then tested for validation by comparing possible local sub-regions of the original array with local additive lengths of fragments. Each validated hypothesis is then output as a possibly correct fragmentation map of the DNA under investigation.

Preferably, multiple possibly correct maps are then ordered as to their probability of correctness by reference to their goodness-of-fit to the data from multiple enzyme digestions.

In an alternative embodiment, a restriction map is constructed by selecting a restriction site as a starting point then selecting all possibly adjacent fragments as candidate neighbors. An extension of this hypothetical map at the distal terminus (if the candidate neighbor fragment is consistent with all available data) is then constructed in a like manner, and the process is reiterated, in essence "growing" the hypothetical map until it is complete, thus arriving at a pre-validated possibly correct fragmentation map. At each step of the growth process, local additivity of the sub-regions of the partial map are used to check validity of the hypothetical map.

DESCRIPTION OF THE PREFERRED EMBODIMENT THEORY AND OPERATION

In accordance with the present invention there is provided a process for constructing maps from fragmentation data. For clarity, the present invention will be described in terms of its application to mapping of DNA molecules fragmented by restriction enzymes, commonly known in the field of molecular biology as restriction mapping. Other types of linear or circular structures and other fragmentation agents could also be mapped by the method.

Objectives of a mapping system

A system for constructing maps should take fragmentation data in the form obtained by the researcher and produce a systematic search of all the possible arrangments of this data to identify maps that are consistent with it. Since, in general, more than one potentially correct map will be found, the system should output any that are consistent with the data. Within this framework the following criteria should be met:

Completeness of solution
Speed of solution
Ability to handle fragment data with ± errors
Ranking of possible maps by quality
Circular and linear maps supported
Experimentally realistic range of data handled.

Completeness of Solution

Since many possible maps may be consistent with a given set of data the system must find them all, although the user might wish to be shown only the best few. It is only the assurance that all possibilities have been found that allows the researcher to have confidence in the method, for if possible solutions failed to be considered, the correct map could be among the missing. The criterion of completeness is of such central importance that it is a definitive requirement for a mapping system and method.

Logical approaches for deriving solutions from data can be thought of as either using negative inference to reject elements of the configuration space because of conflicts with the data or using positive inference to deduce solutions from the data. A method which uses only negative inference is complete if the hypothesis generator exhaustively models the solution space and the rejection criteria never cause rejection of a valid solution. A method which uses only positive inference is complete if the inference rules generate all possible hypotheses fitting the criteria. In choosing an approach for solving a problem, the character of the data, of the configuration space, and of the inference rules which can be used must all be considered. Many known algorithms for problem solving use a combination of both approaches.

The following description discloses two variations of a method for solving restriction mapping problems. First described is an exhaustive hypothesis generator which completely models the configuration space and passes hypotheses one at a time to an evaluator which rejects those inconsistent with the data. It is this complete accuracy of the map generator of the present invention that instills the necessary confidence in its users. Also described are specific positive inference rules which could be used to limit the configuration space.

The preferred embodiment of the invention is termed the "branch and bounds method" and is based on the exhaustive hypothesis generator as limited by positive inference rules. The method uses negative inference to reject many elements of the solution space at once. This is accomplished by intermixing steps of map generation and map testing at a fine level.

Speed of Solution

The second criterion of acceptability is speed. The mapping problem is in the category known as NP complete, which means that there is no known way to solve it in less than exponential time. No matter how efficient a method is employed, the time required to solve increasingly complex maps increases exponentially. Many such problems would be insoluable for all practical purposes, regardless of the computational power available. The impact of an efficient algorithm versus an inefficient one, however, can be worth orders of magnitude in time. In effect, the quantitative difference becomes qualitative, making useful problems soluble that would otherwise be (for all practical purposes) insoluble. The preferred embodiment is an exhaustive map generator that can solve maps commonly encountered in molecular biology at practical speed, even on a personal computer.

Ability to handle fragment data with ± errors

Real (experimentally derived) data has error limits associated with it and a method must allow for the possibility that any fragment in the data deviates from its mean by the allowed amount in either direction. Real maps are one-dimensional and intervals on the map are additive. Fragment sizes are measurements of these intervals. If any proposed map has fragments assigned to intervals such that the additive relationship within error is not maintained, then the map is incorrect.

Ranking of maps by quality

When a large number of possible maps (each reasonably consistent with the data given the error limits) are found by a method, there is considerable difficulty for the user in deciding which is the most probable one. The determination of a "figure of merit" for each map, based on the overall fit of the data to the map, provides a basis for ranking the output. This is a considerable help to the user.

Circular and linear maps supported

Natural DNA is either linear or circular. The ability of a method to handle both cases is therefore a significant benefit.

Experimentally realistic range of data handled

The method of the present invention is not inherently limited in the number of enzymes that can be handled. For example, some prior art methods can handle only two enzymes. Similarly, the method of the present invention does not require that every double enzyme digestion be done in order to solve multi-enzyme maps. There may be used as much double digest data as is available, but only a few double digestion experiments are necessary. The minimum requirement is only enough multiple digests to involve all the enzymes. As more double or multiple digest data are supplied, better results are produced, ie. fewer "possible" maps found in a shorter time.

A map generator and a map evaluator are provided. The generator has the job of enumerating all possible hypotheses (in a combinatoric sense) based on a model of the configuration space. Each hypothesis is then passed to the map evaluator. The evaluator functions to reject maps which are inconsistent with the data and presents all others to the user. The evaluator comprises three parts: the map hypothesis rejector, the site positioner and the map quality evaluator. The hypothesis rejector screens hypotheses produced by the generator and rejects those with an unacceptable level of inconsistency with the data. For each map not rejected, the site positioner assigns numerical positions to each site on the map and the evaluator checks each map against the data for quality of fit. The maps with an acceptable quality are the solutions and they are passed to the user through the output channel. The generator and the elements of the evaluator will be discussed in detail in the following three sections.

The map generator

The map generator can be of any form that produces a complete coverage of all mathmatically possible maps given the single and multiple digest data. A brute force procedure that is a correct but computationally-intensive method for generating all maps is:

(PERMUTE ALL SITES) AND (PERMUTE ALL FRAGMENTS)

This is described in more detail as the steps below.

1. Generate list of all sites in molecule {determine the number of sites Si for each enzyme i by counting the fragments in each single digest (and subtracting one if map is linear)}

2. Determine the total number of sites, N, in the map by adding up the individual totals.

3. While an untried permutation of sites exist {number of permutations of sites is:

$$\frac{N!}{S1! \times S2!\, X \ldots Si!} \Big\}$$

4. Select a permutation of all sites

5. While an untried permutation of fragments in single enzyme digests exists {number of permutations is F1! X F2! X . . . Fi!, where Fi is the number of fragments in digest i}

6. Select a permutation of single digest fragments

7. For fragments in all single digests, assign all fragments (in selected order) to intervals on the map bounded on both ends by sites of the type used in the digest and containing no interior sites of that type.

8. While untried permutation of fragments in multiple enzyme digests exists

9. Select a permutation of multiple digest fragments {number of permutations is M1! X M2! X M3! . . . X Mk!, where M is the number of fragments in multiple digest k}

10. For all fragments in all multiple digests included in the input data, distribute all fragments (in selected order) to the map intervals bounded by sites of any type used in the digest and containing no interior sites of any of these types.

11. Pass this hypothesis to the hypothesis evaluator. {Each configuration defined by the combinations of site orders and combinations of fragment distributions is a theoretically possible hypothesis to be passed to the hypothesis evaluator.}

```
EndWhile {permute all experimentally available multiple digest fragments}
    EndWhile {permute all single digest fragments}
EndWhile {permute all sites}
```

It should be noted that the map generator can be used equally well to generate linear or circular maps. The only detail that must be changed is whether fragments are to be assigned to an interval that spans the end. If the map is linear such assignments must be eliminated from consideration.

Other suitable embodiments of the "brute force" map generator can be obtained by interchanging the order of steps. For example, one could consider the possible ordering of fragments first (in the outer loop) and then consider the ordering of sites. Alternatively, the single fragments could be permuted first, then the sites, and then the multiple fragments. Finally, as discussed below with respect to the preferred embodiment, these steps may be intermixed at a fine level, some fragment permutations being done, then some site permutations, then some more fragments etc. The possible variations in the order of steps are minor modifications of the method of the present invention.

A critical feature of the "brute force" map generator of the present invention is that it does not require that double digest data be available from all the combinations of enzymes of the map. This is important because the number of double digests increases rapidly with the number of single digests. {EX(E-1)/2 , where E is the number of enzymes to be mapped} This can easily lead to a great deal of experimental work for maps with several enzymes. Many methods of the prior art which require all double digest data to set up the map generator are unsuitable because of the experimentally unrealistic requirement that double digest data be available for every pairwise combination of enzymes.

As is common to all methods, that of the present invention requires single digests of all the enzymes to be mapped. These are used to generate the list of sites to be permuted. Fragment permutations are done on the single digest fragments and on only those multiple digests for which experimental data are available.

The hypothesis evaluator

The map hypothesis rejector checks a number of intervals on the hypothesized map for additivity of fragment sizes as explained above. It is important to note that if any interval on the hypothesised map is non-additive, (beyond the error limits of the data), then the map is inconsistent with the data and is considered to be wrong. (It is this fact that is used to reject whole sets of hypotheses in the solution space by the prefered embodiment, the branch and bounds method described below.) Pearson's map rejector looks only at the whole map (sum) deviation of the data, not at individual data points, and rejects those maps whose total deviation is greater than a preset limit. Thus, correct maps may be rejected if most of the intervals are near the error limits of the data since the total error will be high, while obviously incorrect maps may be accepted if most of the intervals are coincidentally close to the data while one diagnostic interval is substantially beyond the acceptable limits of non-additivity.

The site positioner is responsible for assigning each restriction site a numerical position on the "possible" map based on the order of sites that has been selected and fragments have been assigned to the map intervals by the map generator. This step is required because every measurement of fragment length has a ± error associated with it. As a result, the length of the intervals of the map between sites can be determined in many different ways by adding up the lengths of the various combinations of sub-fragments that make it up.

Several alternatives exist for the design of the site positioning algorithm. In accordance with Pearson's method, single digests may be used alone after normalization of the total length of fragments to an average value. This provides a single position for each site, but the method avoids conflicts by throwing away the multiple digestion data. This technique has an adverse effect on accuracy since the single digest fragments, as the longest in the data, have the largest absolute errors.

An alternative method is to use the shortest fragment available to define every map interval. This also throws away data but is more accurate since the data thrown away is the less accurate data rather than the more accurate data.

The preferred method is that disclosed by Schroeder and Blattner. This method makes use of all the data by performing a least squares calculation to minimize the sum of the squares of the error of each fragment length relative to the length of the map interval to which it is assigned. This method gives the optimum map positions in the least squares sense for every site. As a slight variation of this method, it is possible to minimize the sum of squares of the errors weighted by various factors, such as the inverse of the relative error limits of the input data.

The map quality evaluator is used to give possible maps a "figure of merit" so that they may be ranked for the user. Once the site positions have been determined, the deviation of the length of each actual data fragment from the calculated length of its interval may be determined. Any map that predicts a fragment size that lies considerably outside the assigned error limits for that fragment is rejected. (It should be noted that this operation rejects maps. The map rejector described above is not essential nor need it be exhaustive in its rejection of inadequate maps since the function can be done here. However, the least squares assignment of site positions is computationly expensive and it is better to do it only on those very few maps, relative to configuration space, which are qualitatively reasonably consistent with the data.) This leaves the maps that are qualitatively consistent with the data. For these a figure of merit for the overall map is determined by any of several statistical formulae; e.g. the root mean square average deviation, the root mean square average fractional deviation or the corresponding straight averages of absolute values of the deviations or fractional deviations. The figure of merit may, in fact, be the maximum fragment error. It is convenient to store these maps in a sorted list so they may be presented to the user in order of the figure of merit.

In summary, then, the present invention provides a method having a proper map generator (which includes permutation of BOTH sites AND single digest fragments AND multiple digest fragments in all possible combinations), and a hypothesis evaluator which rejects only those maps in which any region is unacceptably (beyond the error limits of the data) non-additive.

The brute force method (wherein the map generator passes one hypothesis at a time to the evaluator) bogs down with maps of modest complexity. The number of trials is far greater than the product of the factorials of the numbers of single digest fragments (as was suggested by Pearson).

Since for a two enzyme linear map (with the double digest) there are A! x B! x (A+B)! permutations of fragments plus the permutations of sites, a brute force method which checks all permutations one at a time becomes rapidly unusable as the number of fragments increases.

Therefore, an efficient map generator/map evaluator combination represents a great improvment. An efficient map generator is one that accomplishes the same result as the "brute force" generator in many fewer computational steps, yet does not fail to consider any of the possibilities that might be correct maps.

The preferred embodiment of the present invention is based on the following three concepts:

1. It is not really necessary to examine all combinations of every permutation of single digest fragments with every permutation of sites ONE AT A TIME. While the order of sites is not uniquely deduceable from the order of single digest fragments unless the data is perfect (0 error), it is possible with linear maps to calculate which site permutations (one to several) are consistent with each proposed permutation of single digest fragments. Thus the configuration space to be exhaustively examined can be significantly reduced by considering only these relative few permutations for each permutation of single digest fragments.

The situation with circular maps is considerably more complicated since possible site orders can be calculated only from permutations of single digest fragments and some (data dependent) assignments of some of the double digest fragments.

2. Once both a single digest fragment permutation and a compatible site permutation (and with circular maps, enough double digest fragments assigned to allow this) are selected, then the distance between any two sites on the map can be calculated. (i.e. we can calculate the size that a fragment assigned to such an interval can be, without conflicting with the already selected fragment and site permutations and assignments.) All unassigned multiple digest fragments must then be assigned in all possible orders to all appropriate intervals. (i.e. Permute multiple digest fragments and assign to intervals—the inside loop of the general description.) For each such permutation (a hypothesis) if any fragment is inconsistent with the calculated allowable size of the interval, then the map is rejected. If no fragments are inconsistent, the map is accepted as possible and output. After all possibilities are tried, the process goes back to the next outside loop and tries the next permutation of single digest fragments AND sites.

2*a*. If no consistent (with the selected single digest permutation and site permutation) permutations of double digest fragments exist, then there are no possible maps for this particular combination. It is not always necessary to enumerate all possible permutations of double digest fragments to discover this. For example: for any interval for which double digest data is available, if no fragment of the appropriate size exists in the appropriate double digest, then no permutation of multiple digest fragments exists which is consistent and the single digest fragment permutation-site permutation combination may be rejected without individually considering all double digest permutations.

The preceeding two rules are examples of positive inference which may be used to limit the hypothsis generator and thus make it more efficient. Using these two rules, it would still be necessary to individually examine all single digest fragment permutations in combination with all consistent possible site permutations, reject some of them by criteria based on the existence or non-existence of particular multiple digest fragments (within error), and examine the rest in combination with multiple digest fragment permutations.

3. If the generator produces maps in the right order, and rejection criteria are applied at intermediate steps in map generation, (not just at the end), an inconsistency in a map may be used to reject entire sets of maps at once. That is, if a map is rejected because it has a particular inconsistent subregion, any and all maps which have the same subregion can be rejected at the same time.

The preferred embodiment specifies a particular arrangment of the steps of fragment and site permutation which can be represented in the form of a tree. Traversal of every branch of the tree from the root to every leaf would be equivalent to the brute force method. (This is equivalent to saying that hypothesis evaluation is applied to complete maps.) But the arrangment of the tree has been chosen to increase the efficiency and to eliminate computational work, by applying the test for local additivity at each branch and rejecting all leaves at once for any branch failing the test.

Starting at the root of the tree and moving outward, the nodes alternate between permuting sites, permuting single fragments, and permuting double fragments. (The term "selection of growing point enzyme" is used herein to describe the act of permuting sites). Because of this alternating arrangment, the order of steps is not only different from the described brute force implementation of the invention, but may differ depending on the data.

Because of the way the tree is designed, every node of it corresponds to a partially completed map, and these are nested so that each step farther out on the tree from the root adds fragments or sites to the end of the map that existed at the preceeding level. With this structure in mind, it is easy to see how the discovery of an inconsistency at any node (a local non-additivity) leads to a simple way of rejecting large numbers of hypotheses at once and thus limits vastly the computational work. In traversing the tree, as soon as a node is encountered whose partial map is inconsistent with the data, everything beyond it need not be traversed because all maps that begin the same way, are rejected.

The equivalence of the growing point selection rule technique to the full permutation of all sites used in the brute force method is clear. The savings accomplished through the use of the more efficient method is quite large in most cases where real data is involved because it is only necessary to apply site permutations in situations where the accumulated error in the positions of restriction sites at the end of the partially completed map of the node overlap. If these positions did not overlap, the permutation would, perforce create a negative fragment. The error control that results from tacking corresponding sites together as the map grows makes this a major savings over the more inefficient brute force method.

The preferred embodiment of the present invention uses a branch and bounds method and is described below. The input data are sets of ordered lists of fragment sizes, corresponding to the sizes of fragments in restriction enzyme digestions and the topology of the molecule (whether the molecule is linear or circular). The method requires that for each enzyme to be mapped, there must be a data list for the single enzyme digest and each enzyme must be involved in at least one multiple enzyme digest. The topology of the configuration space of the mapping problem requires that all pairs of single enzymes can be related through one or more multiple digests. (This is distinct from the first requirement only if there are more than three enzymes to be mapped). In the prefered embodiment, in order to ensure complete coverage of the configuration space of a circular map, there is a further requirement that there must be enough multiple digest data that at least one of the enzymes to be mapped is involved in a multiple digest with every other enzyme.

Overview of procedure

Maps are constructed by building the map up one step at a time. At each step there are a (data dependent) number of choices that could be made. At each step, every possibility must be tried and at each try the result is checked for internal consistency. (Additivity of map intervals within the error bounds of the measured fragment sizes must always be maintained). Any inconsistency causes pruning of that branch. That is, we need not continue any further down the wrong path of map construction but back up and try again with a different choice. If there are no more choices we backup one step further and try again.

There are three different kinds of steps in map construction which are repeated until a complete map is achieved (and/or until all possibilities have been tried and rejected). Pruning rules are applied at each step.

1. Choose a site. The hypothesis to be tested is that this site is the next site on the map. (No intervening sites between the previous site, chosen in the previous cycle, and this one). This site is called the growing point. It is chosen to be consistent with single digest fragments assigned in previous cycles. All possibilities must be tried. No more choices to try causes the method to reject this branch and backup to the previous step. (step 3 in previous cycle).

2. Assign multiple digest fragments which end at this site.

Any multiple digest which involves the enzyme of the growing point type will have a fragment in it that ends at the growing point and maintains additivity of interval on the partially constructed map, if it is correct so far. There may be more than one choice and eventually all choices must be tried. If there are no more choices to try this branch is pruned and the method backs up to the previous step. (step 3 above)

3. Assign a single digest fragment that begins at the growing point and extends into the not yet constructed part of the growing map. (All choices must be eventually tried). If there are no more choices to try this branch is pruned and the method backs up one step. (step 2 above)

These three steps are repeated until the entire configuration space has been covered. Each cycle adds to the growing map, one site, one fragment from each multiple enzyme digest which ends at that site, and one fragment from the single enzyme digest which begins at that site.

The steps of the method are cyclic so the above numbering of the steps (i.e. 1,2,3) is an arbitrary break in the cycle (i.e. 2,3,1,2,3,1, . . . is an equally valid representation). An alternative way to think about the cycle is described below.

Maps are constructed by adding one single digest fragment at a time to the growing map. The fragment is then accepted or rejected by checking the consistency of the map to date with the available multiple digest data. An inconsistency causes rejection of the newly added fragment and the the next available fragment is tried instead. If there are no more available fragments to try, the algorithm backs up one step, removes the last added, tentatively accepted, fragment and tries the next available fragment to add at that point. If the fragment is accepted, the construction process continues, another single-digest fragment is added to the map, accepted or rejected, and so on. A possible map is found when all single-digest fragments have been added to the map and accepted. The map is processed (checked, refined and output). Then the algorithm backs up a step and continues, since we want to find all possible maps which are consistent. A flow chart of the method is given in FIGS. 4,5 and 6. It is described below.

In the preferred embodiment, the overall order in which the map is constructed is from one end toward the other (left to right if ends are known) for linear molecules, and from an arbitrary point for circular maps. Different overall orders are also possible (e.g. right to left, or one end for a while then the other end for a while, or both ends at once with a parallel processor, or from more than one point in a circular map either alternating or in parallel, etc.).

The point to which the method will add another single digest fragment is called the growing point. (It is also the point up to which double digest fragments have been fit in the previous step.) It is defined as the next (from the previous growing point) site on the growing map. It is found as the right end of a single enzyme map which is the leftmost amongst the single digest maps. Since the relative map positions of the endpoints have an inherent uncertainty due to the measurement error of the input data, the relative order of closely spaced sites may not be determinable. When ambiguity of growing points is encountered, all possible growing points are explored, one after the other. Thus the method of the present invention properly handles closly spaced sites, a particular weakness of various prior art methods. A valuable enhancement to the selection of growing point is the use of relative error (relative to a reference point in the accepted part of the growing map) in comparing endpoints. This is described in the Errors section below.

A single digest fragment is added to the end of one of the maps (the growing point) and the recursive procedure BUILDMAP is called to see if this added fragment is accepted and if it is to add another fragment to the (next) growing point.

Figures 7, 7A, 7B, 7C:
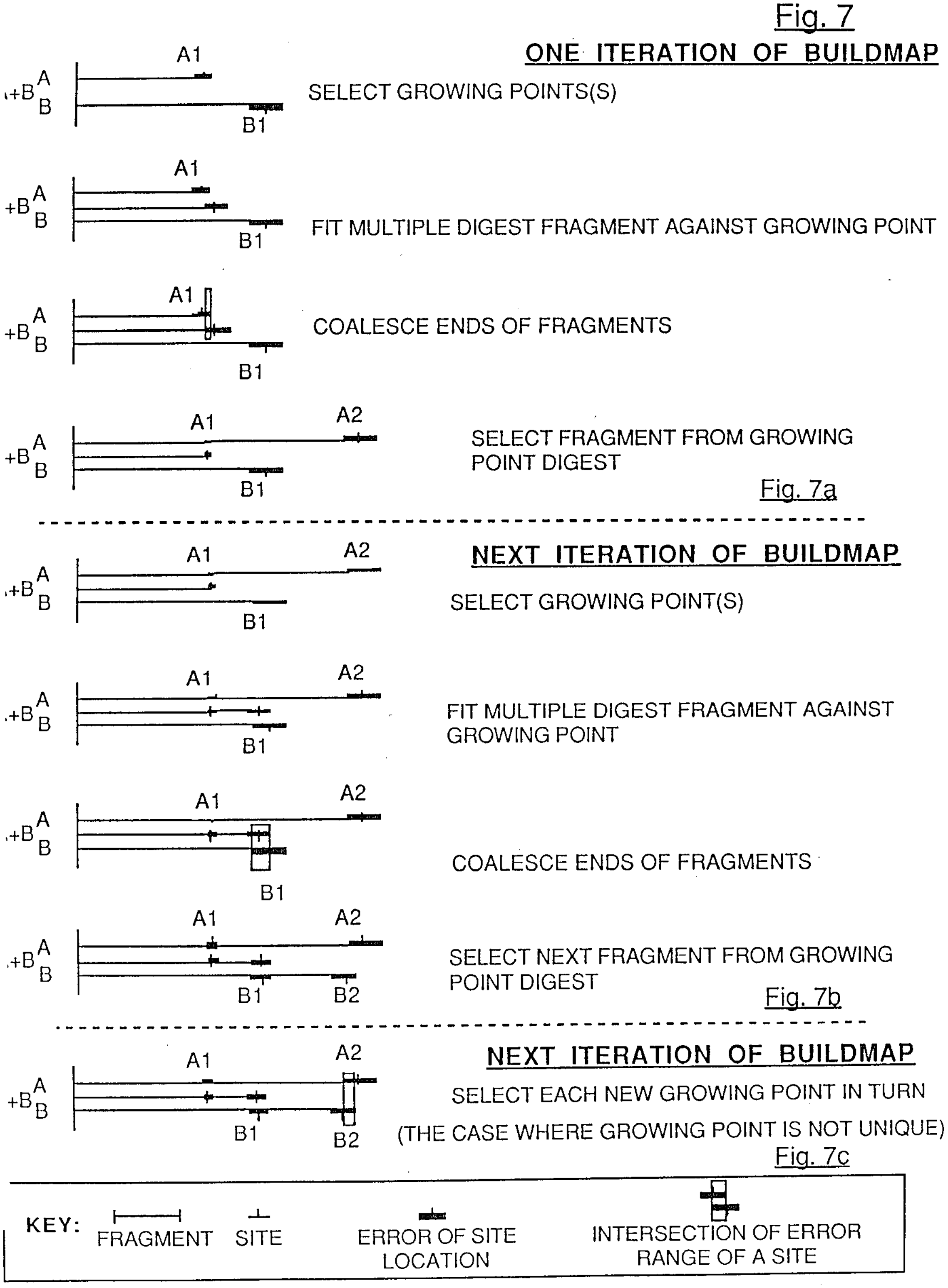
FIG. 7 is a diagramatic representation of the steps (a, b & c) of map construction by the method of the present invention.

The procedure BUILDMAP executes as follows: The new ends are compared (next growing point is determined) and the sizes of fragments to expect from each multiple digest are calculated. The fragment we are trying to find runs from the right end of the double digest map to the just determined (next) growing point (see FIG. 7). Each multiple digest is checked for the existence of a fragment of the appropriate size. Its size must be such that the sum of its length and the lengths of all other fragments assigned to the map from that double digest between the previous end of the growing point enzyme map and the current end equals, within error, the size of the last fragment in the new growing point digest (see FIG. 8). This value range could be calculated in a number of ways. The important point is that the error to be used is local to the region where the fragment is being fit, and includes only the error in fragments which overlap the last fragment in the single digest map of the growing point enzyme. This is a unique and crucial feature of the present invention. If there is not a set (one from each multiple) of fragments which fit, the single-digest fragment is rejected (BUILDMAP returns) and a different single-digest fragment tried.

After the existence of at least one appropriately sized fragment from each appropriate multiple digest is verified, then the added single digest fragment is accepted, one fragment from each multiple digest is assigned to the map, i.e. it can not be used in any other position in this map. If there is more than one fragment which will fit, all possibilities are tried. If more than one multiple digest has more than one fragment which will fit, all permutations—i.e. all sets of one fragment from each multiple—are tried.

When multiple digest fragments which fit are found and assigned to this map position, a coordinate correction is performed on the growing point using the overlapping lengths of (1) the single digest fragment ending at the growing point and (2) the sum of the lengths of the multiple digest fragments contained within it, for each multiple digest involving the growing point enzyme in the data set. The coordinate adjustment employed is to set the coordinate range of the site (growing point) to the intersection of endpoint ranges of the overlapping values. The effect of this is to identify the endpoint of the single digest map and the multiple digest map as the same site by setting the coordinates to the same value. This assignment of the double digest fragments to the growing overlapped regions of the single digest maps, followed by coalescing of the endpoint sites, merges the originally independent single enzyme maps into a single unified map. In the unified map the length of intervals between sites (fragment sizes), both like enzyme sites (single digest fragments and different enzyme sites (multiple digest fragments), are used to set site coordinates (See FIG. 7). As grapically represented in FIG. 7, the growing end of the map is a set of independent, parallel maps, one for each enzyme. As we move along, adding and checking, the parallel maps are linked together.

The practical value of unifying the maps as we proceed is twofold. First, it allows the use of relative error (relative to a reference point in the unified map) for finding the next growing point, thus reducing the ambiguity of relative position of endpoint coordinates enough that all possibilities can be practically explored. Experiments have shown that this increases the efficiency of the algorithm by orders of magnitude.

Second, it could make the calculating of the size of fragment to look for in the double digest slightly more efficient. We could use subtraction of endpoint coordinates (using a reference point in the unified map to get relative, ie. local, error) and compare this value against the query fragment in the multiple digest instead of summing all appropriate fragments (and errors) with the query fragment (with errors) and then comparing this size to the size of the single digest fragment (with errors).

The order of map construction disclosed (trying all possible growing points) is unique to the present invention as is the fitting of double digest fragments using local error. The assignment of all permutations of double digest fragments which fit is unique to the present invention. While not critical, it assures the identification of maps which differ only in the alternative location of double digest fragments (as in FIG. 2) and permits the coalescing of the parallel maps from the different digests. The coalescing of the maps is unique to the present invention, and while not critical to the algorithm in general, it allows for the next point. That is, the method of calculating the next growing point(s) is unique in the use of relative error and increases the efficiency dramatically, making the use of the method on a computer practical.

Error handling for determining growing point

Two unique features of the present invention are the use of local errors to fit fragments from the multiple digest against the single digests and the use of relative error in calculating growing point. The use of local errors in fitting double digest fragments is described above, in FIG. 7, and in the Details section.

The use of relative error in determining the next growing point is important for efficiency. There are various, equivalent ways that the error handling may be implemented. The principle is described here and more details of the preferred embodiment are described in the Details section.

Figure 9:
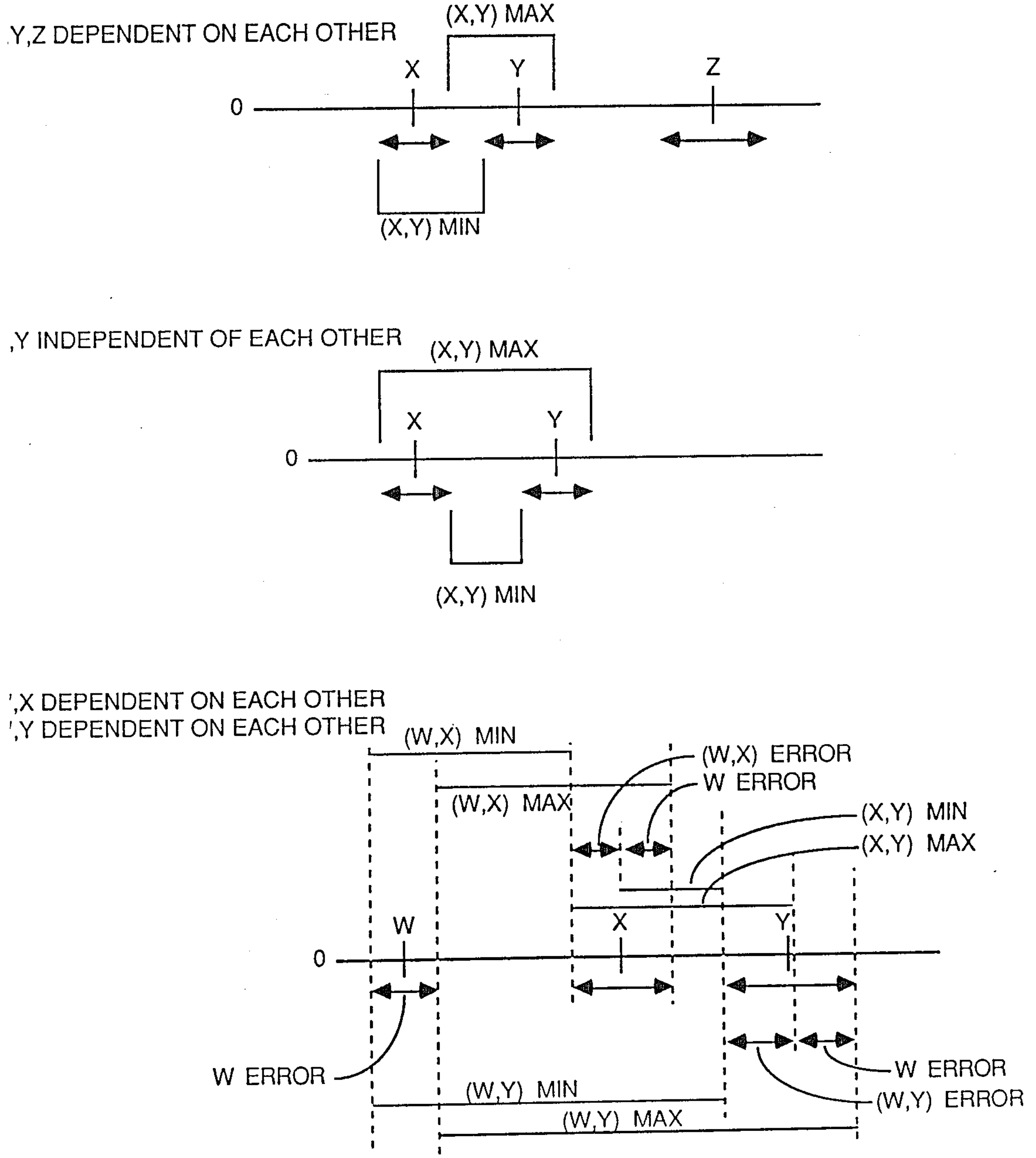
FIG. 9 is a collection of maps showing possible error relationships between sites.

The calculated position error of any two sites on a line might be dependent on each other or independent of each other. For example, if the coordinate and error of a site was determined by adding the length and error of the interval between it and another site to the coordinate and error of the other site, then the positions of the sites are dependent. They can only vary independently over part of the error range. Therefore, the difference between sites which are dependent in this way can be obtained by subtracting the coordinates, and the error on this distance can be obtained by subtracting the errors of the two sites (FIG. 9). On the other hand, two independent sites can vary over the entire range of their errors independently. The distance between these sites is obtained by subtracting the coordinates and the error is arrived at independently by adding the errors. If two sites are not known relative to each other, but each is known relative to a third site, the two sites are not totally independent. The relative position of the two sites may be calculated including only that amount of the site errors which is independent. That is, their relative positions may be determined more accurately by referal to the third site than by subtraction of coodinates and summing of errors. One can subtract the error on the common reference point from each of the sites, before comparing them. The best reference point to use is one closest (fewest intervening steps of dependent sites) to the two sites.

let dist(x,y) be the distance between site x and site y
and x(coord), y(coord), be the locations of x, y
and x(error) and y(error) be the error on the location
The following cases are handled:

Dependent sites:

$$dist(x,y) = y(coord) - x(coord) \pm |y(error) - x(error)|$$

Independent sites:

$$dist(x,y) = y(coord) - x(coord) \pm (y(error) + x(error))$$

Partially dependent sites, by referal to a third site, z, upon which both x and y are dependent:

$$\begin{aligned} dist(x,y) &= dist(z,y) - dist(z,x) \\ &= (y(coord) - z(coord)) - (x(coord) - z(coord)) \pm \\ &\quad (|y(error) - z(error)| + |x(error) - z(error)|) \\ &= y(coord) - x(coord) \pm \\ &\quad (|y(error) - z(error)| + |x(error) - z(error)|) \end{aligned}$$

Applying this to the comparison of two restriction sites for determination of growing point(s) in the algorithm, any two sites on the growing map of the same enzyme type are dependent because the interval between them is known (fragment length of fragment from single digest or sum of more than one fragment) and is used to determine the coordinate and the error. Any two sites of different types are dependent if the double digest for the two enzymes exists, and the fragment between the two sites has been assigned and used to determine the coordinates of the two sites.

Figure 10:
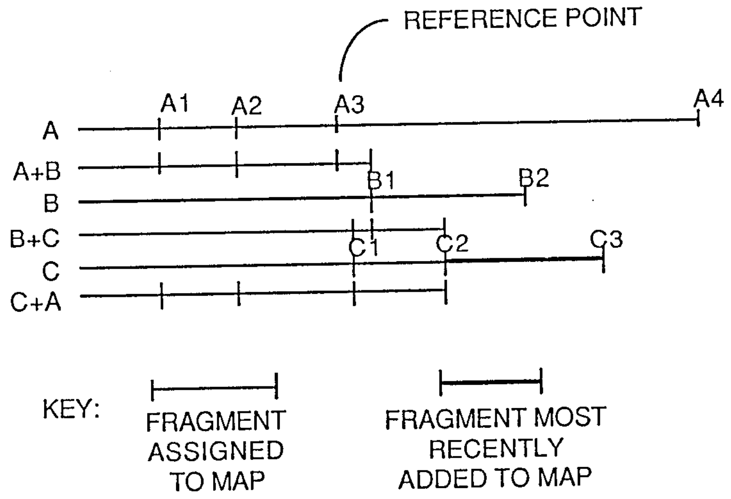
FIG. 10 is a map illustrating how to find reference point.
Figure 11:
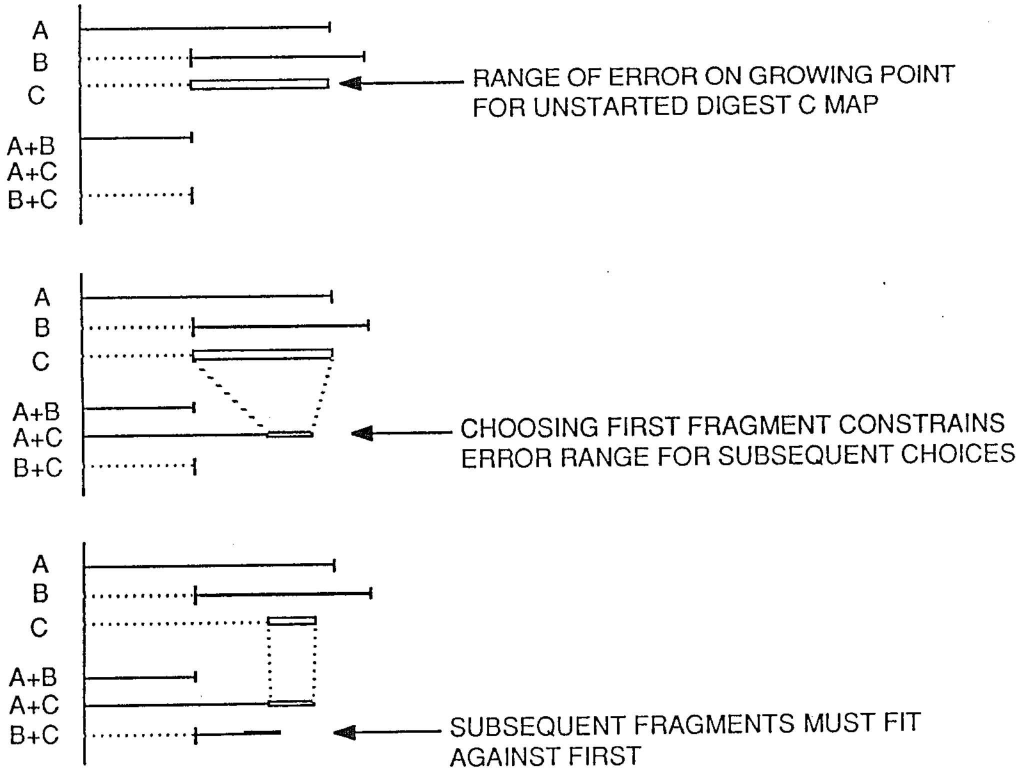
FIG. 11 is a diagram of the special case of starting a circular map.

In order to determine the next growing point, it is necessary to compare right ends of the single digest maps (coordinates of different enzymes). Since the error on these sites generally gets larger and larger as we get further in map construction, using the global error to compare the sites would lead to exploring many "possible" growing points and very slow operation. However, the sites in fact are not totally independent. They can be compared by referal to a third site, a reference point, upon which both of them are dependent, as shown in FIG. 10.

The best reference point to use is the closest. When comparing two map right-end sites (and the double digest for the two enzymes exists), the best reference point is the leftmost previous end of the two maps. If appropriate double digest data doesn't exist, then there is another site from which there is a common path of dependent sites to the two sites being compared. The best reference point is different for any two sites and depends on which double digests exist. For present purposes (reducing ambiguity of growing point) using the best reference point is not essential. Any fairly close reference point will do at the cost of some increased ambiguity. Because finding the best for every pairwise combination of enzymes would be a complex and time consuming step, the closest site which can be a reference point for any two map right ends may be used. (Termed the "greatest-common-whole-map-reference-point"). It is the leftmost of the "best" reference points for pairs, and is found as the leftmost previous end among the single digest maps. Since the input data is reqired to contain multiple digests so that all enzymes are represented in the multiples, the entire set of enzymes is tied together through multiple digest(s) and the use of a single reference point is valid.

Procedure for starting a map

The previous sections describe the process of constructing restriction maps by adding fragments one at a time to a growing map. The following discussion details the procedures for starting a new map.

Linear maps

Linear maps have two sites in common among all the digests, the two ends. To start a linear map, an arbitrary order is imposed on the enzymes' single digests. Only two minor steps need be incorporated into the BUILD-MAP procedure for beginning a map: the method of choosing the growing point and the method of fitting multiple digest fragments. At the begining of a map (i.e. there is at least one single digest with no fragments yet in the map), the growing point is chosen as an unstarted single digest map (arbitraily the next). After choosing such a growing point, no multiple digest fragments need to be fit. The method proceeds by adding a single digest fragment to the selected growing point.

Circular maps

Circular maps create special problems at the beginning and ending of map construction, but once underway can proceed as described above. The method of the present invention can handle circular maps without special user input, except, of course, input of an indication that the DNA is circular.

In determining a growing point, if any single digest map is not started, there is a growing point ambiguity. Possibilities for the growing point include the leftmost site(s) of the started maps and all unstarted enzyme maps. All of these possibilities must be tried.

When the selected growing point belongs to an unstarted map, then fitting multiple digest fragments employs special rules. If all of the other enzymes involved in a multiple digest belong to unstarted maps, then no multiple digest fragment is placed in the map. The fragment that would have been chosen will actually be chosen at the right end of the map, since the left end of this fragment is positioned to the left of our arbitrary starting point and the map is circular. If one or more of the other enzymes involved in the multiple digest belong to started maps, then the fragment chosen from the multiple digest is allowed to fit by much weaker rules than normal. This situation is analogous to guessing where to start the growing point map. Any fragment chosen from the multiple digest will position the first site in the growing point digest, but the method has already made one assumption that must not be contradicted. The position of the growing point must not be to the right of the right end of any other started map (i.e. contradicting the definition of growing point).

Ending a Map

Figure 5:
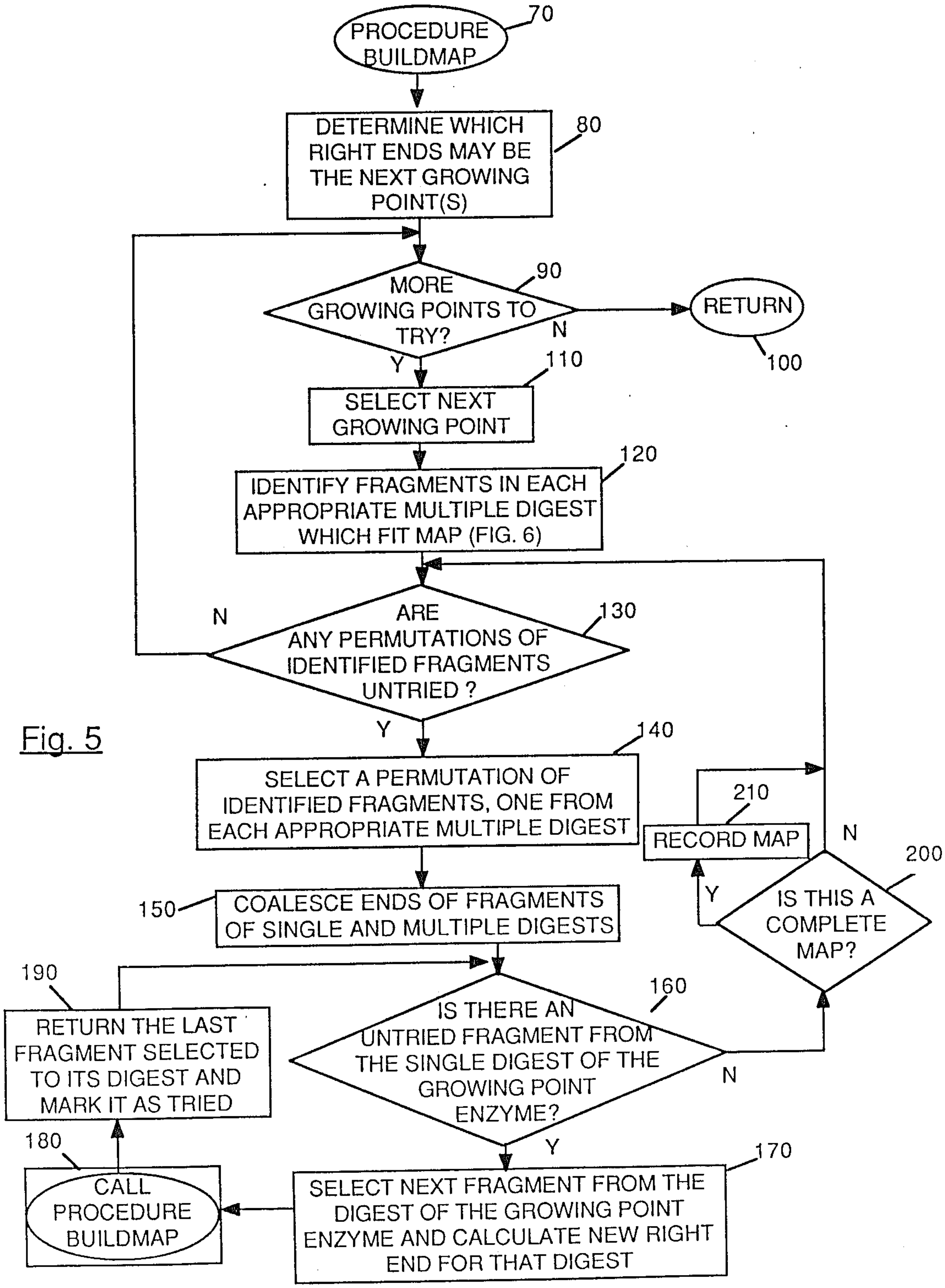
FIG. 5 is a flow chart of recursive procedure BUILDMAP, which is a part of the computer program implementation of the present invention.

For linear problems involving only two enzymes, the method of the present invention always completely solves the map at the step numbered 9 in FIG. 5. Extending the number of enzymes, however, involves some complications.

For linear maps, the method will have chosen one enzyme as the last growing point (which is synonymous with the right end of the map) and will have fit fragments from all multiple digests involving that enzyme. Since the right end is a site which is common to all maps and the growing point enzyme is a site which is not, the method must fit a last fragment into all multiple digest maps that do not contain the growing point enzyme. The fitting procedure is the same as that depicted in FIG. 8, but each of the enzymes involved in the multiple digest maps is hypothesized to be the growing point, one at a time.

For circular maps, the method will always have two loose ends at step 9 of the flowchart in FIG. 5. First, as in linear maps, there is one last fragment to fit in each of the multiple digest maps that do not involve the enzyme at the end of the map (and in this case also at the beginning). Since the maps are circular, the method must use special fitting rules to accomodate the part of the map that extends beyond the arbitrary ending/starting point wrapping around to the first site in the multiple digest map. The difference in starting positions ± error is added to each single digest map when this fragment is fit. In addition, each single digest map must be tested for fit between the part of the map that extends beyond the last growing point and the position in the map where that digest begins. The fitting rules employed are equivalent to rotating the map leftward to each of the single digest starting sites and applying the standard rules for fit.

Evaluating and presenting a map

Once the method of the present invention has produced a site order and an assignment of fragment order in every digest, it has thus produced an assignment of every fragment to a map interval. This is the requirement for use of the method of Schroeder and Blattner to determine the coordinates of the sites of the restriction map (Schröeder and Blattner, 1978). This method assigns map coordinates so as to minimize the sum of the squares of the fractional deviation between the fragment computed length (difference of coordinates) and the fragment measured length. The present invention employs this method to assign map coordinates to the maps constructed. Maps are then sorted in order of best "score".

Score may be defined in a number of ways. The present inventors have used both the normalized standard deviation of fragments and the standard deviation weighted by measurement error. In either case, the smallest score is the best fit. The first uses the sum of squares of the fractional deviation (the same thing which is minimized by the fitting method). The second uses the sum of squares of the fractional deviation weighted by the inverse of % fragment-error for the individual fragments. Thus a difference in an interval whose measurement was known to be bad (proportionally) does not count as much as a fragment whose measurement was known to be good.

Enhancements and Variations

The following variations are alternative embodiments which may be used in combination with the method described herein, or with other methods of map computation.

(1) The method may impose an ordering so as to eliminate inverted (mirror image) maps.

(2) When fitting doubles, the method may check "clues". A fragment labelled as "new" in the double digest (either input by the user or automatically labelled by the program because the size is distinct from all single-digest fragments) is rejected if the method is searching for a fragment with both ends of the same type. Those fragments which can be automatically labeled by the program would automatically be rejected because of size, but "clue" checking is known to be much faster than checking the size. Those which are close in size to a non-new fragment can't be distinguished as new just by size of the input data but the user may be able to tell by inspection of the gel and thus many false maps can be rejected if the ųser also inputs clues where possible.

(3) In trying to add a single-digest fragment, use of clues such as (cut-by enz X) to eliminate some fragments from consideration would be a saving of computational effort.

(4) For linear molecules, use of clues such as: Left end, Right end, or someEnd increases efficiency.

(5) It would be efficient to consider "identical" sized fragments as the same so that both permutations are not output, thus eliminating "identical" (for all practical purposes) maps. The preferred embodiment uses "identical to the last digit", but this may be varied by the user.

(6) It will be useful to extend the method to allow adding of digests using additional enzymes to an existing map. Instead of trying all orderings of single-digest fragments, for a mapped enzyme, the method would allow adding them only in the mapped order.

(6a) Similarly, it will be useful to extend the method to allow use of any available partial mapping information, such as some of the contained-in relationships or a map of part of the molecule such as one has when mapping clones of an unknown DNA in a known vector. This may be done either by constraining the order of adding fragments or by by elimination of maps inconsistent with the partial mapping information.

(7) The existence of "not-visible" fragments is readily detected by consistency rules and easily handled by the present invention. According to the preferred embodiment, the consistency checker (of the data input and editing program) finds out if there are small (not visible) missing fragments and the user is advised to add a small fragment with value < some amount. This could be more automated by letting the method assume existence of such fragments.

(8) For those instances where an experimentor purifies a gel band and redigests, it may be useful to add a "contained_in" clue for those fragments' relationship to other fragments.

(9) The inclusion of some indication of adjacency within a particular digest may be added.

(10) The inclusion of some indication of the existence of fragments obtained by partial (incomplete) digestions consisting of adjacent fragments not cut may be useful. Such an indicator would be used either to eliminate some "close" solutions, or to check additive length of fragments.

Details of the Preferred Embodiment Computer Implementation

An implementation of the method of the present invention, written in the 'C' computer language for the IBM Personal Computer is attached hereto as Appendix A. The system is structured into three major parts: a fragment/digest editor, a map generator and a map viewer.

The fragment/digest editor allows a user to enter digestion data from the keyboard in a convenient manner and will also accept measurements produced by a digitizer. The editor is resposible for determining the overall consistency of the data and identifying conditions that would cause problems for the map generator, such as missing fragments.

The map generator is responsible for producing all maps consistent with the fragment measurements and storing completed maps for review.

The map viewer is a screen oriented system which allows the user to examine the maps produced in various levels of detail and in a variety of formats. Foremost is the ease of comparing any two maps. The viewer also allows the user to further process any selected maps into files compatible with other analysis and formatting tools.

DETAILED DESCRIPTION OF THE PREFERRED EMBODIMENT

Data Structures of RMAP

Figure 4:
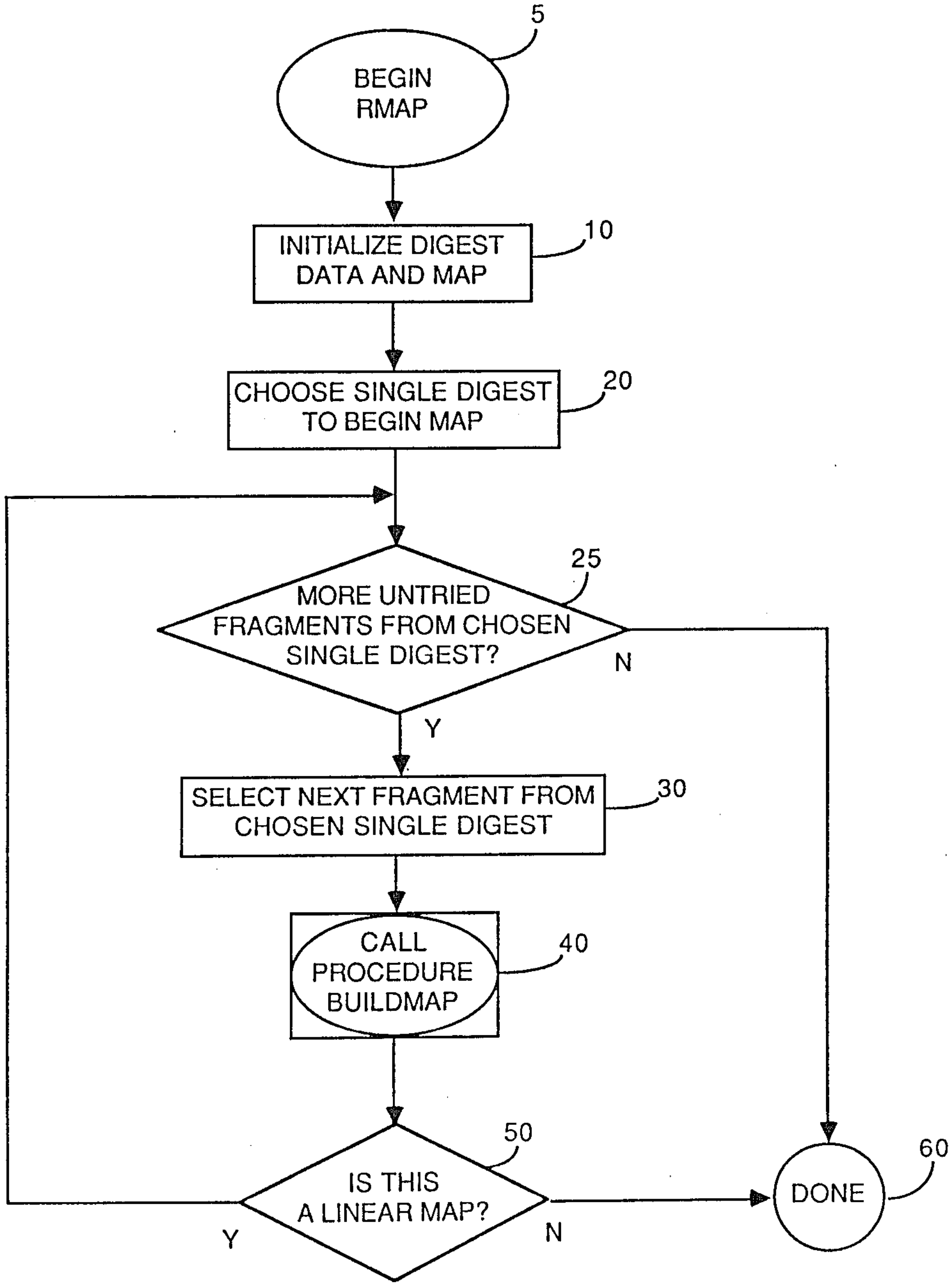
FIG. 4 is a flow chart of the computer program which implements the present invention.

Refering to Block 10 in FIG. 4, there are shown three data structures for the control of the program RMAP during the construction of possible restriction maps.

The FRAGMENT_DATA are a set of ordered lists, one for each different digestion in the input data. Each element of each list contains a fragment size, fragment error, an assigned-or-available flag, and (optionally) any "clues" about the fragment. Each list also has an associated pointer which is the "next-available fragment to try". It means that all available fragments above the pointer have been tried and all available fragments below the pointer have not been tried. Upon rejection of a fragment the program sets the pointer to the next (after the rejected one) available fragment in the ordered list. Upon acceptance of a fragment the program sets the pointer to the beginning of the list (first available fragment) in readiness for the next step of the recursion.

The MAP_TO_DATE is a set of arrays, one for each different digest in the input data. Each element of the array is a fragment identifier. As the program proceeds with map construction each fragment added to the growing map is represented by assigning its identifier to the next element in the array. Each map array has an associated integer, the number of fragments assigned to the map to date, and two associated coordinate ranges, the minimum and maximum values for the right end of the map and for the previous end (i.e. left end of last fragment added).

The HEAP is a dynamic structure which stores the information needed as the program proceeds back and forth through the recursion levels. It is a stack of objects referencing lists of growing points yet to be tried for a specific map position. Each element of the list contains the growing-point enzyme type, right-end coordinate range and previous coordinate range. A new list is created with each recursion and "heaped" upon the last. Each element of the list is examined, in turn, before the algorithm retreats to the previous heap level.

At the completion of a map, the sites of the map may be read from the heap in left to right order by traversing the heap from bottom to top and referencing the first list element at each level.

Reading the Data

Data is read into the program from a data file. This file is created by an editor written especially for the purpose. Input for the editor can be either typed at the keyboard or obtained via measurement by a digitizer tablet. The editor checks fragment consistency using the rules outlined in Table 1.

Starting the map (FIG. 4 Block 20)

To start the map a fragment is selected from one of the single digests. There are some constraints on which single enzyme digest and which fragment from the digest may be used. For linear maps any digest will do. The algorithm tries all fragments as the starting fragment (see flow chart) however, fragment selection for the first fragment is rejected if it conflicts with a "clue". i.e. if "leftend" is labelled in the starting digest, it is the only fragment from that digest which is possible as the starting fragment. Similarly, "right end" is rejected as a starting fragment, or if two directionally unspecified ends are in the data set ("ends") only those two are tried. If clues for endpoints have been specified, then one of the single digests containing clues must be chosen to start the map, otherwise we may inadvertently chose a fragment from an un-clued digest which conflicts with the end clues. All unstarted maps are assigned a range for the position of their right end site of zero±zero.

For circular maps the enzyme digest to start is one which is involved in at least one multiple digest with every other enzyme to be mapped. This ensures complete coverage of the configuration space. If there is not such a digest, an arbitry one is choosen. All unstarted maps are assigned a range for the position of their right end site that spans zero to the length of the first fragment.

Recursive procedure BUILDMAP (FIG. 5)

We have implemented this method as a recursive procedure. However, since the maximum depth of recursion is known for any given data set (total number of single digest fragments) it could be implemented non-recursively. The Pseudocode Listing of Table 2 outlines the computer procedure implementing the mapping method described in FIG. 5.

The details described in the paragraphs below are numbered and formatted in parallel to the Pseudocode Listing so the reader can more easily refer back to the "big picture".

BEGIN BUILDMAP {a recursive procedure which tests to see if a single-digest fragment which has been added to the map is accepted and to try adding another fragment if it is}

1. (a). Determine possible GrowingPoints by finding leftmost right end site(s) by comparing coordinates of the sites (stored on the map-to-date). For this comparison, instead of using the global range (error relative to left end) of the coordinates (stored in map) use the relative error. This is obtained by subtracting the error of the greatest-common reference point for the entire map from the range of each right end coordinate. The site with the leftmost coordinate and any other site(s) whose relative-error-ranges for its coordinate overlap that of the leftmost site are possible growing points.

i.e. Find RightEnd with lowest Low end of range. This is one new GrowingPoint. Compare that G.P. High end with the low end for every other RightEnd site. If G.P.High - RefError>otherLow then the other site is also a potential GrowingPoint OR if G.P.High>otherHigh then other is a potential GrowingPoint.

note: RefError is the error range of the leftmost PreviousEnd of all the single digest maps.

(Special case if just starting a linear map—choose exactly one unstarted map as growing point rather than all that intersect.)

(b). Place a new element on the heap containing a growing point node for each possible growing point.

This contains (i) The enzyme type of the GrowingPoint (ii) The coordinate range (global error) of the growing point (iii) The coordinate range of the previous growing point 2. While untried GrowingPoints, Select Next GrowingPoint at the top of the heap 3. Calculate size of fragments from multiple digests to look for {use local errors}

(a) Examine all multiple digests which contain the growing point enzyme.

(b) Find a fragment which runs from the current right end site of the multiple digest map to the growing point.

(c) Use as the reference point the left end of the single fragment in the growing point enzyme single digest.

(d) Criteria for fit: Sum of fragments with errors in the multiple digest from the reference point rightwards, plus the query fragment with error must intersect the size of the single digest fragment (of growing point type) with its error.

(Note: special case if at beginning of circular map—sum of query fragment minus error and starting position of multiple digest map minus error must be less than the leftmost single digest map right end plus error. This effectively places the first site in the growing point digest map anywhere from the last growing point to the next most likely growing point. After fitting one fragment using this rule all others must fit as if the growing point digest map begins at this position.)

4. While an untried set of fragments which fit exist, Select fragments from multiple digests.

One fragment from each multiple digest 3(*a*) must fit 3(*d*). Existence of set that does fit allows acceptance of single digest fragment added to map in previous recursion and the algorithm can proceed forward. This loop tries all permutations of one fragment from each multiple which fits against the single.

At this point, the single-digest fragment added in the last recursion has been accepted. Now proceed to get ready to add the next fragment to the map.

5. Coalesce end of single digest map with each multiple digest.

Using the set of fragments from multiples selected above (Step 4):

(a) take the intersection of the ranges of all the sums used to fit the multiple digest fragments and the range of the single. If there is an empty intersection, reject this permutation of multiple digest fragments. {continue with step 4}

(b) add this range (a) to the PreviousEnd of the growing point digest. Also sum the errors.

c) adjust the coordinate of the growing point by putting the result (b) in the right end coordinate of the map of the single digest.

Note: this is where the starting position of circular maps of the single digests is determined and why this method can map circular molecules without a specific user input offset. If we are just starting the growing point digest, then we substitute 0±0 for the PreviousEnd in step 5(*b*).

{start at beginning of list of unassigned fragments for single digest of GrowingPoint enzyme. This important point is handled by the selection routine for single digest fragments so the pointer is set to the top of the list in a previous recursion when the last fragment was selected.}

6. Are any single digest fragments untried? if not, then proceed to step 9, otherwise While still untried fragments in single digest of GrowingPoint type, (a) Select next fragment from single digest to try adding to map at GrowingPoint.

(b) Calculate new right end for that map.

(i) save the right-end as PreviousEnd.

(ii) The new right-end is right-end (stored in map)+(fragment size of fragment selected±error on selected fragment).

7. Call BUILDMAP {to see if added fragment is accepted and to try adding another fragment if it is. return here if fragment selected in 6 above is rejected}

8. Remove fragment from Map. Return fragment to fragment list, Set next-frag-to-try pointer to next fragment after this one. Restore PreviousEnd and RightEnd (by reading from heap) end Loop 6 (while still fragments left to try)

9. Query is this a map? If yes, record the map.

Remove multiple digest fragments selected in step 4 from map. Return fragments to fragment list.

end Loop 4 (while still permutations of fragments from each double digest that fit)

remove GrowingPoint node from Heap end Loop 2 (while still untried growing points)

remove top level from heap (contains no more GrowingPoint nodes now)

RETURN {fragment added in previous recursion doesn't fit}

Starting Maps

Figure 6:
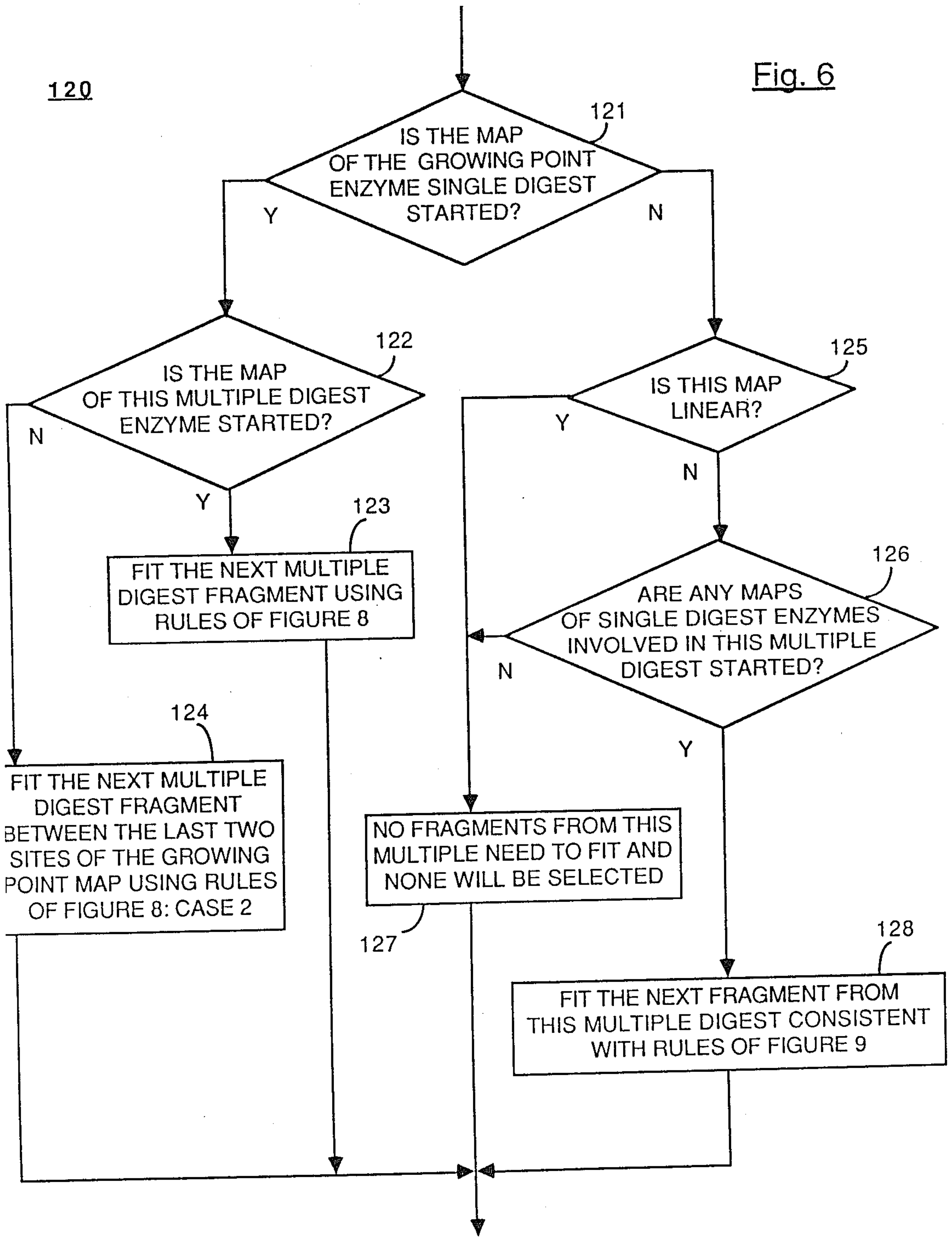
FIG. 6 is a detailed flowchart of step 120 of BUILDMAP showing special cases for starting maps.

FIG. 6 outlines the procedure for fitting double digest fragments. This includes the special cases of just starting a map.

Starting a linear map

When any of the single digest maps are not yet started (i.e. no fragments yet assigned to map) special rules apply to finding the (next) growing point and to fitting fragments. The growing point selected is the next (abitrary order) unstarted digest. Since the growing point is synonymous with the left end, we would look for a fragment of zero length to be fit and obviously no such fragment would be represented in the data. The previously added single digest fragment is accepted (without assigning any multiple digest fragments) and a single digest fragment from the new growing point is added.

Starting a circular map

When any of the single digest maps are not yet started special rules apply to finding the (next) growing point and to fitting fragments. The possible growing points are the leftmost right end site(s) of the started digest map(s) and all unstarted digest maps (eg. at the first call of BUILDMAP all single digest maps are determined to be possible growing points). All possibilities must be tried one after the other.

Special rules also apply to fitting multiple digest fragments. The various cases are flowcharted in FIG. 6 and fitting rules for the special case diagramed in FIG. 10. In order to understand why these rules work it is necessary to realize that the selection of a growing point has made an hypothesis about the order of sites in the map. Since we try all possible growing points this is legitimate. Any multiple digest involving the selected growing point enzyme must be considered. A fragment to be fit is to be placed left of (ending at) the growing point.

If the growing point enzyme map has already been started, there are two cases to consider, the other enzyme maps in the multiple digest have not been started or they (any one) have been started. If both the growing point digest map and (one of) the other enzyme maps have been started, then the regular rules apply. If none of the other enzymes in the multiple digest have started maps then the first site for that enzyme has not yet been encounted and is right of the growing point. Since the growing point enzyme map has started, the fragment to be fit is the same size as the last fragment in the growing point enzyme digest map.

If the growing point enzyme map has not been started then, we don't really know the position of the growing point except that it is right of the previous growing point and left of any other right end in the map. If none of the maps for any of the other enzymes in the double digest have been started, the fragment left of the growing point extends left of the arbitrary starting point for the map and so no fragment needs be fit. (Unlike the case of linear where the concept of a fragment left of the left end is meaningless, there really is such a fragment in a circular map. It is fit at the end of the process.) However, when the growing point digest map has not been started and the other enzyme map has been started, the fragment to be fit runs from the other enzyme to the growing point. Thus the first double digest fragment to be fit has a large error since the uncertainty of the location of the growing point site is large. After the first multiple digest fragment is selected the site location is set using this fragment and fragments to be fit from any other appropriate multiple digests have errors based on the local error of the first (i.e. sum of overlapping fragments).

Ending a Map

When all fragments from single digests have been placed in the map (FIG. 5, Block 200) the algorithm has reached a stage where BUILDMAP has made all the forward progress that it can. In linear maps with two enzymes this stage represents a completed map, but in more complicated maps one last fitting step still remains before we have a complete map.

For linear maps of three or more enzymes, we have chosen only one of the single digest enzymes as the last growing point. Since that site represents the right end of the map, it is a site common to all digests, but we have only fit multiple digest fragments for digests that contain the growing point enzyme. Therefore, we need to determine that the last unchosen fragment from each of the multiple digests NOT containing the growing point enzyme will fit at the right end of the map.

To accomplish that, we scan the set of multiple digests in a predefined order (our implementation uses the order of occurrence in the data). Each multiple digest that contains an unchosen fragment has that fragment chosen and tested against each of the single digest maps for the enzymes it contains. This involves hypothesizing each other enzyme as the last growing point and then applying the fitting rules shown in FIG. 8. If all such fragments fit, then the map is complete and we proceed to Block 210 of FIG. 5.

In order to restore the state of the map in such a way that BUILDMAP can continue we must replace exactly the set of fragments chosen by this last step. This is accomplished by replacing one fragment from the end of each multiple digest map NOT containing the last growing point enzyme in the same predefined order in which these fragments were selected. The ordering is important if any of these fragments fails to fit, since we must replace ONLY those fragments chosen by this last step.

For circular maps of two or more enzymes, we have completed the map for all digests containing the enzyme of the single digest used to begin the map. Although all single digest fragments have been chosen at this step, we still need to fit a fragment from each multiple digest NOT containing the growing point enzyme (same as the enzyme site at the start/end of the map). The procedure for fitting these remaining fragments is much the same as for the linear case detailed above, but only the leftmost of the single digest right ends for enzymes contained in the multiple digest is tested for fit, since all fragments to the right of this point have already been fit at the beginning of the map.

Figure 8A:
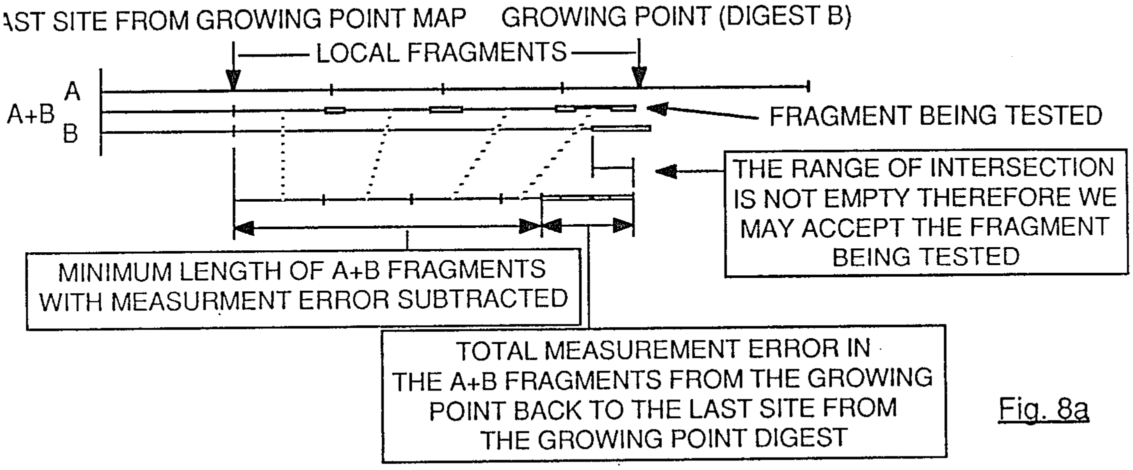
FIG. 8 is a diagramatic representation of the method of fitting double digest fragments (a & b) into the growing map using local error.
Figure 8B:
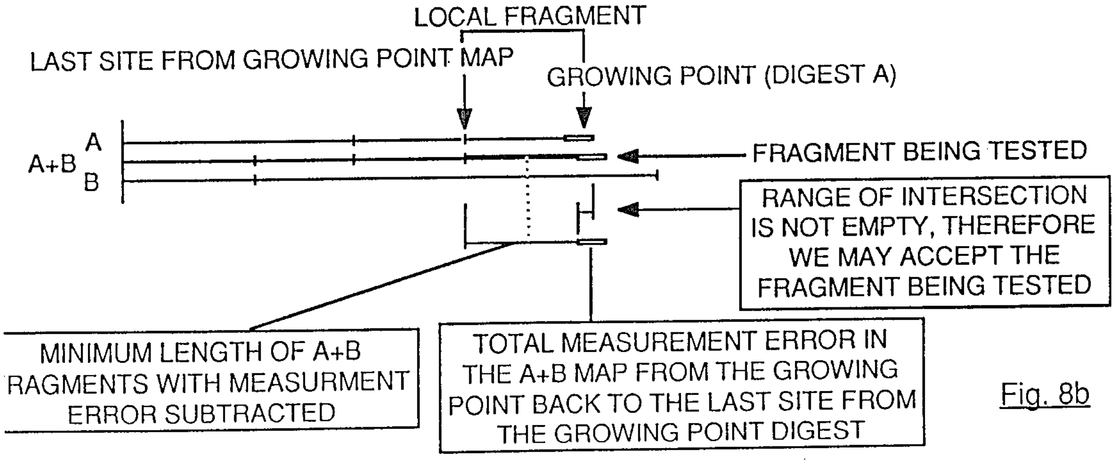
Figure 8:
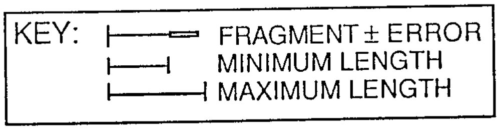

Since circular maps allow weak fitting rules in order to start single digest maps, we are in a position at the end of the map to test this hypothesis using the stronger fitting rules of FIG. 8. Although all fragments have been placed in the map, we may have managed to avoid testing the fit of some single digest fragments that span our arbitrary starting/ending site. The only fragments which have escaped scrutiny are those which span the start/end site and are composed of three or more multiple digest fragments. Rather than identifying these individual cases, our implementation simply tests every one of the rightmost single digest fragments against the multiple digest fragments contained within it using the rules shown in FIG. 8 modified to cycle to the beginning of the map at the start/end site.

Recording a completed map

Once a complete map has been identified, we are in a position to evaluate the quality of the map in relation to the others generated by BUILDMAP. The present invention applies the method of Schroeder and Blattner to compute positions for all map sites based upon the generated order of fragmentation data. A measure of goodness of fit is then calculated using the formula:

$$M = \sqrt{\frac{\Sigma_{i,j}\left(\frac{Fm - Fc}{Fm}\right)^2}{n\,(n-1)}}$$

where:

Fm=measured fragment size from site i to site j

Fc=computed fragment size from site i to site j n=total number of fragments represented in data M=measure of deviation evaluated over all pairs i,j which are measured A perfect map produces a measure of zero and larger measures indicate greater deviation from an optimal map. The preferred embodiment ranks maps in order of increasing measure of deviation and records maps in a randomly accessed file indexed by a file of deviation measures. Purely as a matter of convenience, only up to fifty maps are stored. Beyond fifty maps, measures better than the fiftieth map cause replacement by the current map and an update of the index file maintaining the measures in increasing order.

Each map is represented in the randomly accesed file by a record composed of:

(1) the vector of site coordinates produced by the method.

(2) the order of single digest enzymes corresponding to the sites of (1) that is internally represented by the first element of each heap list.

(3) the generated order of fragment identifiers for each digest map represented in the data.

All other information (such as fragment sizes, error, enzyme names, etc.) is assumed to be reproducible from the input data.

The index contains all references necessary to reproduce the input data (specifically the data pathname), the number of maps stored in the randomly accessed file and a record for each map containing:

(1) the position of the map record in the random file.

(2) the measure of deviation for that map.

Structuring the output this way promotes complete modularity of the reviewing process, therefore it may be implemented as a completely independent program.

Map Consistency

In order to successfully apply the map generation algorithm, several requirements of the input data must be met. These requirements are embodied by the following assumptions:

| | |
|---|---|
| Purity Rule: | (1) The DNA to be mapped is a single molecular strain. |
| Topology Rule: | (2) The DNA is known to be exclusively either circular or linear. |
| Digestion Rule: | (3) Digestion of the DNA has proceeded to completion. |
| Combination Rule: | (4) At least two independent sets of cleavage products are represented, separately and in combination. |
| Orphan Rule: | (5) Each enzyme or proper subset of enzymes involved in a multiple digestion is represented by a separate (single) digestion and identified as such |
| Completeness Rule: | (6) Every fragment has been represented in the data and a measurement and bounding error has been assigned to it. |
| Uniqueness Rule: | (7) Any fragments of identical size are individually represented. |

From these primary assumptions we have formulated tests which may be used to qualify the data for map generation (Table 1). Data failing any one of these tests will guarantee incomplete coverage of the configuration space and will give unsatisfactory (or no) results, therefore, all tests must succeed before any attempt at map generation is made.

The tests in Table 1 apply assumptions 1,2,3,6, and 7 in combination to yield equations relating the number of fragments between single and multiple digests. Any digests not meeting these equalities are assumed to have violated either the Completeness Rule (6) or the Uniqueness Rule (7) and the user is directed to re-examine the experiment in order to identify the cause of the inconsistency.

Application of the Combination Rule (4) involves identifying at least two single digestions and at least one multiple digestion in the data. Once that has been satisfied we may apply the Orphan Rule (5) to determine whether any set of single digestions is missing. Passing this last test qualifies the data for map generation.

STATEMENT OF INDUSTRIAL UTILITY

The present invention may be useful for the generation of restriction maps of DNA or for solutions to similar mapping problems. DNA restriction maps find application in the design of recombinant DNA, and in the elucidation of DNA structures for purposes of genetic comparison, diagnosis, and other such uses.

Glossary of Terms

Decomposition Fragment—See Fragment.

DNA—Deoxyribonucleic Acid. For mapping purposes it is a one-dimensional entity of finite length either linear (two ends) or circular (no ends).

Double-digest—All the fragments produced by incubation of a DNA molecule with two restriction enzymes at once.

Fragment—A subsection of a DNA molecule created by cleaving the DNA with restriction enzyme(s). The ends of the fragment are two restriction sites. The size (length) of the fragment is the distance between the two restriction sites on the DNA molecule from which the fragment was cleaved. Fragments may also be sub-fragments of larger fragments produced by single digests.

Genome—The entire genetic content of an organism. For most organisms, this comprises one or more molecules of DNA. (Exceptions are some viruses, e.g. retroviruses which have RNA genomes.)

Growing Point—The data point used in the construction of maps that according to the present invention which is defined as the site in the restriction map chosen from the set of right ends of all single digest maps which is assumed to be furthest to the left.

Growing Point Enzyme—The enzyme used in the single digest which has been chosen as the growing point.

Map—An enumeration of the sites for one or more restriction enzymes on a particular DNA molecule.

Mapping—The process of deducing the map of a particular DNA molecule for one or more restriction enzymes from single and multiple digests.

Measurement error—The length of fragments can be measured. Methods generally used to obtain fragment sizes for the purposes of mapping have a measurement error roughly proportional to fragment length. (i.e. the error is proportional to fragment length, such as ±5% rather than absolute like ±620)

Multiple-Digest—All the fragments produced by incubation of a DNA molecule with two or more restriction enzymes at once.

Permutation—A unique ordering of objects. (E.g. a permutation of fragments or sites).

Restriction enzyme—An endonuclease which cleaves DNA at one or more specific sites.

Restriction site—A site on a DNA molecule at which a restriction enzyme cleaves. It is usually identified with the name of the enzyme which cleaves at that site and the position of the site (± error) on the DNA molecule in question.

Single-digest—All the fragments produced by incubation of a DNA molecule with any one restriction enzyme.

Reference Point—A site in the restriction map used for the purpose of comparing the right ends of two single digest maps where error is localized.

TABLE 1

FRAGMENT CONSISTENCY RULES let $f_1$ = number of fragments in digest 1
$f_2$ = number of fragments in digest 2
$f_{1,2}$ = number of fragments in 1 + 2 double digest
$s_1$ = number of sites of type 1
$s_2$ = number of sites of type 2
$s_{1,2}$ = number of sites of either type 1 or 2 for linear molecules
$f_1 = s_1 + 1$
$f_2 = s_2 + 1$
$f_{1,2} = s_1 + s_2 + 1 = f_1 + f_2 - 1$ for circular molecules
$f_1 = s_1$
$f_2 = s_2$
$f_{1,2} = f_1 + f_2$ For digests containing "clue" information:
let $cut_1$ = number of fragments of digest 1 cut by enzyme 2
$uncut_1$ = number of fragments of digest 1 not cut by enzyme 2
new = number of fragments in the double digest which are not in either single digest
$cut_1 + uncut_1 = f_1$
$cut_2 + uncut_2 = f_2$
$uncut_1 + uncut_2 + new = f_{1,2}$ assume $s_1$ and $s_2 > 0$,
$1 \leqq cut_1 \leqq s_2$
$1 \leqq cut_2 \leqq s_1$ for linear molecules
$new = cut_1 + cut_2 - 1$
$|f_1 - f_2| - 1 \leqq uncut_1 + uncut_2 \leqq |f_1 - f_2| + 1$
$1 \leqq new \leqq 2^* \min(s_1,s_2)$ for circular molecules
$new = cut_1 + cut_2$
$uncut_1 + uncut_2 = |f_1 - f_2|$
$2 \leqq new \leqq 2^* \min(s_1,s_2)$

TABLE 2

Outline of Procedure Buildmap formated like the implemented C program. This procedure implements the method FlowCharted in FIG. 5. Steps are numbered in accordance with FlowChart in FIG. 5. Terms are defined in the text and the method is explained in text and figures. In this table, messages surounded by brackets are {comments}.
Overview of Recursive Procedure BUILDMAP for constructing restriction maps from fragment size data

```
    Begin BUILDMAP {to see if added fragment is accepted and to try adding another
    fragment if it is}
1.  Determine which right ends may be growing points by finding leftmost right end site(s)
    {by comparing the coordinates using relative error}
While untried GrowingPoints,
        2.  Select GrowingPoint
        3.  Calculate size of fragments from multiple digests to look for {use local errors}
    While a set of untried fragments which fit exist
            4.  Select a permutation fragments from multiple {fragments must fit.
                Existence of set that do allows acceptance of single digest fragment added to
```

TABLE 2-continued

Outline of Procedure Buildmap formated like the implemented C program. This procedure implements the method FlowCharted in FIG. 5. Steps are numbered in accordance with FlowChart in FIG. 5. Terms are defined in the text and the method is explained in text and figures. In this table, messages surounded by brackets are {comments}.
Overview of Recursive Procedure BUILDMAP for constructing restriction maps from fragment size data

```
            map in last recursion}
        5.  rectify maps by coalescing sites {using selected set of fragments from
            multiples which fit to adjust the coordinate of the growing point}
            {start at beginning of list of unassigned fragments for single digest of
            GrowingPoint enzyme. note this is handled by the Select routine}
        While still untried fragments in single digest of GrowingPoint Enzyme
            6.  Select next fragment from single digest to try adding to
                GrowingPoint and Calculate new right end for that map.
            7.  Call BUILDMAP {to see if added fragment is accepted try adding
                another fragment if it is}
                {return to here if reject fragment selected in 6 above}
            8.  Remove fragment (selected in 6) from map, mark it as tried and
                replace it in fragment list
            end while {still fragments left to try}
        9.  Query is this a map? If yes, go to 10. OUTPUT PROCEDURE
            {return here after successful - map output so we can continue and get all maps}
    end while {still permutations of fragments from each double digest that fit}
end while {still untried growing points}
RETURN {fragment added in previous recursion doesn't fit}
```

APPENDIX A

```
/*****************************************************************
 *                                                               *
 *                          Map Viewer                           *
 *                                                               *
 *****************************************************************/

#define MAXMAP          20      /* maximum number of sites in any given map */
#define MAXDEPTH        50      /* maximum depth of the heap (same as max.
                                   number of multiple digest sites) */
#define MAXVIEW         50      /* maximum number of maps saved in archive file */

#define NAMELEN         80                  /* largest digest name */
#define MAXSIN          8                   /* maximum number of single digests */
#define MAXMUL          MAXSIN*2            /* maximum number of multiple digests
                                               (N * 2 is a good approximation
                                                for the largest number of multiple digests) */

#define EMPTY           -1      /* value of an empty heap pointer/map index */
#define USED            1       /* value of 'used' flag indicating already chosen */
#define FREE            0       /* value of 'used' flag indicating availability */
#define START           0       /* where to begin array index scans */
#define TOOBIG          1       /* possible return value from 'fits()' */
#define  FIT            0       /* ditto */
#define TOOSMALL        -1      /* ditto */

#define SIZE            long            /* type of fragment length values */
#define GIANT           2147483647L     /* largest positive value for (SIZE) type */
#define ZERO            0L              /* zero value for (SIZE) type */

#define NONE            0       /* synonymous with empty list */
#define  TRUE           1       /* logic true value */
#define  FALSE          0       /* logic false value */

#define BACKSPACE       8       /* ASCII backspace character */
#define FORWARD         '*'     /* character representing progress */
#define BACKUP          249     /* character representing failure */
#define SUCCESS         ']'     /* character representing map completion */
#define FDCHAR          'A'     /* character representing first single digest on compressed maps */

#define ENDMARK         0x1a    /* control-Z is logical EOF on text files */

#define MAPWIDTH        71
#define SCREENWIDTH     80

#define VERBOSE         1       /* verbose output from fragment measurement formats */
#define COMPACT         0       /* compact output from frag. meas. form. */

#define  boolean int            /* type of functions returning logical values */

#define void int                /* type of functions returning arbitrary values */

typedef struct endp {          /* endpoint range structure, used to store */
                                /* the size of a single digest map */

        SIZE            lo,hi;          /* limits on right map endpoint */
        int             index;          /* what position in single map this corresponds to */
}
        endpoint;

typedef struct hnode {

        int             s_digest;       /* which digest does this represent */
        endpoint        s_pos;          /* value of 'sd_end' at decision point */
        SIZE            s_ref;          /* map reference point (everything left of here is to be believed) */
        struct hnode    *others;        /* next list element */

}
        heap;                   /* decision list type name */

/* The heap is a place where upcoming decisions are stored. Every
 * time a growing point is selected (or more than one), the selection
 * is put onto the heap. This allows a simple method of recording
 * what to try prior to backtracking and when to backtrack. By recording
 * each growing point, a scan of the heap entry nodes will produce a map
 * containing all sites catalogued to the current step.
 */
```

```
VAR heap                *what_next[MAXDEPTH];
VAR int                 heap_top = { EMPTY };

typedef struct dignode {        /* storage node for fragment digests */

        SIZE            frag;           /* measured fragment size (in bases) */
        SIZE            frag_error;     /* measurement error (in bases) */
        boolean                 used;           /* flag signalling whether this fragment */
                                        /* has already been chosen for a map */
}
        digest;

VAR char                comment[NAMELEN];       /* single line comment for project */

/* digest storage for singles */

VAR digest              singles [MAXSIN] [MAXMAP];      /* single digests */
VAR int                 s_dup [MAXSIN] [MAXMAP];        /* fragment groups which look identical to the algorithm */
VAR char                sname [MAXSIN] [NAMELEN];       /* their names */
VAR int                 sptr [MAXSIN];                  /* current fragment */
VAR int                 smax [MAXSIN];                  /* index of last fragment */
VAR int                 nsd = { NONE };                 /* number of single digests */

VAR int                 nsites;                         /* number of sites in the map */

/* digest storage for multiples */

VAR digest              multiples [MAXMUL] [MAXMAP];    /* multiple digests */
VAR int                 m_dup [MAXMUL] [MAXMAP];        /* fragment groups which look identical to the algorithm */
VAR char                mname [MAXMUL] [NAMELEN];       /* their names */
VAR int                 composition [MAXMUL] [MAXSIN];  /* which singles used to cut */
VAR int                 mptr [MAXMUL];                  /* current fragment */
VAR int                 mmax [MAXMUL];                  /* index of last fragment */
VAR int                 nmd = { NONE };                 /* number of multiple digests */

VAR int                 nfrags;                         /* number of multiple digest fragments */

VAR SIZE                lo_factor;              /* error on fragments in % */
VAR SIZE                hi_factor;

VAR SIZE                ave_len = { 0L };       /* average length (circumference) of the total map */

/* single digest maps */

VAR int                 sd_map [MAXSIN] [MAXMAP];       /* maps for all single digests */
VAR endpoint            sd_end [MAXSIN];                /* the endpoint ranges */
VAR int                 sd_mdoff [MAXSIN];              /* the multiple digest containing the offset fragment for this single */
VAR int                 sd_mdfrag [MAXSIN];             /* the fragment in above digest which relates this single to first single */
VAR SIZE                sd_offlen [MAXSIN];             /* length of digest offset */
VAR SIZE                sd_offerr [MAXSIN];             /* error term for offset fragment */
VAR SIZE                ref_point = { ZERO };   /* map position where error begins */

/* multiple digest maps */

VAR int                 md_map [MAXMUL] [MAXMAP];       /* maps for all multiple digests */
VAR int                 md_site [MAXMUL] [MAXMAP];      /* which single digest site cuts at right end of this fragment */
VAR int                 md_end [MAXMUL];                /* map index of end of current map */
VAR int                 md_off [MAXMUL];                /* multiple digest containing offset fragment */
VAR int                 md_frag [MAXMUL];               /* fragment from above digest which relates this digest to to first */
VAR SIZE                md_offlen [MAXMUL];             /* length of digest offset */
VAR SIZE                md_offerr [MAXMUL];             /* error of above length */

VAR FILE                *out;                           /* map output file */
VAR FILE                *arch;                          /* map archive file */

VAR int                 traceflag;                      /* trace toggle */

/* In an attempt to suppress maps that are the reverse of a map we will ordinarily find,
 * we came to this conclusion: by choosing any two fragments from the same single
 * digest and forcing them to occur in a specific left to right order, we could ensure
 * that only maps of one of the two reversed orders would appear. This not only accomplishes
 * that end, but also reduces the number of maps considered by a factor of 2.
 */

VAR int                 force_digest;                   /* the single digest containing the largest fragment */
                                                        /* used as starting point and must not be used to force ordering */

VAR int                 order_map;                      /* the digest to enforce an ordering */
VAR int                 prime5, prime3;                         /* the left and right forced fragments */
```

```
VAR int                 linear = { 0 };                        /* is this map linear? (this version is circular only) */

/* the following data are used in the review process */

VAR int                 view = { 0 };                   /* which map (in best to worst order) is currently being viewed */
VAR float               map_score [MAXVIEW];            /* deviation scores for each archived map */
VAR int                 position [MAXVIEW];             /* file position of each archived map */
VAR int                 max_score = (EMPTY);            /* index of last map in 'map_score' */

VAR long                n_maps = { 0L };                /* total number of maps processed */
VAR long                filespace;                      /* space allocated in bytes to each map in the archive */

VAR char maps [MAXVIEW] [SCREENWIDTH+5];                /* where maps for comparison are written */

VAR int                 hours, minutes, seconds;        /* running time */
#define MAXMAT 50
VAR float         vector [MAXMAT];        /* where the result appears */

#include <stdio.h>

#define VAR

#include <rmap.h>
#include <matrix.h>

SIZE permute();

char fofname[65];
char archname[65];
char indname[65];

extern int _fmode;
int revflag;

main(argc,argv)

int argc;
char **argv;
{
        FILE *inp;
        int ac;


        init();                 /* initialize variables */

        out = stdout;
        revflag = traceflag = 0;

        for(ac = 1; ac < argc; ac++) {
                if( argv[ac][0] == '-' ) {      /* error factor specified */
                        switch(tolower(argv[ac][1])) {
                                case 'l':
                                        linear = TRUE;
                                        break;
                                case 'i':       /* project name */
                                        strcpy(fofname,&argv[ac][2]);
                                        break;
                        }
                }
                else
                        if( argv[ac][0] == '+' ) {      /* error factor specified */
                                sscanf(&argv[ac][1],"%ld", &hi_factor);
                        }
        }

        revflag = 1;

        strcpy(archname,fofname);       /* map archive now named according to project */
        strcpy(indname,fofname);

        new_ext(archname,"maf");        /* construct map archive filenames */
        new_ext(indname,"mix");

        if( inp = fopen( indname, "r" ) ) {

                reload(inp);            /* reload archive index */
                fclose(inp);

                get_fof(fofname);       /* read data */
                permute();      /* document fragment duplication groups */
        }
        else {
```

```c
                printf("\nInput error: no map archive");
                exit(1);
        }
_fmode = 0x8000;                                        /* open the map archive file */
        if( (arch = fopen(archname,"r+")) == NULL ) {
                printf("\nPanic! can't open archive file\n");
                exit(1);
        }
_fmode = 0;

        review();       /* process the output */

        exit(0);

}
#include <stdio.h>

#define VAR extern

#include <rmap.h>
#include <matrix.h>


#undef min      /* cure stupid warnings from bios.h */
#undef max
#undef NULL
#undef BACKSPACE

#include "bios.h"
#include "window.h"


#define MAXLINES MAXVIEW + 3                    /* maximum number of map lines */
#define MAXFRAG MAXDEPTH + 6                    /* maximum number of lines in a fragment map */
#define MAXSCALE MAXSIM + 5                     /* maximum number of lines in a scaled map */
#define MAXSEQ 6                                /* maximum number of lines in a sequential map */

#define CUTLINE 4                               /* line of sequential map showing cuts */
#define XFERPOS 5                               /* first character position transferred from compressed map to sequential */
#define TAGPOS 3                                /* position of tag character in compressed maps */
#define TAG '*'                                 /* character used for tagged maps */
#define UNTAG ' '                               /* character used for untagged maps */
#define SHSTART 8                               /* character position containing beginning of map (SEQMAP format) */
#define SHEND 78                                /* character position containing end of map (SEQMAP format) */

#define MOVE 1                                  /* flag for update on cursor movement only */
#define ALWAYS 0                                /* flag for update on every call */

#define KEYMAX 5                                /*max number of keystrokes to process */
                                                /*in one call to k_vcom() or k_vmap() */
#define MAXWINWID 256
/***************************************************************************/
/*  Declare structures externally to permit initialization                 */
/***************************************************************************/

KEYR keyrec = {0, 0, KEYMAX};           /*see bios.h for definition */

#define STYLES 3        /* number of format styles */
#define SEQMAP 0        /* sequential map style */
#define FRAGMAP 1       /* fragment map style */
#define MINIMAP 2       /* mini-map style */

int width[STYLES] = { 90, 256, 81 };

#define ACTIVE 0        /* window indices (entry screen) */
#define COMP 1
#define LIST 2
#define HELP 3
#define TITLEA 5
#define TITLEC 6
#define TITLEH 7
#define LEGEND 10

#define ACTEX 4         /* window index (expand screen) */
#define FULLSCREEN 11

#define MENU 8          /* window indices (menu and dialog screen) */
#define DIALOG 9

        /* file records for 11 windows */

FREC fr[] = {
```

```
        {"",0,0,0,90,0,0,0},
        {"",0,0,0,90,0,0,0},
        {"",0,0,0,81,0,0,0},
        {"",0,0,0,81,0,0,0},
        {"",0,0,0,90,0,0,0},
        {"",0,0,0,81,0,0,0},
        {"",0,0,0,81,0,0,0},
        {"",0,0,0,81,0,0,0},
        {"",0,0,0,40,0,0,0},
        {"",0,0,0,40,0,0,0},
        {"",0,0,0,81,0,0,0},
        {"",0,0,0,81,0,0,0}
};

        /* 11 windows */

WINDOW wn[] ={ {0,6,0,79,  0,0, NORMAL, 0, NO_WRAP, 0,1, 0,0,&bdr_dln,0,&fr[0]},
               {7,13,0,79, 0,0, NORMAL, 0, NO_WRAP, 0,1, 0,0,&bdr_dln,0,&fr[1]},
               {15,22,0,79,0,0, NORMAL, 0, NO_WRAP, 0,1, 0,0,&bdr_0,  0,&fr[2]},
               {24,24,0,79,0,0, REVERSE,0, NO_WRAP, 0,1, 0,0,&bdr_0,  0,&fr[3]},
               {0,21,0,79, 0,0, NORMAL, 0, NO_WRAP, 0,1, 0,0,&bdr_dln,0,&fr[4]},
               {0,0,1,78,  0,0, NORMAL, 0, NO_WRAP, 0,1, 0,0,&bdr_0,  0,&fr[5]},
               {7,7,1,78,  0,0, NORMAL, 0, NO_WRAP, 0,1, 0,0,&bdr_0,  0,&fr[6]},
               {23,23,0,79,0,0, REVERSE,0, NO_WRAP, 0,1, 0,0,&bdr_0,  0,&fr[7]},
               {0,12,40,79,0,0, NORMAL, 0, WRAP,    0,1, 0,0,&bdr_dln,0,&fr[8]},
               {0,10,0,39, 0,0, NORMAL, 0, WRAP,    0,1, 0,0,&bdr_dln,0,&fr[9]},
               {14,14,0,79,0,0, REVERSE,0, NO_WRAP, 0,1, 0,0,&bdr_0,  0,&fr[10]},
               {0,24,0,79, 0,0, NORMAL, 0, NO_WRAP, 0,1, 0,0,&bdr_0,  0,&fr[11]}
};

int select_line = { 1 };          /* which map below is selected (numbered 1..n) */
char *lineptr[MAXLINES];          /*array for storing addresses of */
                                  /*lines of maps for viewing */

int act_line = { 1 };             /* which map is in the active window */
char *acts[MAXSEQ];               /* window contents for active map */
char *actm[MAXSCALE];
char *actf[MAXFRAG];

char *actall[MAXSEQ+MAXSCALE+MAXFRAG];   /* a big window containing all the active window stuff */

char **actptr[STYLES] = { &acts[0], &actf[0], &actm[0] };

char *comps[MAXSEQ];              /* window contents for comparison map */
char *compm[MAXSCALE];
char *compf[MAXFRAG];

char **compptr[STYLES] = { &comps[0], &compf[0], &compm[0] };

char *helptext[12];               /* help window */
char *helptitle = {
"MMMMMMMMMMMMMMMMMMMMMMMMMMMMMMMMMMMMMHelpMMMMMMMMMMMMMMMMMMMMMMMMMMMMMMMMMMMMM"
};

char *atitle[] = {        /* formatting strings for active window titles */
"MMMMMMMMMMMMMMMMMMMMMMMMMM Active Map %2d Sequential MMMMMMMMMMMMMMMMMMMMMMMMMMM",
"MMMMMMMMMMMMMMMMMMMMMMMMMM Active Map %2d Fragment MMMMMMMMMMMMMMMMMMMMMMMMMMMM",
"MMMMMMMMMMMMMMMMMMMMMMMMMM Active Map %2d  Minimap MMMMMMMMMMMMMMMMMMMMMMMMMMMM"
};

char *ctitle[] = {        /* formatting strings for comparison window titles */
"MMMMMMMMMMMMMMMMMMMMMMMM Comparison Map %2d Sequential MMMMMMMMMMMMMMMMMMMMMMMMM",
"MMMMMMMMMMMMMMMMMMMMMMMM Comparison Map %2d Fragment MMMMMMMMMMMMMMMMMMMMMMMMMM",
"MMMMMMMMMMMMMMMMMMMMMMMM Comparison Map %2d  Minimap MMMMMMMMMMMMMMMMMMMMMMMMMM"
};
char *aextitle[] = {      /* formatting string for expanded screen */
"MMMMMMMMMMMMMMMMMMMMMMMMM Active Map %2d All Forms MMMMMMMMMMMMMMMMMMMMMMMMMMMM"
};

char *htext1[] = {                  /* help text for entry screen */
"    F1    Pull up/down help window           ->,,,<-  Scroll within window\n",
"    PgUp  move cursor up one window          PgDn  move cursor down one window\n",
" \n",
"    E     (E)xpand active map                M     display (M)inimap format\n",
"    F     display (F)ragment format          S     display (S)equential format\n",
"    O     (O)utput tagged maps               T     (T)ag/untag map for processing\n",
"    U     (U)ntag every map                  A     Tag (A)ll maps\n",
"    I     (I)nsert current map as active     <Esc> exit review session\n",
"\0"
};

char *htext2[] = {                  /* help text for active expanded screen */
"    ->,,,<-  Scroll within window      F     display fragment sizes\n",
```

```
"   <Esc>  return to comparison screen\n",
"\0"
};

char *htext3[] = {                  /* help text for the process menu */
" \n",
"   <Enter>     output and return              <Esc>       skip output\n",
" \n",
"    Y          select current format          A           select (A)ll formats\n",
"    N          unselect current format        1           name files automatically\n",
"   ->,,,<-  move to next option            2         . name files manually\n",
"\0"
};

char *empty = { "\002\n" };                 /* empty line (don't reallocate this one) */
char last = { (char) NULL };                /* universal end of window marker */

#define LSPOS 17          /* first splice point for legend line */
#define LSINC 7           /* how many chars per field */

char *legend = {                    /* compressed map description line */
"Map3Deviation3                                                        3"
};

int auto_man = { 1 };               /* automatic/manual file naming (default: auto) */

#define PR_POS 24                   /* string position of print flags in process menu */
#define FI_POS 31                   /* string position of file flags in process menu */
#define UNPICKED '.'                /* character for unpicked option */
#define PICKED 'Y'                  /* character for picked option */
#define MTOP 3                      /* first line of process menu */
#define MBOT 8                      /* last line of process menu */
#define AML 10                      /* line containing the auto_man flag */
#define AMAPOS 24                   /* position of AUTO */
#define AMMPOS 30                   /* position of MAN */

#define SEQFORM MTOP
#define FRAGFORM MTOP+1
#define MINIFORM MTOP+2
#define SIZEFORM MTOP+3
#define LSTFORM MTOP+4
#define RMPFORM MTOP+5


char *menutext[] = {                /* text of process menu */
" \n",
"      What to Process:\n",
"                            Print  File\n",
"      Sequential Map          .      .\n",
"      Fragment Map            .      .\n",
"      Mini-Map                .      .\n",
"      Fragment Sizes          .      .\n",
"      .LST Format             .      .\n",
"      .RMP Format             _      .\n",
" \n",
"      File naming:          AUTO   man\n",
"\0"
};

#define SCALE 72                    /* number of columns in which to scale the pseudo-graphic map */
#define DIVISIONS 10.0              /* maximum number of divisions on the scaled map */
#define SCALEFACTOR 1000.0          /* units on scale are kilobases */

SIZE setms();             /* set the end position for each digest */
char *malloc();           /* memory allocator */

int build_big(a,b,c,d)              /* build a big window at 'a' from windows 'b','c','d' */
char *a[],*b[],*c[],*d[];           /* assume that no allocation or collection takes place at 'a' */
{
        int i,j;
        char time[80];

        i=0;


        sprintf(time,"Running time: %2d:%02d:%02d,   maps generated: %ld\n",hours,minutes,seconds,n_maps);
        attach(a,&i,time);
        a[i++] = empty;

        for(j=0; *b[j]; j++) a[i++] = b[j];
        a[i++] = empty;
       a[i++] = empty;
       for(j=0; *c[j]; j++) a[i++] = c[j];
       a[i++] = empty;
```

```
        a[i++] = empty;
        for(j=0; *d[j]; j++) a[i++] = d[j];

        a[i++] = &last;
        return(i);
}

void make_wn(m)             /* write character counts into the first byte of each string */
char *m[];
{
        int i;

        for( i=0; *m[i]; i++ )
                m[i][0] = (char) strlen(m[i]);
}

int dup_wn(m,n)             /* copy window contents from 'm' to 'n' (assumes destination is large enough) */
char *m[],*n[];             /* returns number of lines copied */
{
        int i,j;
        for( i=j=0; *m[i]; i++ ) attach(n,&j,&m[i][1]);
        attach(n,&j,&last);      /* create the end of window mark */
        return(j);
}

int count_line(m)           /* counts the number of lines in window 'm' */
char *m[];
{
        int i;

        for(i=0; *m[i]; i++ );
        return(i+1);
}

void file_wn(f,m)                   /* write window contents m[] to stream 'f' */
FILE *f;
char *m[];
{
        int i;

        putc( '\n', f );
        for(i=0; *m[i]; i++) fputs( &m[i][1], f );
        putc( '\n', f );
}

void attach(m,mlines,lout)          /* allocate memory and copy string in window format */
char *m[], *lout;
int *mlines;
{
        int ml;
        char *p;

        ml = *mlines;

        if( m[ml] && *m[ml] ) free( m[ml] );

        if( *lout ) {
                if( (m[ml] = malloc(strlen(lout)+2)) != NULL ) {
                        p = m[ml++];
                        *p++ = (char) (strlen(lout)+1);
                        strcpy(p,lout);
                }
        }
        else m[ml++] = lout;

        *mlines = ml;

}

void label(sd,m,pos,c)      /* write text on a sequential map vertically */
char *sd,*m[];              /* this assumes the window text has been allocated by blankseq() */
int pos;
char c;
{
        int i;
        boolean moved;

        if( pos > SMEND ) return;

        moved = FALSE;
        while( m[CUTLINE-1][pos] != ' ' ) {      /* position is already occupied */
                if( m[CUTLINE-1][pos] == '\n' ) return;         /* no place left to put label */
```

```
		pos++;
		moved=TRUE;
	}

	for( i = max((CUTLINE - strlen(sd)), 0); i < CUTLINE; i++ ) {
		if( *sd == NULL ) break;
		m[i][pos] = *sd++;
	}
	if( moved ) {
		if( m[CUTLINE][pos] == '-' ) m[CUTLINE][pos] = '/';
	}
	else m[CUTLINE][pos] = c;
}

void multi_label(this,m,pos,site)	/* write more than one label on map at same place */
int this, pos, *site;
char *m[];
{
	int i,j;

	if( view != this ) {	/* must go to disk */
		view = this;
		free_heap();
		get_map(view);
	}

	for( j = (int) (m[CUTLINE][pos] - '1'), i = *site; j >= 0; j--,i++ ) {
		label(sname[what_next[i]->s_digest],m,pos,'+');
	}

	*site = i;
}

int blankseq(this,m)	/* allocate buffer space for a sequential map and attach to 'm' */
int this;
char *m[];
{
	int i,pos;
	char line[SCREENWIDTH+3];

	for( pos = i = 0; i < CUTLINE; i++ )
		attach(m,&pos,"                                                            \n");
	sprintf(line,"%2d %s",this+1,&maps[this][XFERPOS]);
	attach(m,&pos,line);
	attach(m,&pos,&last);
	return(pos);
}

int lc2seq(this,m)	/* label a linear sequential map */
int this;
char *m[];
{
	int pos,rv,i;

	i=nsd;		/* heap index for current site */

	rv = blankseq(this,m);
	label("LEND",m,SMSTART,'|');
	label("REND",m,SMEND,'|');
	for( pos = SMSTART+1; pos <= SMEND; pos++ )
		if( isalpha(m[CUTLINE][pos]) ) {
			label(sname [m[CUTLINE][pos] - FDCHAR], m, pos,'+');
			i++;
		}
		else if( isdigit(m[CUTLINE][pos]) ) {	/* multiple cuts */
			multi_label(this,m,pos,&i);
		}

	for( pos = SMSTART+1; pos <= SMEND; pos++ )	/* rescan for obscured cuts */
		if( isdigit(m[CUTLINE][pos]) || isalpha(m[CUTLINE][pos]) ) m[CUTLINE][pos] = '/';


	return(rv);
}

int cc2seq(this,m)	/* label a circular sequential map */
int this;
char *m[];
{
	int pos,rv,i;

	i=START;	/* heap index for current site */
```

```
        rv = blankseq(this,m);
        for( pos = SMSTART; pos <= SMEND; pos++ )
                if( isalpha(m[CUTLINE][pos]) ) {
                        label(sname [m[CUTLINE][pos] - FDCHAR], m, pos,'+');
                        i++;
                }
                else if( isdigit(m[CUTLINE][pos]) ) {   /* multiple cuts */
                        --i;
                        multi_label(this,m,pos,&i);
                        ++i;
                }

        for( pos = SMSTART; pos <= SMEND; pos++ )       /* rescan for obscured cuts */
                if( isdigit(m[CUTLINE][pos]) || isalpha(m[CUTLINE][pos]) ) m[CUTLINE][pos] = '/';

        return(rv);
}

int cmp2seq(this,m)     /* construct and label a sequential map */
int this;
char *m[];
{
        if( linear ) return( lc2seq(this,m) );
        return( cc2seq(this,m) );
}

int draw_scale(n,m)     /* print a scaled pseudo-graphic map */
int n;
char *m[];
{
        if( linear ) return(d_l_scale(n,m));
        return(d_c_scale(n,m));
}


static char smap[SCALE+10], lout[SCREENWIDTH+10];

int d_l_scale(n,m)      /* print a linear map in scaled pseudo-graphic form */
int n;
char *m[];
{
        int sd, h;
        float units, tick, iunits, hunits;
        int mlines;


        mlines = 0;
        for( sd = START; sd <= nsd; sd++ ) {                    /* scan singles */
                dup(smap,'-',SCALE);                            /* clear the map buffer */
                for( h = nsd; h < heap_top; h++ ) {             /* scan the map */
                        if( what_next[h]->o_digest == sd ) {    /* the digest cuts here */
                                smap [(int) ( ((double) SCALE * vector [h-nsd+1]) / vector [n-1] )] = '+';     /* show a cut */
                        }
                }
                sprintf(lout,"%4s |%s|\n", sname [sd], smap);
                attach(m,&mlines,lout);
        }

        dup(smap,'-',SCALE);

        for( units = 100.0; vector [n-1] / units > DIVISIONS; units *= 10.0 );
        iunits =  (double) SCALE * units / vector [n-1];
        for( tick = iunits; (int) tick < SCALE; tick += iunits) smap [(int) tick] = '^';

        sprintf(lout,"scale|%s|\n", smap);
        attach(m,&mlines,lout);

        dup(smap,' ',SCALE);

        for( hunits = iunits, tick = units; (int) hunits < SCALE; hunits += iunits ) {
                center( smap, (int) hunits, tick, SCALEFACTOR, 5 );
                tick += units;
        }
        sprintf(lout," kb  |%s|\n", smap);
        attach(m,&mlines,lout);

        dup(smap,'-',SCALE);
        center( smap, SCALE>>1, vector [n-1], 1.0, 15 );
        sprintf(lout,"size |%s|\n", smap);
        attach(m,&mlines,lout);
        attach(m,&mlines,&last);
        return(mlines);
}
```

```
int d_c_scale(n,m)          /* print a circular map in scaled pseudo-graphic form */
int n;
char *m[];
{
        int sd, h, stop, i, q;
        float units, tick, iunits, hunits;
        int ss[MAXSIN],ms[MAXMUL];
        char mark;
        float maplen;
        int mlines;


        mlines = 0;
        setms(ss,ms,&stop);                /* find sites involved in overlap and compute total length */
        maplen = vector[n] + vector[stop+1];     /* map extends more than once around circle */


        q = SCALE - 2;

        for( sd = START; sd <= nsd; sd++ ) {                      /* scan singles */
                dup(smap,'-',SCALE);                              /* clear the map buffer */
                i = EMPTY;
                if( what_next[heap_top]->s_digest == sd ) {       /* this digest starts map */
                        I = START;
                        smap[i] = '|';
                }

                for( h = START; h <= heap_top; h++ ) {            /* scan the map */
                        if( what_next[h]->s_digest == sd ) {      /* the digest cuts here */
                                If( i < START ) {                 /* first site from this digest */
                                        mark = '|';
                                        i = (int) ( ((double) SCALE * vector [h+1]) / maplen );
                                        dup(smap,'.',i);
                                }
                                else {
                                        mark = '+';
                                        i = (int) ( ((double) SCALE * vector [h+1]) / maplen );
                                }
                                smap [i] = mark;        /* show a cut */
                        }
                }

                for( h = START; h <= stop; h++ ) {                /* scan the map overlap */
                        if( what_next[heap_top]->s_digest == sd ) {      /* end of map */
                                I = (int) ( ((double) SCALE * vector [n]) / maplen );

                                smap [i] = '|';
                                dup( &smap [i+1], '.', q - i + 1 );
                                break;
                        }

                        if( what_next[h]->s_digest == sd ) {      /* the digest cuts here */
                                If( h +1 == ss[sd] ) {            /* last site from this digest */
                                        mark = '|';
                                        if( (i = (int) ( ((double) SCALE * (vector [h+1] + vector[n])) / maplen )) >= SCALE ) i = SCALE-1;
                                        dup( &smap[i+1],'.',q - i + 1 );
                                        smap[i] = mark;
                                        break;
                                }
                                else {
                                        mark = '+';
                                        i = (int) ( ((double) SCALE * (vector [h+1] + vector[n])) / maplen );
                                }
                                smap [i] = mark;        /* show a cut */
                        }
                }
                smap [SCALE] = NULL;
                sprintf(lout,"%4s %s\n", sname [sd], smap);
                attach(m,&mlines,lout);
        }

        dup(smap,'-',q);

        for( units = 100.0; maplen / units > DIVISIONS; units *= 10.0 );
        iunits =  (double) q * units / maplen;
        for( tick = iunits; (int) tick < q; tick += iunits) smap [(int) tick] = '^';

        sprintf(lout,"scale|%s|\n", smap);
        attach(m,&mlines,lout);

        dup(smap,' ',q);
```

```
        for( hunits = iunits, tick = units; (int) hunits < q; hunits += iunits ) {
                center( smap, (int) hunits, tick, SCALEFACTOR, 5 );
                tick += units;
        }
        sprintf(lout," kb  |%s|\n", smap);
        attach(m,&mlines,lout);

        i = (int) ( ((double) SCALE * vector [n]) / maplen ) - 1;
        dup(smap,'-',i);
        center( smap, i>>1, vector [n], 1.0, 15 );
        sprintf(lout,"size |%s|\n", smap);
        attach(m,&mlines,lout);

        dup(&smap[i-1],'-',q-i-1);
        dup(smap,' ',i-2);
        smap[i-2] = '|';
        cpnum( smap, maplen - vector[n] );
        sprintf(lout,"overlap %s|\n", smap);
        attach(m,&mlines,lout);

        attach(m,&mlines,&last);
        return(mlines);
}

void lnumsprintf(f,wid,num,fill)                /* do sprintf() with left fill (Lattice doesn't) */
char *f;
int wid;
long num;
char fill;
{
        int size,i;
        char form[50],fo[50];

        size = digits(num);                             /* how many digits in 'num' */
        for( i=0; wid > size; wid--,i++) fo[i]=fill;    /* put in the left fill */
        fo[i] = NULL;
        sprintf(form,"%%%dld",wid);                     /* create the format string */
        strcat(fo,form);
        sprintf(f,fo,num);                              /* put in the number */
}

int draw_map(m)  /* display the map in a window */
char *m[];
{
        if( linear ) return(d_lmap(m));
        else return(d_cmap(m));
}

int d_lmap(m)           /* draw a linear molecule map vertically */
char *m[];
{
        int i,j;
        int sp[MAXSIN],mp[MAXMUL];
        char lout[256],l2[40];
        int mlines;

        mlines = 0;
        strcpy(lout,"------");
        for( i = START; i <= nsd; i++ ) {               /* scan singles */
                strcat(lout,"---------");
        }
        strcat(lout,"---");
        for( i = START; i <= nmd; i++ ) {               /* scan multiples */
                strcat(lout,"-------------");
        }
        strcat(lout,"\n");
        attach(m,&mlines,lout);

        strcpy(lout," map ");
        for( i = START; i <= nsd; i++ ) {               /* scan singles */
                sprintf(l2,"%6s  ",sname[i]);
                strcat(lout,l2);
        }
        strcat(lout," ||");
        for( i = START; i <= nmd; i++ ) {               /* scan multiples */
                sprintf(l2," %9s  ",mname[i]);
                strcat(lout,l2);
        }
        strcat(lout,"\n");
        attach(m,&mlines,lout);
```

```
	strcpy(lout,"------");			/* scan singles */
	for( i = START; i <= nsd; i++ ) {
		strcat(lout,"----------");
		sp[i] = EMPTY;
	}
	strcat(lout,"---");				/* scan multiples */
	for( i = START; i <= nmd; i++ ) {
		strcat(lout,"-------------");
		mp[i] = EMPTY;
	}
	strcat(lout,"\n");
	attach(m,&mlines,lout);

	strcpy(lout," end ");
	for(i = START; i <= nsd; i++) {
		strcat(lout," ________");
	}
	strcat(lout," ||");
	for(i = START; i <= nmd; i++) {		/* print the left end */
		strcat(lout," ____________");
	}
	strcat(lout,"\n");
	attach(m,&mlines,lout);

	for(j = nsd; j <= heap_top; j++) {		/* print fragment data */
		if(j == heap_top) strcpy(lout," end ");
		else {
			sprintf(l2,"%4s ",sname[what_next[j]->s_digest]);
			strcpy(lout,l2);
		}
		for( i = START; i <= nsd; i++ ) {		/* scan singles */
			if( ((j == heap_top) || (what_next[j]->s_digest == i)) && (++sp[i] <= sd_end[i].index) ) {		/* this digest cuts here */
				strcat(lout," ");
				lnumsprintf(l2,7,singles[i][sd_map[i][sp[i]]].frag,'_');
				strcat(lout,l2);
				if(s_dup[i][sd_map[i][sp[i]]]) strcat(lout,"*");
				else strcat(lout,"_");
			}
			else strcat(lout,"         ");
		}
		strcat(lout," ||");
		for( i = START; i <= nmd; i++ ) {		/* scan multiples */
			if( ((j == heap_top) || (composition[i][what_next[j]->s_digest])) && (++mp[i] <= md_end[i]) ) {
				strcat(lout," ");
				lnumsprintf(l2,10,multiples[i][md_map[i][mp[i]]].frag,'_');
				strcat(lout,l2);
				if(m_dup[i][md_map[i][mp[i]]]) strcat(lout,"*");
				else strcat(lout,"_");
			}
			else strcat(lout,"            ");
		}
		strcat(lout,"\n");
		attach(m,&mlines,lout);
	}

	strcpy(lout,"------");			/* scan singles */
	for( i = START; i <= nsd; i++ ) {
		strcat(lout,"----------");
	}
	strcat(lout,"---");				/* scan multiples */
	for( i = START; i <= nmd; i++ ) {
		strcat(lout,"-------------");
	}
	strcat(lout,"\n");
	attach(m,&mlines,lout);

	attach(m,&mlines,&last);
	return(mlines);
}

int d_cmap(m)		/* print a circular molecule map vertically in unwrapped form...only works for complete maps */
char *m[];
{
	heap *look();
	int i,j,stop;
	int sp[MAXSIN],mp[MAXMUL];
	int ss[MAXSIN],ms[MAXMUL];
```

```
mlines = 0;
for( i = START; i <= nsd; i++ ) {                /* clear map markers for singles */
        ss[i] = sp[i] = EMPTY;
}
ss[look()->s_digest] = START;

for( i = START; i <= nmd; i++ ) {                /* clear map markers for multiples */
        ms[i] = mp[i] = EMPTY;
        if( composition[i][look()->s_digest] ) ms[i]= START;
}

for( stop = START; stop <= heap_top; stop++ ) {          /* scan heap for end of map */
        for( i = START; i <= nmd; i++ )
                if( composition [i] [what_next[stop]->s_digest] )        /* multiple has a site here */
                        if( ms [i] == EMPTY ) ms [i] = stop+1;           /* this is the start/end */

        if( ss [what_next[stop]->s_digest] == EMPTY )    /* single digest starts/ends here */
                ss [what_next[stop]->s_digest] = stop+1;

        if( allset(ss,nsd) && allset(ms,nmd) ) break;    /* found all the starts/ends...'stop' is set to last */
}


strcpy(lout,"------");
for( i = START; i <= nsd; i++ ) {                /* scan singles */
        strcat(lout,"----------");
}
strcat(lout,"---");
for( i = START; i <= nmd; i++ ) {                /* scan multiples */
        strcat(lout,"-------------");
}
strcat(lout,"\n");
attach(m,&mlines,lout);

strcpy(lout," map ");
for( i = START; i <= nsd; i++ ) {                /* scan singles */
        sprintf(l2,"%6s   ",sname[i]);
        strcat(lout,l2);
}
strcat(lout," ||");
for( i = START; i <= nmd; i++ ) {                /* scan multiples */
        sprintf(l2," %9s  ",mname[i]);
        strcat(lout,l2);
}
strcat(lout,"\n");
attach(m,&mlines,lout);

strcpy(lout,"------");
for( i = START; i <= nsd; i++ ) {                /* scan singles */
        strcat(lout,"----------");
        sp[i] = EMPTY;
}
strcat(lout,"---");
for( i = START; i <= nmd; i++ ) {                /* scan multiples */
        strcat(lout,"-------------");
        mp[i] = EMPTY;
}
strcat(lout,"\n");
attach(m,&mlines,lout);

sprintf(lout,"%4s ",sname[look()->s_digest]);
for(i = START; i <= nsd; i++) {
        if( ss[i] == START ) strcat(lout," _________");
        else strcat(lout,"    .    ");
}
strcat(lout," ||");
for(i = START; i <= nmd; i++) {                  /* print the left end...first site is top of heap */
        if( ms[i] == START ) strcat(lout," ____________");
        else strcat(lout,"     ..     ");
}
strcat(lout,"\n");
attach(m,&mlines,lout);


for(j = START; j <= heap_top; j++) {                     /* print fragment data, first map cycle */
        sprintf(lout,"%4s ",sname[what_next[j]->s_digest]);
        for( i = START; i <= nsd; i++ ) {                /* scan singles */
                if( ss[i] == j+1 ) strcat(lout," ________");
                else if( ss[i] > j+1 ) strcat(lout,"    .    ");
                else if( (what next[j]->s_digest == i) && (++sp[i] <= sd_end[i].index) ) {          /* this digest cuts here */
```

```
                        strcat(lout," ");
                        lnumsprintf(12,7,singles[i][sd_map[i][sp[i]]].frag,'_');
                        strcat(lout,l2);
                        if(s_dup[i][sd_map[i][sp[i]]]) strcat(lout,"*");
                        else strcat(lout,"_");
                }
                else strcat(lout,"          ");
        }
        strcat(lout," ||");
        for( i = START; i <= nmd; i++ ) {                       /* scan multiples */
                if( ms[i] == j+1 ) strcat(lout," ___________");
                else if( ms[i] > j+1 ) strcat(lout,"      ..      ");
                else if( (composition[i][what_next[j]->s_digest]) && (++mp[i] <= md_end[i]) ) {
                        strcat(lout," ");

                                lnumsprintf(12,10,multiples[i][md_map[i][mp[i]]].frag,'_');
                                strcat(lout,l2);
                                if(m_dup[i][md_map[i][mp[i]]]) strcat(lout,"*");
                                else strcat(lout,"_");
                        }
                        else strcat(lout,"             ");
                }
                strcat(lout,"\n");
                attach(m,&mlines,lout);
        }

        for(j = START; j <= stop; j++) {                        /* print fragment data, overlap map cycle */
                sprintf(lout,"%4s ",sname[what_next[j]->s_digest]);
                for( i = START; i <= nsd; i++ ) {               /* scan singles */
                        if( j >= ss[i] ) strcat(lout,"    .     ");
                        else if( (what_next[j]->s_digest == i) && (++sp[i] <= sd_end[i].index) ) {              /* this digest cuts here */
                                strcat(lout," ");
                                lnumsprintf(12,7,singles[i][sd_map[i][sp[i]]].frag,'_');
                                strcat(lout,l2);
                                if(s_dup[i][sd_map[i][sp[i]]]) strcat(lout,"*");
                                else strcat(lout,"_");
                        }
                        else strcat(lout,"          ");
                }
                strcat(lout," ||");
                for( i = START; i <= nmd; i++ ) {               /* scan multiples */
                        if( j >= ms[i] ) strcat(lout,"      ..      ");
                        else if( (composition[i][what_next[j]->s_digest]) && (++mp[i] <= md_end[i]) ) {
                                strcat(lout," ");
                                lnumsprintf(12,10,multiples[i][md_map[i][mp[i]]].frag,'_');
                                strcat(lout,l2);
                                if(m_dup[i][md_map[i][mp[i]]]) strcat(lout,"*");
                                else strcat(lout,"_");
                        }
                        else strcat(lout,"             ");
                }
                strcat(lout,"\n");
                attach(m,&mlines,lout);
        }


        strcpy(lout,"-----");
        for( i = START; i <= nsd; i++ ) {                       /* scan singles */
                strcat(lout,"----------");
        }
        strcat(lout,"---");
        for( i = START; i <= nmd; i++ ) {                       /* scan multiples */
                strcat(lout,"-------------");
        }
        strcat(lout,"\n");
        attach(m,&mlines,lout);

        attach(m,&mlines,&last);
        return(mlines);
}

void act_update(cursor,tj,cwin)  /* refresh the expanded active screen for current window */
int cursor,tj,cwin;
{

        switch( cwin ) {
                case ACTEX:
                        if( !cursor || (k_vmap(tj, keyrec.kq, &wn[cwin]) != 0) ) {
                                v_mem( &actall[fr[ACTEX].ib],&wn[ACTEX]);
                                title( aextitle, 0, TITLEA, act_line);
```

```
				}
				break;
			case HELP:
				if( !cursor || (k_vmap(tj, keyrec.kq, &wn[cwin]) != 0) )
					v_mem(&helptext[fr[HELP].ib],&wn[HELP]);
				break;
		}
}

int act_screen()		/* do the expanded screen for active map */
{
	int tj,cwin,style;

	fr[HELP].ib = fr[HELP].wfr = fr[HELP].wfc = wn[HELP].r = wn[HELP].c = 0;
	fr[HELP].ln_q = dup_wn(htext2,helptext);		/* move new help text */
	wn[HELP].rb = 23;
	set_wn(&wn[HELP]);
	act_update(ALWAYS,tj,HELP);

	wn[TITLEH].rb = wn[TITLEH].re = 22;
	set_wn(&wn[TITLEH]);
	v_st(helptitle,&wn[TITLEH]);

	fr[ACTEX].ib = fr[ACTEX].wfr = fr[ACTEX].wfc = wn[ACTEX].r = wn[ACTEX].c = 0;
	fr[ACTEX].ln_q = build_big( (char *) actall, (char *) actf, (char *) acts, (char *) actm );
	fr[ACTEX].c_q = MAXWINWID;
	set_wn(&wn[ACTEX]);
	act_update(ALWAYS,tj,ACTEX);

	cwin = ACTEX;
	for(;;) {
		if( (tj = ki_cum(&keyrec)) < 0 ) {	/* extended keys */
			tj = -tj;		/* negate */
			act_update(MOVE,tj,cwin);
		}
		else {
			switch( toupper(tj) ) {		/* interpret keystroke commands */
				case '\033':		/* return */
					wn[HELP].rb = 24;
					wn[TITLEH].rb = wn[TITLEH].re = 23;
					set_wn(&wn[TITLEH]);
					v_st(helptitle,&wn[TITLEH]);
					return(1);
				case 6:			/* catch ^F also */
				case 'F':	/* scroll the fragment sizes by on the full screen */
					set_wn(&wn[FULLSCREEN]);
					cl_wn(&wn[FULLSCREEN]);

					dev_comp(stdout,nsites,VERBOSE,1);	/* scroll with pause */

					unset_wn(&wn[FULLSCREEN]);

					set_wn(&wn[TITLEH]);
					v_st(helptitle,&wn[TITLEH]);

					set_wn(&wn[HELP]);
					act_update(ALWAYS,tj,HELP);

					set_wn(&wn[ACTEX]);
					act_update(ALWAYS,tj,ACTEX);
					break;
			}
		}
	}
}

tag(line)		/* tag/untag the map in 'line' */
int line;
{
	if( maps[--line][TAGPOS] == TAG ) maps[line][TAGPOS] = UNTAG;
	else maps[line][TAGPOS] = TAG;
}

fresh(win,style,m)		/* update FREC and window cursor for new contents */
int win,style;
char **m[];
{
	fr[win].ib = fr[win].wfr = fr[win].wfc = wn[win].r = wn[win].c = 0;
	fr[win].c_q = width[style];
	fr[win].lbp = *m[style];
}
```

```
title( ti, style, win, line)
char *ti[];
int style,win,line;
{
        char s[SCREENWIDTH];

        sprintf(s,ti[style],line);
        wn[win].r = wn[win].c = 0;      /* replace cursor at beginning of window */
        v_st(s,&wn[win]);
}

cur2sel(win)     /* move cursor to select_line position in window */
WINDOW *win;
{
        if( (win->r = select_line - win->frp->wfr - 1) < 0 ) win->r = 0;
}

new_view(style)  /* show new map in comparison window */
int style;
{
        if( (select_line = wn[LIST].r + wn[LIST].frp->wfr + 1) < 1 )
                select_line = 1;

        if(style != SEQMAP) {    /* do this depending on what format is being viewed */
                if( view != select_line-1 ) {
                        view = select_line-1;
                        free_heap();
                        get_map(view);
                }
        }

        fresh( COMP, style, &compptr );
        switch( style ) {
                case SEQMAP:
                        fr[COMP].ln_q = cmp2seq(select_line-1, compptr[style]);
                        break;
                case MINIMAP:
                        fr[COMP].ln_q = draw_scale(nsites, compptr[style]);
                        break;
                case FRAGMAP:
                        fr[COMP].ln_q = draw_map( compptr[style] );
                        break;
        }

        set_wn(&wn[COMP]);
        v_mem( compptr[style],&wn[COMP]);
        title( ctitle, style, TITLEC, select_line);
}

void update(cursor,tj,cwin,style)       /* refresh the screen for current window */
int cursor,tj,cwin,style;
{

        switch( cwin ) {
                case ACTIVE:
                        if( !cursor || (k_vmap(tj, keyrec.kq, &wn[cwin]) != 0) ) {
                                v_mem( actptr[style],&wn[ACTIVE]);
                                title( atitle, style, TITLEA, act_line);
                        }
                        break;
                case COMP:
                        if( !cursor || (k_vmap(tj, keyrec.kq, &wn[cwin]) != 0) ) {
                                v_mem( compptr[style],&wn[COMP]);
                                title( ctitle, style, TITLEC, select_line);
                        }
                        break;
                case LIST:
                        k_vcom(tj, keyrec.kq, &wn[cwin]);
                        new_view(style);
                        v_mem( &lineptr[fr[LIST].ib],&wn[LIST]);
                        break;
                case HELP:
                        if( !cursor || (k_vmap(tj, keyrec.kq, &wn[cwin]) != 0) )
                                v_mem(&helptext[fr[HELP].ib],&wn[HELP]);
                        break;
        }
}

int k_vmenu(tj,kq,wn)    /* process movement for output process menu */
int tj,kq;
WINDOW *wn;
{
```

```
        switch( tj ) {
                case K_UP:
                        pm_move(1,0);
                        return(1);
                case K_DN:
                        pm_move(-1,0);
                        return(1);
                case K_LEFT:
                        pm_move(0,1);
                        return(1);
                case K_RIGHT:
                        pm_move(0,-1);
                        return(1);
                default:
                        return(0);
        }
}
splice(d,s)     /* do strcpy() without NULL */
char *d,*s;
{
        while(*s) *d++ = *s++;
}

auto_sel()      /* show auto/man flag */
{
        if( auto_man ) {        /* auto */
                splice(&menutext[AML][AMAPOS],"AUTO");
                splice(&menutext[AML][AMMPOS],"man");
        }
        else {                  /* man */
                splice(&menutext[AML][AMAPOS],"auto");
                splice(&menutext[AML][AMMPOS],"MAN");
        }
}

pm_clear()      /* unselect all flags */
{
        int i;
        for( i=MTOP; i <= MBOT; i++ ) {
                menutext[i][FI_POS+1] = UNPICKED;
                if( i == MBOT ) break;
                menutext[i][PR_POS+1] = UNPICKED;
        }
        auto_man = 1;
        auto_sel();
}

pick()          /* select at current pos in process menu */
{
        menutext[wn[MENU].r][wn[MENU].c+1] = PICKED;
}

unpick()        /* unselect as above */
{
        menutext[wn[MENU].r][wn[MENU].c+1] = UNPICKED;
}

pm_move(ud,lr)  /* move cursor in MENU window ud (1->up,0->same,-1->down) */
int ud,lr;      /* lr (1->left,0->same,-1->right) */
{
        if(lr) {
                if( wn[MENU].r != MBOT ) {
                        if( wn[MENU].c == FI_POS ) wn[MENU].c = PR_POS;
                        else wn[MENU].c = FI_POS;
                }
        }
        if(ud) {
                if( ud < 0 ) {  /* down */
                        if( wn[MENU].c == PR_POS ) {
                                if( wn[MENU].r == MBOT-1 ) wn[MENU].r = MTOP;
                                else wn[MENU].r++;
                        }
                        else {
                                if( wn[MENU].r == MBOT ) wn[MENU].r = MTOP;
                                else wn[MENU].r++;
                        }
                }
                else {          /* up */
                        if( wn[MENU].r == MTOP ) {
                                if( wn[MENU].c == PR_POS ) wn[MENU].r = MBOT-1;
                                else wn[MENU].r = MBOT;
```

```
                        }
                        else wn[MENU].r--;
                }
        }
        pl_csr(&wn[MENU]);
}

void pm_update(cursor,tj,cwin)    /* refresh the menu screen for current window */
int cursor,tj,cwin;
{

        switch( cwin ) {
                case MENU:
                        if( !cursor || (k_vmenu(tj, keyrec.kq, &wn[cwin]) != 0) )
                                v_mem( &menutext[fr[MENU].ib],&wn[MENU]);
                        break;
                case HELP:
                        if( !cursor || (k_vmap(tj, keyrec.kq, &wn[cwin]) != 0) )
                                v_mem(&helptext[fr[HELP].ib],&wn[HELP]);
                        break;
        }
}

int process()     /* do whatever the user wants with the tagged maps */
{
        int tj,cwin,i,j;


        wn[HELP].rb = 16;
        wn[TITLEH].rb = wn[TITLEH].re = 15;

        fr[HELP].ib = fr[HELP].wfr = fr[HELP].wfc = wn[HELP].r = wn[HELP].c = 0;
        fr[HELP].ln_q = dup_wn(htext3,helptext);          /* move new help text */
        set_wn(&wn[HELP]);
        v_mem(&helptext[fr[HELP].ib],&wn[HELP]);
        set_wn(&wn[TITLEH]);
        v_st(helptitle,&wn[TITLEH]);

        pm_update(ALWAYS,tj,HELP);

        pm_clear();
        fr[MENU].ib = fr[MENU].wfr = fr[MENU].wfc = 0;
        fr[MENU].ln_q = count_line( menutext );
        set_wn(&wn[MENU]);
        wn[MENU].r = MTOP;
        wn[MENU].c = PR_POS;
        pm_update(ALWAYS,tj,MENU);
        pl_csr(&wn[MENU]);

        set_wn(&wn[DIALOG]);
        v_fst("Select processing options using cursor keys and 'Y', then hit <Enter> to process.",&wn[DIALOG]);

        cwin = MENU;

        for(;;) {
                if( (tj = ki_cum(&keyrec)) < 0 ) {        /* extended keys */
                        tj = -tj;         /* negate */
                        pm_update(MOVE,tj,cwin);
                }
                else {
                        switch( toupper(tj) ) {          /* interpret keystroke commands */

                                case '\r':               /* process, then return */
                                        do_process();

                                case '\033':
                                        wn[HELP].rb = 24;
                                        wn[TITLEH].rb=wn[TITLEH].re = 23;
                                        return(1);       /* skip processing */

                                case 'Y':                /* select */
                                        if( cwin == MENU ) {
                                                pick();
                                                pm_update(ALWAYS,tj,cwin);
                                        }
                                        break;
                                case 'N':                /* unselect */
                                        if( cwin == MENU ) {
                                                unpick();
                                                pm_update(ALWAYS,tj,cwin);

                                        }
                                        break;
```

```
                                case 'A':               /* pick all */
                                        if( cwin != MENU) break;
                                        i = wn[MENU].r;         /* save current row */
                                        for(j=0;j<MBOT-MTOP+1;j++) {
                                                pick();
                                                pm_move(-1,0);
                                        }
                                        wn[MENU].r = i;         /* restore row */
                                        pm_update(ALWAYS,tj,cwin);
                                        break;
                                case '1':               /* automatic naming */
                                        auto_man = 1;
                                        auto_sel();
                                        pm_update(ALWAYS,tj,MENU);
                                        if( cwin != MENU ) pm_update(ALWAYS,tj,cwin);
                                        break;
                                case '2':               /* manual naming */
                                        auto_man = 0;
                                        auto_sel();
                                        pm_update(ALWAYS,tj,MENU);
                                        if( cwin != MENU ) pm_update(ALWAYS,tj,cwin);
                                        break;
                        }
                }
        }
}

boolean any_options(flag)       /* returns TRUE if any options selected */
int flag;                       /* flag = 0 -> check printer column, 1 -> check file column */
{
        int i;

        if( flag ) flag = FI_POS+1;
        else flag = PR_POS+1;

        for(i=MTOP; i <= MBOT; i++) if( menutext[i][flag] == PICKED ) return(TRUE);

        return(FALSE);
}

wn_gets(s,prompt)       /* get string from dialog window into 's' */
char *s,*prompt;
{
        cl_wn(&wn[DIALOG]);
        v_fst(prompt,&wn[DIALOG]);
        pl_csr(&wn[DIALOG]);
        gets(s);
        v_fst("\n ",&wn[DIALOG]);
        pl_csr(&wn[DIALOG]);
}

extern char fofname[65];

do_process()    /* process tagged maps according to menutext flags */
{
        FILE *pr, *pfile, *lst, *rmp;
        int i, vsave;
        char s[SCREENWIDTH];
        char pfn[SCREENWIDTH];
        char lstfn[SCREENWIDTH];
        char rmpfn[SCREENWIDTH];

        if( !any_options(0) && !any_options(1) ) return;

        cl_wn(&wn[MENU]);

        set_wn(&wn[DIALOG]);

        pr = pfile = NULL;

        if( any_options(0)  && ((pr = fopen("PRN:","w")) == NULL) ) v_fst("\nCan't open the printer stream!\n",&wn[DIALOG]);

        if( any_options(1) ) {
                if( (menutext [SEQFORM][FI_POS+1] == PICKED) ||
                        (menutext [FRAGFORM][FI_POS+1] == PICKED) ||
                        (menutext [MINIFORM][FI_POS+1] == PICKED) ||
                        (menutext [SIZEFORM][FI_POS+1] == PICKED) ) {   /* a stream file option is picked */
                        if( auto_man ) strcpy(pfn,"rmap.out");
                        else wn_gets(pfn," What file for map output?\n ");
                        if( (pfile = fopen(pfn,"w")) == NULL ) v_fst("\nCan't open map output file!\n",&wn[DIALOG]);
                }
        }
```

```
vsave = view;   /* save current archive map */

for(i=START; i <= max_score; i++) {      /* scan maps */
        if( maps[i][TAGPOS] == TAG ) {  /* this one is tagged */
                sprintf(s,"\n        Processing map %d",i+1);
                v_fst(s,&wn[MENU]);
                pI_csr(&wn[MENU]);

                view = i;
                free_heap();
                get_map(view);            /* load the map */

                if( any_options(0) ) {
                        fprintf(pr,"--------------------------------------------------------------------\n");
                        fprintf(pr," Map: %d    Project: %s    ",view+1,fofname);
                        date(pr);
                        fprintf(pr,"\n--------------------------------------------------------------------\n");
                }

                if( menutext [SEQFORM][PR_POS+1] == PICKED ) {
                        fprintf(pr,"\nSequential map:\n");
                        cmp2seq(i,compptr[SEQMAP]);
                        file_wn(pr,compptr[SEQMAP]);
                }

                if( menutext [FRAGFORM][PR_POS+1] == PICKED ) {
                        fprintf(pr,"\nFragment map:\n");
                        map_print(pr);
                }

                if( menutext [MINIFORM][PR_POS+1] == PICKED ) {
                        fprintf(pr,"\nMini-map:\n");
                        scale_map(pr,nsites);
                }

                if( menutext [SIZEFORM][PR_POS+1] == PICKED ) {
                        dev_comp(pr,nsites,VERBOSE,0);
                }

                if( menutext [LSTFORM][PR_POS+1] == PICKED ) {
                        fprintf(pr,"\nSite positions:\n");
                        fileout(pr);
                }


                if( pfile ) {
                        fprintf(pfile,"--------------------------------------------------------------------\n");
                        fprintf(pfile," Map: %d    Project: %s    ",view+1,fofname);
                        date(pfile);
                        fprintf(pfile,"\n--------------------------------------------------------------------\n");
                                                        {
                        if( menutext [SEQFORM][FI_POS+1] == PICKED ) {
                                fprintf(pfile,"\nSequential map:\n");
                                cmp2seq(i,compptr[SEQMAP]);
                                file_wn(pfile,compptr[SEQMAP]);
                        }

                        if( menutext [FRAGFORM][FI_POS+1] == PICKED ) {
                                fprintf(pfile,"\nFragment map:\n");
                                map_print(pfile);
                        }

                        if( menutext [MINIFORM][FI_POS+1] == PICKED ) {
                                fprintf(pfile,"\nMini-map:\n");
                                scale_map(pfile,nsites);
                        }

                        if( menutext [SIZEFORM][FI_POS+1] == PICKED ) {
                                dev_comp(pfile,nsites,VERBOSE,0);
                        }
                }
                if( menutext [LSTFORM][FI_POS+1] == PICKED ) {          /* .LST file output */

                        if( auto_man ) {         /* auto */
                                sprintf(lstfn,"rmap%d.lst",view+1);
                        }
                        else {
                                sprintf(s," What .LST file name for map %d\n ",view+1);
                                wn_gets(lstfn,s);
                                new_ext(lstfn,"lst");
                        }
```

```
                        if( (lst = fopen(lstfn,"w")) == NULL ) {
                                sprintf(s,"\nCan't open .LST file for map %d!\n",view+1);
                                v_fst(s,&wn[DIALOG]);
                        }
                        else {
                                fileout(lst);
                                putc(ENDMARK,lst);      /* logical EOF */
                                fclose(lst);
                        }
                }
                if( menutext [RMPFORM][FI_POS+1] == PICKED ) {          /* .LST file output */

                        if( auto_man ) {        /* auto */
                                sprintf(rmpfn,"rmap%d.rmp",view+1);
                        }
                        else {
                                sprintf(s," What .RMP file name for map %d\n ",view+1);
                                wn_gets(rmpfn,s);
                                new_ext(rmpfn,"rmp");
                        }

                        if( (rmp = fopen(rmpfn,"w")) == NULL ) {
                                sprintf(s,"\nCan't open .RMP file for map %d!\n",view+1);
                                v_fst(s,&wn[DIALOG]);
                        }
                        else {
                                rmpout(rmp);
                                putc(ENDMARK,rmp);      /* logical EOF */
                                fclose(rmp);
                        }
                }
            }
        }
        view = vsave;
        free_heap();
        get_map(view);
        cmp2seq(view, compptr[SEQMAP]);                 /* restore old window contents */

        if( pr ) fclose(pr);
        if( pfile ) {
                putc(ENDMARK,pfile);    /* logical EOF */
                fclose(pfile);
        }
}

int cm_up(cw)    /* move up one window on comparison screen */
int cw;
{
        if( --cw < ACTIVE ) cw = LIST;
        return(cw);
}

int cm_down(cw)  /* move down one window on comparison screen */
int cw;
{
        if( ++cw > LIST ) cw = ACTIVE;
        return(cw);
}

void make_legend()        /* construct the legend line */
{
        int i,j;
        char s[20];

        for(j=LSPOS,i=START; i<=nsd; i++, j += LSINC ) {
                sprintf(s,"%4s=%c", sname[i], (char) (i+FDCHAR) );
                splice(&legend[j],s);
        }
}

int help_up(cwin,style)  /* expand the help window for entry screen so you can see it all at once */
int cwin,style;
{
        int rv;

        wn[HELP].rb=16;
        wn[TITLEH].rb = wn[TITLEH].re = 15;
```

```
        set_wn(&wn[HELP]);
        v_mem(&helptext[fr[HELP].ib],&wn[HELP]);
        set_wn(&wn[TITLEH]);
        v_st(helptitle,&wn[TITLEH]);

        rv = ki_cum(&keyrec);

        wn[HELP].rb=24;
        wn[TITLEH].rb = wn[TITLEH].re = 23;

        set_wn(&wn[HELP]);
        v_mem(&helptext[fr[HELP].ib],&wn[HELP]);
        set_wn(&wn[TITLEH]);
        v_st(helptitle,&wn[TITLEH]);

        set_wn(&wn[LIST]);
        curTsel(&wn[LIST]);
        if(cwin != LIST) update(ALWAYS,0,LIST,style);

        update(ALWAYS,0,cwin,style);

        return(rv);
}

mapout()
{
        int tj, i, cwin, style, reuse;

        scr_setup();
        scr_cblk();             /* use pcio.lib functions to set block cursor */

        cls();                          /*clear screen */

        make_wn(htext1);                /* initialize static windows */
        make_wn(htext2);
        make_wn(htext3);
        make_wn(menutext);

        fr[LIST].lbp = (char *) &lineptr[0];    /* set up the map list window */
        for( i=0; i <= max_score; i++ ) lineptr[i] = (char *) &maps[i];
        lineptr[max_score+1] = (char *) &last;
        fr[LIST].ln_q = max_score+2;
        fr[LIST].ib = 0;

        /* best map is already resident from review() */
        /* put various formats in windows */

        draw_scale(nsites, actptr[MINIMAP]);    /* write the mini-map */

        draw_map( actptr[FRAGMAP]);             /* write the fragment map */
        fr[ACTIVE].lbp = (char *) acts;
        fr[ACTIVE].ln_q = cmp2seq(view, actptr[SEQMAP]);        /* write the sequential map */
        fr[ACTIVE].ib = 0;

        if( max_score > 0 ) {   /* there are other maps to compare */

                view++;                 /* look at the next best map in comparison window */
                free_heap();
                get_map(view);

                select_line = 2;
                wn[LIST].r = 1;
                fr[LIST].wfr = 0;

                fr[COMP].lbp = (char *) compptr[SEQMAP];
                fr[COMP].ln_q = cmp2seq(view, compptr[SEQMAP]);
                fr[COMP].ib = 0;
        }

        fr[HELP].lbp = (char *) helptext;               /* set up help window */
        fr[HELP].ln_q = dup_wn(htext1,helptext);
        fr[HELP].ib = 0;

        fr[TITLEH].lbp = helptitle;
        fr[TITLEH].ln_q = 1;
        fr[TITLEH].ib = 0;

/*  display entry screen */

        set_wn(&wn[ACTIVE]);
        v_mem(&acts[fr[ACTIVE].ib],&wn[ACTIVE]);
        set_wn(&wn[TITLEA]);
        title(atitle,SEQMAP,TITLEA,act_line);
```

```
set_wn(&wn[COMP]);
v_mem(&comps[fr[COMP].ib],&wn[COMP]);
set_wn(&wn[TITLEC]);
title(ctitle,SEQMAP,TITLEC,select_line);

set_wn(&wn[HELP]);
v_mem(&helptext[fr[HELP].ib],&wn[HELP]);
set_wn(&wn[TITLEH]);
v_st(helptitle,&wn[TITLEH]);

fr[LEGEND].lbp = legend;
fr[LEGEND].ln_q = 1;
fr[LEGEND].ib = 0;

set_wn(&wn[LEGEND]);
make_legend();
v_st(legend,&wn[LEGEND]);


if(set_wn(&wn[LIST]) == NULL)
        printf("\ndefinitions inconsistent for window 2");

cur2sel(&wn[LIST]);
v_mem(&lineptr[fr[LIST].ib],&wn[LIST]);                /*display maps              */


cwin = LIST;
style = SEQMAP;
reuse = FALSE;

for(;;) {                               /*Set up endless loop */

        if( !reuse ) tj = ki_cum(&keyrec);
        else reuse = FALSE;

        if( tj < 0 ) {  /* extended keys */

                tj = -tj;       /* negate */

                if( tj == K_PGUP ) {                    /* move up a window */
                        cwin = cm_up(cwin);
                        pl_csr(&wn[cwin]);
                }
                else if( tj == K_PGDN ) {               /* move down a window */
                        cwin = cm_down(cwin);
                        pl_csr(&wn[cwin]);
                }
                else if( tj == K_F1 ) {                         /* expand help */
                        if( (tj = help_up(cwin,style)) == -(K_F1) ) reuse = FALSE;
                        else reuse = TRUE;
                }
                else update(MOVE,tj,cwin,style);        /* update current window */

        }
        else {
                switch( toupper(tj) ) {         /* interpret keystroke commands */
                        case '\033':
                                cl_wn(&wn0);    /* clear screen */
                                return;
                        case 'E':               /* expand active screen */
                                if( !act_screen() ) {
                                        cl_wn(&wn0);
                                        return;
                                }
        f = fp = START;                         /* begin with first frag */
        while( (fp = next_m_group(d,fp)) > EMPTY ) {                    /* scan for groups of the same size */
                if( fp != f ) {                                                 /* more than one */
                        printf("\nFragments: ");
                        for( ++group_num, scan=f; scan <= fp; scan++ ) {        /* document the group */
                                m_dup [d][scan] = group_num;
                                printf("%d ",multiples [d] [scan].frag);
                        }
                        printf("are members of a duplication group in %s", mname [d] );
                        perms *= factorial( (fp - f) + (SIZE) 1 );
                }
                if( ++fp >= mmax [d] ) break;                           /* done with this digest */
                f = fp;
        }
}

return(perms);
}
```

```
/***************************************************************
 *                                                             *
 *                    Map Generator                            *
 *                                                             *
 ***************************************************************/

#define MAXMAP          20      /* maximum number of sites in any given map */
#define MAXDEPTH        50      /* maximum depth of the heap (same as max.
                                   number of multiple digest sites) */
#define MAXVIEW         50      /* maximum number of maps saved in archive file */

#define NAMELEN         30                      /* largest digest name */
#define MAXSIN          8                       /* maximum number of single digests */
#define MAXMUL          MAXSIN*2                /* maximum number of multiple digests
                                                   (N * 2 is a good approximation
                                                    for the largest number of multiple digests) */

#define EMPTY           -1      /* value of an empty heap pointer/map index */
#define USED            1       /* value of 'used' flag indicating already chosen */
#define FREE            0       /* value of 'used' flag indicating availability */
#define START           0       /* where to begin array index scans */
#define TOOBIG          1       /* possible return value from 'fits()' */
#define  FIT            0       /* ditto */
#define TOOSMALL        -1      /* ditto */

#define SIZE            long            /* type of fragment length values */
#define GIANT           2147483647L     /* largest positive value for (SIZE) type */
#define ZERO            0L              /* zero value for (SIZE) type */

#define NONE            0       /* synonymous with empty list */
#define  TRUE           1       /* logic true value */
#define  FALSE          0       /* logic false value */


#define END             1       /* bit flag for fragment on end attribute       (LINEAR ONLY) */
#define LEND            2       /* bit flag for fragment on left end attribute  (LINEAR ONLY) */
#define REND            4       /* bit flag for fragment on right end attribute         (LINEAR ONLY) */
#define ANYEND          7       /* combined attributes for above three flags */
#define SPECEND         3       /* either specific end */
#define NEW             8       /* bit attribute for multiple fragment not in single    (MULTIPLE ONLY) */
#define CUT             8       /* bit attribute for single fragment not in multiple    (SINGLE ONLY) */
#define CLUE            char    /* type of attribute flags */


#define BACKSPACE       8       /* ASCII backspace character */
#define FORWARD         '*'     /* character representing progress */
#define BACKUP          249     /* character representing failure */
#define SUCCESS         ']'     /* character representing map completion */
#define MAPSTART        '['     /* character representing map start */

#define MAPWIDTH 66
#define SCREENWIDTH 80

#define  boolean int            /* type of functions returning logical values */

#define void int                /* type of functions returning arbitrary values */

typedef struct endp {           /* endpoint range structure, used to store */
                                /* the size of a single digest map */

        SIZE            lo,hi;          /* limits on right map endpoint */
        int             index;          /* what position in single map this corresponds to */
}
        endpoint;

typedef struct hnode {

        int             s_digest;       /* which digest does this represent */
        endpoint        s_pos;          /* value of 'sd_end' at decision point */
        endpoint        s_last;                 /* value of 'last_end' at decision point */
        SIZE            s_ref;          /* map reference point (everything left of here is to be believed) */
        struct hnode    *others;        /* next list element */

}
        heap;                   /* decision list type name */

/* The heap is a place where upcoming decisions are stored. Every
 * time a growing point is selected (or more than one), the selection
 * is put onto the heap. This allows a simple method of recording
 * what to try prior to backtracking and when to backtrack. By recording
 * each growing point, a scan of the heap entry nodes will produce a map
 * containing all sites catalogued to the current step.
 */
```

```
VAR heap                    *what_next[MAXDEPTH];
VAR int                     heap_top = { EMPTY };

typedef struct dignode {         /* storage node for fragment digests */

        SIZE            frag;           /* measured fragment size (in bases) */
        SIZE            frag_error;     /* measurement error (in bases) */
        boolean                 used;           /* flag signalling whether this fragment */
                                        /* has already been chosen for a map */
        CLUE            flags;          /* fragment attributes used for heuristics */
}
        digest;
/* digest storage for singles */

VAR digest                  singles [MAXSIN] [MAXMAP];      /* single digests */
VAR int                     s_dup [MAXSIN] [MAXMAP];        /* fragment groups which look identical to the algorithm */
VAR CLUE                    s_endflag [MAXSIN];             /* place to put end clues for whole digest */
VAR char                    sname [MAXSIN] [NAMELEN];       /* their names */
VAR int                     sptr [MAXSIN];                  /* current fragment */
VAR int                     smax [MAXSIN];                  /* index of last fragment */
VAR int                     nsd = { NONE };                 /* number of single digests */

VAR int                     nsites;                         /* number of sites in the map */

/* digest storage for multiples */

VAR digest                  multiples [MAXMUL] [MAXMAP];    /* multiple digests */
VAR int                     m_dup [MAXMUL] [MAXMAP];        /* fragment groups which look identical to the algorithm */
VAR CLUE                    m_endflag [MAXMUL];             /* place to put end clues for whole digest */
VAR char                    mname [MAXMUL] [NAMELEN];       /* their names */
VAR int                     composition [MAXMUL] [MAXSIN];  /* which singles used to cut */
VAR int                     mptr [MAXMUL];                  /* current fragment */
VAR int                     mmax [MAXMUL];                  /* index of last fragment */
VAR int                     nmd = { NONE };                 /* number of multiple digests */

VAR int                     mfrags;                         /* number of multiple digest fragments */

VAR SIZE                    lo_factor;              /* error on fragments in % */
VAR SIZE                    hi_factor;

VAR SIZE                    ave_len = { 0L };       /* average length (circumference) of the total map */

VAR endpoint                scratch;                /* scratch-pad for endpoint refinement */

/* single digest maps */

VAR int                     sd_map [MAXSIN] [MAXMAP];       /* maps for all single digests */
VAR endpoint                sd_end [MAXSIN];                /* the endpoint ranges */
VAR endpoint                last_end [MAXSIN];              /* previous endpoints (one site back) */
VAR int                     sd_mdoff [MAXSIN];              /* the multiple digest containing the offset fragment for this single */
VAR int                     sd_mdfrag [MAXSIN];             /* the fragment in above digest which relates this single to first single */
VAR SIZE                    sd_offlen [MAXSIN];             /* length of digest offset */
VAR SIZE                    sd_offerr [MAXSIN];             /* error term for offset fragment */
VAR SIZE                    ref_point = { ZERO };   /* map position where error begins */

/* multiple digest maps */

VAR int                     md_map [MAXMUL] [MAXMAP];       /* maps for all multiple digests */
VAR int                     md_site [MAXMUL] [MAXMAP];      /* which single digest site cuts at right end of this fragment */
VAR int                     md_end [MAXMUL];                /* map index of end of current map */
VAR int                     md_off [MAXMUL];                /* multiple digest containing offset fragment */
VAR int                     md_frag [MAXMUL];               /* fragment from above digest which relates this digest to to first */
VAR SIZE                    md_offlen [MAXMUL];             /* length of digest offset */
VAR SIZE                    md_offerr [MAXMUL];             /* error of above length */

VAR FILE                    *out;                           /* map output file */
VAR FILE                    *arch;                          /* map archive file */

VAR int                     traceflag;                      /* trace toggle */

VAR int                     clueflag = { TRUE };            /* flag to use attribute flags */

/* In an attempt to suppress maps that are the reverse of a map we will ordinarily find,
 * we came to this conclusion: by choosing any two fragments from the same single
 * digest and forcing them to occur in a specific left to right order, we could ensure
 * that only maps of one of the two reversed orders would appear. This not only accomplishes
 * that end, but also reduces the number of maps considered by a factor of 2.
 */

VAR int                     force_digest;                   /* the single digest containing the largest fragment */
                                                            /* used as starting point and must not be used to force ordering */
```

```
VAR int                 order_map;                  /* the digest to enforce an ordering */
VAR int                 prime5, prime3;                     /* the left and right forced fragments */

VAR int                 linear = { 0 };                     /* is this map linear? (this version is circular only) */

/* the following data are used in the review process */

VAR int                 view = { 0 };               /* which map (in best to worst order) is currently being viewed */
VAR float               map_score [MAXVIEW];        /* deviation scores for each archived map */
VAR int                 position [MAXVIEW];         /* file position of each archived map */
VAR int                 max_score = {EMPTY};        /* index of last map in 'map_score' */

VAR long                n_maps = { 0L };            /* total number of maps processed */
VAR long                filespace;                  /* space allocated in bytes to each map in the archive */

VAR char                comment[80] = { "" };       /* project description */

VAR int                 hours, minutes, seconds;    /* a place to broadcast the running time */
#define MAXMAT 50
#define MATPLUSVECTOR MAXMAT+1

VAR int         row [MATPLUSVECTOR];    /* row/column indices to record exchanges */
VAR int         col [MATPLUSVECTOR];

VAR float       matrix [MAXMAT] [MATPLUSVECTOR];        /* the coefficient matrix w/vector */
VAR float       vector [MAXMAT];                        /* where the result appears */
/* Copyright (c) 1986 DNASTAR, Inc. */

#include <stdio.h>

#define VAR

#include <rmap.h>
#include <matrix.h>

SIZE permute();
boolean get_fof();

char fofname[65];
char archname[65];
char indname[65];

extern int _fmode;
int revflag;

deinit()
{
        scr_con();
}

main(argc,argv)
int argc;
char **argv;
{
        FILE *inp;
        int ac;


        scr_setup();    /* pcio initialization */
        scr_coff();     /* turn off cursor */

        init();                 /* initialize variables */

        out = stdout;
        revflag = traceflag = 0;

        for(ac = 1; ac < argc; ac++) {
                if( argv[ac][0] == '-' ) {      /* error factor specified */
                        switch(tolower(argv[ac][1])) {
                                case 'i':
                                        if(get_fof(&argv[ac][2])) {     /* read data */
                                                strcpy(fofname, &argv[ac][2]);
                                                sort_out();     /* figure out what digests are related to what */
                                                permute();      /* document fragment duplication groups */
                                        }
                                        else {
                                                printf("\nInput error!");
                                                deinit();
                                                exit(1);
                                        }
                                        break;
                                case 'l':
```

```
                                        linear = TRUE;          /* force linear map */
                                        break;
                                case 't':
                                        traceflag = 1;          /* turn on trace from beginning */
                                        break;
                                case 'c':
                                        clueflag = FALSE;       /* suppress fragment attribute flags */
                                        break;
                        }
                }
        }

        strcpy(archname,fofname);       /* map archive now named according to project */
        strcpy(indname,fofname);

        new_ext(archname,"maf");        /* assign extensions according to function */
        new_ext(indname,"mix");

_fmode = 0x8000;                                        /* open the map archive file */
        if( (arch = fopen(archname,"w+")) == NULL ) {
                printf("\nPanic! can't open archive file\n");
                deinit();
                exit(1);
        }
_fmode = 0;

        unlink(indname);

        disp_init();    /* initialize display functions */

        pick_force();   /* prevent reverse copies */

        do_map();       /* find all the maps */

disp_success(); /* check progress one last time */

        review();       /* process the output */

        deinit();
        exit(0);

}
#include <stdio.h>
#include <rmap.h>

SIZE lo_val(), hi_val();
boolean first_choice(), choose(), s_pick(), larger(), smaller(), sd_done(), decisions();
heap *new(), *look();
int small(), large();
void disp_progress(), disp_backup();

int user_abort = { FALSE };             /* flag used for user controlled interruption */
int level = { 0 };                      /* yoyo recursion level (for trace) */

do_map()        /* initialize all starting conditions for 'yoyo()' */
{
        int this, count;

        if(nmd+1 < MAXMUL) strcpy(mname[nmd+1],"start");        /* name a dummy map for starting offset */

        for ( ave_len = ZERO, this = START; this <= nsd; this++ ) {
                for( count = START; count <= smax[this]; count++ ) {
                        ave_len += singles[this][count].frag;           /* sum all single fragments */
                }
        }

        ave_len /= (nsd+1);     /* average length (circumference) computed */

        printf("\nconstructing maps\n\n");      /* tell us about it */

        time(0);                /* set the elapsed timer to zero */
        disp_start();           /* display the title and timer for map generation */

        sptr[force_digest] = START;

        if( s_endflag [force_digest] & LEND ) {                 /* left end specified...find it */
                for(this = START; this <= smax[force_digest]; this++)
                        if( singles [force_digest][this].flags & LEND ) {       /* found it */
                                sptr [force_digest] = this;
                                break;
                        }
```

```
        }
        while ( sptr[force_digest] <= smax[force_digest] ) {

                level = 0;                              /* yoyo level indicator for trace */

                ref_point = (SIZE) 0;                   /* error reference point is left end */

                for( this = START; this <= nmd; this++ ) {
                        m_clear(this);                  /*initialize multiple digests */
                        m_reset(this);
                        md_end [this] = EMPTY;
                        md_frag[this] = md_off[this] = EMPTY;
                        md_offlen[this] = md_offerr[this] = ZERO;
                        if( linear || composition [this] [force_digest] ) md_off [this] = nmd+1;
                }
                                                                /* pick an offset digest for digests that have no offset, but leave len and err at
                for( this = START; this <= nsd; this++ ) {
                        sd_end [this].lo = ZERO;
                        sd_end [this].index = EMPTY;
                        if(linear) {
                                sd_end [this].hi = ZERO;
                                sd_mdoff [this] = nmd+1;        /* offset fragment from fictitious digest */
                        }
                        else {
                                sd_end [this].hi = singles [force_digest][count].frag;  /* set map endpoint so it competes for growing point */
                                sd_mdoff [this] = EMPTY;
                        }
                        move_end(&sd_end[this],&last_end[this]);
                        sd_mdfrag [this] = EMPTY;
                        sd_offlen [this] = sd_offerr [this] = ZERO;
                }

                if(s_pick(force_digest)) {                      /* place it (or something not violating a rule) */

                        sd_mdoff [force_digest] = nmd+1;        /* set offset to 0 permanently */

                        yoyo();                                         /* do the algorithm */

                        s_replace(force_digest);
                        s_next(force_digest);
                }

                if( !linear || user_abort ) break;      /* all circular permutations have been tried */
                                                        /* linear case needs to try all frags as left end */

        }
}
boolean cut_violation(sd)                       /* return TRUE if this digest violates the CUT rule */
int sd;
{
        if( clueflag ) {                                /* attempt to use heuristics */
                if( sd_end [sd].index > EMPTY ) {       /* something is in this map */
                        if( singles [sd][sd_map [sd][sd_end [sd].index]].flags & CUT ) {        /* this is a cut frag */
                                if(look()->s_digest == sd) {

                                        if(traceflag) printf("\nEliminating %d as growing point...must be cut ",sd);
                                        return(TRUE);                           /* can't be growing point if it contradicts being cut */
                                }
                        }
                }
        }
        return(FALSE);
}

int set_grow()          /*  choose the smallest (or set thereof) single digest(s) and put on the heap */
{
        int select, this;
        heap *p, *q;

        if( sd_done() ) {
                if( linear ) push( new( small() ) );    /* end of map on linear case is irrelevant */
                else push( new( force_digest ) );       /* end of map on circular case is same digest as beginning */
        }
        else {
                select = small();       /* choose what looks like the leftmost single digest */

                if( cut_violation( select ) ) p = NULL;         /* try others since this one contradicts CUT clue */
                else p = new( select );                         /* start list with the (apparent) smallest */

                for( this = nsd; this > EMPTY; this-- ) {

                        if( this == select ) continue;

                        if( !smaller( select, this ) ) {
```

```
                        if( cut_violation( this ) ) continue;

                        if(p) {
                                if( linear && (heap_top < nsd-1) ) break;       /* linear maps don't explore decisions prior to fitting one frag in all singles */
                                q = new(this);
                                q->others = p->others;
                                p->others = q;
                        }
                        else p = new( this );
                }
        }

        if( p ) push(p);                        /* put it on the heap */
        else return(EMPTY);                     /* no growing point possible */
        }
        return( look()->s_digest );
}

move_ref()      /* check left ends of last frag in each single and move the leftmost to ref_point */
{
        SIZE low;
        int scan,pick;

        for( pick = EMPTY, low = GIANT, scan = START; scan <= nsd; scan++ ) {
                if( last_end [scan].lo < low ) {
                        pick = scan;
                        low = last_end [scan].lo;
                }
        }

        if( low > ZERO ) ref_point = last_end [pick].hi - last_end [pick].lo;
        else ref_point = ZERO;
}

boolean consistent()    /* endpoint range reversal indicates an inter-multiple digest inconsistency */
                        /* not found by fitting against single digest */
{
        if( scratch.lo <= scratch.hi ) return(TRUE);
        if(traceflag) printf("\ninter-multiple fitting inconsistency (%ld </= %ld)\n",scratch.lo,scratch.hi);
        return(FALSE);
}

void move_end(se,de)                    /* move endpoint values from 'se' to 'de' */
endpoint *se,*de;
{
        de->lo = se->lo;
        de->hi = se->hi;
}

void localize(gp,se)                    /* move error range for last frag only to 'se' */
int gp;
endpoint *se;
{
        int f;

        if( (f = sd_end [gp].index) >= START ) {

                se->lo = lo_val(gp,sd_map [gp][f]);
                se->hi = hi_val(gp,sd_map [gp][f]);

        }
        else se->lo = se->hi = ZERO;

        if(traceflag) printf("\nLocalize %s(%ld..%ld)\n",sname[gp],se->lo,se->hi);
}

void correlate(gp,se)   /* move correlated error range in 'se' to end of digest 'gp' */
int gp;
endpoint *se;
{
        int f;

        if( (f = sd_end [gp].index) >= START ) {        /* end defined by map */

                sd_end [gp].lo += (se->lo - lo_val(gp,sd_map [gp][f]));
                sd_end [gp].hi += (se->hi - hi_val(gp,sd_map [gp][f]));

        }
        else if( sd_mdoff != EMPTY ) {          /* end defined by offset */

                sd_end [gp].lo = sd_offlen [gp] - sd_offerr [gp] + se->lo;
                sd_end [gp].hi = sd_offlen [gp] + sd_offerr [gp] + se->hi;
```

```
	}
	else {						/* left end is zero */
		sd_end [gp].lo = se->lo;
		sd_end [gp].hi = se->hi;
	}
	if(traceflag) printf("\nCorrelate (%ld..%ld) new end (%ld..%ld)\n",se->lo,se->hi,sd_end [gp].lo,sd_end [gp].hi);
}

boolean check_user()	/* check keyboard for user interruption, return TRUE if abort */
{
	int c;

	if(kbhit()) {	/* user wants something */

		if((c = getch()) == '\033') {	/* get interrupt character */

			printf("\n[ (I)nterrupt or (C)ontinue ]:\n");
			c = getch();		/* get the control character */

			if( toupper(c) == 'I' ) {
				user_abort = TRUE;
				return(TRUE);
			}
			else if( toupper(c) == '?' ) {
				traceflag = !traceflag;
			}

			disp_start();		/* re-display the title line and timer */
		}

	}
	return(FALSE);
}

yoyo()	/* this is the whopper...the main algorithm, notice that it is recursive */
{
	auto int dropout, grow_point;

	level++;
	if(traceflag) printf("\nEnter Yoyo(%d)\n",level);

	if( check_user() ) return;	/* monitor keyboard and respond to potential interrupt */

	if( (grow_point = set_grow()) == EMPTY ) {
		if(traceflag) printf("\nNo growing point possible! ");
		return;		/* pick a growing point (or return if none possible) */
	}

	if(traceflag) {
		printf("\ngrowing point selected is %s", sname[grow_point]);
		if( sd_end[grow_point].index > EMPTY ) printf(" at %ld\n",singles[grow_point][sd_map[grow_point][sd_end[grow_point].index]].frag);
		else printf(" for the first time\n");
	}

	do {		/* try all growing points at this level */

		localize(grow_point,&scratch);				/* localize error back to last site in this digest */

		if(traceflag) {
			trace();
			map_print();
			printf("first_choice()\n");
		}

		if( first_choice(grow_point) ) {	/* multiple digests all fit */

			do {

				if( consistent() ) {

					correlate( grow_point, &scratch );	/* move refined endpoint range back to map */

					if(traceflag) {
						trace();
						map_print();
					}

					while ( s_pick(grow_point) ) {		/* select the next single digest fragment */

						if(traceflag) {
							printf("s_pick()\n");
```

```
                                                trace();
                                        }
                                        disp_progress();        /* let the user see some action */

                                        move_ref();     /* see if the reference point changes */
                                        yoyo();                 /* recurse for another fragment */
                                        if( user_abort ) return;        /* break out of recursion */
                                        disp_backup();          /* undo the action */
                                        if(traceflag) {
                                                trace();
                                                printf("s_replace()\n");
                                        }
                                        s_replace(grow_point);          /* put the fragment back in digest */
                                        if(traceflag) printf("s_next()\n");
                                        s_next(grow_point);             /* step to next */
                                        if(traceflag) trace();
                                }
                                s_reset(grow_point);            /* reposition digest pointer for next choice of multiple digest fragment */
                        }
                        localize( grow_point, &scratch );       /* restore coarse endpoint range to scratchpad */
                        if(traceflag) printf("choose()\n");
                } while ( choose(grow_point) );         /* try any other combinations of multiple digest fragments */
                if(traceflag) trace();
        }
        if(traceflag) printf("old_mults()\n");
        old_mults(grow_point);          /* replace all the multiple digest pointers */

        if(traceflag) {
                trace();
                printf("pop()\n");
        }
        dropout = decisions();          /* any pending alternative growing points? */
        pop();                          /* step back to the previous fragment (or next decision) */
        grow_point = look()->s_digest;  /* try next growing point at this level */
        if(traceflag) {
                printf("\nnext growing point decision is %s", sname[grow_point]);
                if( sd_end[grow_point].index > EMPTY ) printf(" at %ld\n",singles[grow_point][sd_map[grow_point][sd_end[grow_point].index]].frag);
                else printf(" for the first time\n");
        }

    } while(!dropout);
    if(traceflag) printf("\nExit Yoyo(%d)\n",level);
    level--;
}
#include <stdio.h>
#define VAR extern
#include <rmap.h>

heap *look();
boolean md_last();
```

```
void end_calc(p,sd)        /* compute the range of endpoints and put in 'p' */
endpoint *p;               /* for map 'sd' up to point 'p->index' */
int sd;
{
        digest *s;

        move_end( p, &last_end[sd] );                   /* store current value as previous */

        if( p->index == START ) {               /* first fragment...replace endpoint range */
                if( sd_mdoff[sd] != EMPTY ) {   /* range becomes offset */
                        p->lo = sd_offlen[sd] - sd_offerr[sd];
                        p->hi = sd_offlen[sd] + sd_offerr[sd];
                }
                else {                          /* range becomes zero */
                        p->lo = p->hi = ZERO;
                }
        }

        s = &singles [sd][sd_map [sd][sd_end [sd].index]];      /* get a pointer to the fragment data */
        p->lo += (s->frag - s->frag_error);                    /* low end of range */
        p->hi += (s->frag + s->frag_error);                    /* high end of range */

        if(traceflag) printf("\nendcalc length of %d: %ld .. %ld\n",sd,p->lo,p->hi);
}

SIZE serror(sd,fr)         /* lookup error on frag 'fr' from digest 'sd' */
int sd,fr;
{
        return( singles [sd] [fr].frag_error );
}

SIZE merror(md,fr)         /* likewise for multiple digests */
int md,fr;
{
        return( multiples [md] [fr].frag_error );
}

SIZE lo_val(sd,fr)         /* compute the low end of the error range for digest 'sd' */
int sd,fr;                 /* and fragment 'fr' */
{
        return( singles [sd] [fr].frag - serror(sd,fr) );
}

SIZE hi_val(sd,fr)         /* compute the high end of the error range for digest 'sd' */
int sd,fr;                 /* and fragment 'fr' */
{
        return( singles [sd] [fr].frag + serror(sd,fr) );
}

/* map comparison functions */

int large()                /* return the single digest map with the rightmost endpoint */
{
        int this,select;
        SIZE big;

        for( big = (SIZE) 0, this = select = 0; this <= nsd; this++ )
                if( sd_end [this].hi > big ) {
                        big = sd_end [this].hi;
                        select = this;
                }
        return(select);
}

boolean larger(s1,s2)      /* return TRUE if single digest map 's1' is strictly larger than 's2' */
int s1,s2;
{
        if( sd_end [s1].lo > sd_end [s2].hi ) return(TRUE);
        return(FALSE);
}

int small()                /* return the single digest map with the leftmost endpoint */
{
        int this,select;
        SIZE little;

        for( little = GIANT, this = select = 0; this <=nsd; this++ )
                if( sd_end [this].lo < little ) {
                        little = sd_end [this].lo;
                        select = this;
```

```
        }
        return(select);
}

boolean smaller(s1,s2)    /* return TRUE if single digest map 's1' is strictly less than 's2' */
int s1,s2;
{
        if( (sd_end [s1].hi - ref_point > sd_end [s2].lo) || (sd_end [s1].hi > sd_end [s2].hi) ) return(FALSE);
        return(TRUE);
}

boolean m_group_check(md)          /* return FALSE if current frag from digest 'md' */
int md;                            /* violates an heuristic rule */
{
        return(TRUE);    /* deactivated */

/* this stuff isn't working...fix it before using it -----------------
        if( mptr[md] == START ) return(TRUE);    /* head of list is always in correct order */

        if( m_dup[md][mptr[md]] ) {      /* it's a member of a doublet group */
                if( m_dup[md][mptr[md]-1] == m_dup[md][mptr[md]]) {      /* same group */
                        if( multiples [md][mptr[md]-1].used == FREE ) return(FALSE);     /* wrong order */
                }
        }
        return(TRUE);
------------------------------------------*/
}

boolean starting(gp,md)            /* is this a situation where any multiple will fit? */
int gp,md;
{
        int scan;

        for( scan = START; scan <= nsd; scan++ )
                if( composition [md][scan] ) {
                        if( sd_end [scan].index < START ) return(TRUE);
                }

        return(FALSE);
}

boolean sbnp(gp,md)                /* are all composing singles not started other than the growing point? */
int gp,md;
{
        int scan;

        for(scan = START; scan <= nsd; scan++)
                if( composition [md][scan] )
                        if( ( sd_end [scan].index >= START ) && ( gp != scan ) ) return(TRUE);

        return(FALSE);
}

boolean nofrag(gp)                 /* is this digest different from any previous growing point? */
int gp;
{
        int scan;

        if( !linear && (gp == force_digest) ) return(FALSE);     /* digest that started the map always has a previous cut */

        if( heap_top <= START ) return(TRUE);            /* effectively different if no last growing point */

        for( scan = heap_top-1; scan >= START; scan-- ) {        /* scan back through map */
                if( what_next[scan]->s_digest == gp ) return(FALSE);            /* digest has a previous cut */
        }
        return(TRUE);    /* digest has never cut before */
}

boolean fit_frag(gp,md)            /* return TRUE if both digests have been started (or at least selected) */
int gp,md;
{
        if( ((sd_end [gp].index >= START) || (gp == look()->s_digest)) && (md_end [md] >= START) ) return(TRUE);
        return(FALSE);
}

void test_scratch(gp,low,high)    /* reduce error range for growing point by intersection with */
int gp;                           /* new information from multiple digest */
SIZE low,high;
{
        if( high < scratch.hi ) {
                if(traceflag) printf("\nHigh end of endpoint range moves down %ld -> %ld\n",scratch.hi,high);
                scratch.hi = high;
        }
```

```
        if( low > scratch.lo ) {
                if(traceflag) printf("\nLow end of endpoint range moves up %ld -> %ld\n",scratch.lo,low);
                scratch.lo = low;
        }
}

int order_fit(gp,md)            /* return successful fit on any multiple frag consistent with */
int gp,md;                      /* growing points and map endpoints */
{
        int scan,le;
        SIZE len,err,low,sdlen,sderr;

        if(traceflag) printf("\norder_fit()...%s(%ld) into %s(%ld)...",mname[md],multiples[md][mptr[md]].frag,sname[gp],singles[gp][sd_map[gp][sd_end[gp].index]].frag);

        len = err = ZERO;

        for(scan = md_end[md]; scan >= START; scan--) {                /* add up the length of this digest */
                len += multiples [md] [md_map[md][scan]].frag;
                err += merror(md, md_map[md][scan]);
        }

        if( md_off[md] != EMPTY ) {     /* this digest has an offset */
                len += md_offlen [md];
                err += md_offerr [md];
        }

        if( sd_mdoff[gp] == EMPTY ) {   /* no offset...wide variation possible */

                if(traceflag) printf("\nLargeness test: len %ld, err %ld, frag %ld, frag_err %ld, sd_end[gp].hi %ld\n",len,err,multiples[md][mptr[md]].frag,multiples[md]

                if( multiples [md][mptr[md]].frag - merror( md, mptr[md] ) + len - err > sd end[gp].hi ) {      /* multiple is inconsistent with next cut */
                        [mptr[md]].frag_er   if(traceflag) printf("larger than other digests (len %ld, err %ld, p.hi %ld)\n",len,err,sd_end[gp].hi);
                        return(TOOBIG);
                }

                if( heap_top <= START ) {
                        If(traceflag) printf("start of map OK\n");
                        return(FIT);
                }

                le = what_next [heap_top-1]->s_digest;  /* look up previous growing point */

                if( (scan = sd_end [le].index) >= START) {      /* there is a fragment in the map */
                        low = sd_end [le].lo - lo_val( le, sd_map [le][scan] );                 /* compute smallest possible position */
                }
                else low = ZERO;

                if(traceflag) printf("\nSmallness test: low = %ld\n",low);
                if( multiples [md] [mptr[md]].frag + merror( md, mptr[md] ) + len + err < low ) {       /* contradicts growing point */
                        if(traceflag) printf("contradicts growing point (%ld)\n",low);
                        return(TOOSMALL);
                }

        }
        else {          /* offset exists...must fit against the end of the single */
                if(traceflag) printf("\nDependent on previous offset frag %ld, ferr %ld, len %ld, err %ld, .hi %ld, .lo %ld\n",
                multiples [md][mptr[md]].frag,merror( md, mptr[md] ),len,err,sd_offlen[gp]+sd_offerr[gp],sd_offlen[gp]-sd_offerr[gp]);

                sdlen = sderr = ZERO;
                for( scan = sd_end[gp].index; scan >= START; scan-- ) {
                        sdlen += singles [gp][sd_map[gp][scan]].frag;
                        sderr += singles [gp][sd_map[gp][scan]].frag_error;
                }

                if( multiples [md][mptr[md]].frag - merror( md, mptr[md] ) + len - err > sd_offlen[gp] + sd_offerr[gp] + sdlen + sderr ) {
                        if(traceflag) printf("too large\n");                    /* multiple is l... digest ...oint
                        return(TOOBIG);
                }
                if( multiples [md] [mptr[md]].frag + merror( md, mptr[md] ) + len + err < sd_offlen[
                        if(traceflag) printf("too small\n");
                        return(TOOSMALL);                                       /* multiple is smaller than digest endpoint
                }
        }

        if(traceflag) printf("acceptable\n");
        return(FIT);
}

int fit_special(gp,md)          /* fit multiples at beginning of map under special rules */
int gp,md;
{
        if(traceflag) printf("\nfit_special()...%s(%ld) into %s(%ld)...",mname[md],multiples[md][mptr[md]].frag,sname[gp],singles[gp][sd_map[gp][sd_end[gp].index]].frag);
```

```
		if( linear && (sd_end [gp].index < START) ) {
			if(traceflag) printf("linear start, no frag\n");
			return(FIT);	/* no fragment here on linear maps */
		}

		if( sbnp(gp,md) ) {	/* all composing singles have been selected, but one has no fragments */
			return( order_fit(gp,md) );	/* almost any fragment will do */
		}
		else {
			if( !fit_frag(gp,md) && nofrag(gp) ) {
				if(traceflag) printf("digest not started yet\n");
				return(FIT);	/* any fragment fits */
			}

			if( clueflag ) {	/* see if this fragment violates any placement heuristics */
				if( multiples [md][mptr[md]].flags & NEW ) {	/* can't be same site at both ends */
					if( md_site [md][md_end [md]] == gp ) {
						if(traceflag) printf("can't place a new frag here...");
						return(TOOBIG);
					}
				}
			}

			if( multiples [md] [mptr [md]].frag + merror(md,mptr [md]) <		/* contradicts growing point */
				lo_val( gp, sd_map [gp] [sd_end [gp].index] ) ) {
					if(traceflag) printf("contradicts growing point\n");
					return(TOOSMALL);
			}

			if( multiples [md] [mptr [md]].frag - merror(md,mptr [md]) >		/* contradicts end of map */
				hi_val( gp, sd_map [gp] [sd_end [gp].index] ) ) {
					if(traceflag) printf("larger than other digests\n");
					return(TOOBIG);
			}

			if( !m_group_check(md) ) {
				if(traceflag) printf("wrong fragment permutation\n");
				return(TOOBIG);		/* contradicts fragment permutation rule */
			}

			if(traceflag) printf("acceptable\n");

			return(FIT);		/* success */
		}
}

int m_fit(gp,md)		/* use normal error accumulation rules to test fit of this multiple frag */
int gp,md;
{
		int scan;
		SIZE error,length,high,low;

		if(traceflag) printf("\nm_fit()...%s(%ld) into %s(%ld)...",mname[md],multiples[md][mptr[md]].frag,sname[gp],singles[gp][sd_map[gp][sd_end[gp].index]].frag);

		if( md_site [md] [md_end[md]] == gp ) {		/* previous cut is from the same digest */

			if(traceflag) printf("same site at both ends...");

			if( (high = multiples [md] [mptr [md]].frag + merror(md, mptr [md])) < lo_val(gp, sd_map [gp] [sd_end [gp].index]) ) {
				if(traceflag) printf("too small\n");
				return(TOOSMALL);
			}

			if( (low = multiples [md] [mptr [md]].frag - merror(md, mptr [md])) > hi_val(gp, sd_map [gp] [sd_end [gp].index]) ) {
				if(traceflag) printf("too large\n");
				return(TOOBIG);
			}

			if( !m_group_check(md) ) {
				if(traceflag) printf("wrong fragment permutation\n");
				return(TOOBIG);
			}

		}
		else {	/* previous cut is from another digest */
			/* accumulate the error back to the rightmost previous gp digest cut */

			if(traceflag) printf("last cut %s, end %s...",sname[md_site[md][md_end[md]]],sname[gp]);

			error = length = (SIZE) 0;
			for( scan=md_end[md]; (scan >= START) && (md_site [md] [scan] != gp); scan--) {
				length += multiples [md] [md_map [md] [scan]].frag;
				error += merror(md, md_map [md] [scan]);
			}
```

```
		error += merror(md,mptr [md]);  /* error on the fragment itself */

		if( (high = multiples [md] [mptr [md]].frag + length + error) < lo_val(gp, sd_map [gp] [sd_end [gp].index]) ) {
			if(traceflag) printf("too small\n");
			return(TOOSMALL);
		}

		if( (low = multiples [md] [mptr [md]].frag + length - error) > hi_val(gp, sd_map [gp] [sd_end [gp].index]) ) {
			if(traceflag) printf("too large\n");
			return(TOOBIG);
		}

		if( !m_group_check(md) ) {
			if(traceflag) printf("wrong permutation\n");
			return(TOOBIG);
		}

	}
	test_scratch(gp,low,high);	/* refine error range based upon new multiple data */

	if(traceflag) printf("acceptable\n");
	return(FIT);
}

int fits(gp,md)			/* find out if the current fragment from multiple digest 'md' */
int gp,md;			/* fits into the growing point */
{				/* returns values TOOSMALL, FIT, and TOOBIG */

	if( starting(gp,md) ) return( fit_special(gp,md) );	/* fitting at start of circular maps is special */

	if( clueflag ) {		/* see if this fragment violates any placement heuristics */
		if( multiples [md][mptr[md]].flags & NEN ) {	/* can't be same site at both ends */
			if( md_site [md][md_end [md]] == gp ) {
				if( !linear || !md_last(md) ) {
					if(traceflag) printf("can't place a new frag here...");
					return(TOOBIG);
				}
			}
		}
		if( linear && (m_endflag [md] & ANYEND) ) {	/* end flags are set...see if this frag violates any end rule */
			switch( multiples [md][mptr[md]].flags & ANYEND ) {
				case LEND:
					if( md_end[md] != EMPTY ) return(TOOBIG);	/* must be first fragment chosen */
					break;
				case REND:
					if( !md_last(md) ) return(TOOBIG);		/* must be last fragment chosen */
					break;
				case END:
					if( !md_last(md) && (md_end [md] != EMPTY) ) return(TOOBIG);	/* must be either of the above */
					break;
				default:					/* must be other than end if ends are specific */
					if( (m_endflag [md] & LEND) && (md_end [md] == EMPTY) ) return(TOOBIG);		/* about to choose other than
left end as left end */
					if( (m_endflag [md] & REND) && (md_end [md] == mmax[md]-1) ) return(TOOBIG);	/* ditto for right end */
					break;
			}
		}
	}

	return( m_fit(gp,md) );			/* use normal rules otherwise...get rid of following code if this is correct */

}

boolean order_check(sd)		/* look at the single digest 'sd' and see if the forced order frags will be reversed */
int sd;				/* return FALSE if so */
{

/*	return(TRUE);   activated */

	if( sd == order_map ) {		/* this is the correct digest */
		if( sptr [sd] == prime5 ) {	/* we are looking at the left forced frag */
			if( singles [sd] [prime3].used == USED ) {	/* wrong order */
				return(FALSE);
			}
			return(TRUE);
		}

		if( sptr [sd] == prime3 ) {	/* we are looking at the right forced frag */
			if( singles [sd] [prime5].used == FREE ) {	/* wrong order */
				return(FALSE);
			}
			return(TRUE);
		}
```

```
        }
        return(TRUE);
}

boolean find_first(gp,md)          /* find the first (largest) fragment in multiple digest 'md' */
int gp,md;                         /* that fits the growing point 'gp' */
{
        int test;

        if( m_reset(md) == FALSE ) return(FALSE);

        while(TRUE) {

                if(traceflag) printf("\ttrying %ld...",multiples[md][mptr[md]].frag);

                if( (test = fits(gp,md)) == FIT ) {      /* found it */
                        if(traceflag) printf("fits\n");
                        m_pick(gp,md);                   /* put it in the map */
                        return(TRUE);
                }

                if( test == TOOSMALL ) {
                        if(traceflag) printf("too small\n");
                        return(FALSE);  /* there aren't any that fit */
                }

                if(traceflag) printf("too large\n");

                if( !m_next(md) ) {
                        if(traceflag) printf("last one\n");
                        return(FALSE);  /* ran out of fragments */
                }
        }
}

int last_fit()              /* check inter-digest consistency at the right end */
{                           /* and add any remaining multiple digest fragments */
                            /* return value is first multiple that doesn't fit */
        int sd,md,scan,ssd,flag;
        SIZE error, length, s_err, s_len, m_err, m_len;

        if(traceflag) {
                map_print();
                trace();
                printf("\nLast_fit()");
        }

        for( md = START; md <= nmd; md++ ) {     /* scan multiple digests */

                for( sd = START; sd <= nsd; sd++ ) {     /* scan single digests */

                        if(sd == look()->s_digest) continue;     /* fragments involving last single digest already fit */

                        if( !composition [md] [sd] ) continue;  /* don't check against singles that don't cut here */

                        flag = 1;       /* set flag to test overlap */

                        if( md_last(md) ) {      /* still need to fit a fragment */
                                ssd = sd;

                                if( !linear ) {
                                        for(scan = START; scan <= nsd; scan++)          /* use enzyme which cuts most leftward at end */
                                                if( composition [md][scan] && (sd_end[scan].lo < sd_end[ssd].lo) )
                                                        ssd = scan;
                                }
                                else flag = 0;  /* don't bother to test fit later since it's done by 'fit()' */

                                if( fits(ssd, md) == FIT ) {     /* OK...keep going */
                                        if(traceflag) printf("\nFitting last frag %ld in %s ",multiples[md][mptr[md]].frag,mname [md]);
                                        m_pick(ssd, md);
                                }
                                else return(md);
                        }

                        if( flag ) {            /* all fragments in, check fit */

                                m_len = m_err = s_len = s_err = error = length = ZERO;

                                if(traceflag) printf("\nadding...");
```

```
        if( sd_mdoff[sd] != EMPTY ) {               /* digest wraps around the zero point */
                s_err = sd_offerr [sd];                     /* add error from zero point leftward */
                s_len = sd_offlen [sd];                     /* add length from zero point leftward */
        }

        if( md_off[md] != EMPTY ) {                 /* multiple digest also wraps around zero point */
                m_len = md_offlen [md];                     /* add length from zero point leftward */
                m_err = md_offerr [md];                     /* add error from zero point leftward */
        }
        if(traceflag) printf(" s_err = %ld, s_len = %ld, m_err = %ld, m_len = %ld   ",s_err,s_len,m_err,m_len);

        for( scan = md_end [md] - 1; (scan >= START) && (md_site [md] [scan] != sd); scan-- ) {
                if(traceflag) printf("%ld ",multiples [md] [md_map [md] [scan]].frag);
                length += multiples [md] [md_map [md] [scan]].frag;
                error += merror(md, md_map [md] [scan]);
        }

        error += merror(md, md_map [md] [md_end [md]]);                 /* error on the fragment itself */

        if(traceflag) printf("...md end(%ld) sd end(%ld)",multiples [md] [md_map[md][md_end [md]]].frag, singles[sd][sd_map [sd] [sd_end [sd].index]].frag);

        if( multiples [md] [md_map [md] [md_end [md]]].frag - m_len + m_err < (lo_val(sd, sd_map [sd] [sd_end [sd].index]) - length - error - s_len - s_err) ) {
                if(traceflag) printf("...nope!\n");
                return(md);
        }

        if( multiples [md] [md_map [md] [md_end [md]]].frag - m_len - m_err > (hi_val(sd, sd_map [sd] [sd_end [sd].index]) - length + error - s_len + s_err) ) {
                if(traceflag) printf("...nope!\n");
                return(md);
        }
        if(traceflag) printf("...fits\n");
                        }
                }
        }
        return(nmd+1);
}

/* functions used to check for the existence of a complete map */

boolean sd_done()       /* return TRUE if all single digest framents have been assigned */
{
        int i,j;

        for(i=0; i <= nsd; i++)
                for(j=0; j <= smax [i]; j++)
                        if( singles[i][j].used == FREE ) return(FALSE);
        return(TRUE);
}

boolean md_done()       /* return TRUE if all multiple digest framents have been assigned */
{
        int i,j;

        for(i=0; i <= nmd; i++)
                for(j=0; j <= mmax [i]; j++)
                        if( multiples[i][j].used == FREE ) return(FALSE);
        return(TRUE);
}

boolean done()          /* return TRUE if all fragments have been assigned to the map */
{
        return( sd_done() && md_done() );
}

boolean md_last(md)     /* return TRUE if only one fragment remains free */
int md;
{
        int total,this;

        for(this = total = START; this <= mmax [md]; this++ )
                if( multiples [md] [this].used == FREE )
                        if( ++total > 1 ) return(FALSE);
        if(total > START) return(TRUE);
        return(FALSE);
}
/* Copyright (c) 1986 DNASTAR, Inc. */

#include <stdio.h>

#define VAR extern
```

```
#include <rmap.h>

heap *look();
boolean sd_done(), sbnp(), nofrag(), fit_frag(), allset(), order_check();
int last_fit();
SIZE merror();
void disp_backup(), disp_progress();

boolean overlaps()        /* return TRUE if linear or if overhanging end of circle fits its' offset from zero point */
{
        int sd, vend;

        if( linear ) return(TRUE);        /* linear maps don't wrap */

        if(traceflag) printf("\nOverlaps...");

        vend = look()->s_digest;          /* lookup digest at zero point */

        for( sd = START; sd <= nsd; sd++ ) {     /* scan singles */
                if( sd == vend ) continue;       /* digest at zero point doesn't wrap */

                if( sd_mdoff[sd] == EMPTY ) {
                        if(traceflag) printf("fail\n");
                        return(FALSE);  /* contradiction: can't have more than one zero point */
                }

                if( sd_end [sd].hi - sd_end [vend].lo <
                        sd_offlen [sd] - sd_offerr [sd] ) {      /* largest overhang is still less than smallest offset */
                                if(traceflag) printf("fail\n");
                                return(FALSE);
                }

                if( sd_end [sd].lo - sd_end [vend].hi >
                        sd_offlen [sd] + sd_offerr [sd] ) {      /* smallest overhang is still larger than largest offset */
                                if(traceflag) printf("fail\n");
                                return(FALSE);
                }
        }

        if(traceflag) printf("fit\n");

        return(TRUE);             /* all overhangs wrap correctly */
}

void set_off(gp,md)       /* set the offsets for newly selected digests */
int gp,md;
{
        int scan,addup;

        if(linear) return;

        if( sbnp(gp,md) && (sd_end[gp].index < START) ) {
                for( scan = START; scan <= nmd; scan++ )
                        if( composition [scan][gp] && (scan != md) ) {  /* the map begins here */
                                if( md_off[scan] == EMPTY ) {
                                        md_off[scan] = md;
                                        md_frag[scan] = mptr[md];
                                        md_offlen [scan] = multiples [md] [mptr [md]].frag;     /* offset from picked digest fragment */
                                        md_offerr [scan] = merror( md, mptr [md] );
                                        if( md_end[md] > START ) {       /* must add other fragments into offset */
                                                for( addup = md_end[md]-1; addup >= START; addup-- ) {
                                                        md_offlen[scan] += multiples[md][md_map[md][addup]].frag;
                                                        md_offerr[scan] += merror( md, md_map[md][addup] );
                                                }
                                        }
                                        if( md_off[md] != EMPTY ) {                             /* must add offset from picked digest */
                                                md_offlen [scan] += md_offlen [md];
                                                md_offerr [scan] += md_offerr [md];
                                        }
                                }
                        }

                if( sd_mdoff[gp] == EMPTY ) {
                        sd_mdoff[gp] = md;
                        sd_mdfrag[gp] = mptr[md];
                        sd_offlen [gp] = multiples [md] [mptr [md]].frag;       /* offset for growing point digest */
                        sd_offerr [gp] = merror( md, mptr [md] );
                        if( md_end[md] > START ) {      /* must add other fragments into offset */
                                for( addup = md_end[md]-1; addup >= START; addup-- ) {
                                        sd_offlen[gp] += multiples[md][md_map[md][addup]].frag;
                                        sd_offerr[gp] += merror( md, md_map[md][addup] );
```

```
			}
		}
		if( md_off [md] != EMPTY ) {			/* offset from picked digest contributes */
			sd_offlen [gp] += md_offlen [md];
			sd_offerr [gp] += md_offerr [md];
		}
		sd_end[gp].lo = sd_offlen[gp] - sd_offerr[gp];	/* update map endpoint to reflect offset */
		sd_end[gp].hi = sd_offlen[gp] + sd_offerr[gp];
	}
    }
}

unset_off(md)	/* reset digest offsets */
int md;
{
	int scan;

	if(linear) return;

	for( scan = START; scan <= nmd; scan++ )
		if( scan != md ) {
			if( (md_off[scan] == md) && (md_frag[scan] == md_map[md][md_end[md]]) ) {
				md_off[scan] = EMPTY;
			}
		}

	for( scan = START; scan <= nsd; scan++ )
		if( (sd_mdoff[scan] == md) && (sd_mdfrag[scan] == md_map[md][md_end[md]]) ) {
			sd_mdoff[scan] = EMPTY;

			if( scan == look()->s_digest ) {	/* this should be true */
				sd_end[scan].hi = look()->s_pos.hi;
				sd_end[scan].lo = look()->s_pos.lo;
			}
		}
}

int next_mdig(gp,md)	/* find the next multiple digest containing site 'gp' */
int gp,md;		/* starting beyond digest 'md' */
{
	for( ++md; md < MAXMUL; md++ )				/* found one */
		if( composition [md] [gp] ) return(md);		/* no more */
	return(EMPTY);
}

boolean f_c_offset(gp)		/* special case of 'first_choice()' below when single has not started and no offset. */
int gp;				/* the digest that sets the offset must be permuted independently of all others */
{
	int this,test,redo;

	for(this = next_mdig(gp, EMPTY); this > EMPTY; this = next_mdig(gp, this) ) {

		if( !find_first(gp, this) ) {
			release(gp,this);
			return(FALSE);
		}
		if( sd_mdoff[gp] != EMPTY ) {	/* this is the independent digest */
			test = this;
			break;
		}
	}
	/* try all frags from 'test' and first choice from following digests */

	do {
		for(this = next_mdig(gp, test); this > EMPTY; this = next_mdig(gp, this) ) {
			if( !find_first(gp,this) ) {	/* can't find a compatible fragment...bad choice of 'test' frag */
				for( redo = next_mdig(gp,test); redo < this; redo = next_mdig(gp,redo))
					m_replace(redo);
				break;
			}
		}
		if( this == EMPTY ) break;	/* found a frag from each digest */

		m_replace(test);		/* try again from independent digest */

		while( m_next(test) ) {		/* keep trying until TOOSMALL */
			If( (redo = fits(gp,test)) == FIT ) {
				m_pick(gp,test);
				break;
```

```
                        }
                        if( redo == TOOSMALL ) {
                                release(gp,test);
                                return(FALSE);
                        }
                }

                if( mptr[test] > mmax[test] ) {                 /* nothing from m_next() */
                        release(gp,test);               /* replace fragments prior to 'test' */
                        return(FALSE);
                }

        } while ( redo == FIT );

        if( sd_done() ) {
                if( ((test =last_fit()) > nmd) && overlaps() ) map_dump();      /* a successful map */
                last_put(test);
        }

        return(TRUE);
}

boolean first_choice(gp)        /* try to fit one fragment from each multiple */
int gp;                         /* digest containing site 'gp', return FALSE */
{                               /* on failure. */
        int this, test;

        if( !linear && (sd_end[gp].index < START) && (sd_mdoff[gp] == EMPTY) )
                return(f_c_offset(gp));                 /* special case when one fragment choice sets single digest offset */

        for(this = next_mdig(gp, EMPTY); this > EMPTY; this = next_mdig(gp, this) ) {

                if( !find_first(gp, this) ) {
                        release(gp,this);
                        return(FALSE);
                }
        }

        if( sd_done() ) {
                if( ((test =last_fit()) > nmd) && overlaps() ) map_dump();      /* a successful map */
                last_put(test);
        }

        return(TRUE);
}

boolean ch_offset(gp)           /* try to find another combination of multiples that fit 'gp' */
int gp;                         /* in this case, the offset fragment choice affects all others */
{
        int this, test, ftest;

        test = sd_mdoff [gp];   /* offset digest gets permuted last */

        for(this = next_mdig(gp, EMPTY); this > EMPTY; this = next_mdig(gp, this) ) {
                if( this == test ) continue;    /* save offset digest for last attempt */

                if( !sbnp(gp,this) && !fit_frag(gp,this) && nofrag(gp) ) continue;      /* if this multiple didn't get a fragment placed, then */
                                                        /* we must look elsewhere for permutations of multiple fragments */

                m_replace(this);                        /* put last fragment back */

                while( m_next(this) ) {                         /* step to next */
                        if( (ftest = fits(gp, this)) == FIT ) {         /* it fits */
                                m_pick(gp, this);       /* put it into map */
                                if( sd_done() ) {
                                        if( ((test = last_fit()) > nmd) && overlaps() ) map_dump();     /* we have a map...process it */
                                        last_put(test);
                                }
                                return(TRUE);           /* successfully found another combination */
                        }
                        if(ftest == TOOSMALL) break;
                }

                find_first(gp, this);                   /* put original choice back in */

        }

        m_replace(test);        /* try another frag from offset digest */

        while( m_next(test) ) {         /* another exists */

                if( (ftest = fits(gp,test)) == FIT ) {  /* it fits...establish starting frags for all other digests */
```

```
                        m_pick(gp,test);

                        for(this = next_mdig(gp, EMPTY); this > EMPTY; this = next_mdig(gp, this) ) {

                                if( this == test ) continue;

                                m_replace(this);

                                if( !find_first(gp,this) ) {    /* new choice blasts another...try again */
                                        m_reset(this);          /*pick an arbitrary frag from current digest */
                                        m_pick(gp,this);
                                        m_replace(test);        /* put the current independent frag back */
                                        break;
                                }
                        }

                        if( this != EMPTY ) continue;   /* we didn't find a complete set of frags */

                        if( sd_done() ) {
                                if( ((test = last_fit()) > nmd) && overlaps() ) map_dump();     /* we have a map...process it */
                                last_put(test);
                        }

                        return(TRUE);                   /* successfully found another combination */
                }

                if( ftest == TOOSMALL ) break;
        }

        find_first(gp,test);                    /* get original choice */
        release(gp,MAXMUL);                     /* remove all chosen fragments from maps */
        return(FALSE);                          /* couldn't find another combination */
}

boolean choose(gp)              /* try to find another combination of multiples */
int gp;                         /* that fit growing point 'gp' */
{
        int this, test;

        if( linear ) {
                if( sd_end [gp].index < START ) return(FALSE);          /* no permutations on left end of linear maps */
        }
        else {
                if( (sd_end [gp].index < START)
                && (sd_mdoff[gp] != EMPTY)
                && (sd_offlen[gp] > ZERO)) return( ch_offset(gp) );     /* special permutations on offset digests */
        }

        for(this = next_mdig(gp, EMPTY); this > EMPTY; this = next_mdig(gp, this) ) {

                if( !linear && !sbnp(gp,this) && !fit_frag(gp,this) && nofrag(gp) ) continue;   /* if this multiple didn't get a fragment placed, then */
                                                        /* we must look elsewhere for permutations of multiple fragments */

                m_replace(this);                        /* put last fragment back */

                while( m_next(this) ) {                         /* step to next */
                        if( (test = fits(gp, this)) == FIT ) {  /* it fits */
                                m_pick(gp, this);       /* put it into map */
                                if( sd_done() ) {
                                        if( ((test = last_fit()) > nmd) && overlaps() ) map_dump();     /* we have a map...process it */
                                        last_put(test);
                                }
                                return(TRUE);           /* successfully found another combination */
                        }
                        if( test == TOOSMALL ) break;
                }

                find_first(gp, this);                   /* put original choice back in */
        }
        release(gp,MAXMUL);                     /* remove all chosen fragments from maps */
        return(FALSE);                          /* couldn't find another combination */
}

/* functions for manipulating single digest fragments follow */

s_group_check(sd)       /* if about to pick a doublet frag out of order, */
int sd;                 /* move to another */
{
        return;         /* deactivated */

        if( sptr[sd] == START ) return;                 /* head of list is always in the right order */
```

```
	while( sptr[sd] <= smax[sd] ) {			/* while more */
		if( s_dup[sd][sptr[sd]] ) {	/* it's a member of a doublet group */
			if(s_dup[sd][sptr[sd]-1] == s_dup[sd][sptr[sd]]) {	/* it's the same group */
				if( singles[sd][sptr[sd]-1].used == USED ) return;	/* correct order */
				s_next(sd);		/* wrong order...try the next */
			}
			else return;
		}
		else return;
	}
}

s_end_check(gp)		/* see if this fragment choice contradicts end clues */
int gp;
{
	if( clueflag && linear ) {
		if( s_endflag [gp] & ANYEND ) {			/* digest contains end clues */
			switch( singles [gp][sptr [gp]].flags & ANYEND ) {
			case LEND:
				if( sd_end[gp].index != EMPTY ) return(FALSE);	/* can't place left end frag at other than left end */
				break;
			case REND:
				if( sd_end[gp].index != smax[gp]-1 ) return(FALSE);	/* ditto for right end */
				break;
			case END:
				if( (sd_end[gp].index >= START) && (sd_end[gp].index < smax[gp]-1) ) return(FALSE);
				break;
			default:	/* digest has clues for ends, but not this fragment */
				if( (s_endflag [gp] & LEND) && (sd_end[gp].index == EMPTY) ) return(FALSE);	/* can't put other than left end in left end */
				if( (s_endflag [gp] & REND) && (sd_end[gp].index == smax[gp]-1) ) return(FALSE);	/* ditto for right end */
				break;
			}
		}
	}
	return(TRUE);	/* anything goes */
}

boolean s_pick(gp)		/* choose the next fragment from digest 'gp' */
int gp;
{
	int i,p;
	SIZE lo;

	if( !order_check(gp) ) s_next(gp);	/* enforce order check */

	while( !s_end_check(gp) ) s_next(gp);	/* enforce end clues */

	s_group_check(gp);			/* force doublet order */

	if( sptr [gp] <= smax [gp] ) {		/* something left to choose */
		if( ++sd_end [gp].index >= MAXMAP ) {	/* too much data in map */
			printf("\nPanic! single digest '%s' is too large.\n",sname[gp]);
			exit(1);
		}
		if(traceflag) printf(" ... (%ld) from %s\n",singles[gp][sptr[gp]].frag,sname[gp]);
		sd_map [gp] [sd_end [gp].index] = sptr [gp];	/* move fragment to map */
		singles [gp] [sptr [gp]].used = USED;		/* mark as chosen */
		end_calc(&sd_end [gp], gp);			/* measure new map */
		s_reset(gp);					/* move digest pointer back to head of list */
		if( !linear ) {				/* move range of endpoints for unstarted digests */
			lo = GIANT;
			for(p=EMPTY,i=START; i <= nsd; i++) {		/* scan singles */
				if( (sd_end[i].index >= START) && (sd_end[i].hi < lo) ) {	/* potentially the smallest */
					lo = sd_end[i].hi;
					p = i;
				}
			}
			if(p != EMPTY) {	/* something is started */
				for(i=START; i <= nsd; i++) {
					if( sd_end[i].index < START ) {		/* this digests endpoint moves */
						sd_end[i].hi = lo;
					}
				}
			}
		}
		return(TRUE);
	}
	return(FALSE);
}

void s_replace(sd)	/* put fragment at end of map 'sd' back in digest */
```

```
int sd;
{
        heap *p;

        sptr [sd] = sd_map [sd] [sd_end [sd].index];            /* move pointer back to position */
        singles [sd] [sptr [sd]].used = FREE;                   /* mark as unused */
        if( p = look() ) {
                sd_end[p->s_digest].index = p->s_pos.index;     /* restore old map endpoint */
                sd_end[p->s_digest].lo    = p->s_pos.lo;
                sd_end[p->s_digest].hi    = p->s_pos.hi;
                last_end[p->s_digest].lo  = p->s_last.lo;
                last_end[p->s_digest].hi  = p->s_last.hi;

                ref_point = p->s_ref;                           /* restore old reference point */
        }
}

boolean s_reset(sd)      /* find the first unused entry in single digest 'sd' */
int sd;
{
        for( sptr [sd] = START; sptr [sd] <= smax [sd]; sptr [sd]++ )
                if( singles [sd] [sptr [sd]].used == FREE )
                        return(TRUE);

        return(FALSE);
}

boolean s_next(sd)       /* find the next unused entry in single digest 'sd' */
int sd;
{
        for( ++sptr [sd]; sptr [sd] <= smax [sd]; sptr [sd]++ )
                if( singles [sd] [sptr [sd]].used == FREE )
                        return(TRUE);

        return(FALSE);
}

void s_clear(sd)         /* set all entries in single digest 'sd' to unused */
int sd;
{
        int this;

        for( this = START; this <= smax [sd]; this++ )
                singles [sd] [this].used = FREE;
}

/* functions for manipulating multiple digest fragments follow */

void m_pick(gp,md)       /* select the current fragment from multiple digest 'md' */
int gp,md;               /* it is cut by site 'gp' */
{
        if( linear ) {
                if( sd_end [gp].index < START ) return;                         /* condition where no fragment is picked */
        }
        else if( !abnp(gp,md) && !fit_frag(gp,md) && nofrag(gp) ) return;       /* condition where no fragment is picked */

        if( ++md_end [md] >= MAXMAP ) {
                printf("\nPanic! Multiple digest map '%s' is too large!\n",mname [md]);
                exit(1);
        }

        disp_progress();                                /* display some progress */

        set_off(gp,md);                                         /* check possibility that this */
                                                        /* fragment sets the map position relative to zero */
        md_map [md] [md_end [md]] = mptr [md];          /* move the fragment to map */
        multiples [md] [mptr [md]].used = USED;                 /* mark it as in use */
        m_reset(md);                                    /* move pointer to top of list */
        md_site [md] [md_end [md]] = gp;                /* save what cuts here */
}

void m_replace(md)       /* put the fragment at the end of the 'md' map back into a digest */
int md;
{
        if( md_end [md] < START ) return;       /* no fragment to replace (corresponds to not being picked above) */

        disp_backup();                          /* display the situation */

        unset_off(md);                          /* release relative map positions undone by this replacement */
```

```
        mptr [md] = md_map [md] [md_end [md]];          /* move pointer back to position */
        multiples [md] [mptr [md]].used = FREE;                 /* mark as unused */
        md_end [md]--;                                  /* map is one fragment shorter */
}

boolean m_reset(md)         /* move pointer to topmost unused fragment */
int md;                     /* return FALSE if none found */
{
        for(mptr [md] = START; mptr [md] <= mmax [md]; mptr [md]++)
                if( multiples [md] [mptr [md]].used == FREE )
                        return(TRUE);
        return(FALSE);
}

boolean m_next(md)          /* find the next unused entry in single digest 'sd' */
int md;

{
        for( ++mptr [md]; mptr [md] <= mmax [md]; mptr [md]++ )
                if( multiples [md] [mptr [md]].used == FREE )
                        return(TRUE);

        return(FALSE);
}

void m_clear(md)            /* set all entries in multiple digest 'md' to unused */
int md;
{
        for(mptr [md] = START; mptr [md] <= mmax [md]; mptr [md]++)
                multiples [md] [mptr [md]].used = FREE;
}

void release(gp,last)       /* replace fragments chosen from all multiple digests */
int gp,last;                /* from START up to, but not including 'last' */
{
        int this;

        for(this = next_mdig(gp, EMPTY); (this > EMPTY) && (this < last); this = next_mdig(gp, this) )
                        m_replace(this);

}

void last_put(mmd)          /* release all multiple digest fragments at end of map */
int mmd;                    /* that do not contain the site at the top of the heap */
{                           /* but are less than 'mmd' */
        int md;

        if(traceflag) {
                map_print();
                trace();
                printf("\nLast_put()");
        }

        for( md = START; md < mmd; md++ ) {     /* scan multiple digests */

                if( composition [md] [look()->s_digest] ) continue;     /* will be released later, continue */

                if(traceflag) printf("\nreplacing %ld in %s ",multiples[md][md_map[md][md_end[md]]].frag,mname[md]);

                m_replace(md);                  /* put the fragment back */
        }
}

void old_mults(gp)          /* restore multiple digest pointers to initial state */
int gp;
{
        int this;

        for(this = next_mdig(gp, EMPTY); this > EMPTY; this = next_mdig(gp, this) )
                m_reset(this);

}

boolean all_checked(sp)             /* see if all members of array 'sp' are non-zero */
int sp [MAXSIN];
{
        int i;

        for( i=START; i <= nsd; i++ ) if( sp[i] == FALSE ) return(FALSE);
        return(TRUE);
}
```

```
int common_digest(first)          /* identify the first digest common to the set of multiples */
int first;                        /* this is necessary only for circular maps */
{
        int i,j,k;
        int score_pad [MAXSIN];
        for( i = first; i <= nsd; i++ ) {                      /* pick a single digest */
                for( j=START; j <= nsd; j++ ) score_pad [j] = FALSE;    /* clear score chart */
                score_pad [i] = TRUE;                          /* check off chosen single */
                for( j=START; j <= nsd; j++ ) {                        /* scan multiple digests */
                        if( composition [j] [i] ) {            /* this multiple contains chosen single */
                                for( k=START; k <= nsd; k++ ) {        /* check off digests connected through this multiple */
                                        score_pad [k] |= composition [j] [k];
                                }
                        }
                }
                if( all_checked(score_pad) ) return(i);        /* this digest is connected to all others through multiples */
        }
        return(EMPTY);                                  /* return value for no connection */
}

void pick_force()         /* select the enforced order digest and fragments from among singles */
{
        SIZE m;
        int this,that,nobetter,careful;
        int connects[MAXSIN];

        if( linear ) {
                for( careful = FALSE, this = START; this <= nsd; this++ )
                        if( s_endflag [this] & SPECEND ) careful = TRUE;        /* must be careful about choosing order */
        }

        m = ZERO;
        that = this = EMPTY;

        if( linear ) {

                for( force_digest = 0; force_digest <= nsd; force_digest++ ) {
                        /* just pick first digest with more than 1 frag for now... */
                        /* we may need to be more careful if we include endpoint information */

                        if( smax [force_digest] > START ) {      /* OK...this one will do */
                                if( singles [force_digest][START].frag > m ) {  /* potentially the largest one */

                                        if( (careful) && ((s_endflag [force_digest] & SPECEND) == 0) ) continue;        /* can't use this one */

                                        this = force_digest;
                                        m = singles [this][START].frag;
                                }
                        }
                }

                order_map = this;       /* linear maps must use the selected digest for ordering */

                if( this != EMPTY ) {
                        prime5 = prime3 = EMPTY;
                        force_digest = this;    /* use the digest with the largest fragment to start */

                        if( careful ) {              /* must choose frags with end flags for ordering */
                                for( that = START; that <= smax[this]; that++ ) {
                                        if( singles [this][that].flags & LEND ) prime5 = that;
                                        else if( singles [this][that].flags & REND ) prime3 = that;
                                }
                        }

                        if( prime5 == EMPTY ) prime5 = 0;               /* largest frag is leftmost */
                        if( prime3 == EMPTY ) prime3 = 1;               /* next largest is rightmost */
                        return;
                }
        }
        else {

                for(this = START; this <= nsd; this++) connects[this] = FALSE;

                this = nobetter = EMPTY;

                while ( (this = common_digest(this+1)) != EMPTY ) {     /* find a single digest that connects to all others and has >=3 frags */
                        if( smax [this] > START+1 ) {                   /* this digest is just fine */
                                that = this;
                        }
                        else {
                                if( smax[this] > START ) nobetter = this;       /* this digest connects, but doesn't have enough frags */
```

```
                }
                connects [this] = TRUE;                                 /* record any digests that connect */
        }

        if( that != EMPTY ) {
                order_map = force_digest = that;        /* use the connecting digest to start */
                prime5 = 1;                             /* second largest frag is leftmost */
                prime3 = 2;                             /* next largest is rightmost */
                return;
        }

        if( nobetter != EMPTY ) {
                order_map = force_digest = nobetter;    /* use the connecting digest even though it can't prevent reversals */
                prime5 = prime3 = START;
                return;
        }

        for( this = START; this <= nsd; this++ ) {      /* see if any digest connects */
                if( connects[this] ) {
                        order_map = force_digest = this;
                        prime5 = prime3 = START;
                        return;
                }
        }

        printf("\n\n\007Not enough multiple digests to guarantee solution!\n\nHit a key to continue\n\n");
        getch();
        exit(1);
    }

    /* none of the single digests contain appropriate data for preventing reversals */
    force_digest = START;               /* well...just pick the first one then */
    prime5 = prime3 = START;            /* order is automatically enforced if both fragments are the same */
}
#include <stdio.h>

#define VAR extern

#include <rmap.h>

char *malloc();

heap *new(sd)    /* allocate a heap node pointing at the end of single digest map 'sd' */
int sd;
{
        heap *p;

        if( ( p = (heap *) malloc(sizeof(heap)) ) != NULL ) {
                p->s_digest = sd;
         p->s_pos.lo = sd_end [sd].lo;
         p->s_pos.hi = sd_end [sd].hi;
         p->s_pos.index = sd_end [sd].index;
         p->s_last.lo = last_end[sd].lo;
         p->s_last.hi = last_end[sd].hi;
         p->s_ref = ref_point;
         p->others = NULL;
         return( p );
    }
    else {
         printf("\n\007Panic! Memory allocation error for heap\n");
         exit(1);
    }
}

int old(p)              /* free a heap node */
heap *p;
{
    return( free( (char *) p ) );
}

void push(p)            /* push node list 'p' onto the heap */
heap *p;
{
    if(++heap_top < MAXDEPTH) {
         what_next [heap_top] = p;
    }
    else {
         printf("\n\007Panic! heap overflow (see programmer)\n");
         exit(1);
    }
}
```

```
boolean pop()           /* release a heap node from the top/head of heap */
{
        heap *p;

        if(heap_top > EMPTY) {
                if( (p = what_next [heap_top]) != NULL) {       /* traverse list */
                        if( p->others != NULL ) {
                                what_next [heap_top] = p->others;
                        }
                        else {
                                heap_top--;
                        }
                        old(p);
                        if(heap_top > EMPTY) return(TRUE);      /* something remains on heap */
                        return(FALSE);                          /* heap is empty */
                }
                else {
                        printf("\n\007Panic! Corrupt heap!");
                        exit(1);
                }
        }
        return(FALSE);                  /* heap is empty */
}

heap *look()    /* return a pointer to the top/head of the heap */
{
        if(heap_top > EMPTY) return(what_next[heap_top]);
        return(NULL);
}

boolean decisions()     /* return TRUE if there are no more growing point decisions */
{                       /* at the current heap level */
        if( look()->others == NULL ) return(TRUE);
        return(FALSE);
}
#include <stdio.h>

#define VAR extern

#include <rmap.h>
#include <matrix.h>

extern int ref_times;   /* number of recursions of least squares routine */

double dev_comp();
void disp_success();


boolean allset(a,p)     /* report TRUE when all members of array 'a' are set up to index 'p' */
int p, a[];
{
        for( ; p >= START; p-- ) if( a[p] == EMPTY ) return(FALSE);
        return(TRUE);
}

void to_l_mapper()      /* set up the data for the least squares module (linear) */
{
        int d, i, j;
        int mpos[MAXMUL], spos[MAXSIN], sp[MAXSIN], mp[MAXMUL];
        boolean foundinvert;


        foundinvert=FALSE;
        for( d = START; d <= nsd; d++) {
                spos[d] = nsd-1;
                sp[d] = EMPTY;

}
for( d = START; d <= nmd; d++) {
        mpos[d] = nsd-1;
        mp[d] = EMPTY;
}

init_mat(nsites);                       /* clear the matrix */

for(j = nsd; j <= heap_top; j++) {              /* insert fragment data in matrix */
        for( i = START; i <= nmd; i++ ) {                       /* scan multiples */
                if( ((j == heap_top) || (composition[i][what_next[j]->s_digest])) && (++mp[i] <= md_end[i]) ) {
                        if( multiples[i][md_map[i][mp[i]]].frag > multiples[i][md_map[i][mp[i]]].frag_error )          /* do not use measurements with 100% error */
                                in_mat(mpos[i]-nsd+1,j-nsd+1,multiples[i][md_map[i][mp[i]]].frag,nsites);
                        else {
                                if( vector[mpos[i]-nsd+1] > vector[j-nsd+1] ) {
                                        in_mat(mpos[i]-nsd+1,j-nsd+1,(SIZE) 1,nsites);
                                        foundinvert = TRUE;
```

```
                        }
                }
                mpos[i] = j;
        }
        }
        for( i = START; i <= nsd; i++ ) {                    /* scan singles */
                if( ((j == heap_top) || (what_next[j]->s_digest == i)) && (++sp[i] <= sd_end[i].index) ) {          /* this digest cuts here */
                        if( singles[i][sd_map[i][sp[i]]].frag > singles[i][sd_map[i][sp[i]]].frag_error )         /* do not use measurements with 100% error */
                                in_mat(spos[i]-nsd+1,j-nsd+1,singles[i][sd_map[i][sp[i]]].frag,nsites);
                        else {
                                if( vector[spos[i]-nsd+1] > vector[j-nsd+1] ) {
                                        in_mat(spos[i]-nsd+1,j-nsd+1,(SIZE) 1,nsites);
                                        foundinvert = TRUE;
                                }
                        }
                        spos[i] = j;
                }
        }
}
if( (vector[1] > 0.0) && !foundinvert ) {       /* this is the second recursion, but we didn't find the negative fragment in the data, invent some */
        for(i=1; i < nsites; i++) {             /* scan the vector looking for the inverted fragment */
                if( vector[i] < vector[i-1] ) break;    /* found it */
        }
        in_mat(i-1, i, (SIZE) 1, nsites);       /* force the reversal by inventing a small positive fragment */
}
if(gauss(nsites)) {             /* solve the system of equations */
        save_map(dev_comp(nsites,0));   /* compute, but don't display the deviation from measured data */
}
else fprintf(out,"\nPanic! Matrix is singular!\n");
}

void to_c_mapper()      /* set up the data for the least squares module (circular) */
{
        SIZE setms();
        heap *look();
        int save_digest;
        int d,i,j,stop;
        int ss[MAXSIN],ms[MAXMUL];
        int mpos[MAXMUL], spos[MAXSIN], sp[MAXSIN], mp[MAXMUL];
        boolean foundinvert;

        foundinvert = FALSE;
        save_digest = look()->s_digest;
        if( save_digest != force_digest ) {     /* top of heap must agree with other end of map otherwise many things break */
                look()->s_digest = force_digest;        /* force it temporarily */
        }

        init_mat(nsites);                       /* clear the matrix */

        setms(ss,ms,&stop);                             /* find start/end of all digests */

        for( i = START; i <= nsd; i++ ) {       /* adjust map markers for singles */
                ss[i]--;
                spos[i] = ss[i];
                sp[i] = EMPTY;
        }

        for( i = START; i <= nmd; i++ ) {               /* adjust map markers for multiples */
                ms[i]--;
                mpos[i] = ms[i];
                mp[i] = EMPTY;
        }

        for(j = START; j <= heap_top; j++) {                    /* get fragment data, first map cycle */
                for( i = START; i <= nmd; i++ ) {               /* scan multiples */
                        if( (ms[i] < j) && (composition[i][what_next[j]->s_digest]) && (++mp[i] <= md_end[i]) ) {
                                if( multiples[i][md_map[i][mp[i]]].frag > multiples[i][md_map[i][mp[i]]].frag_error )     /* do not use measurements with 100% error */
                                        in_mat(mpos[i]+1,(j==heap_top) ? 0 : j+1,multiples[i][md_map[i][mp[i]]].frag,nsites);
                                else {
                                        if( j != heap_top ) {
                                                if( vector [mpos[i]+1] > vector [j+1] ) {
                                                        in_mat(mpos[i]+1,j+1,(SIZE) 1,nsites);
                                                        foundinvert=TRUE;
                                                }
                                        }
                                }
```

```
                        mpos[i] = j;
                }
        }
        for( i = START; i <= nsd; i++ ) {                       /* scan singles */
                if( (ss[i] < j) && (what_next[j]->s_digest == i) && (++sp[i] <= sd_end[i].index) ) {            /* this digest cuts here */
                        if( singles[i][sd_map[i][sp[i]]].frag > singles[i][sd_map[i][sp[i]]].frag_error )               /* do not use measurements with 100% error */
                                in_mat(spos[i]+1,(j==heap_top) ? 0 : j+1,singles[i][sd_map[i][sp[i]]].frag,nsites);
                        else {
                                if( j != heap_top ) {
                                        if( vector [spos[i]+1] > vector [j+1] ) {
                                                in_mat(spos[i]+1,j+1,(SIZE) 1,nsites);
                                                foundinvert=TRUE;
                                        }
                                }
                        }
                        spos[i] = j;
                }
        }
}
for(j = START; j <= stop; j++) {                                /* print fragment data, overlap map cycle */
        for( i = START; i <= nmd; i++ ) {                       /* scan multiples */
                if( (j <= ms[i]) && (composition[i][what_next[j]->s_digest]) && (++mp[i] <= md_end[i]) ) {
                        if( multiples[i][md_map[i][mp[i]]].frag > multiples[i][md_map[i][mp[i]]].frag_error )           /* do not use measurements with 100% error */
                                in_mat(mpos[i]+1,j+1,multiples[i][md_map[i][mp[i]]].frag,nsites);
                        mpos[i] = j;
                }
        }
        for( i = START; i <= nsd; i++ ) {                       /* scan singles */
                if( (j <= ss[i]) && (what_next[j]->s_digest == i) && (++sp[i] <= sd_end[i].index) ) {           /* this digest cuts here */
                        if( singles[i][sd_map[i][sp[i]]].frag > singles[i][sd_map[i][sp[i]]].frag_error )               /* do not use measurements with 100% error */
                                in_mat(spos[i]+1,j+1,singles[i][sd_map[i][sp[i]]].frag,nsites);
                        spos[i] = j;
                }
        }
}
if( (vector[1] > 0.0) && !foundinvert ) {       /* this is the second recursion, but we didn't find the negative fragment in the data, invent some */
        for(i=START; i <= nsites; i++) {                /* scan the vector looking for the inverted fragment */
                if( vector[i+1] < vector[i] ) break;    /* found it */
        }
        if( i+1 == nsites ) in_mat(i,0, (SIZE) 1, nsites);       /* fragment spans starting point */
        else in_mat(i, i+1, (SIZE) 1, nsites);  /* force the reversal by inventing a small positive fragment */
}

if(gauss(nsites)) {                     /* solve the system of equations */
        save_map(dev_comp(nsites,0));   /* compute, but don't display the deviation from measured data */
}
else fprintf(out,"\nPanic! Matrix is singular!\n");

look()->s_digest = save_digest;
}

int digits(n)   /* return the number of digits in 'n' */
long n;
{
        int dc;

        for( dc=0; n > 0; dc++ ) n = n / 10L;
        return(dc);
}

void lnumprintf(f,wid,num,fill)         /* do fprintf() with left fill (Lattice doesn't) */
FILE *f;
int wid;
long num;
char fill;
{
        int size;
        char form[10];

        size = digits(num);                             /* how many digits in 'num' */
        for( ; wid > size; wid--) putc(fill,f);                 /* put in the left fill */
        sprintf(form,"%%%dld",wid);                     /* create the format string */
        fprintf(f,form,num);                            /* put in the number */
}

void to_map()
{
        if( linear ) to_l_mapper();
        else to_c_mapper();
```

```
}
void map_dump()           /* process an acceptable map */
{
        ref_times = 0;  /* this is the first time */

        init_voc(nsites);

        /* now do the least squares refinement */
        to_map();

        disp_success();          /* indicate that we have a map on screen */
}

void map_print()          /* display the map up to this point (it is effectively the heap) */
{
        if( linear ) lmap();
        else cmap();
}

lmap()            /* print a linear molecule map vertically */
{
        int i,j;
        int sp[MAXSIN],mp[MAXMUL];

        fprintf(out,"\n-----");
        for( i = START; i <= nmd; i++ ) {                 /* scan multiples */
                fprintf(out,"-------------");
        }
        fprintf(out,"---");
        for( i = START; i <= nsd; i++ ) {                 /* scan singles */
                fprintf(out,"----------");
        }
        fprintf(out,"\n map ");

                                              /* print names */
        for( i = START; i <= nmd; i++ ) {                 /* scan multiples */
                fprintf(out," %9s  ",mname[i]);
        }
        fprintf(out," ||");
        for( i = START; i <= nsd; i++ ) {                 /* scan singles */
                fprintf(out,"%6s    ",sname[i]);
        }
        fprintf(out,"\n-----");


        for( i = START; i <= nmd; i++ ) {                 /* scan multiples */
                fprintf(out,"-------------");
                mp[i] = EMPTY;
        }
        fprintf(out,"---");
        for( i = START; i <= nsd; i++ ) {                 /* scan singles */
                fprintf(out,"----------");
                sp[i] = EMPTY;
        }

        fprintf(out,"\n end ");
        for(i = START; i <= nmd; i++) {                   /* print the left end */
                fprintf(out," ___________");
        }
        fprintf(out," ||");
        for(i = START; i <= nsd; i++) {
                fprintf(out," ________");
        }
        putc('\n',out);


        for(j = nsd; j <= heap_top; j++) {                /* print fragment data */
                if(j == heap_top) fprintf(out," end ");
                else fprintf(out,"%4s ",sname[what_next[j]->s_digest]);
                for( i = START; i <= nmd; i++ ) {                 /* scan multiples */
                        if( ((j == heap_top) || (composition[i][what_next[j]->s_digest])) && (++mp[i] <= md_end[i]) ) {
                                putc('|',out);
                                lnumprintf(out,10,multiples[i][md_map[i][mp[i]]].frag,'_');
                                if(m_dup[i][md_map[i][mp[i]]]) putc('*',out);
                                else putc('_',out);
                        }
                        else fprintf(out,"            ");
```

```
        }
        fprintf(out," ||");
        for( i = START; i <= nsd; i++ ) {                    /* scan singles */
                if( ((j == heap_top) || (what_next[j]->s_digest == i)) && (++sp[i] <= sd_end[i].index) ) {          /* this digest cuts here */
                        fprintf(out," ");
                        lnumprintf(out,7,singles[i][sd_map[i][sp[i]]].frag,'_');
                        if(s_dup[i][sd_map[i][sp[i]]]) putc('*',out);
                        else putc('_',out);
                }
                else fprintf(out,"          ");
        }
        putc('\n',out);
    }

    fprintf(out,"------");
    for( i = START; i <= nmd; i++ ) {                /* scan multiples */
            fprintf(out,"-------------");
    }
    fprintf(out,"---");
    for( i = START; i <= nsd; i++ ) {                /* scan singles */
            fprintf(out,"----------");
    }
    putc('\n',out);
}

cmap()          /* print a circular molecule map vertically in unwrapped form...only works for complete maps */
{

    heap *look();
    int i,j,stop;
    int sp[MAXSIN],mp[MAXMUL];
    int ss[MAXSIN],ms[MAXMUL];
    for( i = START; i <= nsd; i++ ) {                /* clear map markers for singles */
            ss[i] = sp[i] = EMPTY;
    }
    ss[look()->s_digest] = START;

    for( i = START; i <= nmd; i++ ) {                /* clear map markers for multiples */
            ms[i] = mp[i] = EMPTY;
            if( composition[i][look()->s_digest] ) ms[i]= START;
    }

    for( stop = START; stop <= heap_top; stop++ ) {          /* scan heap for end of map */
            for( i = START; i <= nmd; i++ )
                    if( composition [i] [what_next[stop]->s_digest] )        /* multiple has a site here */
                            if( ms [i] == EMPTY ) ms [i] = stop+1;           /* this is the start/end */

            if( ss [what_next[stop]->s_digest] == EMPTY )   /* single digest starts/ends here */
                    ss [what_next[stop]->s_digest] = stop+1;

            if( allset(ss,nsd) && allset(ms,nmd) ) break;   /* found all the starts/ends...'stop' is set to last */
    }


    fprintf(out,"\n-----");
    for( i = START; i <= nmd; i++ ) {                /* scan multiples */
            fprintf(out,"-------------");
    }
    fprintf(out,"---");
    for( i = START; i <= nsd; i++ ) {                /* scan singles */
            fprintf(out,"----------");
    }
    fprintf(out,"\n map ");

                                                      /* print names */
    for( i = START; i <= nmd; i++ ) {                /* scan multiples */
            fprintf(out," %9s  ",mname[i]);
    }
    fprintf(out," ||");
    for( i = START; i <= nsd; i++ ) {                /* scan singles */
            fprintf(out,"%6s   ",sname[i]);
    }
    fprintf(out,"\n-----");

    for( i = START; i <= nmd; i++ ) {                /* scan multiples */
            fprintf(out,"-------------");
```

```
}
fprintf(out,"---");
for( i = START; i <= nsd; i++ ) {                /* scan singles */
        fprintf(out,"----------");
}

fprintf(out,"\n%4s ",sname[look()->s_digest]);
for(i = START; i <= nmd; i++) {                  /* print the left end...first site is top of heap */
        if( ms[i] == START ) fprintf(out," ____________");
        else fprintf(out,"      ..      ");
}
fprintf(out," ||");
for(i = START; i <= nsd; i++) {
        if( ss[i] == START ) fprintf(out," _________");
        else fprintf(out,"     .     ");
}
putc('\n',out);


for(j = START; j <= heap_top; j++) {                     /* print fragment data, first map cycle */
        fprintf(out,"%4s ",sname[what_next[j]->s_digest]);
        for( i = START; i <= nmd; i++ ) {                /* scan multiples */
                if( ms[i] == j+1 ) fprintf(out," ____________");
                else if( ms[i] > j+1 ) fprintf(out,"      ..      ");
                else if( (composition[i][what_next[j]->s_digest]) && (++mp[i] <= md_end[i]) ) {
                        putc(' ',out);
                        lnumprintf(out,10,multiples[i][md_map[i][mp[i]]].frag,'_');
                        if(m_dup[i][md_map[i][mp[i]]]) putc('*',out);
                        else putc('_',out);
                }
                else fprintf(out,"             ");
        }
        fprintf(out," ||");
        for( i = START; i <= nsd; i++ ) {                /* scan singles */
                if( ss[i] == j+1 ) fprintf(out," _________");
                else if( ss[i] > j+1 ) fprintf(out,"     .     ");
                else if( (what_next[j]->s_digest == i) && (++sp[i] <= sd_end[i].index) ) {       /* this digest cuts here */
                        fprintf(out," ");
                        lnumprintf(out,7,singles[i][sd_map[i][sp[i]]].frag,'_');
                        if(s_dup[i][sd_map[i][sp[i]]]) putc('*',out);
                        else putc('_',out);
                }
                else fprintf(out,"          ");
        }
        putc('\n',out);
}

for(j = START; j <= stop; j++) {                         /* print fragment data, overlap map cycle */
        fprintf(out,"%4s ",sname[what_next[j]->s_digest]);
        for( i = START; i <= nmd; i++ ) {                /* scan multiples */
                if( j >= ms[i] ) fprintf(out,"      ..      ");

                        else if( (composition[i][what_next[j]->s_digest]) && (++mp[i] <= md_end[i]) ) {
                                putc(' ',out);
                                lnumprintf(out,10,multiples[i][md_map[i][mp[i]]].frag,'_');
                                if(m_dup[i][md_map[i][mp[i]]]) putc('*',out);
                                else putc('_',out);
                        }
                        else fprintf(out,"             ");
                }
                fprintf(out," ||");
                for( i = START; i <= nsd; i++ ) {        /* scan singles */
                        if( j >= ss[i] ) fprintf(out,"     .     ");
                        else if( (what_next[j]->s_digest == i) && (++sp[i] <= sd_end[i].index) ) {       /* this digest cuts here */
                                fprintf(out," ");
                                lnumprintf(out,7,singles[i][sd_map[i][sp[i]]].frag,'_');
                                if(s_dup[i][sd_map[i][sp[i]]]) putc('*',out);
                                else putc('_',out);
                        }
                        else fprintf(out,"          ");
                }
                putc('\n',out);
        }

        fprintf(out,"------");
        for( i = START; i <= nmd; i++ ) {                /* scan multiples */
                fprintf(out,"-------------");
        }
        fprintf(out,"---");
        for( i = START; i <= nsd; i++ ) {                /* scan singles */
                fprintf(out,"----------");
        }
        putc('\n',out);
```

```
}

trace()            /* print digest status */
{

        int i,j;
        heap *p;

        printf("********************************\n");
        printf("nsd = %d, msd = %d\n",nsd,nmd);
        for(i=START; i <= nmd; i++) {
                printf("%10s | mptr(%d) free( ",mname[i],mptr[i]);
                for(j=START; j <= mmax[i]; j++)
                        if(multiples [i][j].used == FREE) printf("%d ",j);
                if( md_off[i] != EMPTY ) printf(")    offset (%ld)\n", md_offlen[i]);
                else printf(")\n");
        }
        for(i=START; i <= nsd; i++) {
                printf("%10s | sptr(%d) free( ",sname[i],sptr[i]);
                for(j=START; j <= smax[i]; j++)
                        if(singles [i][j].used == FREE) printf("%d ",j);
                printf(") end(%ld..%ld) index(%d)",sd_end[i].lo,sd_end[i].hi,sd_end[i].index);
                if( sd_mdoff[i] != EMPTY ) printf("    offset (%ld)\n", sd_offlen[i]);
                else printf("\n");
        }
        printf("reference point = %ld\nheap( ", ref_point);
        for(i=START; i <= heap_top; i++) {
                if(what_next[i]->others) {
                        printf("[ ");
                        for( p = what_next[i]; p; p = p->others ) {
                                printf("%s ",sname[p->s_digest]);
                        }
                        printf("] ");
                }
                else {
                        printf("%s ",sname[what_next[i]->s_digest]);
                }
        }
        printf(")\n");
        printf("********************************\n");

}
#include <stdio.h>

#define VAR extern

#include <rmap.h>
#include <matrix.h>

#define SCALE 72                 /* number of columns in which to scale the pseudo-graphic map */
#define DIVISIONS 10.0           /* maximum number of divisions on the scaled map */
#define SCALEFACTOR 1000.0       /* units on scale are kilobases */

boolean allset();
double fabs();

extern int rejectflag;           /* flag used to broadcast refinement errors to other modules */

void in_mat(ls,rs,len,n)         /* place one fragment into matrix */
int ls,rs,n;
SIZE len;
{
        float term,term2;

        if(traceflag) printf("\ninserting fragment (%d,%d) of length %ld into matrix",ls,rs,len);

        term = 1.0 / (float) len;
        term2 = term / (float) len;

        matrix [ls] [rs]        -= term2;
        matrix [rs] [rs]        += term2;
        matrix [ls] [ls]        += term2;
        matrix [rs] [ls]        -= term2;

        matrix [ls] [n]                 -= term;
        matrix [rs] [n]                 += term;

        if( ls < rs ) return;

        matrix [ls] [n-1]       -= term2;
        matrix [rs] [n-1]       += term2;
        matrix [n-1] [rs]       += term2;
        matrix [n-1] [ls]       -= term2;
```

```
        matrix [n-1] [n]          += term;
        matrix [n-1] [n-1]        += term2;

}

void init_mat(n)          /* clear the matrix */
int n;
{
        int i,j;

        for( j = 0; j <= n; j++ )
                for( i = 0; i < n; i++ )
                        matrix [i] [j] = 0.0;

}

void init_vec(n)          /* clear the result vector */
int n;
{
        int i;

        for( i=0; i<=n; i++ ) vector [i] = 0.0;
}

double dev_term(ls,rs,len,err,verbose)   /* compute one deviation term from 'vector' */
int ls,rs,verbose;
SIZE len,err;
{
        double dif;             /* this version weights the deviation terms by 1/(fragment error) */

        if( ls < rs ) {
                dif = ((double) len - vector [rs] + vector [ls]);
                if(verbose) fprintf(out,"%10ld%10.0f%10.1lf %%\n", len, (vector[rs] - vector[ls]), (- (dif * (double) 100.0 / (double) len)) );
        }
        else {  /* fragment spans origin */
                dif = len - vector [rs] + vector [ls] - vector[nsites];
                if(verbose) fprintf(out,"%10ld%10.0f%10.1lf %%\n", len, (vector[rs] + vector[nsites] - vector[ls]), (- (dif * (double) 100.0 / (double) len)) );
        }

/* This seems to be rejecting too many things-------------------------------
        if( fabs(dif) > (double) err ) rejectflag = TRUE;       /* reject this map since these deviations exceed the error specified */
                                                                /* this situation occurs when many multiples individually add up to their corresponding singles */
                                                                /* but when cross referenced they contradict somewhere (combinations not examined by the algorithm) */
----------------------------------------------------------------------------- */

/*----------------------weighting factor is inversely proportional to specified error
        if( err > (double) 0.0 ) dif /= (double) err;
------------- */

        dif = dif / (double) len;

        if(traceflag) printf("\nfrag (%d,%d) old len = %ld, new len = %6.0f, dif = %6.0lf\n", ls, rs, len, ( rs > ls) ? (vector [rs] - vector [ls]) : (vector[rs] +
                                                                                                                                  vector[nsites] - vector
        return( dif * dif );
}

double dev_l_comp(n,verbose)     /* compute and display the deviation (linear) */
int n,verbose;
{
        int i, j, nfrags;
        int mpos[MAXMUL], spos[MAXSIN], sp[MAXSIN], mp[MAXMUL];
        double deviation;
        double sqrt();

        for( i = START; i <= nsd; i++) {
                sp[i] = EMPTY;
                spos[i] = nsd-1;
        }
        for( i = START; i <= nmd; i++) {
                mp[i] = EMPTY;
                mpos[i] = nsd-1;
        }

        deviation = (double) 0.0;
        nfrags = 0;

        if(verbose) fprintf(out,"\n     Digest       Enzymes       Measured  Computed    %% Error\n");
```

```
for(j = nsd; j <= heap_top; j++) {                /* insert fragment data in matrix */
        for( i = START; i <= nmd; i++ ) {                    /* scan multiples */
                if( ((j == heap_top) || (composition[i][what_next[j]->s_digest])) && (++mp[i] <= md_end[i]) ) {
                        if(verbose) fprintf(out,"%12s   %4s - %4s  ", mname[i], (mpos[i] == EMPTY) ? " end" : sname[what_next[mpos[i]]->s_digest],
                                (j == heap_top) ? " end" : sname[what_next[j]->s_digest]);
                        deviation += dev_term(mpos[i]-nsd+1,j-nsd+1,multiples[i][md_map[i][mp[i]]].frag,multiples[i][md_map[i][mp[i]]].frag_error,verbose);
                        mpos[i] = j;
                        nfrags++;
                }
        }
        for( i = START; i <= nsd; i++ ) {                    /* scan singles */
                if( ((j == heap_top) || (what_next[j]->s_digest == i)) && (++sp[i] <= sd_end[i].index) ) {             /* this digest cuts here */
                        if(verbose) fprintf(out,"%12s   %4s - %4s  ", sname[i], (spos[i] == EMPTY) ? " end" : sname[i], (j == heap_top) ? " end" : sname[i]);
                        deviation += dev_term(spos[i]-nsd+1,j-nsd+1,singles[i][sd_map[i][sp[i]]].frag,singles[i][sd_map[i][sp[i]]].frag_error,verbose);
                        spos[i] = j;
                        nfrags++;
                }
        }
}

deviation = sqrt( deviation / ((double) nfrags * (double) nfrags) );

return( deviation );
}

double dev_c_comp(n,verbose)      /* compute and display the deviation (circular) */
int n,verbose;
{
        int i, j, nfrags;
        int stop;
        int ss[MAXSIN],ms[MAXMUL];
        int mpos[MAXMUL], spos[MAXSIN], sp[MAXSIN], mp[MAXMUL];
        double deviation;
        double sqrt();
        SIZE setms();
        heap *look();

        deviation = (double) 0.0;
        nfrags = 0;

        if(verbose) fprintf(out,"\n     Digest       Enzymes       Measured  Computed    %% Error\n");

        setms(ss,ms,&stop);                              /* find start/end of all digests */

        for( i = START; i <= nsd; i++ ) {         /* adjust map markers for singles */
                ss[i]--;
                spos[i] = ss[i];
                sp[i] = EMPTY;
        }

        for( i = START; i <= nmd; i++ ) {                /* adjust map markers for multiples */
                ms[i]--;
                mpos[i] = ms[i];
                mp[i] = EMPTY;
        }

        for(j = START; j <= heap_top; j++) {                 /* get fragment data, first map cycle */
                for( i = START; I <= nmd; i++ ) {            /* scan multiples */
                        if( (ms[i] < j) && (composition[i][what_next[j]->s_digest]) && (++mp[i] <= md_end[i]) ) {
                                if(verbose) fprintf(out,"%12s   %4s - %4s  ", mname[i], (mpos[i] == EMPTY) ? " end" : sname[what_next[mpos[i]]->s_digest],
                                        (j == heap_top) ? " end" : sname[what_next[j]->s_digest]);
                                deviation += dev_term(mpos[i]+1,(j==heap_top) ? 0 : j+1,multiples[i][md_map[i][mp[i]]].frag,multiples[i][md_map[i][mp[i]]].frag_error,
                                                                                                                                                    verbose);
                                mpos[i] = j;
                                nfrags++;
                        }
                }

                for( i = START; i <= nsd; i++ ) {            /* scan singles */
                        if( (ss[i] < j) && (what_next[j]->s_digest == i) && (++sp[i] <= sd_end[i].index) ) {          /* this digest cuts here */
                                if(verbose) fprintf(out,"%12s   %4s - %4s  ", sname[i], (spos[i] == EMPTY) ? sname[look()->s_digest] : sname[i], sname[i]);
                                deviation += dev_term(spos[i]+1,(j==heap_top) ? 0 : j+1,singles[i][sd_map[i][sp[i]]].frag,singles[i][sd_map[i][sp[i]]].frag_error,verbose);
                                spos[i] = j;
                                nfrags++;
                        }
                }
        }
```

```
for(j = START; j <= stop; j++) {                        /* print fragment data, overlap map cycle */
        for( i = START; i <= nmd; i++ ) {               /* scan multiples */
                if( (j <= ms[i]) && (composition[i][what_next[j]->s_digest]) && (++mp[i] <= md_end[i]) ) {
                        if(verbose) fprintf(out,"%12s   %4s - %4s  ", mname[i], (mpos[i] == EMPTY) ? " end" : sname[what_next[mpos[i]]->s_digest],
                                (j == heap_top) ? " end" : sname[what_next[j]->s_digest]);
                        deviation += dev_term(mpos[i]+1,(j==heap_top) ? 0 : j+1,multiples[i][md_map[i][mp[i]]].frag,multiples[i][md_map[i][mp[i]]].frag_error,verbose);
                        mpos[i] = j;
                        nfrags++;
                }
        }

        for( i = START; i <= nsd; i++ ) {               /* scan singles */
                if( (j <= ss[i]) && (what_next[j]->s_digest == i) && (++sp[i] <= sd_end[i].index) ) {          /* this digest cuts here */
                        if(verbose) fprintf(out,"%12s   %4s - %4s  ", sname[i], (spos[i] == EMPTY) ? sname[look()->s_digest] : sname[i], sname[i]);
                        deviation += dev_term(spos[i]+1,(j==heap_top) ? 0 : j+1,singles[i][sd_map[i][sp[i]]].frag,singles[i][sd_map[i][sp[i]]].frag_error,verbose);
                        spos[i] = j;
                        nfrags++;
                }
        }
}

        deviation = sqrt( deviation / ((double) nfrags * (double) nfrags) );

        return( deviation );
}

double dev_comp(n,verbose)      /* compute and display deviation */
int n,verbose;
{
        rejectflag = FALSE;     /* innocent until proven guilty */

        if( linear ) return( dev_l_comp(n,verbose) );
        return( dev_c_comp(n,verbose) );
}

void breakout(n)        /* extract a vector from the last column of 'matrix', */
int n;                  /* put it in 'vector' and adjust to begin at zero */
{
        int i,j;
        float leftend;

        vector [col [n-1]] = matrix [row [n-1]] [col [n]];

        for( i = n-2; i >= 0; i-- ) {
                vector [col [i]] = matrix [row [i]] [col [n]];
                for( j = n-1; j > i; j-- )
                        vector [col [i]] -= matrix [row [i]] [col [j]] * vector [col [j]];
        }

        for( leftend = vector [0], i = 0; i < n; i++ )
                vector [i] -= leftend;

        vector[n] = vector[n-1] + leftend;
}

boolean gauss(n)        /* solve the system of 'n' equations in 'matrix' */
int n;                  /* using Gaussian elimination */
{
        int i, j, k;    /* loop indices */
        double pivot;   /* current largest term */
        int pr, pc;     /* row and column of pivot */
        int swap;       /* place to exchange row/column pointers */

        for( i = 0; i <= n; i++ ) row [i] = col [i] = i;        /* initialize row/column pointers */

        for( k = 0; k < n; k++ ) {                                      /* main loop */

                pivot = 0.0;

                for( i = k; i < n; i++ ) {                              /* select pivot */
                        for( j = k; j < n; j++ ) {
                                if( pivot < fabs( matrix [row [i]] [col [j]] ) ) {
                                        pivot = fabs( matrix [row [i]] [col [j]] );
                                        pr = i;
                                        pc = j;
                                }
                        }
                }
```

```
		if( (pivot = matrix [row [pr]] [col [pc]]) == (double) 0.0 ) return(FALSE);	/* singular matrix */

		swap = col [pc];	col [pc] = col [k];	col [k] = swap;
		swap = row [pr];	row [pr] = row [k];	row [k] = swap;

		for( j = k+1; j <= n; j++ ) {					/* divide by pivot */
			if( matrix [row [k]] [col [j]] != 0.0 ) {		/* but not if zero */
				matrix [row [k]] [col [j]] = matrix [row [k]] [col [j]] / pivot;
			}
		}

		if( k == n-1 ) {	/* done...break out the vector */
			breakout(n);
			return(TRUE);
		}

		for( i = k+1; i < n; i++ ) {	/* subtract pivot equation */
			for( j = k+1; j <= n; j++ ) {
				if( matrix [row [k]] [col [j]] != 0.0 )
					matrix [row [i]] [col [j]] -= matrix [row [i]] [col [k]] * matrix [row [k]] [col [j]];
			}
		}
	}
	return(FALSE);	/* we should never end here */
}

void dup(s,c,n)		/* flush 'n' copies of character 'c' into buffer 's' */
char *s,c;
int n;
{
	while( n-- > 0 ) *s++ = c;
	*s = NULL;	/* null terminate as a convenience */
}

void cpnum(s,n)	/* put a float 'n' into a buffer 's' */
char *s;
double n;
{
	char *p, temp[10];

	if( n > 1.0 ) sprintf(temp,"%.0lf",n);
	else sprintf(temp,"%3.1lf",n);

	p = temp;
	while( *p ) *s++ = *p++;
}

int cdigits(n)	/* compute the number of digits to print for a float */
float n;
{
	int i;

	if( n < 1.0 ) return(3);
	for( i = 1; n > 1.0; i++ ) n /= 10.0;
	return(i);
}

void center(s,p,val,denom,field)		/* insert a floating point number 'val' into string 's' */
char *s;					/* centered around position 'p' and scaled by 'denom' */
int p,field;
double val,denom;
{
	val /= denom;				/* compute the number to print */
	if( (p = p - (cdigits(val) >> 1)) < 0 ) p = 0;	/* compute the beginning of the number */
	cpnum(&s[p], val);			/* put in the number */
}

SIZE setms(ss,ms,maxp)		/* set the end position for each digest */
int ss[MAXSIN],ms[MAXMUL];
int *maxp;
{
	heap *look();
	int i,j;

	for( i=START; i <= nsd; i++ ) ss[i] = EMPTY;	/* clear start indices */
	for( i=START; i <= nmd; i++ )
		if( composition[i][look()->s_digest] ) ms[i] = START;
		else ms[i] = EMPTY;

	ss[look()->s_digest] = START;			/* zero point */
```

```
	for(*maxp = i = START; i <= heap_top; i++ ) {			/* scan heap */
		for(j = START; j <= nmd; j++ ) {		/* scan multiples */
			if( composition [j][what_next[i]->s_digest]
				&& ( ms[j] == EMPTY ) ) ms[j] = i+1;
		}
		if( ss[what_next[i]->s_digest] == EMPTY ) {
			ss[what_next[i]->s_digest] = i+1;
			*maxp = i;
		}
		if( allset(ss,nsd) && allset(ms,nmd) ) break;
	}

	return( ave_len );
}

void scale_map(n)		/* print a scaled pseudo-graphic map */
int n;
{
	if( linear ) l_scale_map(n);
	else c_scale_map(n);
}

void l_scale_map(n)		/* print a linear map in scaled pseudo-graphic form */
int n;
{
	int sd, h;
	float units, tick, iunits, hunits;
	char smap[SCALE+5];

	putc('\n',out);

	for( sd = START; sd <= nsd; sd++ ) {				/* scan singles */
		dup(smap,'-',SCALE);					/* clear the map buffer */
		for( h = nsd; h < heap_top; h++ ) {			/* scan the map */
			if( what_next[h]->s_digest == sd ) {		/* the digest cuts here */
				smap [(int) ( ((double) SCALE * vector [h-nsd+1]) / vector [n-1] )] = '+';		/* show a cut */
			}
		}
		fprintf(out,"%4s |%s|\n", sname [sd], smap);
	}

	dup(smap,'-',SCALE);

	for( units = 100.0; vector [n-1] / units > DIVISIONS; units *= 10.0 );
	iunits =  (double) SCALE * units / vector [n-1];
	for( tick = iunits; (int) tick <= SCALE; tick += iunits) smap [(int) tick] = '^';

	fprintf(out,"scale|%s|\n", smap);

	dup(smap,' ',SCALE);

	for( hunits = iunits, tick = units; (int) hunits <= SCALE; hunits += iunits ) {
		center( smap, (int) hunits, tick, SCALEFACTOR, 5 );
		tick += units;
	}
	fprintf(out," kb  |%s|\n", smap);

	dup(smap,'-',SCALE);
	center( smap, SCALE>>1, vector [n-1], 1.0, 15 );
	fprintf(out,"size |%s|\n\n", smap);
}

void c_scale_map(n)		/* print a circular map in scaled pseudo-graphic form */
int n;
{
	int sd, h, stop, i, q;
	float units, tick, iunits, hunits;
	char smap[SCALE+5], mark;
	int ss[MAXSIN],ms[MAXMUL];
	float maplen;

	setms(ss,ms,&stop);			/* find sites involved in overlap and compute total length */
	maplen = vector[n] + vector[stop+1];	/* map extends more than once around circle */

	q = SCALE - 2;

	putc('\n',out);

	for( sd = START; sd <= nsd; sd++ ) {				/* scan singles */
		dup(smap,'-',SCALE);					/* clear the map buffer */
		i = EMPTY;
		if( what_next[heap_top]->s_digest == sd ) {		/* this digest starts map */
			i = START;
			smap[i] = '|';
```

```
        }
        for( h = START; h <= heap_top; h++ ) {          /* scan the map */
                if( what_next[h]->s_digest == sd ) {    /* the digest cuts here */
                        if( i < START ) {               /* first site from this digest */
                                mark = '|';
                                i = (int) ( ((double) SCALE * vector [h+1]) / maplen );
                                dup(smap,'.',i);
                        }
                        else {
                                mark = '+';
                                i = (int) ( ((double) SCALE * vector [h+1]) / maplen );
                        }
                        smap [i] = mark;        /* show a cut */
                }
        }
        for( h = START; h <= stop; h++ ) {              /* scan the map overlap */
                if( what_next[heap_top]->s_digest == sd ) {     /* end of map */
                        i = (int) ( ((double) SCALE * vector [n]) / maplen );
                        smap [i] = '|';
                        dup( &smap [i+1], '.', q - i + 1 );
                        break;
                }

                if( what_next[h]->s_digest == sd ) {    /* the digest cuts here */
                        if( h +1 == ss[sd] ) {          /* last site from this digest */
                                mark = '|';
                                if( (i = (int) ( ((double) SCALE * (vector [h+1] + vector[n])) / maplen )) >= SCALE ) i = SCALE-1;
                                dup( &smap[i+1],'.',q - i + 1 );
                                smap[i] = mark;
                                break;
                        }
                        else {
                                mark = '+';
                                i = (int) ( ((double) SCALE * (vector [h+1] + vector[n])) / maplen );
                        }
                        smap [i] = mark;        /* show a cut */
                }
        }
        smap [SCALE] = NULL;
        fprintf(out,"%4s %s\n", sname [sd], smap);
    }
    dup(smap,'-',q);

    for( units = 100.0; maplen / units > DIVISIONS; units *= 10.0 );
    iunits =  (double) q * units / maplen;
    for( tick = iunits; (int) tick < q; tick += iunits) smap [(int) tick] = '^';

    fprintf(out,"scale|%s|\n", smap);

    dup(smap,' ',q);

    for( hunits = iunits, tick = units; (int) hunits < q; hunits += iunits ) {
            center( smap, (int) hunits, tick, SCALEFACTOR, 5 );
            tick += units;
    }
    fprintf(out," kb  |%s|\n", smap);

    i = (int) ( ((double) SCALE * vector [n]) / maplen ) - 1;
    dup(smap,'-',i);
    center( smap, i>>1, vector [n], 1.0, 15 );
    fprintf(out,"size |%s|\n", smap);

    dup(&smap[i-1],'-',q-i-1);
    dup(smap,' ',i-2);
    smap[i-2] = '|';
    cpnum( smap, maplen - vector[n] );
    fprintf(out,"overlap %s|\n\n", smap);
}
#include <stdio.h>
#define VAR extern

#include <rmap.h>
#include <matrix.h>

int rejectflag;             /* global flag used to communicate with 'refine' module */

#define MAXREFINE 2         /* maximum number of recursions for least squares refinement */
int ref_times;              /* global counter for number of refinements */
```

```
boolean same_map();
heap *look();

boolean order_correct(n)          /* are the vector values in increasing order from 0..n */
int n;
{
        int i;

        if( !linear ) ++n;        /* include the whole circle */

        for( i=1; i < n; i++ ) {
                if(traceflag) printf("\n%6.0f < %6.0f\n",vector[i-1],vector[i]);
                if( vector[i] < vector[i-1] ) return(FALSE);
        }
        return(TRUE);
}

bump(p)             /* move save data from insertion point back */
int p;
{
        int q;

        for( q = max_score; q > p; q-- ) {
                map_score [q] = map_score [q-1];
                position [q] = position [q-1];
        }
}

int next_spot()           /* find the least valuable or an empty spot in archive file */
{
        if( max_score < MAXVIEW-1 ) max_score++;          /* more room */
        return( position [max_score] );
}

int bsins(dev)            /* return an insertion point in array map_score */
double dev;               /* using a binary search */
{
        int p,q,pp;
        float dt;

        for( dt = (float) dev, p = START, q = max_score; q != p+1; ) {

                pp = (p+q) >> 1;                          /* cut remaining partition in half */
                if( dt > map_score [pp] ) p = pp;         /* decide which half contains 'dev' */
                else q = pp;

        }
        return(q);
}

double fabs();

boolean same_score(x,y)  /* return TRUE if the floats x and y are very close (equal) */
double x,y;
{
        if( fabs( x-y ) <= 1.0E-6 ) return(TRUE);
        return(FALSE);
}

int in_view(dev)          /* return an ordered array position for score 'dev' or EMPTY */
double dev;
{
        int p;

        if( (max_score < START) ||                                  /* nothing saved yet */
                ( (float) dev <= map_score [START]) ) {
                        if( same_score(dev, (double) map_score [START]) ) {
                                If( same_map(START) ) return(EMPTY);               /* duplicate score indicates doublet permutation */
                        }
                        return(START);                      /* best score so far */
        }

        if( (float) dev >= map_score [max_score] ) {                 /* worst score so far */
                if( max_score >= MAXVIEW-1 ) return(EMPTY);          /* no room */
                if( same_score(dev, (double) map_score [max_score]) ) {              /* another permutation? */
                        If( same_map(max_score) ) return(EMPTY);
                }
                return(max_score+1);
        }

        p = bsins(dev);                 /* do a binary search for the position */

        if( same_score(dev, (double) map_score[p]) ) {
                If( same_map(p) ) return(EMPTY);         /* duplicate score indicates a doublet permutation */
```

```
	}
	return(p);
}

void save_map(dev)		/* archive the current map if 'dev' is small enough */
double dev;
{
	int pos, filepos;

/* must review this method of rejection...don't use for now
	if(rejectflag) return;	whoops...no we don't, it's not internally consistent */

	if( !order_correct(nsites) ) {
		if( ++ref_times < MAXREFINE ) to_map();
		return;		/* inverted sites indicate internal inconsistency ... re-run the refinement */
	}

	n_maps++;		/* we have another map */

	if( (pos = in_view(dev)) > EMPTY ) {	/* it's a good score */
		filepos = next_spot();		/* find a place in the archive file */
		bump(pos);			/* shift the other maps into position */
		map_score [pos] = (float) dev;	/* record score and file position */
		position [pos] = filepos;
		archive(filepos);		/* write the map to disk */
	}
}

archive(pos)	/* dump the current map to archive file at block number 'pos' */
int pos;
{
	int i;

	fseek(arch, filespace * (long) pos, 0);

	fwrite( (char *) vector, sizeof(float), nsites+1, arch );

	for( i = (linear) ? nsd : START; i <= heap_top; i++ )
		fwrite( (char *) &(what_next [i]->s_digest), sizeof(int), 1, arch );

	for( i = START; i <= nsd; i++ ) {
		fwrite( (char *) sd_map [i], sizeof(int), smax [i]+1, arch );
	}

	for( i = START; i <= nmd; i++ ) {
		fwrite( (char *) md_map [i], sizeof(int), mmax [i]+1, arch );
	}

}

boolean pop();

free_heap()	/* re-allocate all current heap nodes */
{
	while( pop() );
}

heap *new();


boolean same_map(pos)	/* inspect the map from archive file at block number 'pos' */
int pos;		/* return TRUE if maps agree other than identical fragments */
{
	int i,j,s,heapsize;


	pos = position [pos];

		/* seek past the vector part */

	fseek(arch, (filespace * (long) pos) + ( ((long) nsites+1L) * sizeof(float)), 0);

	if(linear) heapsize = nsites+nsd-1;
	else heapsize = nsites;

	for( i = (linear) ? nsd : START; i < heapsize; i++ ) {			/* compare site order */
		fread( (char *) &s, sizeof(int), 1, arch );
		if( linear && (i == heapsize-1) ) break;
		if( s != what_next[i]->s_digest ) return(FALSE);
	}
```

```
	for( i = START; i <= nsd; i++ ) {		/* compare all single digest frags */
		for( j=START; j <= smax[i]; j++ ) {
			fread( (char *) &s, sizeof(int), 1, arch );
			if( !s_dup[i][sd_map[i][j]] && (s != sd_map[i][j]) ) return(FALSE);
		}
	}

	for( i = START; i <= nmd; i++ ) {		/* compare all multiple digest frags */
		for( j=START; j <= mmax[i]; j++ ) {
			fread( (char *) &s, sizeof(int), 1, arch );
			if( !m_dup[i][md_map[i][j]] && (s != md_map[i][j]) ) return(FALSE);
		}
	}

	return(TRUE);	/* maps agree */

extern char fofname[];
extern char indname[];

save_ind()	/* write the map index to 'rmap.ind' */
{
	FILE *f;
	int i;

	if( f = fopen(indname,"w") ) {
		fprintf(f,"%ld %d %d %d\n",n_maps,hours,minutes,seconds);
		fprintf(f,"%d\n", max_score);
		for(i=0; i <= max_score; i++ )
			fprintf(f,"%4d %12.6f\n", position[i], map_score[i]);
		fclose(f);
	}
}

extern int revflag;

review()	/* process the summary output */
{
	int c;

	save_ind();	/* write the map index */

	printf("\nTotal number of maps generated: %ld\nNumber of maps saved for review: %d\n",n_maps,max_score+1);

	if(max_score < 0) {
		printf("\nBetter luck next time.\n");
		exit(2);
	}
}
#include <stdio.h>

#define VAR extern	/* not the main module */

#include <rmap.h>

void init()	/* initialize all map and digest pointers to show empty */
{
	int i,j;

	for(i=0; i < MAXSIN; i++) {
		sd_mdoff [i] = sd_mdfrag [i] = EMPTY;
		sptr [i] = START;
		smax [i] = EMPTY;
		*sname [i] = NULL;
		sd_end [i].index = EMPTY;
		sd_end [i].lo = sd_end [i].hi = (SIZE) 0;
		s_endflag [i] = (CLUE) NONE;
		for(j=0; j < MAXMAP; j++) {
			singles [i] [j].used = FREE;
			s_dup [i] [j] = START;
			singles [i] [j].flags = (CLUE) NONE;
		}
	}

	for(i=0; i < MAXMUL; i++) {
		md_off [i] = md_frag [i] = EMPTY;
		mptr [i] = START;
		mmax [i] = EMPTY;
		*mname [i] = NULL;
		md_end [i] = EMPTY;
		m_endflag [i] = (CLUE) NONE;
		for(j=0; j < MAXSIN; j++) {
			composition [i] [j] = FALSE;
```

```
	}
	for(j=0; j < MAXMAP; j++) {
		multiples [i] [j].used = FREE;
		m_dup [i] [j] = START;
		multiples [i] [j].flags = (CLUE) NONE;
	}
	}
/*
	hi_factor = lo_factor = (SIZE) 10;	/* set error at 10% */
*/
	ref_point = (SIZE) 0;

	for( i = START; i < MAXVIEW; i++ ) position [i] = i;	/* set up initial file positions */

}

#define TBUF 80

int dcomp(f1,f2)			/* compare the sizes of fragments stored in nodes 'f1','f2' */
digest *f1,*f2;
{
	if (f2->frag > f1->frag) return(1);
	if (f2->frag < f1->frag) return(-1);
	return(0);
}

char *scan_past(p,c)			/* scan past the first occurrence of char 'c' in string 'p' */
char *p,c;
{
	while(*p) {
		if( *p == c) return(++p);
		++p;
	}
	return(p);
}

get_project(pn)			/* read in a project from file 'pn' */
char *pn;
{
	FILE *f;
	char *p;
	char b[TBUF],clu[TBUF];
	int i,j,t;

	if( f = fopen(pn,"r") ) {

		init();

		fgets(b,TBUF,f);
		trim(b);
		strcpy(comment,b);

		fgets(b,TBUF,f);
		if( toupper( b[0] ) == 'L' ) linear = TRUE; else linear = FALSE;

		fgets(b,TBUF,f);
		sscanf(b,"%d",&nmd);

		for(i=START; i<=nmd; i++) {

			fgets(b,TBUF,f);
			trim(b);
			strcpy(mname[i],b);

			fgets(b,TBUF,f);
			sscanf(b,"%d",&mmax[i]);

			for(j=START; j<=mmax[i]; j++) {
				fgets(b,TBUF,f);
				clu[0] = NULL;
				sscanf(b,"%ld, %ld, %s",&multiples[i][j].frag,&multiples[i][j].frag_error,clu);
				p = clu;
				while( *p ) {
					switch( toupper(*p++) ) {
					case 'A':	/* auto new frag */
					case 'N':	/* new frag */
						multiples[i][j].flags  |= (CLUE) NEW;
						break;
					case 'E':	/* any end */
						multiples[i][j].flags |= (CLUE) END;
						m_endflag[i] |= (CLUE) END;
						break;
```

```
                    case 'L':       /* left end */
                            multiples[i][j].flags |= (CLUE) LEND;
                            m_endflag[i] |= (CLUE) LEND;
                            break;
                    case 'R':       /* right end */
                            multiples[i][j].flags |= (CLUE) REND;
                            m_endflag[i] |= (CLUE) REND;
                            break;
                    }
                }

                mfrags++;
            }
        }

        fgets(b,TBUF,f);
        sscanf(b,"%d",&nsd);

        for(i=START; i<=nsd; i++) {

            fgets(b,TBUF,f);
            trim(b);
            strcpy(sname[i],b);

            fgets(b,TBUF,f);
            sscanf(b,"%d",&smax[i]);

            for(j=START; j<=smax[i]; j++) {
                fgets(b,TBUF,f);
                clu[0] = NULL;
                sscanf(b,"%ld, %ld, %s",&singles[i][j].frag,&singles[i][j].frag_error,clu);
                p = clu;
                while( *p ) {
                    switch( toupper(*p++) ) {
                    case 'C':
                        singles[i][j].flags |= (CLUE) CUT;
                        break;
                    case 'E':       /* any end */
                        singles[i][j].flags |= (CLUE) END;
                        s_endflag[i] |= (CLUE) END;
                        break;
                    case 'L':       /* left end */
                        singles[i][j].flags |= (CLUE) LEND;
                        s_endflag[i] |= (CLUE) LEND;
                        break;
                    case 'R':       /* right end */
                        singles[i][j].flags |= (CLUE) REND;
                        s_endflag[i] |= (CLUE) REND;

                            break;
                        }
                    }

                    nsites++;
                }
            }
            fclose(f);

            return(1);

        }
        return(0);
}

get_fof(pn)                     /* read file 'inp' and follow instructions */
char *pn;
{
        int this;
        char b[TBUF];

        nsites = mfrags = 0;

        if(get_project(pn)) {

                if( linear ) nsites = nsites - nsd + 1;         /* correct for sites coinciding with end */

                if(linear) filespace = (long) (nsites+1) * sizeof(float)
                        + ((long) (mfrags + nsites + nsites + nsd - 2)) * sizeof(int);
                else filespace = (long) (nsites+1) * sizeof(float)
                        + ((long) (mfrags + nsites + nsites)) * sizeof(int);
```

```
                return(1);
        }

        return(0);
}

sort_out()      /* figure out what multiples are composed of what singles */
{
        char b[TBUF],*p;
        int i,j,nd;

        for( i = START; i <= nmd; i++ )         {       /* scan multiple digests */

                printf("\n%s contains: ",mname[i]);

                for( nd = j = START; j <= nsd; j++ ) {  /* scan single digests */
                        strcpy(b,sname[j]);
                        strcat(b," ,");                         /* look for 'sname[],' imbedded in mname[] */
                        if( stcpm( mname[i], b, &p ) ) {        /* found it */
                                composition [i] [j] = TRUE;
                                printf("%s%s", (nd) ? " and " : "" , sname [j]);
                                nd++;
                                continue;
                        }
                        strcpy(b,", ");                         /* look for ',sname[]' imbedded in mname[] */
                        strcat(b,sname[j]);
                        if( stcpm( mname[i], b, &p ) ) {        /* found it */
                                composition [i] [j] = TRUE;
                                printf("%s%s", (nd) ? " and " : "" , sname [j]);
                                nd++;
                                continue;
                        }
                }
        }

        putchar('\n');
}

trim(s)         /* remove trailing newline if there */
char *s;
{
        if( *s ) {
                if( s[strlen(s)-1] == '\n' ) s[strlen(s)-1] = NULL;
        }
}

/* ----- this stuff is just for debugging ------------------

md_dump(md)     /* dump the digest data to stdout */
int md;
{
        int this;

        printf("\n%s: ", mname [md]);

        for(this = START; this <= mmax [md]; this++ )
                printf("\n%ld+-(%ld%%) %d", multiples [md] [this].frag, (multiples [md] [this].frag_error * 100L / multiples [md][this].frag),multiples[md][this].flags );

}

sd_dump(sd)     /* dump the digest data to stdout */
int sd;
{
        int this;

        printf("\n%s: ", sname [sd]);

        for(this = START; this <= smax [sd]; this++ )
                printf("\n%ld+-(%ld%%) %d", singles [sd] [this].frag, (singles [sd] [this].frag_error * 100L / singles [sd] [this].frag),singles[sd][this].flags );
}

------------------ end debug */#include <stdio.h>

#define VAR extern

#include <rmap.h>


SIZE factorial(n)       /* compute the factorial of 'n' */
SIZE n;
{
```

```
        if( n > (SIZE) 1 ) return( n * factorial( n - (SIZE) 1 ) );
        return( (SIZE) 1 );
}

boolean s_same(sd,f1,f2)          /* return TRUE if single digest fragments */
int sd,f1,f2;                     /* f1 and f2 are exactly the same size */
{
        if( singles [sd] [f1].frag != singles [sd] [f2].frag ) return(FALSE);
        return(TRUE);
}

boolean m_same(md,f1,f2)          /* return TRUE if multiple digest fragments */
int md,f1,f2;                     /* f1 and f2 are exactly the same size */
{
        if(multiples [md][f1].frag != multiples[md][f2].frag) return(FALSE);
        return(TRUE);
}

int next_s_group(d,f)             /* return the end of the size group starting with frag 'f' */
int d,f;
{
        int fp;

        if( (fp = f+1) > smax[d] ) return(EMPTY);
        while( s_same(d,f,fp) ) {
                if( ++fp > smax [d] ) break;
        }
        return(--fp);
}

int next_m_group(d,f)             /* return the end of the size group starting with frag 'f' */
int d,f;
{
        int fp;

        if( (fp = f+1) > mmax[d] ) return(EMPTY);
        while( m_same(d,f,fp) ) {
                if( ++fp > mmax [d] ) break;
        }
        return(--fp);
}

SIZE permute()   /* document the number of permuted maps to expect as similarity groups */
{
        int d,f,fp;
        int group_num, scan;
        SIZE perms;

        perms = (SIZE) 1;         /* there must be at least one perutation */

        for( group_num = d = START; d <= nsd; d++ ) {   /* scan single digests */
                f = fp = START;                         /* begin with first frag */
                while( (fp = next_s_group(d,fp)) > EMPTY ) {            /* scan for groups of the same size */
                        if( fp != f ) {                                         /* more than one of this size */
                                printf("\nFragment duplication of %ld in %s",singles [d][f].frag,sname[d]);
                                for( ++group_num, scan=f; scan <= fp; scan++ ) {        /* document the group */
                                        s_dup [d][scan] = group_num;
                                }
                                perms *= factorial( (fp - f) + (SIZE) 1 );
                        }
                        if( ++fp >= smax [d] ) break;                   /* done with this digest */
                        f = fp;
                }
        }                                       /* done computing single digest permutations */

        for( group_num = d = START; d <= nmd; d++ ) {   /* scan multiple digests */
                f = fp = START;                         /* begin with first frag */
                while( (fp = next_m_group(d,fp)) > EMPTY ) {            /* scan for groups of the same size */
                        if( fp != f ) {                                         /* more than one */
                                printf("\nFragment duplication of %ld in %s",multiples[d][f].frag,mname[d]);
                                for( ++group_num, scan=f; scan <= fp; scan++ ) {        /* document the group */
                                        m_dup [d][scan] = group_num;
                                }
                                perms *= factorial( (fp - f) + (SIZE) 1 );
                        }
                        if( ++fp >= mmax [d] ) break;                   /* done with this digest */
                        f = fp;
                }
        }

        putchar('\n');
```

```
        return(perms);
}
/* Copyright (c) 1986 DNASTAR, Inc. */

#include <stdio.h>

#define VAR extern

#include <rmap.h>
#include <dos.h>

#define MAXBAR 32          /* number of chars in bar graph */

extern int level;          /* counter of the current tree level */

#define LEVELS MAXMAP

long buckets [LEVELS];     /* steps at every level of the tree */
double maxperms;           /* maximum number of expected steps */
                           /* (I will explain this later, when I understand it) */


#define STEPS 600          /* update every 600 steps */

union REGS tstart;         /* elapsed time save area */

int t_day = { 0 };                  /* how many days have elapsed (not many I hope) */
int t_trigger = { 0 };              /* is 24 hour clock wrap imminent? */
int d_trigger = { STEPS };          /* flag for how often clock display gets updated (in yoyo() steps) */

void ptime(out)  /* dump IBM format time to stdout */
union REGS *out;
{
        if(t_trigger) {                  /* the clock may have wrapped */
                if( out->h.ch == 0 ) {   /* it did */
                        t_day++;         /* another day has passed */
                        t_trigger = FALSE;
                }
        }
        else {                   /* see if the clock is going to wrap soon */
                if( out->h.ch == 23 ) {          /* it is */
                        t_trigger = TRUE;
                }
        }

        hours = (int) out->h.ch;
        minutes = (int) out->h.cl;
        seconds = (int) out->h.dh;

        if( (seconds -= (int) tstart.h.dh) < 0 ) {       /* seconds fixup */
                seconds += 60;
                minutes--;
        }

        if( (minutes -= (int) tstart.h.cl) < 0 ) {       /* minutes fixup */
                minutes += 60;
                hours--;
        }

        hours = hours - (int) tstart.h.ch + 24 * t_day;

        putch('\r');     /* move carriage (archane idea) to left margin */

        printf("  %2d:%02d:%02d", hours, minutes, seconds );
}

void time(verbose)        /* displays the current time to stdout */
int verbose;
{
        union REGS in,out;

        in.x.ax = 0x2c21;        /* get time vector from MSDOS */
        intdos(&in,&out);                /* do it */

        if(verbose) ptime(&out);
        else {
                tstart.x.cx = out.x.cx;
                tstart.x.dx = out.x.dx;
        }
}
```

```
void gmaps()            /* display the number of maps found so far */
{
        printf("%14ld%14d       ",n_maps,max_score+1);
}

void disp_success()     /* display successful completeion of a map on the screen */
{

        time(1);
        gmaps();
        progress_dump();

}
void disp_backup()      /* display failure of a step */
{

}

void disp_progress()    /* display progress of a step */
{

        buckets [level]++;      /* document depth */

        if( !( --d_trigger) ) {                 /* time to display */
                d_trigger = STEPS;
                disp_success();
        }

}

void disp_start()       /* display start of map */
{

        printf("Time Elapsed   Maps Generated   Maps Saved              Progress\n");

        time(1);
        gmaps();
        progress_dump();
}

void disp_init()        /* initialize display functions */
{
        int i,j, frags;
        SIZE factorial();
        double log(), sqrt(), ave_err, ave, t, q, scatter;

        for( i=0; i < LEVELS; i++ ) buckets [i] = 0L;

        maxperms = (double) 1.0;
        scatter = ave = ave_err = (double) 0.0;
        frags = 0;

        for( i = START; i <= nsd; i++ ) {
                for( j = START; j <= smax[i]; j++ ) {
                        ave_err += ((double) singles[i][j].frag_error / (double) singles[i][j].frag);
                        ave += (double) singles[i][j].frag;
                }
                frags += (smax[i]+1);
                ave /= (double) (smax[i]+1);

                q = 0.0e0;
                for( j = START; j <= smax[i]; j++ ) {
                        t = (double) singles[i][j].frag - ave;
                        t *= t;
                        t = 1.0e0 / t;
                        q += t;
                }
                q = log( 1e0 / q );
/*
                scatter += q;
*/
        }
/*
        scatter /= (double) (nsd+1);    /* scatter is now average scatter */
*/

        ave_err /= (double) frags;      /* we now have the average error ratio in per cent */
        ave_err *= (double) 100.0;      /* average error is a general indicator of how combinatorically inclined this run is */

        maxperms = sqrt(ave_err) * (double) frags * (double) frags / (double) (nsd+1);
```

```
/*
        printf("\nmaxperms = %g, average error = %g, scatter = %g\n",maxperms,ave_err,scatter);
*/

}

do_meter(v)       /* display a bar graph with value 'v' (0.0 .. 1.0) */
double v;
{
        int val, unval;

        v *= (double) MAXBAR;   /* scale to size of meter */

        val = (int) v;          /* the bar part of the meter */
        unval = MAXBAR - val;   /* the other part of the meter */

        putchar('^');                   /* put up beginning wall */
        for( ; val--; ) putchar('[');   /* draw done part */
        for( ; unval--; ) putchar('1');         /* draw undone part */
        putchar(']');                   /* put up end wall */

}
progress_dump()           /* compute and display progress meter */
{
        int i;
        long total;
        double meter,temp, log();

        total = 0L;

        meter = (double) 1.0;

        for( i=1; i < LEVELS; i++ ) {           /* treat level counters as a polynomial of logarithms */
                if( buckets [i] > 0L ) {
/*
printf("\n%d: %ld",i,buckets[i]);
*/
                        total += buckets[i];
                        meter += ( meter * (log( (double) buckets[i]) / ((double) i * maxperms)) );
                }
                else break;
        }

        temp = (log( (double) 100.0 * meter ) - 4.6E0) * 3.333E0;              /* attempt to linearize the concavity */

        if( temp < (double) 0.0 ) temp = (double) 0.0;          /* keep function in (0.0 .. 1.0) range */
        else if( temp > (double) 1.0 ) temp = (double) 1.0;     ,

        do_meter(temp);
}
/*************************************************************
 *                                                           *
 *                    Fragment Editor                        *
 *                                                           *
 *************************************************************/
/* Copyright (c) 1986, DNASTAR, Inc. */

#define MAXMAP          20      /* maximum number of sites in any given map */
#define MAXDEPTH        50      /* maximum depth of the heap (same as max.
                                   number of multiple digest sites) */
#define MAXVIEW         50      /* maximum number of maps saved in archive file */

#define MAXPATH         68                      /* longest pathname */
#define NAMELEN         30                      /* largest digest name */
#define MAXSIN          8                       /* maximum number of single digests */
#define MAXMUL          MAXSIN*2                /* maximum number of multiple digests
                                                   (N * 2 is a good approximation
                                                    for the largest number of multiple digests) */

#define EMPTY           -1      /* value of an empty heap pointer/map index */
#define USED            1       /* value of 'used' flag indicating already chosen */
#define FREE            0       /* value of 'used' flag indicating availability */
#define START           0       /* where to begin array index scans */
#define TOOBIG          1       /* possible return value from 'fits()' */
#define  FIT            0       /* ditto */
#define TOOSMALL        -1      /* ditto */
#define MULTIPLE        2       /* return value for multiple digest read in */
#define SINGLE          1       /* return value for single digest read in */

#define SIZE            long            /* type of fragment length values */
#define GIANT           2147483647L     /* largest positive value for (SIZE) type */
#define ZERO            0L              /* zero value for (SIZE) type */
```

```
#define NONE            0       /* synonymous with empty list */
#define  TRUE           1       /* logic true value */
#define  FALSE          0       /* logic false value */

#define BACKSPACE       8       /* ASCII backspace character */
#define FORWARD         '*'     /* character representing progress */
#define BACKUP          249     /* character representing failure */
#define SUCCESS         ']'     /* character representing map completion */
#define MAPSTART        '['     /* character representing map start */

#define MAPWIDTH 66
#define SCREENWIDTH 80

#define EEND            1       /* bit flag for fragment on end attribute       (LINEAR ONLY) */
#define LEND            2       /* bit flag for fragment on left end attribute  (LINEAR ONLY) */
#define REND            4       /* bit flag for fragment on right end attribute         (LINEAR ONLY) */
#define ANYEND          7       /* combined attributes for above three flags */
#define SPECEND         3       /* either specific end */
#define NEW             8       /* bit attribute for multiple fragment not in single    (MULTIPLE ONLY) */
#define CUT             8       /* bit attribute for single fragment not in multiple    (SINGLE ONLY) */
#define AUTONEW         16      /* bit flag for new frags assigned automatically */
#define CLUE            char    /* type of clue attribute */

#ifndef IBM                             /* this is a function on the IBM */
#define rawout(c) putch(c)              /* raw screen output */
#endif

#define CUP     'H'             /* cursor keys */
#define CDOWN   'P'
#define LEFT    'K'
#define RIGHT   'M'
#define PGUP    'I'
#define PGDN    'Q'
#define HOME    'G'
#define END     'O'
#define INS     'R'
#define DEL     'S'

#define ABORT '\033'
#define CR '\r'

#define  boolean int            /* type of functions returning logical values */

#define void int                /* type of functions returning arbitrary values */

typedef struct endp (           /* endpoint range structure, used to store */
                                /* the size of a single digest map */

        SIZE            lo,hi;          /* limits on right map endpoint */
        int             index;          /* what position in single map this corresponds to */
)
        endpoint;

typedef struct hnode (

        int             s_digest;       /* which digest does this represent */
        endpoint        s_pos;          /* value of 'sd_end' at decision point */
        SIZE            s_ref;          /* map reference point (everything left of here is to be believed) */
        struct hnode    *others;        /* next list element */

)
        heap;                   /* decision list type name */

typedef struct dignode (        /* storage node for fragment digests */

        SIZE            frag;           /* measured fragment size (in bases) */
        SIZE            frag_error;     /* measurement error (in bases) */
        boolean                 used;           /* flag signalling whether this fragment */
                                        /* has already been chosen for a map */
        CLUE            flags;
)
        digest;

/* storage used for project mergers */

VAR char                m_s_name [MAXSIN][NAMELEN];     /* names of single digests in merge project */
VAR int                 m_s_pick [MAXSIN];              /* which (if any) have been selected */
VAR char                m_m_name [MAXMUL][NAMELEN];     /* names of single digests in merge project */
VAR int                 m_m_pick [MAXMUL];              /* which (if any) have been selected */
VAR int                 m_nmd,m_nsd;                    /* number of single/multiple digests */
VAR int                 m_topology;                     /* topology of merge project */
```

```
/* temporary digest storage (used for input and editing) */

VAR digest              tdigest [MAXMAP];
VAR char                tname [NAMELEN];
VAR char                tfile [MAXPATH];
VAR CLUE                tclue;
VAR int                 tmax;
VAR int                 tptr;

/* digest storage for singles */

VAR digest              singles [MAXSIN] [MAXMAP];      /* single digests */
VAR char                sname [MAXSIN] [NAMELEN];       /* their names */
VAR char                sfile [MAXSIN] [MAXPATH];       /* what file they came from */
VAR CLUE                s_endflag [MAXSIN];             /* place to put end clues for whole digest */
VAR int                 sptr [MAXSIN];                  /* current fragment */
VAR int                 smax [MAXSIN];                  /* index of last fragment */
VAR int                 nsd = { NONE };                 /* number of single digests */

VAR int                 nsites;                         /* number of sites in the map */

/* digest storage for multiples */

VAR digest              multiples [MAXMUL] [MAXMAP];    /* multiple digests */
VAR char                mname [MAXMUL] [NAMELEN];       /* their names */
VAR char                mfile [MAXSIN] [MAXPATH];       /* what file they came from */
VAR CLUE                m_endflag [MAXMUL];             /* place to put end clues for whole digest */
VAR int                 composition [MAXMUL] [MAXSIN];  /* which singles used to cut */
VAR int                 mptr [MAXMUL];                  /* current fragment */
VAR int                 mmax [MAXMUL];                  /* index of last fragment */
VAR int                 nmd = { NONE };                 /* number of multiple digests */

VAR int                 mfrags;                         /* number of multiple digest fragments */

VAR SIZE                lo_factor;              /* error on fragments in % */
VAR SIZE                hi_factor;

VAR SIZE                ave_len = { 0L };       /* average length (circumference) of the total map */

/* single digest maps */

VAR int                 linear = { 0 };                 /* is this map linear? (this version is circular only) */

VAR int                 clueflag = { TRUE };            /* flag to use attribute flags */

VAR char                mp_name[MAXPATH] = { "" };      /* name of project */

VAR char                comment[80] = { "" };           /* description of project */

VAR int                 change_flag = { FALSE };        /* have any changes been made to current project */
/**
 *
 * The following symbols are used for the "open" and "creat" functions.
 *
 **/
#define O_RDONLY 0          /* Read-only value (right byte of mode word) */
#define O_WRONLY 1          /* Write-only value */
#define O_RDWR 2            /* Read-write value */

#define O_NDELAY 4          /* Non-blocking I/O flag */
#define O_APPEND 8          /* Append mode flag */
#define O_CREAT 0x0100      /* File creation flag */
#define O_TRUNC 0x200       /* File truncation flag */
#define O_EXCL 0x400        /* Exclusive access flag */

#define O_RAW 0x8000        /* Raw I/O flag (Lattice feature) */

/**
 *
 * The following symbols are used for the "fcntl" function.
 *
 */
#define F_DUPFD 0           /* Duplicate file descriptor */
#define F_GETFD 1           /* Get file descriptor flags */
#define F_SETFD 2           /* Set file descriptor flags */
#define F_GETFL 3           /* Get file flags */
#define F_SETFL 4           /* Set file flags */

/* Copyright (c) 1986 DNASTAR, Inc. */

#include <stdio.h>

#define VAR
```

```
#include <redit.h>

#include <bios.h>
#include <window.h>

WINDOW wn[] = {
                {0,24,0,40, 0,0, NORMAL, 0, NO_WRAP, 0,1, 0, 0, &bdr_dln,NULL},
                {0,11,41,79,0,0, NORMAL, 0,    WRAP, 0,1, 0, 0, &bdr_dln,NULL},
                {0,24,0,79, 0,0, NORMAL, 0, NO_WRAP, 0,1, 0, 0, &bdr_0,  NULL},
                {12,24,41,79,0,0,NORMAL, 0,    WRAP, 0,1, 0, 0, &bdr_dln,NULL}
};

int cur_window = { 0 };          /* which window is active for raw I/O */

#define STATUS          12       /* line containing full screen status transactions */


#define EDIT            0        /* edit window */
#define EMENU           1        /* edit menu window */
#define PICK            2        /* file pick screen */
#define CLUEHELP        3        /* clue help window */

/* fields in digest selection screen */

#define DS_SC           10
#define DS_MC           50
#define DS_HEADING      1
#define DS_TITLE        3
#define DS_TOP          5

int ds_type = { SINGLE };
int ds_pick = { EMPTY };

/* fields in fragment editor screen */

#define SC_TOP          4        /* top of fragment list */
#define SC_WIDTH        8        /* width of following fields */
#define SC_FRPOS        5
#define SC_ERPOS        14
#define SC_PCPOS        23
#define SC_CLPOS        35
#define SC_TITLE        1
#define SC_HEADING      3
#define SC_FIPOS        40
#define SC_MAPOS        4


#define FRAG            0        /* values for tcol */
#define ERR             1
#define PCENT           2
#define CLUCOL          3

VAR int tcol = { FRAG };         /* which column of fragment edit screen */

extern char *fn_get();           /* file pick function */
extern char **fn_list();         /* multi-file pick function */

#define PM_TITLE        3        /* title line of project menu */
#define PM_TC           20       /* starting column of title */
#define PM_TOP          6        /* top row of items on project menu */
#define PM_COL          27       /* starting column of menu items */
#define PM_MAX          7        /* largest number of items on project menu - 1 */

VAR int pm_row = { 0 };          /* project menu row */

VAR char *pm_title = { "Restriction Mapping Project Manager Ver 1.1" };

VAR char *pm_text[] = {
"C   (C)reate new project",
"O   (O)pen existing project",
"R   (R)esume current project",
"S   (S)ave project",
"B   (B)ackup current project",
"G   (G)et project from backup",
"N   give project new (N)ame",
"E   (E)xit to system"
};

VAR int op_row = { 0 };
```

```
#define LINPOS 12
#define TOPOLINE 15
#define OP_TITLE 3
#define OP_TOP 5
#define OP_MAX 8
#define OP_COL 23

VAR char *topology = {
"Topology:   Circular"
};

char *op_text[] = {
"I   (I)nput digest from .gel file",

"G   (G)et digests from another project",
"E   (E)dit/create/view/delete digest",
"A   (A)nalyze project consistency",
"M   (M)ake restriction maps",
"V   (V)iew restriction maps",
"L   set (L)inear topology",
"C   set (C)ircular topology",
"R   (R)eturn to project menu"
};

pm_menu()                    /* show project menu */
{
        int i;

        cur_window = PICK;
        set_wn(&wn[PICK]);

        gotoxy(PM_TC,PM_TITLE);
        rawputs(pm_title);

        for(i=0;i<=PM_MAX;i++) {
                gotoxy(PM_COL,PM_TOP+i);
                if( pm_row == i ) reverse();
                rawputs(pm_text[i]);
                if( pm_row == i ) normal();
        }
}

pm_on(r)            /* highlight the row 'r' on the project menu */
int r;
{
        cur_window = PICK;
        gotoxy(PM_COL,PM_TOP+r);
        reverse();
        rawputs(pm_text[r]);
        normal();

}

pm_off(r)           /* unhighlight the row 'r' on the project menu */
int r;
{
        cur_window = PICK;
        gotoxy(PM_COL,PM_TOP+r);
        rawputs(pm_text[r]);
}

boolean pm_select()                /* pick an item from the project menu */
{
        pm_menu();

        while(1) {
                switch(toupper(rawin())) {
                        case 0:
                                switch(rawin()) {
                                        case CUP:
                                                pm_off(pm_row);
                                                if( --pm_row < 0 ) pm_row = PM_MAX;
                                                pm_on(pm_row);
                                                break;
                                        case CDOWN:
                                                pm_off(pm_row);
                                                if( ++pm_row > PM_MAX ) pm_row = 0;
                                                pm_on(pm_row);
                                                break;
                                        case HOME:
                                        case PGUP:
```

```
                                        pm_off(pm_row);
                                        pm_row = 0;
                                        pm_on(pm_row);
                                        break;
                                case PGDN:
                                case END:
                                        pm_off(pm_row);
                                        pm_row = PM_MAX;
                                        pm_on(pm_row);
                                        break;
                        }
                        break;
                case CR:
                        return( (pm_row != PM_MAX) );
                case 'C':
                        pm_row = 0;
                        return(TRUE);
                case 'O':
                        pm_row = 1;
                        return(TRUE);
                case 'R':
                        pm_row = 2;
                        return(TRUE);
                case 'S':
                        pm_row = 3;
                        return(TRUE);
                case 'B':
                        pm_row = 4;
                        return(TRUE);
                case 'G':
                        pm_row = 5;

                        return(TRUE);
                case 'N':
                        pm_row = 6;
                        return(TRUE);
                case 'X':
                        return(FALSE);
                }
        }
}

SIZE round(n)           /* convert a float to SIZE (long) by rounding to nearest value */
float n;
{
        SIZE t,tp1;

        t = (SIZE) n;
        tp1 = t+1;
        if( (n - (float) t) > ( (float) tp1 - n) ) return(tp1);
        return(t);
}

boolean cwhite(c)       /* is this char whitespace (including comma) */
char c;
{
        if( (c == ' ') || (c == '\t') || (c == ',') ) return(TRUE);
        return(FALSE);
}


commatize(s)            /* compress whitespace and insert commas */
char *s;
{
        char *p;
        boolean skipping;

        for( p = s; *p && cwhite(*p); p++ );    /* skip whitespace at beginning */
        skipping = FALSE;

        while( *p ) {
                if( cwhite(*p) ) {
                        skipping = TRUE;
                        p++;
                }
                else {
                        if( skipping ) {
                                *s++ = ',';
                                skipping = FALSE;
                        }
                        *s++ = *p++;
                }
        }
        *s = NULL;
```

```
}

get_csr(x,y)            /* compute where cursor should be on the screen given 'tcol' and 'tptr' */
int *x,*y;
{
        if(tptr == EMPTY) {     /* in the name field */
                *x = SC_NAPOS+8;
                *y = SC_TITLE;
                return;
        }

        switch(tcol) {
                case FRAG:      *x = SC_FRPOS;  break;
                case ERR:       *x = SC_ERPOS;  break;
                case PCENT:     *x = SC_PCPOS;  break;
                case CLUCOL:    *x = SC_CLPOS;  break;
        }

        *y = SC_TOP + tptr;
}

ed_menu()               /* display the editor menu */
{
        set_wn(&wn[EMENU]);
        v_st("          Fragment Editor\n",&wn[EMENU]);
        v_st("   <Ins>    add new fragment\n",&wn[EMENU]);
        v_st("   <Del>    delete current fragment\n",&wn[EMENU]);
        v_st("   number   update current entry\n",&wn[EMENU]);
        v_st("    '%'     set global error bound\n",&wn[EMENU]);
        v_st("    '<'     ceiling on small frag.\n",&wn[EMENU]);
        v_st("    ^D      duplicate current frag.\n",&wn[EMENU]);
        v_st("    ^A      abandon changes\n",&wn[EMENU]);
        v_st("   <Esc>    save changes\n",&wn[EMENU]);
}

clue_on()               /* put up the clue menu */
{
        set_wn(&wn[CLUEHELP]);

        v_st("          Mapping Clues\n",&wn[CLUEHELP]);
        v_st("\n",&wn[CLUEHELP]);
        if( stpchr(tname,',') ) {       /* multiple digest */
                v_st("  N  The fragment is new in the\n",&wn[CLUEHELP]);
                v_st("     multiple digest.\n",&wn[CLUEHELP]);
        }
        else {                          /* single digest */
                v_st("  C  The fragment is cut by another\n",&wn[CLUEHELP]);

                v_st("     enzyme in a multiple digest.\n",&wn[CLUEHELP]);
        }

        v_st("  X  Erase clues for this fragment.\n",&wn[CLUEHELP]);

        if( linear ) {                  /* linear clue help */
                v_st(" L/R The fragment is known to be\n",&wn[CLUEHELP]);
                v_st("     positioned at the (L)eft (5')\n",&wn[CLUEHELP]);
                v_st("     or (R)ight (3') end.\n",&wn[CLUEHELP]);
                v_st("  E  The fragment is known to be\n",&wn[CLUEHELP]);
                v_st("     positioned at one of the ends\n",&wn[CLUEHELP]);
                v_st("     of the map.\n",&wn[CLUEHELP]);
        }
}

clue_off()              /* take down the clue menu */
{
        unset_wn(&wn[CLUEHELP]);
}

show(all)               /* display the temporary digest full screen */
int all;
{
        char s[SCREENWIDTH];
        int i;
        boolean smallfrag;

        if(all) {
                clears();

                gotoxy(SC_NAPOS,SC_TITLE);
                rawputs("Digest: ");

                gotoxy(SC_FRPOS-2,SC_HEADING);
                rawputs("Fragment  Error  in Per Cent  Clues");
        }
```

```
	if(tptr == EMPTY) reverse();
	gotoxy(SC_NAPOS+8,SC_TITLE);
	rawputs(tname);
	if(tptr == EMPTY) normal();

	if( (tptr != EMPTY) && (tcol == CLUCOL) ) clue_on();
	else clue_off();

	for(i=START; i<=tmax; i++) {

		gotoxy(SC_FRPOS,SC_TOP+i);
		if( (tdigest[i].frag != 0) && (tdigest[i].frag == tdigest[i].frag_error) ) {
			sprintf(s,"< %ld",tdigest[i].frag * (SIZE) 2);
			smallfrag = TRUE;
		}
		else {
			sprintf(s,"%ld",tdigest[i].frag);
			smallfrag = FALSE;
		}

		if( (i==tptr) && (tcol==FRAG) ) reverse();
		rawputs(s);
		if( (i==tptr) && (tcol==FRAG) ) normal();

		gotoxy(SC_ERPOS,SC_TOP+i);
		if( smallfrag ) strcpy(s,"----");
		else sprintf(s,"%ld",tdigest[i].frag_error);

		if( (i==tptr) && (tcol==ERR) ) reverse();
		rawputs(s);
		if( (i==tptr) && (tcol==ERR) ) normal();


		gotoxy(SC_PCPOS,SC_TOP+i);
		if( smallfrag ) strcpy(s,"(----)");
		else sprintf(s,"(%.1f%%)",( (float) tdigest[i].frag_error * 100.0) / (float) tdigest[i].frag);

		if( (i==tptr) && (tcol==PCENT) ) reverse();
		rawputs(s);
		if( (i==tptr) && (tcol==PCENT) ) normal();

		gotoxy(SC_CLPOS,SC_TOP+i);

		if( (i==tptr) && (tcol==CLUCOL) ) reverse();
		if( !tdigest[i].flags ) rawputs(" ");	/* show an empty space so we know where the cursor is */
		else {
			if( tdigest[i].flags & NEW ) {	/* this is either 'N' or 'C' depending on whether the digest is a multiple or single */
				if( stpchr(tname,',') ) rawputs("N");
				else rawputs("C");
			}
			if( tdigest[i].flags & AUTONEW ) rawputs("n");
			if( linear ) {
				if( tdigest[i].flags & LEND ) rawputs("L");
				else if( tdigest[i].flags & REND ) rawputs("R");
				else if( tdigest[i].flags & EEND ) rawputs("E");
			}
		}
		if( (i==tptr) && (tcol==CLUCOL) ) normal();
		if( tcol == CLUCOL ) rawputs(" ");	/* erase field following */
	}
show_on()		/* turn on a field */
{
	char s[SCREENWIDTH];
	int smallfrag;

	switch(tptr) {
		case EMPTY:	/* name line */
			gotoxy(SC_NAPOS+8,SC_TITLE);
			reverse();
			rawputs(tname);
			normal();
			break;
		default:	/* a fragment line */
			switch(tcol) {
				case FRAG:	/* fragsize column */
					gotoxy(SC_FRPOS,SC_TOP+tptr);
					if( (tdigest[tptr].frag != 0) && (tdigest[tptr].frag == tdigest[tptr].frag_error) ) sprintf(s,"< %ld",tdigest[tptr].frag *
					(SIZE)2); else sprintf(s,"%ld",tdigest[tptr].frag);
					reverse();
					rawputs(s);
					normal();
					break;
				case ERR:	/* absolute error column */
```

```
                        gotoxy(SC_ERPOS,SC_TOP+tptr);
                        if(  (tdigest[tptr].frag != 0) && (tdigest[tptr].frag == tdigest[tptr].frag_error) ) strcpy(s,"----");
                        else sprintf(s,"%ld",tdigest[tptr].frag_error);
                        reverse();
                        rawputs(s);
                        normal();
                        break;
                case PCENT:     /* per cent error column */
                        gotoxy(SC_PCPOS,SC_TOP+tptr);
                        if(  (tdigest[tptr].frag != 0) && (tdigest[tptr].frag == tdigest[tptr].frag_error) ) strcpy(s,"(----)");
                        else sprintf(s,"(%.1f%%)",( (float) tdigest[tptr].frag_error * 100.0) / (float) tdigest[tptr].frag);
                        reverse();
                        rawputs(s);
                        normal();
                        break;
                case CLUCOL:    /* clue column */
                        clue_on();
                        gotoxy(SC_CLPOS,SC_TOP+tptr);
                        reverse();
                        if( !tdigest[tptr].flags ) rawputs(" ");        /* show an empty space so we know where the cursor is */
                        else {
                                if( tdigest[tptr].flags & NEW ) {       /* this is either 'N' or 'C' depending on whether the digest is a multiple or
                                        if( stpchr(tname,',') ) rawputs("N");
                                        else rawputs("C");                                                                    single */
                                }
                                if( tdigest[tptr].flags & AUTONEW ) rawputs("n");
                                if( linear ) {
                                        if( tdigest[tptr].flags & LEND ) rawputs("L");
                                        else if( tdigest[tptr].flags & REND ) rawputs("R");
                                        else if( tdigest[tptr].flags & EEND ) rawputs("E");
                                }
                        }
                        normal();
                        rawputs(" ");   /* erase field following */
                        break;
                }
                break;
        }
}
show_off()      /* turn off a field */
{
        char s[SCREENWIDTH];

        switch(tptr) {
        case EMPTY:     /* name line */
                gotoxy(SC_NAPOS+8,SC_TITLE);
                rawputs(tname);
                break;
        default:        /* a fragment line */
                switch(tcol) {
                case FRAG:      /* fragsize column */
                        gotoxy(SC_FRPOS,SC_TOP+tptr);
                        if(  (tdigest[tptr].frag != 0) && (tdigest[tptr].frag == tdigest[tptr].frag_error) ) sprintf(s,"< %ld",tdigest[tptr].frag *
                                else sprintf(s,"%ld",tdigest[tptr].frag);
                        rawputs(s);
                        break;
                case ERR:       /* absolute error column */
                        gotoxy(SC_ERPOS,SC_TOP+tptr);
                        if(  (tdigest[tptr].frag != 0) && (tdigest[tptr].frag == tdigest[tptr].frag_error) ) strcpy(s,"----");
                        else sprintf(s,"%ld",tdigest[tptr].frag_error);
                        rawputs(s);
                        break;
                case PCENT:     /* per cent error column */
                        gotoxy(SC_PCPOS,SC_TOP+tptr);
                        if(  (tdigest[tptr].frag != 0) && (tdigest[tptr].frag == tdigest[tptr].frag_error) ) strcpy(s,"(----)");
                        else sprintf(s,"(%.1f%%)",( (float) tdigest[tptr].frag_error * 100.0) / (float) tdigest[tptr].frag);
                        rawputs(s);
                        break;
                case CLUCOL:    /* clue column */
                        clue_off();
                        gotoxy(SC_CLPOS,SC_TOP+tptr);
                        if( !tdigest[tptr].flags ) rawputs(" ");        /* show an empty space so we know where the cursor is */
                        else {

                                if( tdigest[tptr].flags & NEW ) {       /* this is either 'N' or 'C' depending on whether the digest is a multiple or
                                        if( stpchr(tname,',') ) rawputs("N");
                                        else rawputs("C");
                                }
                                if( tdigest[tptr].flags & AUTONEW ) rawputs("n");
                                if( linear ) {
                                        if( tdigest[tptr].flags & LEND ) rawputs("L");
                                        else if( tdigest[tptr].flags & REND ) rawputs("R");
                                        else if( tdigest[tptr].flags & EEND ) rawputs("E");
```

```
                                        }
                                }
                                rawputs(" ");   /* erase field following */
                                break;
                        }
                        break;
                }
}

void get_error()                /* set global error bound */
{
        char s[SCREENWIDTH];
        SIZE pce;
        float pcef;
        int i;

        set_wn(&wn[CLUEHELP]);
        cur_window = CLUEHELP;

        gotoxy(2,2);
        rawputs("Specify global error bound");
        gotoxy(2,3);
        rawputs("or <esc> to skip: ");
        block();

        if( rawgets(s) > 0 ) {
                sscanf(s,"%f",&pcef);
                if( pcef > 0.0 ) {
                        for( i = START; i <= tmax; i++ ) {
                                tdigest[i].frag_error = (SIZE) ( ((float) tdigest[i].frag * pcef) / 100.0 );
                        }
                }
        }

        invisible();
        unset_wn(&wn[CLUEHELP]);
        cur_window = EDIT;
}

extern int dcomp();

ed_frags(sorm,dig)              /* edit the digest in the temporary space */
int sorm,dig;
{
        int x,y;
        char c, s[SCREENWIDTH], *p;
        float pcnt;
        SIZE fr;

        set_wn(&wn[EDIT]);

        ed_menu();

        cur_window = EDIT;

        switch(sorm) {
                case MULTIPLE:
                        mul2ed(dig);
                        break;
                case SINGLE:
                        sin2ed(dig);
                        break;
                case NONE:
                        return(FALSE);
        }

        invisible();            /* turn off cursor */

        show(1);                /* update temp digest full screen */

        if( tmax == EMPTY ) {   /* new digest maybe? */
                tptr = EMPTY;
                c = 1;
                s[0] = NULL;
                while( c && (*tname == NULL) ) {        /* name digest first */
                        get_csr(&x,&y);                 /* get screen position */
                        gotoxy(x,y);
                        crepeat('_',NAMELEN-3);
                        gotoxy(x,y);
                        block();

                        switch( arawgets(s) ) {
                        default:
```

```
                        commatize(s);
                        uppercase(s);
                        strcpy(tname,s);
                case ABORT:
                case -2:
                case -1:
                case 0:
                        c = 0;
                        break;
                }
        }
        invisible();
        show(1);
}

while(1) {

        c = rawin();

        switch( c ) {
        case 0:
                switch(rawin()) {
                case CUP:
                        show_off();
                        if( --tptr < EMPTY ) tptr = tmax;
                        show_on();
                        break;
                case CDOWN:
                        show_off();
                        if( ++tptr > tmax ) tptr = EMPTY;
                        show_on();
                        break;
                case LEFT:
                        show_off();
                        if( --tcol < FRAG ) tcol = CLUCOL;
                        show_on();
                        break;
                case RIGHT:
                        show_off();
                        if( ++tcol > CLUCOL ) tcol = FRAG;
                        show_on();
                        break;
                case HOME:
                        show_off();
                        tcol = FRAG;
                        tptr = START;
                        show_on();
                        break;
                case PGUP:
                        show_off();
                        tptr = START;
                        show_on();
                        break;
                case END:
                        show_off();
                        tcol = CLUCOL;
                        tptr = tmax;
                        show_on();
                        break;
                case PGDN:
                        show_off();
                        tptr = tmax;
                        show_on();
                        break;

                case 'R':       /* insert */
                        if( ++tmax < MAXMAP ) {
                                tdigest [tmax].frag = (SIZE) 0;
                                tdigest [tmax].frag_error = (SIZE) 0;
                                tdigest [tmax].flags = (CLUE) NONE;
                                tptr = tmax;
                                tcol = FRAG;
                        }
                        else --tmax;
                        show(1);
                        break;
                case 'S':       /* delete */
                        if( tmax > EMPTY ) {
                                for( x = tptr + 1; x <= tmax; x++ ) {
                                        tdigest [x-1].frag = tdigest [x].frag;
                                        tdigest [x-1].frag_error = tdigest [x].frag_error;
                                        tdigest [x-1].flags = tdigest [x].flags;
```

```
                                }
                                tmax--;
                                if( tptr > tmax ) tptr = tmax;
                                show(1);
                        }
                        break;
                }
                break;
        case 4:                         /* duplicate (^D) */
                if( tptr < START ) break;
                if(++tmax >= MAXMAP) tmax--;
                else {
                        tdigest[tmax].frag = tdigest[tptr].frag;
                        tdigest[tmax].frag_error = tdigest[tptr].frag_error;
                        tdigest[tmax].flags = tdigest[tptr].flags;
                        qsort( &tdigest[0], tmax+1, sizeof(digest), &dcomp );
                        show(1);
                }
                break;
        case '%':                       /* global error set */
                get_error();
                show(1);
                break;
        case '<':                       /* small frag */
        case '>':                       /* just for safety */
                if( (tcol == FRAG) && (tptr > EMPTY) && (tmax > EMPTY) ) {
                        get_car(&x,&y);             /* get screen position */
                        gotoxy(x,y);        /* make certain the cursor is there */
                        crepeat(' ',SC_WIDTH);
                        gotoxy(x,y);
                        block();

                        if( tdigest[tptr].frag == 0 ) strcpy(s,"< ");
                        else sprintf(s,"< %ld",tdigest[tptr].frag * (SIZE) 2);

                        switch( arawgets(s) ) {

                        default:
                                p = s;
                                while(*p && !isdigit(*p)) p++;
                                if( stpchr(p,'.') ) {   /* contains decimal point...must be in kilobases */
                                        sscanf(p,"%f",&pcnt);
                                        fr = round(pcnt * 1000.0);
                                }
                                else sscanf(p,"%ld",&fr);
                                tdigest[tptr].frag_error = fr / (SIZE) 2;
                                tdigest [tptr].frag = fr / (SIZE) 2;
                                tdigest [tptr].used = USED;
                                qsort( &tdigest[0], tmax+1, sizeof(digest), &dcomp );
                                for( tptr=START; tptr <= tmax; tptr++ ) {
                                        if( tdigest[tptr].used == USED ) {
                                                tdigest[tptr].used = FREE;
                                                break;
                                        }
                                }

                                if( tdigest [tptr].frag < (SIZE) 0 ) tdigest [tptr].frag = -tdigest [tptr].frag;
                                if( tdigest [tptr].frag_error < (SIZE) 0 ) tdigest [tptr].frag_error = -tdigest [tptr].frag_error;
                        case -2:
                        case -1:
                        case ABORT:
                        case 0:
                                break;
                        }

                        invisible();
                        show(1);
                }
                break;
        case 1:                         /* abandon (^A) */
                invisible();
                return(FALSE);

        case ABORT:                     /* save */
                if(norm==MULTIPLE) {

                        if( tmax < START ) del_mul(dig);
                        else {
                                if( stpchr(tname,',') ) {       /* still a multiple */
                                        if(dig == EMPTY) {
                                                if( nmd < MAXMUL-1 ) ed2mul(++nmd);
```

```
				}
				else ed2mul(dig);
			}
			else {			/* user pulled a switcheroo */
				if( nsd < MAXSIN-1 ) {	/* room for it */
					ed2sin(++nsd);
				}
				else {			/* no more digest space, return to edit */
					cl_wn(&wn[EMENU]);
					v_fst("\n  Maximum number of single digests exceeded!\n  Save as a multiple digest please!\n  (Hit a key to continue)",&wn[E     );
					pl_csr(&wn[EMENU]);
					rawin();
					ed_menu();
					show(1);
					break;
				}
				del_mul(dig);		/* delete old multiple */
			}
		}
	}
	else {
		if( tmax < START ) del_sin(dig);
		else {
			if( stpchr(tname,',') ) {	/* switched to multiple */
				if( nmd < MAXMUL-1 ) {	/* room for it */
					ed2mul(++nmd);
				}
				else {			/* no more digest space, return to edit */
					cl_wn(&wn[EMENU]);
					v_fst("\n  Maximum number of multiple digests exceeded!\n  Save as a single digest please!\n  (Hit a key to continue)",&wn[EMENU]);
					pl_csr(&wn[EMENU]);
					rawin();
					ed_menu();
					show(1);
					break;
				}
				del_sin(dig);		/* delete old single */
			}
			else {
						if( dig == EMPTY ) {
							if( nsd < MAXSIN-1 ) ed2sin(++nsd);
						}
						else ed2sin(dig);
					}
				}
			}
			sort_out();
			invisible();
			return(TRUE);

		default:			/* maybe a new value? */
			if( c == CR ) {		/* edit current value */
				if( tptr == EMPTY ) {
					strcpy(s,tname);
					c = 'a';
				}
				else {
					c = '1';
					switch( tcol ) {
						case FRAG:
							sprintf(s,"%ld",tdigest[tptr].frag);
							break;
						case ERR:
							sprintf(s,"%ld",tdigest[tptr].frag_error);
							break;
						case PCENT:
							sprintf(s,"%.1f",((float) tdigest[tptr].frag_error * 100.0) / (float) tdigest[tptr].frag);
							break;
						case CLUCOL:
							c = CR;			/* can't edit this field */
							break;
					}
				}
			}
			else {
				s[0] = c;
				s[1] = NULL;		/* create string containing character */
			}
			if( isdigit(c) && (tptr > EMPTY) && (tmax > EMPTY) ) {
				get_csr(&x,&y);			/* get screen position */
				gotoxy(x,y);		/* make certain the cursor is there */
				crepeat('_',SC_WIDTH);
				gotoxy(x,y);
				block();
```

```
	switch( arawgets(s) ) {

	default:
		if( tcol == PCENT ) {
			sscanf(s,"%f",&pcnt);
			tdigest[tptr].frag_error = (SIZE) (((float) tdigest[tptr].frag * pcnt) / 100.0);
		}
		else if( tcol == FRAG ) {
			if( stpchr(s,'.') ) {   /* contains decimal point...must be in kilobases */
				sscanf(s,"%f",&pcnt);
				fr = round(pcnt * 1000.0);
			}
			else sscanf(s,"%ld",&fr);
			tdigest[tptr].frag_error = (SIZE) (((float) fr * (float) tdigest [tptr].frag_error) / (float) tdigest [tptr].frag);
			tdigest [tptr].frag = fr;
			tdigest [tptr].used = USED;
			qsort( &tdigest[0], tmax+1, sizeof(digest), &dcomp );
			for( tptr=START; tptr <= tmax; tptr++ ) {
				if( tdigest[tptr].used == USED ) {
					tdigest[tptr].used = FREE;
					break;
				}
			}
		}
		else if( tcol==ERR ) {
			sscanf(s,"%ld",&tdigest[tptr].frag_error);
		}

		if( tdigest [tptr].frag < (SIZE) 0 ) tdigest [tptr].frag = -tdigest [tptr].frag;
		if( tdigest [tptr].frag_error < (SIZE) 0 ) tdigest [tptr].frag_error = -tdigest [tptr].frag_error;
	case -2:
	case -1:
	case ABORT:
	case 0:
		break;
	}

	invisible();
	show(1);
}
else if( isalpha(c) ) {
	if( tptr == EMPTY ) {   /* update digest name */
		get_csr(&x,&y);                 /* get screen position */
		gotoxy(x,y);            /* make certain the cursor is there */
		crepeat('_',NAMELEN-3);
		gotoxy(x,y);
		block();

		switch( arawgets(s) ) {
		default:
			commatize(s);
			uppercase(s);

				strcpy(tname,s);
			case ABORT:
			case -1:
			case -2:
			case 0:
				break;
			}

			invisible();
			show(1);
	}
	else if( tcol == CLUCOL ) {                /* it's the clue field */
			switch( toupper(c) ) {
			case 'N':       /* new frag */
				if( stpchr(tname,',') ) {       /* it's a multiple...OK */
					tdigest[tptr].flags |= (CLUE) NEW;
				}
				break;
			case 'C':       /* cut frag */
				if( !stpchr(tname,',') ) {      /* it's a single...OK */
					tdigest[tptr].flags |= (CLUE) CUT;
				}
				break;
			case 'L':       /* left end */
				if( linear ) {
					for(x=START;x<=tmax;x++) tdigest[x].flags &= (CLUE) ~LEND;
					tdigest [tptr].flags |= (CLUE) LEND;    /* this must be the only left end */
```

```
					}
					break;
				case 'R':	/* right end */
					if( linear ) {
						for(x=START;x<=tmax;x++) tdigest[x].flags &= (CLUE) ~REND;
						tdigest [tptr].flags |= (CLUE) REND;	/* this must be the only right end */
					}
					break;
				case 'E':	/* any end */
					if( linear ) {
						tdigest [tptr].flags &= (CLUE) ~ANYEND;
						tdigest [tptr].flags |= (CLUE) EEND;
					}
					break;
				case 'X':	/* clear flags */
					tdigest [tptr].flags = (CLUE) NONE;
					break;
				}
				show(0);
			}
		}
		break;
	}
	}
}

del_sin(n)	/* delete single digest 'n' */
int n;
{
	int i,j;

	if( nsd < START ) return;
	if( n < START ) return;

	change_flag = TRUE;	/* project has been modified */

	for( i = n + 1; i <= nsd; i++ ) {
		for( j = START; j <= smax[i]; j++ ) {
			singles [i-1][j].frag = singles [i][j].frag;
			singles [i-1][j].frag_error = singles [i][j].frag_error;
			singles [i-1][j].flags = singles [i][j].flags;
			strcpy(sname[i-1],sname[i]);
			strcpy(sfile[i-1],sfile[i]);
		}
		smax [i-1] = smax [i];
	}
	nsd--;

	sort_out();
}

del_mul(n)	/* delete multiple digest 'n' */
int n;
{
	int i,j;

	if( nmd < START ) return;
	if( n < START ) return;

	change_flag = TRUE;	/* project has been modified */

	for( i = n + 1; i <= nmd; i++ ) {
		for( j = START; j <= mmax[i]; j++ ) {
			multiples [i-1][j].frag = multiples [i][j].frag;
			multiples [i-1][j].frag_error = multiples [i][j].frag_error;
			multiples [i-1][j].flags = multiples [i][j].flags;
			strcpy(mname[i-1],mname[i]);
			strcpy(mfile[i-1],mfile[i]);
		}
		mmax [i-1] = mmax [i];
	}
	nmd--;
```

```
        sort_out();     /* figure out what's missing */
}

boolean check_change(sorm,dig)          /* see if the temp digest and the specified digest are the same */
int sorm, dig;                          /* return TRUE if different */
{
        int i;

        if( sorm == MULTIPLE ) {

                if( tmax != mmax[dig] ) return(TRUE);   /* check number of frags. */

                if( strcmp(tname,mname[dig]) != 0 ) return(TRUE);       /* check name */

                for( i = START; i <= tmax; i++ ) {      /* check each fragment */
                        if( tdigest[i].frag != multiples[dig][i].frag ) return(TRUE);
                        if( tdigest[i].frag_error != multiples[dig][i].frag_error ) return(TRUE);
                        if( tdigest[i].flags != multiples[dig][i].flags ) return(TRUE);
                }

        }
        else {

                if( tmax != smax[dig] ) return(TRUE);   /* check number of frags. */

                if( strcmp(tname,sname[dig]) != 0 ) return(TRUE);       /* check name */

                for( i = START; i <= tmax; i++ ) {      /* check each fragment */
                        if( tdigest[i].frag != singles[dig][i].frag ) return(TRUE);
                        if( tdigest[i].frag_error != singles[dig][i].frag_error ) return(TRUE);
                        if( tdigest[i].flags != singles[dig][i].flags ) return(TRUE);
                }

        }
        return(FALSE);  /* no change */
}

sin2ed(n)       /* copy single digest into temp */
int n;
{
        int i;

        for( i=START; i <= smax[n]; i++ ) {
                tdigest[i].frag = singles[n][i].frag;
                tdigest[i].frag_error = singles[n][i].frag_error;
                tdigest[i].flags = singles[n][i].flags;
        }

        strcpy(tname,sname[n]);
        strcpy(tfile,sfile[n]);
        tmax = smax[n];
        tptr=START;
}

mul2ed(n)       /* copy multiple digest into temp */
int n;
{
        int i;

        for( i=START; i <= mmax[n]; i++ ) {
                tdigest[i].frag = multiples[n][i].frag;
                tdigest[i].frag_error = multiples[n][i].frag_error;
                tdigest[i].flags = multiples[n][i].flags;
        }

        strcpy(tname,mname[n]);
        strcpy(tfile,mfile[n]);
        tmax = mmax[n];
        tptr=START;
}

ed2sin(n)       /* copy temp into single digest */
int n;
{
        int i;

        if( !check_change( SINGLE, n ) ) return;        /* digest has not changed...don't bother */

        change_flag = TRUE;     /* project has been modified */

        for( i=START; i <= tmax; i++ ) {
                singles[n][i].frag = tdigest[i].frag;
                singles[n][i].frag_error = tdigest[i].frag_error;
                singles[n][i].flags = tdigest[i].flags;
```

```
	}
	strcpy(sname[n],tname);
	strcpy(sfile[n],tfile);
	smax[n] = tmax;
}

ed2mul(n)		/* copy temp into multiple digest */
int n;
{
	int i;

	if( !check_change( MULTIPLE, n ) ) return;	/* digest has not changed...don't bother */

	change_flag = TRUE;	/* project has been modified */

	for( i=START; i <= tmax; i++ ) {
		multiples[n][i].frag = tdigest[i].frag;
		multiples[n][i].frag_error = tdigest[i].frag_error;
		multiples[n][i].flags = tdigest[i].flags;
	}

	strcpy(mname[n],tname);
	strcpy(mfile[n],tfile);
	mmax[n] = tmax;
}

int get_gel(wc)		/* get a digest from a file like 'wc' */
char *wc;
{
	char **p;
	int i, rv;

	set_wn(&wn[PICK]);
	cur_window = PICK;

	if( p = fn_list("Gel files contained in ", wc) ) {
		clears();
		for( rv = 0, i=0; p[i]; i++ ) {
			if( get_dig(p[i]) == 0 ) rv = 1;
		}
		if( rv ) {
			gotoxy(1,1);
			printf("\nHit a key to continue\n");
			rawin();
		}
	}
	return(NONE);
}

get_new(p,cflag)
char *p;
int cflag;
{
	static char s[SCREENWIDTH], b[SCREENWIDTH];
	char *q;
	FILE *save;
	int rv;

	cur_window = PICK;
	set_wn(&wn[PICK]);

	gotoxy(20,STATUS-5);
	rawputs(p);

	if( rawgets(s) > 0 ) {

		if(cflag) {
			if( change_flag ) {	/* current project not saved...try to help */
				clears();
				gotoxy(20,15);
				rawputs("Current project is not saved...save first? (Y/N) ");
				if( rawgets(b) > 0 ) {	/* got a response */
					q = b;
					while( *q && !isalpha(*q) ) q++;
					if( toupper(*q) == 'Y' ) {	/* OK...save it */
						clears();
						gotoxy(1,1);
						if( (save = fopen(mp_name,"w+")) ) {
							put_project(save,0);
							fclose(save);
						}
					}
```

```
                        }
                }
                init();                         /* clear digest area */
        }

        complete(b,s);
        new_ext(b,".mpf");

        if( save = fopen(b,"r") ) {      /* already one of that name */
                fclose(save);

                clears();
                gotoxy(15,15);
                rawputs("A project of that name already exists...Overwrite? (Y/N) ");
                if( (rv = rawgets(s)) > 0 ) {
                        q = s;
                        while( *q && !isalpha(*q) ) q++;

                        if( toupper(*q) != 'Y' )        /* OK...overwrite it */
                                return(FALSE);

                }
                else return(FALSE);
        }
        strcpy(mp_name,b);

        clears();
        gotoxy(16,10);

        rawputs("Type one line of description of new project:");
        gotoxy(20,12);
        rawputs("Project: ");
        rawputs(mp_name);

        gotoxy(1,14);
        crepeat(' ',SCREENWIDTH);
        gotoxy(1,14);

        if( rawgets(comment) <= 0 ) comment[0] = NULL;

        change_flag = TRUE;     /* force a save */

        return(TRUE);
    }
    return(FALSE);
}

int get_old()           /* load a mapping project */
{
    char *p, *q, b[SCREENWIDTH];
    int rv;
    FILE *save;

    cur_window = PICK;
    set_wn(&wn[PICK]);


    if( p = fn_get("Project files contained in ","*.mpf") ) {
        clears();

        if( change_flag ) {     /* current project not saved...try to help */
                gotoxy(20,15);
                rawputs("Current project is not saved...save first? (Y/N) ");
                if( rawgets(b) > 0 ) {  /* got a response */
                        q = b;
                        while( *q && !isalpha(*q) ) q++;
                        if( toupper(*q) == 'Y' ) {      /* OK...save it */
                                clears();
                                gotoxy(1,1);
                                if( (save = fopen(mp_name,"w+")) ) {
                                        put_project(save,0);
                                        fclose(save);
                                }
                        }
                }
        }

        init();
        complete(mp_name,p);
        if( (rv = get_project(p,0)) ) sort_out();
        return(rv);
```

```
        }
        return(NONE);
}

get_merge()     /* merge from another mapping project */
{
        char *p;
        int rv;

        cur_window = PICK;
        set_wn(&wn[PICK]);

        if( p = fn_get("Project files contained in ","*.mpf") ) {
                if( skim(p) ) {
                        if( pick_merge("merge") ) {
                                if( rv = merge(p) ) {
                                        sort_out();
                                        return(rv);
                                }
                        }
                }
        }
        return(NONE);
}

show_digests(s) /* display a selection of entered digests */
char *s;        /* 's' says what will be done with it */
{
        int i;

        gotoxy(DS_SC+10,DS_HEADING);
        rawputs("Select a digest to ");
        rawputs(s);
        gotoxy(DS_SC-4,DS_TITLE);
        rawputs("Single digests");
        gotoxy(DS_MC-4,DS_TITLE);
        rawputs("Multiple digests");

        for( i=EMPTY; i<=nsd; i++ ) {   /* scan singles */

                gotoxy(DS_SC,DS_TOP+i);

                if((ds_type == SINGLE) && (ds_pick == i)) reverse();

                if(i==EMPTY) {
                        highint();
                        rawputs("New");
                        normal();
                }
                else rawputs(sname[i]);

                if((ds_type == SINGLE) && (ds_pick == i)) normal();
        }

        for( i=EMPTY; i<=nmd; i++ ) {   /* scan mulitples */

                gotoxy(DS_MC,DS_TOP+i);

                if((ds_type == MULTIPLE) && (ds_pick == i)) reverse();

                if(i==EMPTY) {
                        highint();
                        rawputs("New");
                        normal();
                }
                else rawputs(mname[i]);

                if((ds_type == MULTIPLE) && (ds_pick == i)) normal();
        }
}

ds_up()
{
        if( --ds_pick < EMPTY ) {
                switch(ds_type) {
                        case MULTIPLE:
                                ds_pick = nmd;
                                break;
                        case SINGLE:
                                ds_pick = nsd;
                                break;
                        default:
                                ds_pick = EMPTY;
                                break;
```

```
                        }
                }
}

ds_down()
{
        switch( ds_type ) {

                case SINGLE:
                        if( ++ds_pick > nsd ) ds_pick = EMPTY;
                        break;

                case MULTIPLE:
                        if( ++ds_pick > nmd ) ds_pick = EMPTY;
                        break;
        }
}

int pick_digest(dig,s)  /* select one digest; return value is type of digest (NONE,SINGLE,MULTIPLE) */
int *dig;               /* 'dig' returns index of chosen digest, 's' tells what will be done with it */
char *s;
{
        cur_window = PICK;
        set_wn(&wn[PICK]);

        if( ds_type == SINGLE ) {
                if( ds_pick > nsd ) ds_pick = nsd;
        }
        else {
                if( ds_pick > nmd ) ds_pick = nmd;
        }

        show_digests(s);

        while(1) {
                switch(rawin()) {
                case CR:
                        *dig = ds_pick;
                        return(ds_type);
                case NULL:
                        switch(rawin()) {
                                case CUP:
                                        ds_up();
                                        break;
                                case CDOWN:
                                        ds_down();
                                        break;
                                case LEFT:
                                case RIGHT:
                                        if( ds_type == MULTIPLE ) {
                                                ds_type = SINGLE;
                                                if( ds_pick > nsd ) ds_pick = nsd;
                                        }
                                        else {
                                                ds_type = MULTIPLE;
                                                if( ds_pick > nmd ) ds_pick = nmd;
                                        }
                                        break;
                                case DEL:
                                        if( ds_type == MULTIPLE ) {
                                                del_mul(ds_pick);

                                                if( ds_pick > nmd ) ds_pick = nmd;
                                        }
                                        else {
                                                del_sin(ds_pick);
                                                if( ds_pick > nsd ) ds_pick = nsd;
                                        }
                                        clears();
                                        break;
                        }
                        show_digests(s);
                        break;
                case ABORT:
                        return(NONE);
                }
        }
}

splice(d,s)     /* do strcpy() without NULL */
char *d,*s;
{
        while(*s) *d++ = *s++;
}
```

```
set_topo()        /* update topology string to reflect current status */
{
        if(linear) splice(&topology[LINPOS],"Linear  ");
        else splice(&topology[LINPOS],"Circular");
}

int same(sdf, sde, mdf, mde)     /* are these fragments close enough to be the same size */
SIZE sdf,sde,mdf,mde;
{
        if( ( sdf + sde >= mdf - mde ) && ( mdf + mde >= sdf - sde ) ) return(TRUE);
        return(FALSE);
}

int next_sdig(sd,md)      /* scan to the next single digest composing 'md' */
int sd,md;
{
        for( ++sd; sd <= nsd; sd++)
                if( composition [md][sd] ) return(sd);
        return(EMPTY);
}

int findmatch(sd,sf,md,mf)        /* find the largest fragment from 'md' starting with 'mf' that */
int sd,sf,md, mf;                 /* is the same size as 'sf' from 'sd' within error */
{
        for( ; mf <= mmax[md]; mf++ ) {
                if( same( singles[sd][sf].frag, singles[sd][sf].frag_error, multiples[md][mf].frag, multiples[md][mf].frag_error ) )
                        return(mf);
                if( singles[sd][sf].frag > multiples[md][mf].frag )      /* multiple frags beyond this point are too small */
                        return(mf);
        }
        return(EMPTY);            /* all frags in multiple are larger than single frag */
}

boolean findgroup(sd,sf,md,mf)   /* see if any combination of frags from 'md' starting with 'mf' */
int sd,sf,md,mf;                 /* are the same as 'sf' from 'sd' within error */
{
        int p[MAXMAP+1];
        int k,m,n;
        SIZE hi,lo,chi,clo;

        lo = singles[sd][sf].frag - singles[sd][sf].frag_error;
        hi = singles[sd][sf].frag + singles[sd][sf].frag_error;

        clo = chi = (SIZE) 0;

        for( n=1, m=mmax[md]; m >= mf; m--, n++ ) {      /* put a bound on the number of fragments in the set */
                clo += multiples[md][m].frag - multiples[md][m].frag_error;
                chi += multiples[md][m].frag + multiples[md][m].frag_error;
                if( clo > hi ) break;                    /* 'n' is the maximum number of fragments */
                if( chi > lo ) return(TRUE);             /* no need to look further...this is a fit */
                if( m == mf ) return(FALSE);             /* sum of all frags. smaller than 'sf' is still smaller than 'sf'...can't fit */
        }

        while( n-- > 1 ) {       /* for all sets of 'n' frags */

                for( m=0, p[0]=mmax[md]; m < n; m++ ) p[m+1] = p[m]-1;  /* start with the smallest possible set */
                p[n+1] = mf - 2;         /* set up a terminating condition */

                do {     /* loop until too large or combinations exhausted */

                        clo = chi = (SIZE) 0;

                        for( m=0; m <= n; m++ ) {
                                clo += multiples[md][p[m]].frag;
                                chi += multiples[md][p[m]].frag_error;
                        }

                        if( same( singles[sd][sf].frag, singles[sd][sf].frag_error, clo, chi ) ) return(TRUE);  /* matching combination */


                        for( m=0; m <= n; m++ ) {
                                if( p[m] > p[m+1]+1 ) {                   /* a place to decrement */
                                        p[m]--;
                                        for( k=0; k < m; k++ )
                                                p[k] = mmax[md] - k;      /* move all the preceeding pointers back to small end */

                                        break;
                                }
                        }

                        if( p[n] < mf ) break;  /* past last combination */

                } while (TRUE);
```

```
        }
        return(FALSE);
}

boolean check_frags()    /* check fragments to see if any don't add up */
{
        int sd,sf,md,mf;
        boolean rv;

        rv = TRUE;

        for( sd=START; sd <= nsd; sd++ ) {
                for( md=START; md <= nmd; md++ ) {
                        if( composition[md][sd] ) {
                                mf = START;
                                for( sf=START; sf <= smax[sd]; sf++ ) {

                                        if( (mf = findmatch(sd,sf,md,mf)) == EMPTY ) {
                                                mf = START;
                                                printf("\n%ld from %s is smaller than anything in %s", singles[sd][sf].frag, sname[sd], mname[md]);
                                                rv = FALSE;
                                                break;
                                        }
                                        if( !same( singles[sd][sf].frag, singles[sd][sf].frag_error, multiples[md][mf].frag, multiples[md][mf].frag_error ) ) {
                                                if( !findgroup(sd,sf,md,mf) ) {                 /* no combination fits either */
                                                        printf("\n%ld from %s doesn't fit any combination of fragments from %s", singles[sd][sf].frag, sname[sd], mname[md]);
                                                        rv = FALSE;
                                                }
                                        }
                                }
                        }
                }
        }
        return(rv);
}

auto_clue()      /* set NEW flag for obvious fragments */
{
        int md,sd,n,looks_the_same;

        for(md=START; md <= nmd; md++) {                                        /* try all multiples */
                mul2sd(md);                                                     /* move to temporary space */
                for(tptr = START; tptr <= tmax; tptr++) {                       /* all frags in multiple */
                        tdigest[tptr].flags &= ~AUTONEW;                        /* clear the auto new flags */
                        if( tdigest[tptr].flags & NEW ) continue;               /* already flagged as new */
                        looks_the_same = FALSE;
                        for( sd = next_sdig(EMPTY,md); sd > EMPTY; sd = next_sdig(sd,md) ) {     /* all composing single digests */
                                for(n=START; n <= smax[sd]; n++) {                              /* each frag. in single */
                                        if( same( singles[sd][n].frag, singles[sd][n].frag_error, tdigest[tptr].frag, tdigest[tptr].frag_error) ) {
                                                looks_the_same = TRUE;
                                                break;
                                        }
                                }
                                if( looks_the_same ) break;
                        }
                        if( !looks_the_same ) {
                                if( (tdigest[tptr].flags & ANYEND) == NULL ) {  /* end fragments must not be new */
                                        tdigest[tptr].flags |= AUTONEW;                 /* not the same as any single -> new frag */
                                        printf("\n%s fragment %ld is being tagged as NEW",tname,tdigest[tptr].frag);
                                }
                        }
                }
                sd2mul(md);                     /* move back */
        }
}

SIZE sabs(s)     /* absolute value for type SIZE */
SIZE s;
{
        if( s < (SIZE) 0 ) return( -s );
        return(s);
}

boolean all_checked(sp)          /* see if all members of array 'sp' are non-zero */
int sp [MAXSIN];
{
        int i;

        for( i=START; i <= nsd; i++ ) if( sp[i] == FALSE ) return(FALSE);
        return(TRUE);
}
```

```
int common_digest(first)         /* identify the first digest common to the set of multiples */
int first;                       /* this is necessary only for circular maps */
{
        int i,j,k;
        int score_pad [MAXSIN];

        for( i = first; i <= nsd; i++ ) {                          /* pick a single digest */
                for( j=START; j <= nsd; j++ ) score_pad [j] = FALSE;    /* clear score chart */
                score_pad [i] = TRUE;                              /* check off chosen single */

                for( j=START; j <= nmd; j++ ) {                            /* scan multiple digests */
                        if( composition [j] [i] ) {                /* this multiple contains chosen single */
                                for( k=START; k <= nsd; k++ ) {            /* check off digests connected through this multiple */
                                        score_pad [k] |= composition [j] [k];
                                }
                        }
                }
                if( all_checked(score_pad) ) return(i);            /* this digest is connected to all others through multiples */
        }
        return(EMPTY);                                  /* return value for no connection */
}


analyse()       /* check consistency of project, return TRUE if consistent */
{
        boolean whoops;
        int i,j,nc,ns;
        char s[SCREENWIDTH];
        SIZE smw[MAXSIN], smwe[MAXSIN];
        SIZE mmw[MAXMUL], mmwe[MAXMUL];
        SIZE average;
        SIZE dif, s_dif, m_dif;
        SIZE most_ave, m_ave_error;
        int s_ave, m_ave;

        whoops = TRUE;

        if( nmd < START ) {
                printf("\nNo multiple digests");
                whoops = FALSE;
        }

        if( nsd < 1 ) {                 /* need at least 2 singles */
                printf("\nNeed at least two single digests");
                whoops = FALSE;
        }

        for(i=START; i<=nsd; i++) {     /* scan singles */
                for(nc = j=START; j<=nmd; j++) {        /* scan multiples */
                        if(composition[j][i]) {
                                nc++;
                                break;
                        }
                }
                if( !nc ) {     /* orphan single digest */
                        printf("\nSingle digest %s is not in any multiple digest",sname[i]);
                        whoops = FALSE;
                }
        }

        average = (SIZE) 0;
        for( i=START; i <= nsd; i++ ) {
                smw[i] = smwe[i] = (SIZE) 0;
                for( j=START; j <= smax[i]; j++ ) {
                        smw[i] += singles[i][j].frag;
                        smwe[i] += singles[i][j].frag_error;
                }
                average += smw[i];
        }

        for( i=START; i <= nmd; i++ ) {
                mmw[i] = mmwe[i] = (SIZE) 0;
                for( j=START; j <= mmax[i]; j++ ) {
                        mmw[i] += multiples[i][j].frag;
                        mmwe[i] += multiples[i][j].frag_error;
                }
                average += mmw[i];
        }

        average /= (nsd+nmd+2);                 /* now we have an average molecular weight */
```

```
s_dif = GIANT;
for( i=START; i <= nsd; i++ ) {
        if( (dif = sabs( smw[i] - average )) < s_dif ) {
                s_dif = dif;
                s_ave = i;
        }
}

m_dif = GIANT;
for( i=START; i <= nmd; i++ ) {
        if( (dif = sabs( mmw[i] - average )) < m_dif ) {
                m_dif = dif;
                m_ave = i;
        }
}

if( s_dif < m_dif ) {
        most_ave = smw[s_ave];
        m_ave_error = smwe[s_ave];
}
else {
        most_ave = mmw[m_ave];
        m_ave_error = mmwe[m_ave];
}

for( i = START; i <= nsd; i++ ) {
        if( !same(most_ave,m_ave_error,smw[i],smwe[i]) ) {
                if( most_ave > smw[i] ) printf("\n%s molecular weight is too small by %ld\n",sname[i], most_ave - smw[i]);

                else printf("\n%s molecular weight is too large by %ld",sname[i], smw[i] - most_ave);
                whoops = FALSE;
        }
}

for( i = START; i <= nmd; i++ ) {
        if( !same(most_ave,m_ave_error,mmw[i],mmwe[i]) ) {
                if( most_ave > mmw[i] ) printf("\n%s molecular weight is too small by %ld\n",mname[i], most_ave - mmw[i]);
                else printf("\n%s molecular weight is too large by %ld",mname[i], mmw[i] - most_ave);
                whoops = FALSE;
        }
}

if( whoops ) {                  /* check connectivity */
        if( !linear ) {                 /* only if circular */
                if( (i = common_digest(START)) == EMPTY ) {     /* not connected */
                        printf("\nNo single digest connects to all other singles\n");
                        whoops = FALSE;
                }
                else printf("\n%s connects to all other single digests\n", sname[i]);
        }
}
for(i=START; i<=nmd; i++) {     /* scan multiples */
        for(nc = ns = j = START; j<=nsd; j++)
                if( composition[i][j] ) {
                        ns += (smax[j]+1);
                        nc++;
                }

        if( nc < 2 ) {          /* not enough composing singles */
                printf("\nMultiple digest %s is composed of missing single digests",mname[i]);
                whoops = FALSE;
        }

        if( linear ) {          /* sum(mf) = sum(sf) - sd + 1 */
                if( mmax[i] > ns-nc ) {
                        printf("\n%d too many fragments in %s",mmax[i]-ns-nc,mname[i]);
                        whoops = FALSE;
                }
                else if( mmax[i] < ns-nc ) {
                        printf("\n%d too few fragments in %s",ns-nc-mmax[i],mname[i]);
                        whoops = FALSE;
                }
        }
        else {                  /* sum(mf) = sum(sf) */
                if( mmax[i]+1 > ns ) {
                        printf("\n%d too many fragments in %s",mmax[i]+1-ns,mname[i]);
                        whoops = FALSE;
                }
                else if( mmax[i]+1 < ns ) {
                        printf("\n%d too few fragments in %s",ns-mmax[i]-1,mname[i]);
                        whoops = FALSE;
                }
        }
```

```
	}
	if( whoops ) whoops = check_frags();

	if( whoops ) auto_clue();

	return(whoops);
}

do_op()		/* perform one of the operations */
{
	FILE *rma;
	int dig,dtype;
	static char parm[SCREENWIDTH],viewpath[MAXPATH];

	switch(op_row) {
		case 0:			/* input */
			get_gel("*.gel");
			break;
		case 1:			/* merge */
			get_merge();
			break;
		case 2:			/* edit */
			while( dtype = pick_digest(&dig,"edit/view/delete") ) ed_frags(dtype,dig);
			break;
		case 3:			/* analyze */
			cl_wn(&wn[cur_window]);
			gotoxy(1,1);
			pl_csr(&wn[cur_window]);
			if( !analyse() ) {
				printf("\n(Hit a key to return to menu)");
				rawin();
			}
			else {
				printf("\nProject is consistent.\nOK to map.\n");
				printf("\n(Hit a key to return to menu)");
				rawin();
			}
			break;
		case 4:			/* map */
			cl_wn(&wn[cur_window]);
			gotoxy(1,1);
			pl_csr(&wn[cur_window]);

			if(analyse()) {			/* analysis uncovers no inconsistency */
				printf("\n");
				if( (rma = fopen(mp_name,"w+")) ) {
					put_project(rma,0);	/* save project */
					fclose(rma);
				}

				strcpy(parm,"rmap -i");
				strcat(parm,mp_name);	/* pass project name to mapping program */
				system(parm);		/* run the mapper */

				strcpy(viewpath,mp_name);	/* construct index file pathname */
				new_ext(viewpath,"mix");

				if( rma = fopen( viewpath, "r") ) {	/* check the index to see if anything was saved */
					fgets(parm,SCREENWIDTH,rma);
					fscanf(rma,"%d",&dig);
					if( dig >= 0 ) {			/* something saved */
						strcpy(parm,"mapout -i");
						strcat(parm,mp_name);
						system(parm);	/* run the viewer */
					}
				}
			}
			else {
				printf("\n(Hit a key to return to menu)");
				rawin();
			}
			break;
		case 5:			/* view */
			cl_wn(&wn[cur_window]);
			gotoxy(1,1);
			pl_csr(&wn[cur_window]);

			strcpy(viewpath,mp_name);	/* construct index file pathname */
			new_ext(viewpath,"mix");
```

```
                if( rma = fopen( viewpath, "r") ) {      /* check the index to see if anything was saved */
                        fgets(parm,SCREENWIDTH,rma);
                        fscanf(rma,"%d",&dig);
                        if( dig >= 0 ) {                 /* something saved */
                                strcpy(parm,"mapout -i");
                                strcat(parm,mp_name);
                                system(parm);   /* run the viewer */
                        }
                }
                break;
        case 6:                         /* set Linear */
                change_flag = TRUE;
                linear = TRUE;
                set_topo();
                break;
        case 7:                         /* set Circular */
                change_flag = TRUE;
                linear = FALSE;
                set_topo();
                break;
        }
}

op_menu()       /* show operation menu */
{
        int i;

        cur_window = PICK;
        set_wn(&wn[PICK]);

        invisible();

        gotoxy(PM_TC,OP_TITLE);
        rawputs("Current Project: ");
        rawputs(mp_name);

        for( i=0; i <= OP_MAX; i++ ) {
                gotoxy(OP_COL,OP_TOP+i);
                if( i == op_row ) reverse();
                rawputs(op_text[i]);
                if( i == op_row ) normal();
        }

        gotoxy(OP_COL,TOPOLINE);
        rawputs(topology);
}

op_on()
{
        gotoxy(OP_COL,OP_TOP+op_row);
        reverse();
        rawputs(op_text[op_row]);
        normal();
}

op_off()
{
        gotoxy(OP_COL,OP_TOP+op_row);
        rawputs(op_text[op_row]);
}

op_select()     /* operate the program */
{
        set_topo();
        op_menu();

        while(1) {
                switch(toupper(rawin())) {
                        case 0:
                                switch(rawin()) {
                                        case CUP:
                                                op_off();
                                                if( --op_row < 0 ) op_row = OP_MAX;
                                                op_on();
                                                break;
                                        case CDOWN:
                                                op_off();
                                                if( ++op_row > OP_MAX ) op_row = 0;
                                                op_on();
                                                break;
                                }
                                break;
```

```
                case CR:        /* select current */
                        if( op_row == OP_MAX ) return;
                        do_op();
                        op_menu();
                        break;
                case 'I':
                        op_row = 0;
                        do_op();
                        op_menu();
                        break;
                case 'G':
                        op_row = 1;
                        do_op();
                        op_menu();
                        break;
                case 'E':
                        op_row = 2;
                        do_op();
                        op_menu();
                        break;
                case 'A':
                        op_row = 3;
                        do_op();
                        op_menu();
                        break;
                case 'M':
                        op_row = 4;
                        do_op();
                        op_menu();
                        break;
                case 'V':
                        op_row = 5;
                        do_op();
                        op_menu();
                        break;
                case 'L':
                        op_row = 6;
                        do_op();
                        op_menu();
                        break;
                case 'C':
                        op_row = 7;
                        do_op();
                        op_menu();
                        break;
                case 'R':
                case ABORT:
                        return;
                }
        }
}

main()
{
        int dtype,d;
        FILE *save;
        char *p, b[SCREENWIDTH];

        if( !keydisk() ) exit(1);

        init();

        scr_setup();
        setbreak();     /* disable DOS break */

        invisible();

        cur_window = PICK;
        set_wn(&wn[PICK]);

        while(pm_select()) {
                switch( pm_row ) {
                case 0:                         /* create */
                        if(get_new("Name of new project: ",TRUE)) op_select();
                        break;
                case 1:                         /* open */
                        if(get_old()) op_select();
                        break;
                case 2:                         /* resume */
                        if(*mp_name) op_select();
                        break;
                case 3:                         /* save */
```

```
			if( !change_flag ) break;	/* don't need to */
			clears();
			gotoxy(1,1);
			if( (save = fopen(mp_name,"w+")) ) {
				put_project(save,0);
				fclose(save);
			}
			break;
		case 4:				/* backup */
			if(*mp_name) {
				clears();
				gotoxy(1,1);
				archive();
			}
			break;
		case 5:				/* restore */
			restore();
			break;
		case 6:				/* rename */
			if(*mp_name) {
				clears();
				gotoxy(1,1);
				get_new("New name for project: ",FALSE);
			}
			break;
		}
	}

	if( change_flag ) {	/* something not written to disk...try to recover */
		clears();
		gotoxy(20,15);
		rawputs("Current project is not saved...save first? (Y/N) ");
		if( rawgets(b) > 0 ) {  /* got a response */
			p = b;
			while( *p && !isalpha(*p) ) p++;
			if( toupper(*p) == 'Y' ) {	/* OK...save it */
				clears();
				gotoxy(1,1);
				if( (save = fopen(mp_name,"w+")) ) {
					put_project(save,0);
					fclose(save);
				}
			}
		}
	}

	visible();
	exit(0);
}
#include <stdio.h>

#define VAR extern

#include <redit.h>

void init()	/* initialize all map and digest pointers to show empty */
{
	int i,j;

	change_flag = FALSE;

	nmd = nsd = EMPTY;

	for(i=0; i < MAXSIN; i++) {
		sptr [i] = smax [i] = EMPTY;
		sname [i][0] = NULL;
		sfile [i][0] = NULL;
		for(j=0; j < MAXMAP; j++) {
			singles [i] [j].used = FREE;
			singles [i] [j].flags = (CLUE) NONE;
		}
	}

	tptr = tmax = EMPTY;
	tname[0] = NULL;
	tfile[0] = NULL;
	for( j = 0; j < MAXMAP; j++ ) {
		tdigest [j].used = FREE;
		tdigest [j].flags = (CLUE) NONE;
	}
```

```
        for(i=0; i < MAXMUL; i++) {
                mptr [i] = mmax [i] = EMPTY;
                mname [i][0] = NULL;
                mfile [i][0] = NULL;
                for(j=0; j < MAXSIN; j++) {
                        composition [i] [j] = FALSE;
                }
                for(j=0; j < MAXMAP; j++) {
                        multiples [i] [j].used = FREE;
                        multiples [i] [j].flags = (CLUE) NONE;
                }
        }

        lo_factor = 10L;
}

#define TBUF 80

int dcomp(f1,f2)                /* compare the sizes of fragments stored in nodes 'f1','f2' */
digest *f1,*f2;
{
        if (f2->frag > f1->frag) return(1);
        if (f2->frag < f1->frag) return(-1);
        return(0);
}

char *scan_past(p,c)            /* scan past the first occurrence of char 'c' in string 'p' */
char *p,c;
{
        while(*p) {
                if( *p == c) return(++p);
                ++p;
        }
        return(NULL);
}

int get_dig(s)          /* read in a digest from file 's' */
char *s;
{
        FILE *inp;
        char b[TBUF], *p;
        int sorm;

        for(sorm=START;sorm < MAXMAP;sorm++) tdigest[sorm].flags = (CLUE) NONE;

        if( (inp = fopen(s,"r")) == NULL ) {    /* not at home */
                                                /* try stripping path */
                local(b,s);
                if( (inp = fopen(b,"r")) == NULL ) {    /* not there either */
                        printf("\nFile error!\n");
                        return(0);
                }
        }
        else strcpy(b,s);               /* the path that worked into 'b' */

        complete(tfile,b);              /* construct complete pathname */

        tmax = EMPTY;

        fgets(b,NAMELEN,inp);           /* read digest name */
        trim(b);

        uppercase(b);                   /* map to upper case alphabetics */

        if( scan_past(b,',') ) {
                sorm = MULTIPLE;        /* multiple digest */
                if( ++nmd >= MAXMUL ) {
                        nmd--;
                        printf("\nToo many multiple digests!\n");
                        return(0);
                }
        }
        else {
                sorm = SINGLE;
                if( ++nsd >= MAXSIN ) {
                        nsd--;
                        printf("\nToo many single digests!\n");
                        return(0);
                }
        }
        strcpy(tname,b);
```

```
while(fgets(b,TBUF,inp)) {                              /* read fragment sizes */
        trim(b);
        if( *b == NULL ) break;
        tmax++;                                         /* one more */
        sscanf(b,"%ld", &tdigest [tmax].frag);  /* extract size */
        if( tdigest [tmax].frag == (SIZE) 0 ) {
                tmax--;
                break;
        }
        if( p = scan_past(b,',') ) {
                p = scan_past(p,' ');
                sscanf(p,"%ld", &tdigest [tmax].frag_error);    /* extract error */
        }
        else tdigest [tmax].frag_error = tdigest [tmax].frag * lo_factor / (SIZE) 100;

        if( p = scan_past(p,',') ) {    /* clue field is present */
                p = scan_past(p,' ');
                while( *p ) {
                        switch( toupper(*p++) ) {
                        case 'A':       /* auto new frag */
                                tdigest [tmax].flags |= (CLUE) AUTONEW;
                                break;
                        case 'N':       /* new frag */
                                tdigest [tmax].flags  |= (CLUE) NEW;
                                break;
                        case 'C':
                                tdigest [tmax].flags |= (CLUE) CUT;
                                break;
                        case 'E':       /* any end */
                                tdigest [tmax].flags |= (CLUE) EEND;

                                tclue |= (CLUE) EEND;
                                break;
                        case 'L':       /* left end */
                                tdigest [tmax].flags |= (CLUE) LEND;
                                tclue |= (CLUE) LEND;
                                break;
                        case 'R':       /* right end */
                                tdigest [tmax].flags |= (CLUE) REND;
                                tclue |= (CLUE) REND;
                                break;
                        }
                }
        }
}

fclose(inp);

qsort( &tdigest[0], tmax+1, sizeof(digest), &dcomp );

if( sorm == MULTIPLE ) ed2mul(nmd);     /* copy to multiple */
else ed2sin(nsd);                       /* copy to single */

sort_out();

return(sorm);
}

int get_project(inp,bak)        /* read file 'inp' and follow instructions */
char *inp;
int bak;
{
        FILE *f;
        int this,i,j;
        char *p;
        static char b[TBUF], clu[TBUF];

        if( f = fopen(inp,"r") ) {
                init();

                fgets(b,TBUF,f);        /* description line */
                trim(b);
                strcpy(comment,b);

                if(bak) {               /* recover project pathname too */
                        fgets(b,TBUF,f);
                        trim(b);
                        strcpy(mp_name,b);
                }

                fgets(b,TBUF,f);
                if( toupper( b[0] ) == 'L' ) linear = TRUE; else linear = FALSE;
```

```
fgets(b,TBUF,f);
sscanf(b,"%d",&nmd);

for(i=START; i<=nmd; i++) {

        fgets(b,TBUF,f);
        trim(b);
        strcpy(mname[i],b);

        fgets(b,TBUF,f);
        sscanf(b,"%d",&mmax[i]);

        for(j=START; j<=mmax[i]; j++) {
                fgets(b,TBUF,f);
                clu[0] = NULL;
                sscanf(b,"%ld, %ld, %s",&multiples[i][j].frag,&multiples[i][j].frag_error,clu);
                p = clu;
                while( *p ) {
                        switch( toupper(*p++) ) {
                        case 'A':       /* auto new frag */
                                multiples[i][j].flags |= (CLUE) AUTONEW;
                                break;
                        case 'N':       /* new frag */
                                multiples[i][j].flags  |= (CLUE) NEW;
                                break;
                        case 'E':       /* any end */
                                multiples[i][j].flags |= (CLUE) EEND;
                                m_endflag[i] |= (CLUE) EEND;
                                break;
                        case 'L':       /* left end */
                                multiples[i][j].flags |= (CLUE) LEND;
                                m_endflag[i] |= (CLUE) LEND;
                                break;
                        case 'R':       /* right end */
                                multiples[i][j].flags |= (CLUE) REND;
                                m_endflag[i] |= (CLUE) REND;
                                break;
                        }
                }
        }
}
fgets(b,TBUF,f);
sscanf(b,"%d",&nsd);

for(i=START; i<=nsd; i++) {
        fgets(b,TBUF,f);
        trim(b);
        strcpy(sname[i],b);

        fgets(b,TBUF,f);
        sscanf(b,"%d",&smax[i]);

        for(j=START; j<=smax[i]; j++) {

                fgets(b,TBUF,f);
                clu[0] = NULL;
                sscanf(b,"%ld, %ld, %s",&singles[i][j].frag,&singles[i][j].frag_error,clu);

                p = clu;
                while( *p ) {
                        switch( toupper(*p++) ) {
                        case 'C':
                                singles[i][j].flags |= (CLUE) CUT;
                                break;
                        case 'E':       /* any end */
                                singles[i][j].flags |= (CLUE) EEND;
                                s_endflag[i] |= (CLUE) EEND;
                                break;
                        case 'L':       /* left end */
                                singles[i][j].flags |= (CLUE) LEND;
                                s_endflag[i] |= (CLUE) LEND;
                                break;
                        case 'R':       /* right end */
                                singles[i][j].flags |= (CLUE) REND;
                                s_endflag[i] |= (CLUE) REND;
                                break;
                        }
                }
        }
}
```

```
                fclose(f);

                return(TRUE);
        }
        else return(FALSE);             /* project isn't here */
}

put_project(f,bak)          /* write current project to disk */
FILE *f;
int bak;                    /* if TRUE this is a backup */
{
        int i,j;
        static char fn[MAXPATH],ext[NAMELEN];

        printf("\nSaving project: %s",mp_name);

        fprintf(f,"%s\n",comment);
        if( bak ) fprintf(f,"%s\n",mp_name);
        fprintf(f,"%s\n", (linear) ? "Linear" : "Circular" );
        fprintf(f,"%d\n",nmd);
        for( i = START; i <= nmd; i++ ) {
                fprintf(f,"%s\n",mname[i]);
                fprintf(f,"%d\n",mmax[i]);
                for( j = START; j <= mmax[i]; j++ ) {

                        fprintf(f,"%ld, %ld",multiples[i][j].frag,multiples[i][j].frag_error);

                        if( multiples[i][j].flags ) {
                                fprintf(f,", ");

                                if( linear ) {
                                        if( multiples[i][j].flags & EEND ) putc('E',f);
                                        else if( multiples[i][j].flags & LEND ) putc('L',f);
                                        else if( multiples[i][j].flags & REND ) putc('R',f);
                                }

                                if( multiples[i][j].flags & NEW ) putc('N',f);
                                if( multiples[i][j].flags & AUTONEW ) putc('A',f);
                        }

                        fprintf(f,"\n");
                }

        }
        fprintf(f,"%d\n",nsd);
        for( i = START; i <= nsd; i++ ) {
                fprintf(f,"%s\n",sname[i]);
                fprintf(f,"%d\n",smax[i]);
                for( j = START; j <= smax[i]; j++ ) {
                        fprintf(f,"%ld, %ld",singles[i][j].frag,singles[i][j].frag_error);
                        if( singles[i][j].flags ) {
                                fprintf(f,", ");
                                if( linear ) {
                                        if( singles[i][j].flags & EEND ) putc('E',f);
                                        else if( singles[i][j].flags & LEND ) putc('L',f);
                                        else if( singles[i][j].flags & REND ) putc('R',f);
                                }
                                if( singles[i][j].flags & NEW ) putc('C',f);
                        }
                        fprintf(f,"\n");
                }
        }


        if( !bak ) change_flag = FALSE;
}

archive()           /* save a project in a backup file */
{
        static char desc[SCREENWIDTH+2],bname[MAXPATH];
        char *p;
        FILE *f;
        int i,j;

        gotoxy(20,12);
        rawputs("Name of backup: ");
        block();

        if( rawgets(bname) > 0 ) {

                new_ext(bname,".mpb");
```

```
        if( f = fopen(bname,"r") ) {
                fclose(f);

                clears();
                gotoxy(15,15);
                rawputs("A backup of that name already exists...Overwrite? (Y/N) ");
                if( (i = rawgets(desc)) > 0 ) {                 /* some response */
                        p = desc;
                        while( *p && !isalpha(*p) ) p++;
                        if( toupper(*p) != 'Y' ) {      /* negative response */
                                invisible();
                                return;
                        }
                }
                else {
                        invisible();            /* abort means negative response */
                        return;
                }
        }

        if( comment[0] == NULL ) {

                clears();

                gotoxy(16,10);
                rawputs("Type one line of description of this backup:");

                gotoxy(1,14);
                crepeat('_',SCREENWIDTH);
                gotoxy(1,14);

                rawgets(desc);
                strcpy(comment,desc);
        }

        if( f = fopen(bname,"w") ) {
                put_project(f,1);       /* flag as a backup */
                fclose(f);
        }
        else {
                clears();
                gotoxy(29,12);
                rawputs("Can't open backup file!");
                gotoxy(29,14);
                rawputs("(Hit a key to continue)");
                rawin();
        }

    }
    invisible();
}
restore()       /* read in a project from backup */
{
    FILE *f;
    char *p;
    char b[TBUF],clu[TBUF];
    int i,j,t;

    if( p = fn_get("Project backup files contained in ","*.mpb") ) {
        clears();

        if(get_project(p,1)) {
                sort_out();
        }
        else {
                printf("\nCan't open backup file!");
                printf("\n\n(Hit a key to continue)\n");
                rawin();
        }
    }

}

sort_out()      /* figure out what multiples are composed of what singles */
{
    char b[TBUF],*p;
    int i,j,nd;
```

```
	for( i = START; i <= nmd; i++ )		{	/* scan multiple digests */

		for(j=START;j<MAXSIN;j++) composition[i][j] = FALSE;

		for( nd = j = START; j <= nsd; j++ ) {	/* scan single digests */
			strcpy(b,sname[j]);
			strcat(b," *,");			/* look for 'sname[],' imbedded in mname[] */
			if( stcpm( mname[i], b, &p ) ) {	/* found it */
				composition [i] [j] = TRUE;
				nd++;
				continue;
			}
			strcpy(b,", *");			/* look for ',sname[]' imbedded in mname[] */
			strcat(b,sname[j]);
			if( stcpm( mname[i], b, &p ) ) {	/* found it */
				composition [i] [j] = TRUE;
				nd++;
				continue;
			}
		}
	}
}

trim(s)		/* remove trailing newline if there */
char *s;
{
	if( *s ) {
		if( s[strlen(s)-1] == '\n' ) s[strlen(s)-1] = NULL;
	}
}

md_dump(md)	/* dump the digest data to stdout */
int md;
{
	int this;

	printf("\n%s: ", mname [md]);

	for(this = START; this <= mmax [md]; this++ )
		printf("%ld+-(%ld%%) ", multiples [md] [this].frag, (multiples [md] [this].frag_error * 100L / multiples [md][this].frag) );
}

sd_dump(sd)	/* dump the digest data to stdout */
int sd;
{
	int this;

	printf("\n%s: ", sname [sd]);

	for(this = START; this <= smax [sd]; this++ )
		printf("%ld+-(%ld%%) ", singles [sd] [this].frag, (singles [sd] [this].frag_error * 100L / singles [sd] [this].frag) );
}

/* Copyright (c) 1986 DNASTAR, Inc. */

#include <stdio.h>

#define VAR extern

#include <redit.h>
#include <fcntl.h>
#include <dos.h>

#define SEQLEFT 10
#define SEQTOP 3
#define SEQSPACE 10
#define SEQMID 10

#define RYMAX 10		/* maximum values for the rack of sequence files */
#define RXMAX 6

#define MAXFILES 64		/* maximum number of files in pick screen */

char	*gel_rack [MAXFILES];	/* the rack of filenames used to select stored sequences */
char	pick_flag [MAXFILES];	/* flag for each indicating selection status */
int	rack_x, rack_y;			/* the rack coordinates of the current filename */
int	mxr = ( -1 );		/* the end of the rack */
int	myr = ( -1 );		/* ditto */
char	gel_dir [MAXPATH];	/* path to the rack */
```

```
load_rack(path,wcard)     /* put all the '.gel' files into the sequence rack */
char *path,*wcard;        /* 'path' is the requested path, 'wcard' is a filename mask */
{
        char where[MAXPATH];
        int total;

        strcpy(where,path);             /* contruct a wildcard for the sequence files */
        if( path && (*path) && (path[strlen(path)-1] != '\\') && (path[strlen(path)-1] != ':')) strcat(where,"\\");

        if( *where && !path_check(where) ) {    /* doesn't exist */

                do {
                        clears();

                        gotoxy(12,19);
                        rawputs("That directory doesn't exist, try another.");

                        gotoxy(22,17);
                        rawputs("Hit <esc> to abort");
                        gotoxy(15,15);
                        rawputs("Another directory? (please specify): ");
                        if( rawgets(where) > 0 ) {      /* a new place */
                                if( (where[strlen(where)-1] != '\\') && (where[strlen(where)-1] != ':')) strcat(where,"\\");
                        }
                        else where[0] = NULL;   /* try current */

                } while( *where && !path_check(where) );
        }

        strcpy(gel_dir,where);          /* save it globally */
        strcat(where,wcard);

        clear_rack();
        rack_x = rack_y = mxr = myr = -1;       /* clear rack and set current to first */

        total = expand(gel_rack,where) - 1;

        if( total >= 0 ) {
                rack_x = rack_y = 0;
                mxr = total / RYMAX;
                myr = total % RYMAX;
        }
}

clear_rack()    /* free the data attached to the sequence rack */
{
        int i,j,ent;
        for(ent = 0, i=0; i <= mxr; i++) {
                for(j=0; j <= myr; j++) {
                        if(gel_rack [ent]) free(gel_rack [ent]);
                        gel_rack [ent] = NULL;
                        pick_flag [ent] = (char) 0;
                        ent++;
                }
        }
}

clear_flags()   /* reset pick flags on rack */
{
        int i;
        for( i=0; i < MAXFILES; i++ ) pick_flag[i] = (char) 0;
}

char *no_ext(s) /* remove the extension from a local filename */
char *s;
{
        static char temp[13];
        char *p;

        strcpy(temp,s);
        for(p = temp; *s; p++)
                if( *s++ == '.' ) *p = NULL;

        return(temp);
}

int r_select()  /* convert 'rack_x and 'rack_y' into an entry index */
{
        if( myr < 0 ) return(-1);
        return( rack_x * RYMAX + rack_y );
}
```

```
out_rack()        /* un-reverse the current entry in the rack on the screen */
{
        gotoxy( (rack_x*SEQSPACE)+SEQLEFT, rack_y+SEQTOP );
        if( myr < 0 ) {
                gotoxy(SEQLEFT,SEQTOP);
                rawputs("None");
        }
        rawputs( no_ext( gel_rack [r_select()] ) );

}

in_rack()         /* reverse the current entry in the rack on the screen */
{
        if( myr < 0 ) return;

        gotoxy( (rack_x*SEQSPACE)+SEQLEFT, rack_y+SEQTOP );
        reverse();
        rawputs( no_ext( gel_rack [r_select()] ) );
        normal();
}

pick1help()       /* display a help menu for single pick screen */
{
        gotoxy(6,RYMAX+SEQTOP+3);
        rawputs("IMMMMMMMMMMMMMMMKMMMMMMMMMMMMMMMKMMMMMMMMMMMMMMMMMMMMMMMMMMMMMMMMMMM;");
        gotoxy(6,RYMAX+SEQTOP+4);
        rawputs(":   <-   left   :     up      :  <ret>     to select              :");
        gotoxy(6,RYMAX+SEQTOP+5);
        rawputs(":   ->   right  :     down    :  <space>   to view file           :");
        gotoxy(6,RYMAX+SEQTOP+6);
        rawputs("LMMMMMMMMMMMMMMMJMMMMMMMMMMMMMMMJMMMMMMMMMMMMMMMMMMMMMMMMMMMMMMMMMMM9");
        gotoxy(6,RYMAX+SEQTOP+7);
        rawputs(": <esc> to abandon    ? help     <other> choose another directory :");
        gotoxy(6,RYMAX+SEQTOP+8);
        rawputs("HMMMMMMMMMMMMMMMMMMMMMMMMMMMMMMMMMMMMMMMMMMMMMMMMMMMMMMMMMMMMMMMMMMM<");
}

pickhelp()        /* display a help menu for multiple pick screen */
{
        gotoxy(6,RYMAX+SEQTOP+3);
        rawputs("IMMMMMMMMMMMMMMMKMMMMMMMMMMMMMMMKMMMMMMMMMMMMMMMMMMMMMMMMMMMMMMMMMMM;");
        gotoxy(6,RYMAX+SEQTOP+4);
        rawputs(":   <-   left   :     up      :  <Ins>     to select              :");
        gotoxy(6,RYMAX+SEQTOP+5);
        rawputs(":   ->   right  :     down    :  <Del>     to unselect            :");
        gotoxy(6,RYMAX+SEQTOP+6);
        rawputs("LMMMMMMMMMMMMMMMJMMMMMMMMMMMMMM9  <space>   to view file           :");
        gotoxy(6,RYMAX+SEQTOP+7);
        rawputs(": <ret> to accept choices      HMMMMMMMMMMMMMMMMMMMMMMMMMMMMMMMMMMM9");
        gotoxy(6,RYMAX+SEQTOP+8);
        rawputs(": <esc> to abandon    ? help     <other> choose another directory :");
        gotoxy(6,RYMAX+SEQTOP+9);
        rawputs("HMMMMMMMMMMMMMMMMMMMMMMMMMMMMMMMMMMMMMMMMMMMMMMMMMMMMMMMMMMMMMMMMMMM<");
}

see_rack(s,many)          /* display the sequence rack on the screen */
char *s;
{
        int i,j,ent;

        clears();

        gotoxy(SEQLEFT+10,1);
        rawputs(s);
        if(*gel_dir) rawputs(gel_dir);
        else rawputs("current directory");

        if( myr < 0 ) {
                gotoxy(SEQLEFT,SEQTOP);
                rawputs("None");
        }
        else {
                for(ent = 0, i=0; i <= mxr; i++) {
                        for(j=0; j < RYMAX; j++) {

                                if( (i == mxr) && (j > myr) ) break;

                                gotoxy( (i*SEQSPACE)+SEQLEFT, j+SEQTOP);

                                if( (i == rack_x) && (j == rack_y) ) {  /* current selection */
                                        reverse();
                                        rawputs( no_ext(gel_rack [ent]) );
                                        normal();
```

```
                                }
                                else    rawputs( no_ext(gel_rack [ent]) );

                                if( many && pick_flag[ent] ) {
                                        highint();
                                        rawputs("*");
                                        normal();
                                }
                                else rawputs(" ");

                                ent++;

                        }
                }
        }

        if( many ) pickhelp();
        else pick1help();
}

q_see_rack(s,many)      /* quick display of the sequence rack on the screen */
char *s;
{
        int i,j,ent;

        if( myr < 0 ) {
                gotoxy(SEQLEFT,SEQTOP);
                rawputs("None");
        }
        else {
                for(ent = 0, i=0; i <= mxr; i++) {
                        for(j=0; j < RYMAX; j++) {

                                if( (i == mxr) && (j > myr) ) break;

                                gotoxy( (i*SEQSPACE)+SEQLEFT, j+SEQTOP);

                                if( (i == rack_x) && (j == rack_y) ) {  /* current selection */
                                        reverse();
                                        rawputs( no_ext(gel_rack [ent]) );
                                        normal();
                                }
                                else    rawputs( no_ext(gel_rack [ent]) );

                                if( many && pick_flag[ent] ) {
                                        highint();
                                        rawputs("*");
                                        normal();
                                }
                                else rawputs(" ");

                                ent++;

                        }
                }
        }
}

mdr()           /* move down one entry in rack */
{
        if( myr < 0 ) return;

        if( (rack_x == mxr) && (rack_y == myr) ) rack_x = rack_y = 0;
        else {
                if( ++rack_y >= RYMAX ) {
                        rack_y = 0;
                        if(++rack_x >= RXMAX) rack_x = 0;
                }
        }
}

mur()           /* move up one entry in rack */
{
        if( myr < 0 ) return;

        if( (rack_x == 0) && (rack_y == 0) ) {
                rack_x = mxr;
                rack_y = myr;
        }
        else {
```

```
                if( --rack_y < 0 ) {
                        rack_y = RYMAX-1;
                        rack_x--;
                }
        }
}

mlr()   /* move left in rack */
{
        if( myr < 0 ) return;

        if( rack_x == 0 ) {
                if( myr >= rack_y ) rack_x = mxr;
                else rack_x = mxr-1;
        }
        else --rack_x;
}

mrr()   /* move right in rack */
{
        if( myr < 0 ) return;

        if( myr >= rack_y ) {
                if( rack_x < mxr ) rack_x++;
                else rack_x = 0;
        }
        else {
                if( ++rack_x >= mxr ) rack_x = 0;
        }
}

rack_move(s,wcard,many)  /* move current selection in rack according to cursor keys */
char *s,*wcard;
int many;
{
        static char t[MAXPATH];
        static char c;
        static int i;
        FILE *fd;

        t[0] = NULL;    /* terminate path */

        while(1) {
                switch( (c = rawin()) ) {

                        case 0:                 /* cursor prefix key */
                                out_rack();
                                switch(rawin()) {
                                        case CUP:
                                                mur();
                                                break;
                                        case CDOWN:
                                                mdr();
                                                break;
                                        case LEFT:
                                                mlr();
                                                break;
                                        case RIGHT:
                                                mrr();
                                                break;
                                        case INS:
                                                if( !many ) break;
                                                if( (i = r_select()) < 0 ) break;
                                                pick_flag[i] = !pick_flag[i];
                                                q_see_rack(s,many);

                                                break;
                                        case DEL:
                                                if( !many ) break;
                                                if( (i = r_select()) < 0 ) break;
                                                pick_flag[i] = 0;
                                                q_see_rack(s,many);
                                                break;
                                }
                                in_rack();
                                break;

                        case ABORT:
                                return(-1);

                        case CR:
                                return(r_select());
```

```
		case ' ':
			r_view(r_select());
			see_rack(s,many);
			break;

		case '?':
			if( fd = fopen("subdir.hlp","r") ) {
				clears();
				more(fd);
				fclose(fd);
			}
			else {
				see_rack(s,many);
			}
			break;

		default:		/* presumably the user wants another directory */
			t[0] = c;	/* prepend the character */
			t[1] = NULL;

			clears();
			gotoxy(22,17);
			rawputs("Hit <esc> to abort");
			gotoxy(15,15);
			rawputs("Another directory? (please specify): ");
			visible();
			if( arawgets(t) > 0 ) {		/* a new place */
				load_rack(t,wcard);	/* look there */
			}
			invisible();
			see_rack(s,many);
			break;
		}
	}
}
r_view(ent)	/* view the sequence in rack number 'ent' */
int ent;
{
	FILE *f;
	static char fn[MAXPATH];
	char sb[SCREENWIDTH];
	int fv;
	long len,beg,end,k;

	if(ent < 0) return;

	clears();

	strcpy(fn,gel_dir);
	strcat(fn,gel_rack [ent]);


	if( f = fopen(fn,"r") ) {	/* view it */
		more(f);
		fclose(f);
	}
	else {
		rawputs("Can't open the file!\n");
	}

}
char *fn_get(s,wcard)	/* look up the 'wcard' files in this directory and view */
char *s,*wcard;		/* 's' is a screen title */
{
	int pick;
	static char t[MAXPATH];
	static char wc[MAXPATH];

	strcpy(wc,wcard);
	load_rack(NULL,wc);
	see_rack(s,0);

	if( (pick = rack_move(s,wc,0)) < 0 ) return(0);
	else {
		strcpy(t,gel_dir);
		strcat(t,gel_rack [pick]);
		return(t);
	}
}
```

```
char **fn_list(s,wcard)  /* look up the 'wcard' files in this directory and view */
char *s,*wcard;          /* 's' is a screen title */
{
        static char t[MAXPATH];
        static char wc[MAXPATH];
        int pick,i,top;
        char *malloc();

        strcpy(wc,wcard);
        load_rack(NULL,wc);
        see_rack(s,1);

        if( (pick = rack_move(s,wc,1)) < 0 ) return(0);
        else {
                for( top = mxr * RYMAX + myr, i = -1, pick = 0; pick <= top; pick++ ) {
                        if(pick_flag[pick]) {
                                i++;
                                strcpy(t,gel_dir);
                                strcat(t,gel_rack[pick]);
                                free(gel_rack[pick]);
                                gel_rack[i] = malloc(strlen(t)+1);
                                strcpy(gel_rack[i],t);
                                if( i != pick ) gel_rack[pick] = NULL;
                                pick_flag[pick] = (char) 0;
                        }
                        else {
                                free(gel_rack[pick]);
                                gel_rack[pick] = NULL;
                        }
                }
                gel_rack[++i] = NULL;
                return(gel_rack);
        }
}

int ch_dir(p)     /* change current directory to 'p'; return 1 if OK else 0 */
char *p;
{
        union REGS in,out;

        in.x.ax = 0x3B21;         /* DOS interrupt for set path */
        in.x.dx = (int) p;               /* the path */
        intdos(&in,&out);

        return( ((int) out.h.al == 0) ? 1 : 0 );
}

int path_check(path)      /* check pathname for existence */
char *path;
{
        int drive;
        static char pn[MAXPATH];
        static char pn2[MAXPATH];
        char *d;

        drive = get_dr_let();

        d = pn;
        *d++ = drive;   /* drive spec */
        *d++ = ':';
        *d++ = '\\';
        if(get_path(d, drive)) *(--d) = NULL;   /* build current pathway in 'pn'*/

        strcpy(pn2,path);
        if(isdrive(pn2)) {       /* drive specified */
                if( pn2[strlen(pn2)-1] == ':' ) {
                        strcat(pn2,"\\");
                }
                else {
                        if( (strlen(pn2) > 3) && (pn2[strlen(pn2)-1] == '\\') ) pn2[strlen(pn2)-1] = NULL;
                }
        }
        else {
                if( (strlen(pn2) > 1) && (pn2[strlen(pn2)-1] == '\\') ) pn2[strlen(pn2)-1] = NULL;
        }

        if( ch_dir(pn2) ) {      /*  path exists */
                ch_dir(pn);      /* reset old path */
                return(1);
        }
        else return(0);                  /* no path...current directory still in effect */
```

```
}
#include <stdio.h>

#define VAR extern

#include <redit.h>

#include <bios.h>

VAR WINDOW wn[];

extern int dcomp();

#define TBUF 80

VAR int cur_window = { 0 };             /* which window is active for raw I/O */

#define STATUS          12      /* line containing full screen status transactions */

#define EDIT            0       /* edit window */
#define EMENU           1       /* edit menu window */
#define PICK            2       /* file pick screen */
#define CLUEHELP        3       /* clue help window */

/* fields in digest selection screen */

#define DS_SC           10
#define DS_MC           50
#define DS_HEADING      1
#define DS_TITLE        3
#define DS_TOP          5

VAR int ds_type = { SINGLE };
VAR int ds_pick = { EMPTY };


void m_init()    /* initialize all merge digest data */
{
        int i;

        m_nmd = m_nsd = EMPTY;

        for(i=0; i < MAXSIN; i++) {
                m_s_name [i][0] = NULL;
                m_s_pick [i] = 0;
        }

        for(i=0; i < MAXMUL; i++) {
                m_m_name [i][0] = NULL;
                m_m_pick [i] = 0;
        }

}

char *skip_1(inp)               /* read past next digest in file 'inp' */
FILE *inp;
{
        int i;
        static char b[TBUF], dn[TBUF];

        fgets(dn,TBUF,inp);     /* read name */

        fgets(b,TBUF,inp);      /* number of frags */
        sscanf(b,"%d",&i);
        for( ; i >= 0; i-- ) fgets(b,TBUF,inp);

        return(dn);
}

boolean skim(mpf)        /* get digest names out of named project */
char *mpf;
{
        FILE *inp;
        char b[TBUF], *p;
        int i;

        if( inp = fopen(mpf,"r") ) {

                m_init();               /* clear data area */

                fgets(b,TBUF,inp);      /* read comment line */
```

```
		fgets(b,TBUF,inp);		/* read topology line */
		if( toupper(b[0]) == 'C' ) m_topology = 0; else m_topology = 1;
		if( m_topology != linear ) {	/* project topologies do not agree */
			clears();
			gotoxy(25,15);
			rawputs("Project topologies do not agree!");
			gotoxy(15,17);
			sprintf(b,"Current project is %s, merge project is %s",linear ? "Linear" : "Circular", m_topology ? "Linear" : "Circular" );
			rawputs(b);
			gotoxy(29,19);
			rawputs("Go ahead anyway? (Y/N) ");
			if( rawgets(b) > 0 ) {
				for( p = b; *p && !isalpha(*p); p++ );
				if( toupper(*p) == 'N' ) {	/* skip */
					fclose(inp);
					return(FALSE);
				}
			}
		}

		fgets(b,TBUF,inp);		/* number of multiple digests */
		sscanf(b,"%d",&m_nmd);

		for( i=START; i <= m_nmd; i++ ) {	/* read digest names */

			p = skip_1(inp);
			trim(p);
			uppercase(p);
			strcpy(m_m_name[i],p);
		}

		fgets(b,TBUF,inp);		/* number of single digests */
		sscanf(b,"%d",&m_nsd);

		for( i=START; i <= m_nsd; i++ ) {	/* read digest names */

				p = skip_1(inp);
				trim(p);
				uppercase(p);
				strcpy(m_s_name[i],p);
			}

			fclose(inp);
			return(TRUE);
		}
		else {
			clears();
			gotoxy(20,15);
			rawputs("Unable to open merge project");
			gotoxy(20,17);
			rawputs("Hit a key to continue");
			rawin();
			return(FALSE);
		}
}

int comp_test(c)		/* compare composition of multiple digests against 'c' */
int c[MAXSIN];			/* return index of first match */
{
		int i,j;
		boolean yes;

		for( i = START; i <= nmd; i++ ) {
			yes = TRUE;
			for( j = START; j <= nsd; j++ ) {
				if( composition [i][j] != c[j] ) {
					yes = FALSE;
					break;
				}
			}
			if( yes ) return(i);
		}
		return(EMPTY);
}

comp_calc(c,s)	/* compute composition in standard format */
int c[MAXSIN];
char *s;
{
		int j;
		static char b[TBUF];
		char *p;
```

```
        for(j=START;j<MAXSIN;j++) c[j] = FALSE;

        for( j = START; j <= nsd; j++ ) {        /* scan single digests */
                strcpy(b,sname[j]);
                                                         /* look for 'sname[],' imbedded in mname[] */
                strcat(b," ,");
                if( stcpm( s, b, &p ) ) {        /* found it */
                        c[j] = TRUE;
                        continue;
                }
                strcpy(b,", ");                          /* look for ',sname[]' imbedded in mname[] */
                strcat(b,sname[j]);
                if( stcpm( s, b, &p ) ) {        /* found it */
                        c[j] = TRUE;
                        continue;
                }
        }
}

/* NOTE: modify this at some point to delete conflicting digests and look for other funny business */

int merge_1(inp)          /* read in a digest from file 'inp' at current position */
FILE *inp;
{
        char b[TBUF], *p;
        int sorm,ttop;
        boolean tcomp[MAXSIN];

        for(sorm=START;sorm < MAXMAP;sorm++) tdigest[sorm].flags = (CLUE) NONE;

        tfile[0] = NULL;                   /* don't use this data any more */
        tmax = EMPTY;

        fgets(b,NAMELEN,inp);              /* read digest name */
        trim(b);

        uppercase(b);                      /* map to upper case alphabetics */

        if( scan_past(b,',') ) {
                sorm = MULTIPLE;           /* multiple digest */
                if( ++nmd >= MAXMUL ) {
                        nmd--;
                        printf("\nToo many multiple digests!\n");
                        return(0);
                }
        }
        else {
                sorm = SINGLE;
                if( ++nsd >= MAXSIN ) {
                        nsd--;
                        printf("\nToo many single digests!\n");
                        return(0);
                }
        }
        strcpy(tname,b);

        fgets(b,TBUF,inp);                 /* get number of fragments */
        sscanf(b,"%d",&ttop);

        for( ; tmax < ttop; ) {
                fgets(b,TBUF,inp);                       /* read fragment sizes */
                trim(b);
                if( *b == NULL ) break;
                                                                 /* one more */
                tmax++;
                sscanf(b,"%ld", &tdigest [tmax].frag);   /* extract size */
                if( tdigest [tmax].frag == (SIZE) 0 ) {
                        tmax--;
                        break;
                }
                if( p = scan_past(b,',') ) {
                        p = scan_past(p,' ');
                        sscanf(p,"%ld", &tdigest [tmax].frag_error);    /* extract error */
                }
                else tdigest [tmax].frag_error = tdigest [tmax].frag * lo_factor / (SIZE) 100;

                if( p = scan_past(p,',') ) {     /* clue field is present */
                        p = scan_past(p,' ');
                        while( *p ) {
                                switch( toupper(*p++) ) {
                                case 'A':         /* auto new frag */
                                        tdigest [tmax].flags |= (CLUE) AUTONEW;
                                        break;
                                case 'N':         /* new frag */
```

```
                        tdigest [tmax].flags  |= (CLUE) NEW;
                        break;
                    case 'C':
                        tdigest [tmax].flags |= (CLUE) CUT;
                        break;
                    case 'E':       /* any end */
                        tdigest [tmax].flags |= (CLUE) EEND;
                        tclue |= (CLUE) EEND;
                        break;
                    case 'L':       /* left end */
                        tdigest [tmax].flags |= (CLUE) LEND;
                        tclue |= (CLUE) LEND;
                        break;
                    case 'R':       /* right end */
                        tdigest [tmax].flags |= (CLUE) REND;
                        tclue |= (CLUE) REND;
                        break;
                    }
                }
            }
        }

        qsort( &tdigest[0], tmax+1, sizeof(digest), &dcomp );

/* consistency with current project should be implemented here */

        if( sorm == MULTIPLE ) {
            comp_calc(tcomp,tname);                             /* extract enzyme composition */
            if( (ttop = comp_test(tcomp)) > EMPTY ) {       /* some other digest has same composition */
                del_mul(ttop);                              /* delete it */
            }
            ed2mul(nmd);                    /* copy to multiple */
        }
        else {
            for(ttop = START; ttop <= nsd; ttop++) {        /* compare names of other singles */
                if( !strcmp(sname[ttop],tname) ) {      /* found another one */
                    del_sin(ttop);
                    break;
                }
            }
            ed2sin(nsd);                    /* copy to single */
        }

        sort_out();

        return(sorm);
}

merge(mpf)              /* merge selected digests from mapping project in file 'mpf' */
char *mpf;
{
        FILE *inp;
        char b[TBUF], *p;
        int i;

        if( inp = fopen(mpf,"r") ) {
            fgets(b,TBUF,inp);      /* skip comment, topology, number of multiple digests */
            fgets(b,TBUF,inp);      /* skip comment, topology, number of multiple digests */
            fgets(b,TBUF,inp);      /* skip comment, topology, number of multiple digests */

            for(i=START; i <= m_nmd; i++) {
                if( m_m_pick[i] ) merge_1(inp);
                else p = skip_1(inp);
            }

            fgets(b,TBUF,inp);      /* skip number of single digests */

            for(i=START; i <= m_nsd; i++) {
                if( m_s_pick[i] ) merge_1(inp);
                else p = skip_1(inp);
            }

        }
        else {
            clears();
            gotoxy(25,15);
            rawputs("Error reading project to merge");
            gotoxy(30,17);
            rawputs("Hit a key to continue");
            rawin();
```

```
		}
}
show_merge(s)	/* display a selection of entered digests */
char *s;	/* 's' says what will be done with it */
{
	int i;

	gotoxy(DS_SC+10,DS_HEADING);
	rawputs("Select digests to ");
	rawputs(s);
	gotoxy(DS_SC-4,DS_TITLE);
	rawputs("Single digests");
	gotoxy(DS_MC-4,DS_TITLE);
	rawputs("Multiple digests");

	for( i=START; i<=m_nsd; i++ ) {		/* scan singles */

		gotoxy(DS_SC,DS_TOP+i);

		if((ds_type == SINGLE) && (ds_pick == i)) reverse();

		rawputs(m_s_name[i]);

		if((ds_type == SINGLE) && (ds_pick == i)) normal();

		if( m_s_pick[i] ) {
			highint();
			rawputs("*");
			normal();
		}
		else rawputs(" ");
	}

	for( i=START; i<=m_nmd; i++ ) {		/* scan mulitples */

		gotoxy(DS_MC,DS_TOP+i);

		if((ds_type == MULTIPLE) && (ds_pick == i)) reverse();

		rawputs(m_m_name[i]);

		if((ds_type == MULTIPLE) && (ds_pick == i)) normal();

		if( m_m_pick[i] ) {
			highint();
			rawputs("*");
			normal();
		}
		else rawputs(" ");
	}
}

m_ds_up()
{
	if( --ds_pick < START ) {
		switch(ds_type) {
			case MULTIPLE:
				ds_pick = m_nmd;
				break;
			case SINGLE:
				ds_pick = m_nsd;
				break;
			default:
				ds_pick = EMPTY;
				break;
		}
	}
}

m_ds_down()
{
	switch( ds_type ) {

		case SINGLE:
			if( ++ds_pick > m_nsd ) ds_pick = START;
			break;

		case MULTIPLE:
			if( ++ds_pick > m_nmd ) ds_pick = START;
			break;
	}
```

```
}

p_m_help()                  /* display help box on merge digest pick screen */
{
        gotoxy(6,DS_TOP+15);
        rawputs("IMMMMMMMMMMMMKMMMMMMMMMMMMKMMMMMMMMMMMMMMMMMMMKMMMMMMMMMMMMMMMMMM;");
        gotoxy(6,DS_TOP+16);
        rawputs(":  <-   left  :    up     :  <ret> to merge   :  <Ins> to select :");
        gotoxy(6,DS_TOP+17);
        rawputs(":  ->   right :    down   :  <esc> to abandon :  <Del> to cancel :");
        gotoxy(6,DS_TOP+18);
        rawputs("HMMMMMMMMMMMMJMMMMMMMMMMMMJMMMMMMMMMMMMMMMMMMMJMMMMMMMMMMMMMMMMMM<");
}

int pick_merge(s)           /* select digests to merge */
char *s;                    /* 's' tells what will be done with it */
{
        cur_window = PICK;
        set_wn(Lwn[PICK]);

        if( ds_pick < START ) ds_pick = START;

        if( ds_type == SINGLE ) {
                if( ds_pick > m_nsd ) ds_pick = m_nsd;
        }
        else {
                if( ds_pick > m_nmd ) ds_pick = m_nmd;
        }

        show_merge(s);
        p_m_help();

        while(1) {
                switch(rawin()) {
                case CR:
                        return(ds_type);
                case NULL:
                        switch(rawin()) {
                                case CUP:
                                        m_ds_up();
                                        break;
                                case CDOWN:
                                        m_ds_down();
                                        break;
                                case LEFT:
                                case RIGHT:
                                        if( ds_type == MULTIPLE ) {
                                                if( m_nsd == EMPTY ) break;
                                                ds_type = SINGLE;
                                                if( ds_pick > m_nsd ) ds_pick = m_nsd;
                                        }
                                        else {
                                                if( m_nmd == EMPTY ) break;
                                                ds_type = MULTIPLE;
                                                if( ds_pick > m_nmd ) ds_pick = m_nmd;
                                        }
                                        break;
                                case DEL:
                                        if( ds_type == MULTIPLE ) {
                                                m_m_pick[ds_pick] = 0;
                                        }
                                        else {
                                                m_s_pick[ds_pick] = 0;
                                        }
                                        break;
                                case INS:
                                        if( ds_type == MULTIPLE ) {
                                                m_m_pick[ds_pick] = !m_m_pick[ds_pick];
                                        }
                                        else {
                                                m_s_pick[ds_pick] = !m_s_pick[ds_pick];
                                        }
                                        break;
                        }
                        show_merge(s);
                        break;
                case ABORT:
                        return(NONE);
                }
        }
```

```
}
#include <stdio.h>
#include <dos.h>

int get_dr_let()          /* return the current drive letter as an int */
{
        union REGS in,out;

        in.x.ax = 0x1921;         /* DOS interrupt for current disk */
        intdos(&in,&out);
        return( (int) (out.h.al + 'a') );

}

get_path(s,d)       /* return the current pathway from the root, but no drive */
char *s;            /* where to put it */
int d;              /* drive letter */
{
        union REGS in,out;

        in.x.ax = 0x4721;          /* DOS interrupt for get current path */
        in.x.si = s;               /* where to put the result */
        in.h.dl = toupper(d) - 'A' + 1;           /* which drive */
        intdos(&in,&out);

        return( (int) out.h.al );
}

isdrive(s)          /* does this pathname contain a drive spec? */
char *s;
{
        return( (s[1] == ':') ? 1 : 0 );
}

complete(d,s)       /* fill in missing parts of complete pathname for 's' and put in 'd' */
char *s,*d;
{
        int drive;

        if(isdrive(s)) {                      /* drive specified */
                if( s[2] == '\\' ) {          /* pathway too */
                        strcpy(d,s);          /* just copy */
                }
                else {                        /* no path...find out what it is */
                        *d++ = s[0];          /* drive spec */
                        *d++ = ':';
                        *d++ = '\\';
                        if(get_path(d, (int) s[0])) *d = NULL;
                        else {
                                if(d[strlen(d)-1] != '\\')
                                        strcat(d,"\\");
                        }
                        strcat(d,&s[2]);              /* add the filename */
                }
        }
        else {
                drive = get_dr_let();         /* what drive is it? */

                if( s[0] == '\\' ) {          /* path from default root specified */
                        *d++ = drive;         /* drive spec */
                        *d++ = ':';
                        strcpy(d,s);          /* copy the rest */
                }
                else {                        /* no drive or path */
                        *d++ = drive;         /* drive spec */
                        *d++ = ':';
                        *d++ = '\\';
                        if(get_path(d, drive)) *d = NULL;
                        else {
                                if(d[strlen(d)-1] != '\\')
                                        strcat(d,"\\");
                        }
                        strcat(d,s);                  /* add the filename */
                }
        }
}

local(d,s)          /* strip the path prefix from 's' and put in 'd' */
char *s,*d;
{
        char *p;
```

```
        for(p=&s[strlen(s)-1]; p != s; --p)
                if( (*p == ':') || (*p == '\\') ) {
                        p++;
                        break;
                }
        strcpy(d,p);
}
#include <stdio.h>

#include <dos.h>

#define alloc(c) malloc(c)

struct fcb {
         char dum[21];
        char atr;
        int  time;
        int  date;
        long size;
         char f_name[13];
};


#define         SEARCH_FIRST    0x4E       /* BDOS calls */
#define         SEARCH_NEXT     0x4F
#define          DTA             0x1A
#define         CDRIVE          0x19

#define         MAXFILEWIDTH    19
#define          MAXLINE                50

#define         TRUE            1
#define         FALSE            0

#define          ERROR           0
#define          OK              1

#define          PATHLEN                64              /* maximum pathname size on MSDOS is 64 chars */

uppercase(s)
char *s;
{
        while(*s) {
                *s = toupper(*s);
                s++;
        }
}

int vcmp(x,y)    /* compare two strings indirectly */
char **x,**y;
{
        return(strcmp(*x,*y));
}


/*
 * expands ambiguous pathname afnp
 * and returns an argv array at 'farg' and function value is number of files
 */

expand(fargs, afnp)
char *fargs[64];
char *afnp;      /* possibly ambiguous file name*/
{

        struct fcb dta;
         union REGS reg;
        char *q;
        int srch, filecount;
        char x[PATHLEN];

        int vcmp();


        /* build fcb   */
         uppercase(afnp);
         bdos(DTA,&dta);

        /* Search disk directory for all ufns which match afn*/
        for(filecount=0;; filecount++) {
```

```
/* the following call is Lattice C specific */

                reg.h.ah = filecount ? SEARCH_NEXT : SEARCH_FIRST;
                reg.x.dx = afnp;
                reg.x.cx = 0;           /* see only regular files */
                srch=intdos(&reg,&reg);         /* call MSDOS */
                if( reg.x.ax == 18 ) break;
        /* end Lattice */

                /*Copy filename from directory*/
                strcpy(x,dta.f_name);

                if( (q = alloc(strlen(x) + 1)) == NULL) {
                        printf("Out of Memory for pathname expansion\n");
                        return ERROR;
                }

                fargs[filecount] = q;
                strcpy(q,x);

        }

        qsort(fargs, filecount, sizeof( char * ) , vcmp);

        return (filecount);
}
#include <stdio.h>


#define EXIT            '\033'
#define PAGESIZE        23

pages(f)        /* read lines from a file 'f' for one screen page and display a continuation prompt */
FILE *f;
{
        int i,endoffile;
        char line[150];

        /* erase any preceeding prompt message */
        printf("\r                                                          \r");

        for(i=PAGESIZE,endoffile=0; i>0; i--) {

                if(!endoffile) {

                        if( ! fgets(line,79,f) ) {
                                endoffile = 1;
                        }
                        else {
                                line[79]=NULL;
                                printf("%s",line);
                        }

                }
                else printf("\n");
        }

        if(endoffile) {
                printf("End...hit <esc> to exit");
                return(0);
        }
        else {
                printf("Hit <esc> to exit or any other key for more ");
                return(1);
        }
}


more(f)         /* print a file on the screen stopping for a user prompt every page */
FILE *f;        /* file 'f' is assumed to be open and readable */
{
        int c;

        while(pages(f)) {
                if( (c = rawin()) == EXIT ) return;
        }
        rawin();
}
#include <stdio.h>

#include <bios.h>
```

```
extern WINDOW wn[];         /* array of windows */
extern int cur_window;      /* which window do these function act upon? */

#define IBM 1

/*                          exchange the comment brackets with the IBM definition
                            to switch from the ANSI screen mode to the Apricot VT52 mode
#define APRICOT 1
*/

#ifdef IBM                  /* these are ANSI strings that work with IBM's ANSI.SYS driver */

#define LEADIN "\033["
#define BETWEEN ";"
#define TRAIL "H"
#define OFFSET 0
#define DECIMAL 1
#define ISBETWEEN 1
#define ISTRAIL 1

#define CLEAR   "\033[2J"       /* erase an ANSI screen */
#define TOP     "\033[1;1H"     /* ANSI for go to upper left corner */

#define GOREV "\033[7m"          /* reverse character attribute */
#define GOBLIND "\033[5m"        /* blink character attribute */
#define EXREV "\033[0m"          /* clear all character attributes */

#define ERASELINE "\033[2K"      /* erase cursor line */

#define CURSORON ""              /* these are ANSI standard control strings that IBM */
#define CURSOROFF ""             /* in its infinite wisdom decided not to support */
#define BLOCKCURSOR ""

#define HOME 'G'            /* cursor keys for IBM */
#define LEFT 'K'
#define END 'O'
#define CUP 'H'
#define CDOWN 'P'
#define PGUP 'I'
#define RIGHT 'M'
#define PGDN 'Q'
#define INSERT 'R'
#define DELETE 'S'

#endif

#ifdef APRICOT              /* these work with the Apricot screen driver (VT52) */

#define LEADIN "\033Y"
#define OFFSET 0x1A
#define ISBETWEEN 0
#define ISTRAIL 0
#define DECIMAL 0

#define CLEAR "\033E"
#define TOP "\033Y  "

#define GOREV "\033p"
#define GOBLIND ""
#define EXREV "\033q"

#define ERASELINE "\033l"

#define CURSORON "\033y\005"      /* set cursor on */
#define CURSOROFF "\033x\005"     /* set cursor off */
#define BLOCKCURSOR "\033x\004"   /* set cursor to reverse block */
#define rawout(c) putch(c)

#endif

#define SPACE 32
#define CNTLC 3
#define CNTLD 4
#define CNTLR 18
#define CNTLU 21
#define CNTLX 24
#define ESC 27
#define LF 10
#define BS 8
#define RETURN 13
#define DEL 127
#define HELP '?'
```

```
rawin()
{
        getch();
}

reverse()       /* switch screen into reverse video */
{
        wn[cur_window].att |= REVERSE;
        wn[cur_window].att ^= NORMAL;   /* not normal if reversed */
}

blink()         /* set blink attribute */
{
        wn[cur_window].att |= BLINK;
}

highint()       /* set high intensity attribute */
{
        wn[cur_window].att |= HIGH_INT;
}

normal()
{
        wn[cur_window].att = NORMAL;
}

eraseline()     /* send an ANSI erase entire line command */
{
        static char *n = { "\n" };

        v_st_rw(n,80,&wn[cur_window]);
}

visible()       /* ANSI make cursor visible */
{
        scr_con();              /* must dig down to the BIOS system level on the IBM */
}

invisible()     /* ANSI make cursor invisible */
{
        scr_coff();             /* must dig down to the BIOS system level on the IBM */
}

block()         /* set to block cursor */
{
        scr_cblk();
}

gotoxy(x,y)     /* move to screen pos (x,y) */
int x,y;
{
        wn[cur_window].r = y-1;
        wn[cur_window].c = x-1;
        pl_csr(&wn[cur_window]);
}

getxy(x,y)      /* return screen pos (x,y) */
int *x,*y;
{
        *x = wn[cur_window].c + 1;
        *y = wn[cur_window].r + 1;
}

clears()        /* clear the screen */
{
        cl_wn(&wn[cur_window]);
}

int rawgets(s)                  /* get a string from rawio functions, but provide simple editing */
char *s;                        /* return the length of 's' ; -1 is returned if ABORT is typed */
                                /* -2 is returned if help is requested */
{
        char c, *p;
        int len;


        len = 0;
        p = s;

        while(1) {      /* get characters repeatedly, until a terminating key is hit */
```

```
		switch( c = rawin() ) {

			case LF:	/* line feed == return key */
			case RETURN:	/* return key */
				*p = 0;
				return(len);

			case DEL:	/* delete */
			case BS:	/* backspace */
				if(len > 0) {
					len--;
					p--;
					rawout(BS);
					rawout(SPACE);
					rawout(BS);
				}
				break;

			case CNTLX:	/* kill line */
				if(len > 0)
					for( ;len > 0; len-- ) {
						p--;
						rawout(BS);
						rawout(SPACE);
						rawout(BS);
					}
				break;

			case ESC:	/* return abort code */
				*p = 0;
				return(-1);

			case HELP:	/* return help code */
				*p = 0;
				return(-2);

			default:	/* some kind of char */
				if( c >= SPACE ) {		/* it's visible, accept it */
					*p++ = c;
					rawout(c);
					len++;
				}
				break;
		}
	}
}

int arawgets(s)			/* get a string from rawio functions, but provide simple editing */
char *s;			/* return the length of 's' ; -1 is returned if ABORT is typed */
				/* -2 is returned if help is requested */
{
	char c, *p, *q, temp[80];
	int len,x,y,sx,sy;

	len = strlen(s);
	p = &s[strlen(s)];

	pl_csr(&wn[cur_window]);

	getxy(&sx,&sy);			/* get initial screen position */
	rawputs(s);

	while(1) {	/* get characters repeatedly, until a terminating key is hit */

		switch( c = rawin() ) {

			case 0:		/* cursor key prefix */
				getxy(&x,&y);

				switch(rawin()) {

					case LEFT:
						if( p == s ) break;
						gotoxy(x-1,y);
						--p;
						break;
					case RIGHT:
						if( *p == 0 ) break;
						gotoxy(x+1,y);
						p++;
						break;
					case HOME:
```

```
                gotoxy(sx,sy);
                p = s;
                break;
        case END:
                p = &s[strlen(s)];
                gotoxy(sx,sy);
                rawputs(s);
                break;
        case DELETE:
                if( (len > 0) && (*p != 0) ) {
                        q = &p[1];
                        strcpy(p,q);
                        rawputs(p);
                        rawout('_');
                        gotoxy(x,y);
                        --len;
                                }
                                break;
                        case INSERT:    /* take as a cue to leave */
                                return(len);
                                break;
                }
                break;

         case LF:        /* line feed == return key */
         case RETURN:    /* return key */
                return(len);

         case DEL:       /* delete */
         case BS:        /* backspace */

                if(len > 0) {
                        if( p == s ) break;     /* can't delete left beyond beginning */
                        rawout(BS);             /* move cursor back */
                        getxy(&x,&y);           /* get screen pos */
                        q = p;                  /* save end of string pos */
                        --p;                    /* move insertion pointer */
                        --len;                  /* string is shorter */
                        strcpy( p, q );                 /* copy back end */
                        rawputs(p);             /* display it */
                        rawout('_');            /* erase the last char */
                        gotoxy(x,y);
                }
                break;

         case CNTLX:     /* kill line */
                if(len > 0)
                        gotoxy(sx,sy);
                        for( ;len > 0; len-- ) rawout('_');
                        p = s;
                        *p = 0;
                        gotoxy(sx,sy);
                break;

         case ESC:       /* return abort code */
                return(-1);

         case HELP:      /* return help code */
                return(-2);

         default:        /* some kind of char */
                if( c >= SPACE ) {              /* it's visible, accept it */
                        strcpy(temp,p);                 /* save end */
                        *p++ = c;               /* insert char */
                        strcpy(p,temp);                 /* copy end */
                        rawout(c);
                        getxy(&x,&y);           /* get screen pos */
                        rawputs(temp);          /* update following text */
                        gotoxy(x,y);            /* restore cursor */
                        len++;
                }
                break;
            }
        }
}

rawputs(s)      /* send a string to the screen 'raw' */
char *s;
{
        int wr,wc;
```

```
		wr=wn[cur_window].r;
		wc=wn[cur_window].c+strlen(s);
		v_st_rw(s,strlen(s),&wn[cur_window]);
		wn[cur_window].r=wr;
		wn[cur_window].c=wc;
		pl_csr(&wn[cur_window]);
}

crepeat(c,n)		/* send 'n' copies of character 'c' to screen 'raw' */
char c;
int n;
{
		for(; n > 0; n--) rawout(c);
}


rawint(i)		/* send an integer in the range (1..132) to the screen as ASCII */
register int i;
{
		register int mi;

		if( i >= 100 ) {
			rawout('1');
			i -= 100;
		}

		if( i >= 10 ) {
			mi = i/10;		/* speed this up if possible */
			rawout( mi + '0' );
			i -= (mi + mi + (mi << 3));	/* quick ( * 10 ) */
		}

		rawout( i + '0' );
}
rawout(c)
char c;
{
		int wc,wr;

		if( c == BS ) {
			if( wn[cur_window].c ) wn[cur_window].c--;
			pl_csr(&wn[cur_window]);
		}
		else {
			wr=wn[cur_window].r;
			wc=wn[cur_window].c+1;
			v_st_rw(&c,1,&wn[cur_window]);
			wn[cur_window].r=wr;
			wn[cur_window].c=wc;
			pl_csr(&wn[cur_window]);
		}

}
```

What is claimed is:

1. A method for constructing fragmentation maps of molecules of DNA comprising the steps of (a) digesting molecules of the DNA with at least two digesting agents which fragment the DNA at characteristics restriction sites, said digesting being conducted with each agent separately as well as with both agents together;

(b) analyzing the approximate length of the fragments created by the digesting step; and (c) entering the approximate length values for the fragments into a digital computer programmed with the steps of (i) permuting incrementally from a beginning fragment form digestion by a first of the agents arrangements of additional sites and fragments from digestion by a second and by both of the agents to construct a plurality of hypotheses for correct additions to the fragmentation map begun with the beginning fragment;

(ii) testing each hypothesis by computing local additive lengths of the additions to said map hypothesis and testing for the existence of additional fragments of a length corresponding to said computed length;

(iii) rejecting each of said hypotheses for which no such additional fragment is found of the correct length;

(iv) accepting incrementally each of said map hypotheses for which said additional fragment is found of the correct length; and (v) outputting all the accepted map hypotheses which utilize all the fragments as possibly correct fragmentation maps.

2. The method of calim 1, wherein in step (i) for all sites calculated from said digestion by the first agent, every permutation of said sites each in combination with every permutation of the fragments from the digestion by the first agent, and each in combination with every permutation of the fragments from the digestion by both agents is generated as an hypothesis for a possibly correct fragmentation map.

3. The method of claim 1, wherein in step (i) every permutation of the fragments from the digestion by the first agent in combination with every permutation of said sites which combination is consistent with the sizes of said fragments from the digestion by the first agent within predetermined error limits, and each in combination with every permutation of the fragments from the digestion by both agents is generated as an hypothesis for a possibly correct fragmentation map.

4. The method of claim 3 further including the step of evaluating said permutations on the basis of consistency with the length of the fragments from the digestion with both agents, and rejecting any combination which is inconsistent with said data.

5. A method for constructing fragmentation maps of DNA molecules comprising the steps of (a) digesting the DNA molecules separately with two different enzymes which cut the DNA at characteristic sites into fragments and also digesting the DNA molecules together with both enzymes;

(b) analyzing the approximate length of the fragments created by the digesting step; and (c) entering the approximate lengths of the fragments into a digital computer programmed to perform the steps of (i) generating each permutation of all fragments from digestion by one enzyme in combiantion with all permutations of sites which are consistent with the lengths of said fragments from digestion by one enzyme within predetermined error limits, (ii) computing the minimum and maximum possible sizes for each interval between sites in said combinations by summing the lengths and the possible error, (iii) selecting fragments from the fragments from digestion by the other enzyme and by both enzyme that are consistent with said computed sizes within possible error, (iv) generating all possible permutation of the order of the fragments so selected, and (v) evaluating the overall cumulative error of the fit of said selected orders of fragments to provide an indication of overall probability of said orders to a user.

6. A method of constructing fragmentation maps of DNA molecules comprising the step of (a) digesting the DNA molecules separately with at least first and second digestion agents, and jointly with both agents, each agent cutting the DNA molecule at a characteristic site;

(b) analyzing the lengths of the fragments created by the digestions; and (c) entering the lengths of the fragments into a digital computer programmed to perform the steps of (i) maintaining three parallel tentative maps of the order of the fragments from the digestion by the first agent, by the second agent, and by both agents, (ii) beginning with a fragment from the digestion by the first agent;

(iii) selecting a site for addition to the tentative maps, the site being selected as the end of the shorter of the two maps from digestion with one of the first and second agents, (iv) tentatively adding to the site a fragment selected from the fragments from the digest by the respective agent for that map, to thus create a hypothesis, (v) testing the hypothesis by testing for the existence of fragments from the digestion by both agents for addition to the map for both agents which is consistent with the hypothesis, (vi) if the testing of the hypothesis fails, repeat steps (iv) and (v) for each remaining fragment for the respective map, (vii) if the testing of the hypothesis proceeds, repeat steps (iii) through (vi) until all fragments from all digests are assigned to one of the fragmentation maps, and (viii) providing as an output to the user all sets of fragmentation maps which use all fragments and which tested correctly.

7. The method of claim 6 wherein the computer is programmed before step (viii) with the step of if no set of fragmentation maps is generated which uses all fragments and tests correctly, then selecting a different fragment from the digestion by the first agent as the beginning in step (ii) and repeating step (iii) through (vii).

8. The method of claim 6 wherein an error is assigned to the lengths of each of the fragments in the step of analyzing, which error is entered into the computer and wherein the computer is further programmed to sum the combined error for each complete set of fragmentation maps and to indicate to the user the relative combined error for each such set.

9. The method of claim 6 wherien the computer is further programmed to, as a result of the testing, to reject all additional hypotheses which are mirror images or which are additions to each hypothesis which fails the test in step (v).

10. The method of claim 6 wherein the user may input constraining information into the computer to constrain the selection in steps (ii), (iii) or (iv).

11. The method of claim 10 wherein the constraining information comprises at least one of a fragment occupying a defined position on a map, a fragment is cut by a selected agent, a fragment from the digestion by both agents is contained in a certain fragment from the digestion by a single agent, a fragment is adjacent a certain fragment, a fragment from one digest is identical to a certain fragment from another digest, and a fragment has a size such that its length has not been determined.

* * * * *

UNITED STATES PATENT AND TRADEMARK OFFICE

CERTIFICATE OF CORRECTION

PATENT NO. : 4,771,384

DATED : September 13, 1988

INVENTOR(S) : Donna L. Daniels, John L. Schroeder, Frederick R. Blattner, Michael Waterman It is certified that error appears in the above-indentified patent and that said Letters Patent is hereby corrected as shown below:

Column 1, before line 5, please insert the following text:

--This invention was made with government support under SBIR Grant R44GM33107 awarded by the National Institutes of Health. The government has certain rights in the invention.--

Signed and Sealed this

Eighteenth Day of March, 1997

Attest:

BRUCE LEHMAN

*Attesting Officer*

*Commissioner of Patents and Trademarks*